US008759297B2

(12) United States Patent
Pardridge et al.

(10) Patent No.: US 8,759,297 B2
(45) Date of Patent: *Jun. 24, 2014

(54) GENETICALLY ENCODED MULTIFUNCTIONAL COMPOSITIONS BIDIRECTIONALLY TRANSPORTED BETWEEN PERIPHERAL BLOOD AND THE CNS

(75) Inventors: William M. Pardridge, Pacific Palisades, CA (US); Ruben J. Boado, Agoura Hills, CA (US)

(73) Assignee: ArmaGen Technologies, Inc., Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/841,541

(22) Filed: Aug. 20, 2007

(65) Prior Publication Data

US 2008/0152645 A1  Jun. 26, 2008

Related U.S. Application Data

(60) Provisional application No. 60/822,825, filed on Aug. 18, 2006.

(51) Int. Cl.
| | | |
|---|---|---|
| *A61K 39/44* | (2006.01) | |
| *A61K 39/395* | (2006.01) | |
| *C07K 16/46* | (2006.01) | |
| *C07K 19/00* | (2006.01) | |
| *C07K 16/28* | (2006.01) | |
| *C07K 16/18* | (2006.01) | |

(52) U.S. Cl.
USPC ... 514/17.7; 424/139.1; 424/1.49; 424/136.1; 530/387.1; 530/387.3; 530/388.15; 530/388.22; 530/388.24

(58) Field of Classification Search
None
See application file for complete search history.

(56) References Cited

U.S. PATENT DOCUMENTS

| | | |
|---|---|---|
| 4,801,575 A | 1/1989 | Pardridge |
| 4,902,505 A | 2/1990 | Pardridge et al. |
| 4,946,778 A * | 8/1990 | Ladner et al. ............... 435/69.6 |
| 5,154,924 A | 10/1992 | Friden |
| 5,180,820 A | 1/1993 | Barde et al. |
| 5,182,107 A * | 1/1993 | Friden ........................ 424/179.1 |
| 5,229,500 A | 7/1993 | Barde et al. |
| 5,438,121 A | 8/1995 | Barde et al. |
| 5,453,361 A | 9/1995 | Yancopoulos et al. |
| 5,527,288 A | 6/1996 | Gross et al. |
| 5,527,527 A | 6/1996 | Friden |
| 5,562,903 A | 10/1996 | Co et al. |
| 5,610,279 A | 3/1997 | Brockhaus et al. |
| 5,618,920 A | 4/1997 | Robinson et al. |
| 5,656,284 A | 8/1997 | Balkin |
| 5,672,683 A | 9/1997 | Friden et al. |
| 5,693,762 A | 12/1997 | Queen et al. |
| 5,824,782 A | 10/1998 | Holzer et al. |
| 5,837,231 A | 11/1998 | Low et al. |
| 5,848,991 A | 12/1998 | Gross et al. |
| 5,977,307 A | 11/1999 | Friden et al. |
| 5,997,501 A | 12/1999 | Gross |
| 6,015,662 A | 1/2000 | Hackett |
| 6,041,775 A | 3/2000 | Century |
| 6,060,069 A | 5/2000 | Hill et al. |
| 6,153,190 A | 11/2000 | Young et al. |
| 6,165,783 A | 12/2000 | Weiss et al. |
| 6,201,105 B1 | 3/2001 | Smith et al. |
| 6,248,262 B1 | 6/2001 | Kubotera et al. |
| 6,284,262 B1 | 9/2001 | Place |
| 6,287,792 B1 | 9/2001 | Pardridge et al. |
| 6,322,808 B1 | 11/2001 | Trautman et al. |
| 6,329,508 B1 | 12/2001 | Friden |
| 6,348,210 B1 | 2/2002 | Gale |
| 6,361,760 B1 | 3/2002 | Murata |
| 6,372,250 B1 | 4/2002 | Pardridge |
| 6,375,975 B1 | 4/2002 | Modi |
| 6,531,309 B1 | 3/2003 | Hu et al. |
| 6,541,610 B1 | 4/2003 | Smith |
| 6,582,945 B1 | 6/2003 | Raso |
| 6,583,272 B1 | 6/2003 | Bailon |
| 6,709,833 B2 | 3/2004 | Fukul et al. |
| 6,743,427 B1 | 6/2004 | Schenk |
| 6,858,206 B2 | 2/2005 | Kakkis |
| 7,053,202 B2 | 5/2006 | O'Keefe et al. |

(Continued)

FOREIGN PATENT DOCUMENTS

| | | | |
|---|---|---|---|
| EP | 0613007 A2 | 8/1994 | |
| EP | 0613007 A3 | 10/1995 | |

(Continued)

OTHER PUBLICATIONS

Barth et al. Boron neutron capture therapy of brain tumors: an emerging therapeutic modality. Neurosurgery. Mar. 1999;44(3):433-50; discussion 450-1.
Buchli, et al. Inhibition of Nogo: a key strategy to increase regeneration, plasticity and functional recovery of the lesioned central nervous system. Ann Med. 2005;37(8):556-67.
Chen, et al. In vitro scanning saturation mutagenesis of all the specificity determining residues in an antibody binding site. Protein Engineering. 1999; vol. 12, No. 4, 349-356.
Chung et al. Antibodies against West Nile Virus nonstructural protein NS1 prevent lethal infection through Fc gamma receptor-dependent and -independent mechanisms. J Virol. Feb. 2006;80(3):1340-51.

(Continued)

*Primary Examiner* — Jeffrey Stucker
*Assistant Examiner* — Aurora M Fontainhas
(74) *Attorney, Agent, or Firm* — Wilson Sonsini Goodrich & Rosati

(57) ABSTRACT

Provided herein are compositions for increasing transport of agents across the blood-brain barrier, in some embodiments in both directions, while allowing their activity once across the barrier to remain substantially intact. The agents are transported across the blood-brain barrier via one or more endogenous receptor-mediated transport systems. In some embodiments the agents are therapeutic, diagnostic, or research agent. Also provided herein are nucleic acids encoding proteins contained in the compositions.

23 Claims, 49 Drawing Sheets

(56) References Cited

U.S. PATENT DOCUMENTS

| | | |
|---|---|---|
| 7,078,376 B1 | 7/2006 | Thompson |
| 7,214,658 B2 | 5/2007 | Tobinick |
| 7,226,758 B1 | 6/2007 | Lin et al. |
| 7,294,704 B2 | 11/2007 | Simone et al. |
| 7,309,687 B1 | 12/2007 | Brines et al. |
| 7,388,079 B2 | 6/2008 | Pardridge et al. |
| 7,741,446 B2 | 6/2010 | Pardridge et al. |
| 8,053,569 B2 | 11/2011 | Pardridge et al. |
| 8,124,095 B2 | 2/2012 | Pardridge et al. |
| 8,142,781 B2 | 3/2012 | Pardridge et al. |
| 8,497,246 B2 | 7/2013 | Pardridge et al. |
| 2002/0052311 A1 | 5/2002 | Solomon et al. |
| 2002/0137684 A1 | 9/2002 | Tchistiakova et al. |
| 2002/0169109 A1 | 11/2002 | Plata-Salaman et al. |
| 2003/0129186 A1 | 7/2003 | Beliveau et al. |
| 2003/0165853 A1 | 9/2003 | Pardridge et al. |
| 2004/0072291 A1 | 4/2004 | Carr et al. |
| 2004/0101904 A1 | 5/2004 | Pardridge et al. |
| 2004/0102369 A1 | 5/2004 | Wu et al. |
| 2004/0229250 A1 | 11/2004 | Figura et al. |
| 2004/0248197 A1 | 12/2004 | Holtzman et al. |
| 2005/0142141 A1 | 6/2005 | Pardridge |
| 2007/0081992 A1 | 4/2007 | Pardridge et al. |
| 2007/0082380 A1 | 4/2007 | Pardridge et al. |
| 2007/0275882 A1 | 11/2007 | Meijer et al. |
| 2007/0280940 A1 | 12/2007 | Winkles et al. |
| 2008/0003211 A1 | 1/2008 | Fogh et al. |
| 2008/0051564 A1 | 2/2008 | Pardridge et al. |
| 2008/0170994 A1 | 7/2008 | Pardridge et al. |
| 2008/0171055 A1 | 7/2008 | Pardridge et al. |
| 2008/0292639 A1 | 11/2008 | Shen et al. |
| 2009/0053219 A1 | 2/2009 | Pardridge et al. |
| 2009/0068206 A1 | 3/2009 | Pardridge et al. |
| 2009/0156498 A1 | 6/2009 | Pardridge et al. |
| 2009/0238789 A1 | 9/2009 | Guyon et al. |
| 2010/0077498 A1 | 3/2010 | Pardridge et al. |
| 2010/0098693 A1 | 4/2010 | Pardridge et al. |
| 2010/0172919 A1 | 7/2010 | Grimm et al. |
| 2010/0261647 A1 | 10/2010 | Pardridge et al. |
| 2010/0290985 A1 | 11/2010 | Pardridge et al. |
| 2011/0110935 A1 | 5/2011 | Pardridge et al. |
| 2012/0269807 A1 | 10/2012 | Pardridge et al. |
| 2013/0142794 A1 | 6/2013 | Pardridge et al. |
| 2013/0287773 A1 | 10/2013 | Pardridge et al. |

FOREIGN PATENT DOCUMENTS

| | | | |
|---|---|---|---|
| JP | 6-228199 | 8/1994 | |
| WO | WO 99/00150 A2 | 1/1999 | |
| WO | WO 99/00951 A1 | 1/1999 | |
| WO | WO 99/00150 A3 | 4/1999 | |
| WO | WO 99/66951 A1 | 12/1999 | |
| WO | WO 00/15759 A1 | 3/2000 | |
| WO | WO 03/074081 A1 * | 9/2003 | ........... A61K 39/395 |
| WO | WO 03/074081 A1 | 12/2003 | |
| WO | WO 2004/050016 A2 | 6/2004 | |
| WO | WO 2006/081171 A1 | 8/2006 | |
| WO | WO 2007/022416 A2 | 2/2007 | |
| WO | WO 2007/044323 A2 | 4/2007 | |
| WO | WO 2007/022416 A3 | 5/2007 | |
| WO | WO 2008/022349 | 2/2008 | |
| WO | WO 2009/018122 | 2/2009 | |
| WO | WO 2007/044323 A3 | 5/2009 | |
| WO | WO 2009/070597 A2 | 6/2009 | |

OTHER PUBLICATIONS

Coloma, M. Josephina, et al. 1999. Transport Across the Primate Blood-Brain Barrier of a Genetically Engineered Chimeric Monoclonal Antibody to the Human Insulin Receptor. *Pharmaceutical Research* 17 (3): 266-274.

Duchnowska, et al. Central nervous system metastases in breast cancer patients administered trastuzumab. Cancer Treat Rev. Jun. 2005;31(4):312-8.

Fukuda et al. In vitro evolution of single-chain antibodies using mRNA display. Nucleic Acids Research, 2006; 34(19):e127.

Hansson et al. Prediction of Alzheimer's disease using the CSF Abeta42/Abeta40 ratio in patients with mild cognitive impairment, Dement Geriatr Cogn Disord. 2007;23(5):316-20.

Henikoff et al.Predicting the effects of amino Acid substitutions on protein function. Annu Rev Genomics Hum Genet. 2006;7:61-80.

Martin et al. Crystal structure at 2.8 A of an FcRn/heterodimeric Fc complex: mechanism of pH-dependent binding. Mol Cell. Apr. 2001;7(4):867-77.

McLendon et al. Radiotoxicity of systemically administered, 211λt-labeled human/mouse chimeric monoclonal antibody: a long-term survival study with histologic analysis. Int J Radiat Oncol Biol Phys. Sep. 1, 1999:45(2):491-9.

Ober, et al. Differences in promiscuity for antibody-FcRn interactions across species: implications for therapeutic antibodies. Int Immunol, Dec. 2001;13(12):1551-9.

Sampson et al. Unarmed, tumor-specific monoclonal antibody effectively treats brain tumors. Proc Natl Acad Sci U S A. Jun. 20, 2000;97(13):7503-8.

Schlachetzki, et al. Expression of the neonatal Fc receptor (FCRn) at the blood-brain barrier. J Neurochem. Apr. 2002;81(1):203-6.

Warrington et al. Human monoclonal antibodies reactive to oligodendrocytes promote remyelination in a model of multiple sclerosis. Proc Natl Acad Sci U S A. Jun. 6, 2000;97(12)6820-5.

Zhang, et al. Mediated efflux of IgG molecules from brain to blood across the blood-brain barrier. J Neuroimmunol. Mar. 1, 2001;114(1-2):168-72.

Deane, et al. IgG-assisted age-dependent clearance of Alzheimer's amyloid beta peptide by the blood-brain barrier neonatal Fc receptor. J Neurosci; 2005; 25(50):11495-503.

Manoutcharian, et al. Amyloid-beta peptide-specific single chain Fv antibodies isolated from an immune phage display library. J Neuroimmunol. 2003; 145(1-2):12-7.

Arndt, et al. Generation of a highly stable, internalizing anti-CD22 single-chain Fv fragment for targeting non-Hodgkin's lymphoma. Int J Cancer. Dec. 10, 2003;107(5):822-829.

Boado et al, Genetic engineering, expression, and activity of a fusion protein of a human neurotrophin and a molecular Trojan horse for delivery across the human blood-brain barrier. Biotechnology and Bioengineering. 2007;97:1376-1386.

Boado et al. Fusion Antibody for Alzheimer's Disease with Bi-Directional Transport Across the Blood-Brain Barrier and Abeta Fibril Disaggregation. Bioconjug Chem. 2007;18(2):447-455.

Boado et al. Humanization of anti-human insulin receptor antibody for drug targeting across the human blood-brain barrier. Biotechnology and Bioengineering. 2007;96:381-391.

Boado, et al. Engineering and expression of a chimeric transferrin receptor monoclonal antibody for blood-brain barrier delivery in the mouse. Biotechnol Bioeng. Mar. 1, 2009;102(4):1251-8.

Brummell, et al. Probing the combining site of an anti-carbohydrate antibody by saturation-mutagenesis: role of the heavy-chain CDR3 residues. Biochemistry. 1993; 32(4):1180-7.

Coloma, et al. Design and production of novel tetravalent bispecific antibodies. Nat Biotechnol. Feb. 1997;15(2):159-63.

Coloma, et al. The hinge as a spacer contributes to covalent assembly and is required for function of IgG. J Immunol. Jan. 15, 1997;158(2):733-40.

Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.

Ferber, D. Bridging the blood-brain barrier: new methods improve the odds of getting drugs to the brain cells that need them. PLoS Biol. Jun. 2007;5(6):e169: 1191-1194.

Forough, et al. Differential transforming abilities of non-secreted and secreted forms of human fibroblast growth factor-1. J Biol Chem. Feb. 5, 1993;268(4):2960-8.

Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.

International search report dated Feb. 27, 2009 for PCT Application No. US08/71121.

(56) References Cited

OTHER PUBLICATIONS

International search report dated Jul. 1, 2008 for PCT Application No. US06/38587.
International Search Report dated Sep. 16, 2008 for PCT Application No. US2007/76316.
Lai, et al. Structural determinants of Trk receptor specificities using BDNF-based neurotrophin chimeras. J Neurosci Res. Dec. 1, 1996;46(5):618-29.
Marvin, et al. Recombinant approaches to IgG-like bispecific antibodies. Acta Pharmacol Sin. Jun. 2005;26(6):649-58.
McGrath, et al. Bifunctional fusion between nerve growth factor and a transferrin receptor antibody. J Neurosci Res. Jan. 15, 1997;47(2):123-33.
Office Action dated Jan. 15, 2008 for U.S. Appl. No. 11/245,710.
Office Action dated Jan. 15, 2009 for U.S. Appl. No. 11/841,623.
Office Action dated Jan. 23, 2009 for U.S. Appl. No. 11/245,546.
Office Action dated Apr. 13, 2007 for U.S. Appl. No. 11/245,710.
Office Action dated Jun. 3, 2008 for U.S. Appl. No. 11/245,710.
Office Action dated Jul. 2, 2008 for U.S. Appl. No. 11/245,546.
Office Action dated Jul. 2, 2009 for U.S. Appl. No. 11/245,710.
Office Action dated Jul. 31, 2009 for U.S. Appl. No. 12/179,806.
Office Action dated Aug. 20, 2009 for U.S. Appl. No. 12/323,232.
Office Action dated Sep. 20, 2007 for U.S. Appl. No. 11/245,710.
Office Action dated Sep. 24, 2009 for U.S. Appl. No. 11/841,623.
Office Action dated Oct. 15, 2007 for U.S. Appl. No. 11/245,710.
Office Action dated Oct. 20, 2009 for U.S. Appl. No. 11/245,546.
Office Action dated Oct. 30, 2009 for U.S. Appl. No. 11/841,592.
Office Action dated Nov. 8, 2007 for U.S. Appl. No. 11/245,546.
Office Action dated Nov. 10, 2008 for U.S. Appl. No. 11/245,710.
Office Action dated Nov. 13, 2006 for U.S. Appl. No. 11/245,710.
Padlan, et al. Identification of specificity-determining residues in antibodies. FASEB J. 1995; 9(1):133-9.
Pardridge, et al. 1998, Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582.
Park, et al. Production and characterization of fusion proteins containing transferrin and nerve growth factor. J Drug Target. 1998;6(1):53-64.
Raghavan, et al. Analysis of the pH dependence of the neonatal Fc receptor/immunoglobulin G interaction using antibody and receptor variants. Biochemistry. Nov. 14, 1995;34(45):14649-57.
Triguero et al. Capillary depletion method for quantification of blood-brain barrier transport of circulating peptides and plasma proteins. J Neurochem. 1990; 54(6):1882-8.
Zhang, et al. Rapid transferrin efflux from brain to blood across the blood-brain barrier. J Neurochem: Mar. 2001;76(5):1597-600.
Frenkel, et al. Modulation of Alzheimer's beta-amyloid neurotoxicity by site-directed single-chain antibody. J Neuroimmunol. Jul. 1, 2000;106(1-2):23-31.
Fukuchi, et al. Amelioration of amyloid load by anti-Abeta single-chain antibody in Alzheimer mouse model. Biochem Biophys Res Commun. May 26, 2006;344(1):79-86.
Liu, et al. Single chain variable fragments against beta-amyloid (Abeta) can inhibit Abeta aggregation and prevent abeta-induced neurotoxicity. Biochemistry. Jun. 8, 2004;43(22):6959-67.
Notice of Allowance dated Oct. 28, 2011 for U.S. Appl. No. 12/688,842.
Notice of Allowance dated Oct. 31, 2011 for U.S. Appl. No. 11/245,546.
Office action dated Oct. 18, 2011 for U.S. Appl. No. 11/245,546.
Office Action dated Oct. 30, 2009 for U.S. Appl. No. 11/841,594.
Office Action dated Feb. 2, 2010 for U.S. Appl. No. 11/245,710.
Office Action dated Mar. 10, 2010 for U.S. Appl. No. 12/179,806.
Office Action dated Mar. 26, 2010 for U.S. Appl. No. 12/323,232.
Office Action dated Mar. 26, 2010 for U.S. Appl. No. 11/841,594.
Boado, et al. Drug delivery of antisense molecules to the brain for treatment of Alzheimer's disease and cerebral AIDS. J Pharm Sci. Nov. 1998;87(11):1308-15.

European search report and search opinion dated Dec. 2, 2010 for Application No. 07841110.5.
European search report dated Feb. 23, 2010 for Application No. 6825389.7.
International search report dated Sep. 7, 2010 for PCT Application No. US10-27882.
Lee, et al. Drug targeting to the brain using avidin-biotin technology in the mouse; (blood-brain barrier, monoclonal antibody, transferrin receptor, Alzheimer's disease). J Drug Target. 2000;8(6):413-24.
Liu, et al. Anti beta-amyloid (Abeta) Scfv inhibits Abeta aggregation and neurotoxicity (P4-354). Neurobiology of Aging, Tarrytown, NY. 2004;25:S575-S576.
Office action dated Feb. 16, 2011 for U.S. Appl. No. 11/893,281.
Office action dated Feb. 16, 2011 for U.S. Appl. No. 12/150,983.
Office action dated Mar. 18, 2011 for U.S. Appl. No. 12/574,571.
Office Action dated Mar. 7, 2011 for U.S. Appl. No. 12/558,348.
Office action dated Apr. 6, 2011 for U.S. Appl. No. 11/245,710.
Office action dated May 12, 2010 for U.S. Appl. No. 11/893,281.
Office action dated May 13, 2011 for U.S. Appl. No. 12/688,842.
Office action dated Jun. 27, 2011 for U.S. Appl. No. 11/245,546.
Office Action dated Jul. 1, 2010 for U.S. Appl. No. 11/245,546.
Office action dated Sep. 15, 2010 for U.S. Appl. No. 12/150,983.
Office Action dated Oct. 12, 2010 for U.S. Appl. No. 11/245,710.
Office action dated Oct. 13, 2009 for U.S. Appl. No. 11/893,281.
Pardridge, et al. Drug and gene targeting to the brain with molecular Trojan horses. Nat Rev Drug Discov. Feb. 2002;1(2):131-9.
Wu, et al. Neuroprotection with noninvasive neurotrophin delivery to the brain. Proc Natl Acad Sci U S A. Jan. 5, 1999;96(1):254-9.
Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.
Al, et al., 2003. Intraputamenal Infusion of GDNF in Aged Rhesus Monkeys: Distribution and Dopaminergic Effects. The Journal of Comparative Neurology 461: 250-261.
Airavaara, et al. Effects of repeated morphine on locomotion, place preference and dopamine in heterozygous glial cell line-derived neurotrophic factor knockout mice. Genes Brain Behay. Apr. 2007;6(3):287-98.
Al Sawaf, et al. Neurological findings in Hunter disease: pathology and possible therapeutic effects reviewed. J Inherit Metab Dis. Aug. 2008:31(4):473-80.
Albayrak, et al. Effect of transient focal ischemia on blood-brain barrier permeability in the rat: Correlation to Cell Injury. Acta Neuropathol 1997;94:158-63.
Alberts, et al. Molecular Biology of the Cell. 3rd Edition. Garland Publishing Inc. New York. 1994; pp. 1206-1207.
Altschul, et al. Optimal sequence alignment using affine gap costs. Bulletin of Mathematical Biology. 1986; 48(5-6):603-16.
Altschul, et al. Basic Local Alignment Search Tool. J. Mol. Biol. 1990;215:403-410.
Altschul, et al. Gapped BLAST and PSI-BLAST: a new generation of protein database search programs. Nucleic Acids Res. 1977;25:3389-402.
Ausubel, et al. Current Protocols in Molecular Biology. John Wiley & Sons, New York, 1995 supplement.
Baloh, et al. Functional mapping of receptor specificity domains of glial cell line-derived neurotrophic factor (GDNF) family ligands and production of GFRalphal RET-specific agonists. J Biol Chem. Feb. 4, 2000;275(5):3412-20.
Beck, et al. 1994. Brain-Derived Neurotropic Factor Protects Against Ischemic Cell Damage in Rat Hippocampus. Journal of Cerebral Blood Flow and Metabolism 14: 689-92.
Bifare, et al. 2005. Brain-Derived Neurotropic Factor Protects against Multiple Forms of Brain Injury in Bacterial Meningitis. The Journal of Infectious Diseases 191: 40-45.
Boado, et al. AGT-181: expression in CHO cells and pharmacokinetics, safety, and plasma iduronidase enzyme activity in Rhesus monkeys. Oct. 2009; 144(2):135-41.
Boado, et al. CHO cell expression, long-term stability, and primate pharmacokinetics and brain uptake of an IgG-paroxonase-1 fusion protein. Biotechnol Bioeng. Jan. 2011;108(1):186-96.

(56) References Cited

OTHER PUBLICATIONS

Boado, et al. GDNF fusion protein for targeted-drug delivery across the human blood-brain barrier. Biotechnol Bioeng. Jun. 1, 2008;100(2):387-96.
Boado, et al. Genetic engineering of a lysosomal enzyme fusion protein for targeted delivery across the human blood-brain barrier. Biotechnology and Bioengineering. 2008; 99:475-84.
Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.
Boado, et al. Selective targeting of a TNFR decoy receptor pharmaceutical to the primate brain as a receptor-specific IgG fusion protein. J Biotechnol. Mar. 2010;146(1-2):84-91.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Brines, et al. Erythropoetin crosses the blood-brain barrier to protect against experimental brain injury, Proc Natl Acad Sci USA. 2000; 97:10526-10531.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Carnicella, et al. GDNF is a fast-acting potent inhibitor of alcohol consumption and relapse. Proc Natl Aced Sci U S A. Jun. 10, 2008;105(23):8114-9.
Casset, et al. A peptide mimetic of an anti-CD4 monoclonal antibody by rational design. Biochem Biophys Res Commun. Jul. 18, 2003;307(1):198-205.
Cassol, et al. Stability of dried blood spot specimens for detection of human immunodeficiency virus DNA by polymerase chain reaction. J Clin Microbiol. Dec. 1992;30(12):3039-42.
Cheng, et al. 1997. Marked Age-dependent Neuroprotection by Brain-derived Neurotropic Factor Against Neonatal Hypoxic-Ischemic Brain Injury. Annals of Neurology 41 (4): 521-29.
Cheng, et al. 2004. Neuroprotection for Ischemic Stroke: Two Decades of Success and Failure. The Journal of the American Society for Experimental Neuro Therapeutics 1: 36-45.
Chothia, et al. Canonical structures for the hypervariable regions of immunoglobulins. J Mol Biol. Aug. 20, 1987;196(4):901-17.
Colman, P.M. Effects of amino acid sequence changes on antibody-antigen interactions. Res Immunol. Jan. 1994:145(1):33-6.
Cowen, et al. 2004. Neuropeptides: implications for alcoholism. Journal of Neurochemistry 89: 273-85.
Dawson, et al. A comparative assessment of the efficacy and side-effect liability of the neuroprotective compounds in experimental stroke. 2001. Brain Research 892: 344-50.
De Pascalis, et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.
Dreier, et al. Recombinant immunocytokines targeting the mouse transferrin receptor: construction and biological activities. Bioconjug Chem. Jul.-Aug. 1998;9(4):482-9.
Duffy, et al. 1987. Blood-brain barrier transcytosis of insulin in developing rabbits. Brain Research 420: 32-38.
Durrington, et al. Paraoxonase and atherosclerosis. Arterioscler Thromb Vasc Biol. Apr. 2001;21(4):473-80.
Ehrenreich, et al. Erythropoietin therapy for acute stroke is both safe and beneficial. Mol Med. Aug. 2002;8(8):495-505.
Eketjall, et al. Distinct structural elements in GDNF mediate binding to GFRalpha1 and activation of the GFRalpha1-c-Ret receptor complex. EMBO J. Nov. 1, 1999;18(21):5901-10.
Elliott, et al. Control of rHuEPO biological activity: the role of carbohydrate. Exp Hematol. Dec. 2004;32(12):1146-55.
EP Appl. No. 08796594.3 Search Report and opinion dated Mar. 16, 2012.
Eslamboli, et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005:25:769-77.
Fillebeen, et al. Receptor-mediated transcytosis of lactoferrin through the blood-brain barrier. J Biol Chem. Mar. 12, 1999;274(11):7011-17.
Flowmen, et al. Determination of the organisation of coding sequences within the iduronate sulphate sulphatase (IDS)gene. Hum. Mol. Genet. 1993;2(1):5-10.
Friden, et al. Blood-brain barrier penetration and in vivo activity of an NGF conjugate. Science. Jan. 15, 1993;259(5093):373-77.
Fu, et al. Neuroprotection in stroke in the mouse with intravenous erythropoietin-Trojan horse fusion protein. Brain Res. Jan. 19, 2011;1369:203-7. Epub Oct. 31, 2010.
Gillies, et al. Bi-functional cytokine fusion proteins for gene therapy and antibody-targeted tratment of cancer. 2002, Cancer Immunology and Immunotherapy, vol. 51, pp. 449-460.
Golden, et al. Human blood-brain barrier leptin receptor. Binding and endocytosis in isolated human brain microvessels. J Clin Invest. Jan. 1, 1997;99(1):14-8.
Grasso, et al. Neuroprotection by erythropoietin administration after experimental traumatic brain injury. Brain Res. Nov. 28, 2007:1182:99-105.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003:18(7):2093-8.
Habgood, et al. Changes in blood-brain barrier permeability to large and small molecules following traumatic brain injury in mice. Eur J Neurosci. Jan. 2007;25(1):231-8.
He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-22.
He, et al. Glial cell line-derived neurotrophic factor mediates the desirable actions of the anti-addiction drug ibogaine against alcohol consumption. J Neurosci. Jan. 19, 2005;25(3):619-28.
Henikoff, et al. Amino acid substitution matrices from protein blocks. Proc Natl Acad Sci U S A. 1992; 89(22):10915-9.
Hetman, et al. Neuroprotection by Brain-derived Neurotropic Factor Is Mediated by Extracellular Signal-regulated Kinase and Phoshatidylinositol 3-Kinase. The J of Bio Chem. 1999. 274 (32): 22569-80.
Holliger, et al. Engineered antibody fragments and the rise of single domains. Nat Biotechnol. Sep. 2005;23(9):1126-36.
Hoshaw, et al. Central administration of IGF-I and BDNF leads to long-lasting antidepressant-like effects. Brain Res. 2005. 1037: 204-8.
Pardridge, et al. 1987. Human Blood-Brain Barrier Transferrin Receptor. Metabolism 36: 892-95.
Pardridge, et al. 1989. Transport of histone through the blood-brain barrier. J Pharmacol Exp Ther. Dec.;251(3):821-6.
Pardridge, et al. 1993. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46.
Pardridge, et al. 1995 Human insulin receptor monoclonal antibody undergoes high affinity binding to human brain capillaries in vitro and rapid transcytosis through the blood-brain barrier in vivo in the primate. Pharm Res. 12(6):807-16.
Patel, et al. Intraputamenal infusion of glial cell line-derived neurotrophic factor in PD: A two-year outcome study. Annals of Neurology. 2005;57:298-302.
PCT Application No. US10/52113 ISR dated Feb. 22, 2011.
PCT Application No. US11/21418 ISR and Written Opinion dated Apr. 8, 2011.

(56) References Cited

OTHER PUBLICATIONS

Pearson, et al. Improved Tools for Biological Sequence Comparison. Proc. Nat'l Acad. Sci. USA. 1988;85:2444-48.
Pearson, Rapid and sensitive sequence comparison with FASTP and FASTA. Meth. Enzymol. 1990;183:63-98.
Pencea, et al. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 2001 21 (17): 6706-17.
Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-26.
Pluckthun, A. Antibodies from *Escherichia coli*. in the Pharmacology of Monoclonal Antibodies. vol. 113, Rosenburg and Moore eds. Springer-Verlag, New York. 1994;pp. 269-315.
Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.
Preston, et al. 1997. Evidence for pore-like opening of the blood-brain barrier following forebrain ischemia in rats. Brain Research 761: 4-10.
Ratliff-Schaub, et al. 2005. Randomized controlled trial of transdermal secretion on behavior of children with autism. Autism 9 (3): 256-65.
Reiber, et al. Protein transfer at the blood cerebrospinal fluid barrier and the quantitation of the humoral immune response within the central nervous system. Clin Chim Acta. Mar. 30, 1987;163(3):319-28.
Robinson, et al. The structures of the neurotrophin 4 homodimer and the brain-derived neurotrophic factor / neurotrophin 4 heterodimer reveal a common Trk-binding site. Protein Science 1999 8: 2589-97.
Rochu, et al. Human paraoxonase: a promising approach for pretreatment and therapy of organophosphorus poisoning. Toxicology. Apr. 20, 2007;233(1-3):47-59.
Rossolini, et al. Use of deoxyinosine-containing primers vs degenerate primers for polymerase chain reaction based on ambiguous sequence information. Mol. Cell. Probes. 1994;8(2):91-98.
Ruiz-Leon, et al. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120;2003:1019-26.
Sakanaka, et al. In vivo evidence that erythropoietin protects neurons from ischemic damage. Proc Natl Acad Sci U S A. Apr. 14, 1998;95(8):4635-40.
Sakane, et al. Carboxyl-directed Pegylation of Brain-derived Neurotrophic Factor Markedly Reduces Systemic Clearance with Minimal Loss of Biologic Activity. Pharmaceutical Research 1997 14(8):1085-1091.
Sariola, et al. Novel functions and signalling pathways for GDNF. J Cell Sci. Oct. 1, 2003;116(Pt 19):3855-62.
Schabitz, et al. Intraventricular Brain-Derived Neurotrophic Factor Reduces Infarct Size After Focal Cerebral Ischemia in Rats. Journal of Cerebral Blood Flow and Metabolism 1997;17: 500-6.
Schlachetzki, et al. Gene therapy of the brain: the trans-vascular approach. Neurology. Apr. 27, 2004;62(8):1275-81.
Schwartz, et al. A superactive insulin: [B10-aspartic acid]insulin(human). Proc Natl Acad Sci U S A. Sep. 1987;84(18):6408-11.
Sellers, On the theory and computation of evolutionary distances. SIAM Journal on Applied Mathematics. 1974;26:787.
Selmayr, et al. Induction of tumor immunity by autologous B lymphoma cells expressing a genetically engineered idiotype. Gene Ther. May 1999;6(5):778-84.
Shanafelt, et al. Identification of critical amino acid residues in human and mouse granulocyte-macrophage colony-stimulating factor and their involvement in species specificity. J Biol Chem. Jul. 25, 1991;266(21):13804-10.
Shin, et al. Transferrin-antibody fusion proteins are effective in brain targeting, Proceedings of the Natinal Academy of Sciences, 1995. vol. 92, pp. 2820-2824.

Sifuentes, et al. A follow-up study of MPS I patients treated with laronidase enzyme replacement therapy for 6 years. Mol Genet Metab. Feb. 2007;90(2):171-80. Epub Sep. 29, 2006.
Siren, et al., Erythropoetin prevents neuronal apoptosis after cerebral ischemia and metabolic stress. Proc Natl Acad Sci U S A. Mar. 27, 2001;98(7):4044-9.
Skolnick, et al. From genes to protein structure and function: novel applications of computational approaches in the genomic era. Trends Biotechnol. Jan. 2000; 18(1):34-9. Review.
Soukharev, et al. A fluorogenic substrate for detection of organophosphatase activity. Anal Biochem. Apr. 1, 2004;327(1):140-8.
Spina, et al., Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry1992;59 (1): 99-106.
Strauss, et al., Brain-derived neurotrophic factor variants are associated with childhood-onset mood disorder: confirmation in a Hungarian sample. Molecular Psychiartry 2005;10: 861-67.
Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.
Takahashi, et al., Inhibition of cell growth and tumorigenesis of human glioblastoma cells by a neutralizing antibody against human basic fibroblast growth factor. Federation of European Biochemical Societies 1991;288 (1,2):65-71.
The BDNF Study Group (Phase III). A controlled trial of recombinant methionyl human BDNF in ALS. Neurology 1999;52: 1427-33.
Thoenen, et al. Neurotrophins: from enthusiastic expectations through sobering experiences to rational therapeutic approaches. Nature Neuroscience Supplement 5;2002:1046-50.
Tomatsu, et al. Murine model (GaIns(tm(C76S)slu)) of MPS IVA with missense mutation at the active site cystein conserved among sulfatase proteins. Mol Genet Metab. Jul. 2007;91(3):261-8.
Tougou, et al. Paraoxonase has a major role in the hydrolysis of prulifloxacin (NM441), a prodrug of a new antibacterial agent. Drug Metab Dispos. Apr. 1998;26(4):355-9.
Tsukahara, et al. The Role of Brain-derived Neurotrophic Factor in Transient Forebrain Ischemia in the Rat Brain. Neurosurgery 34 (2);1994:323-31.
U.S. Appl. No. 10/307,165 Office Action dated Feb. 10, 2006.
U.S. Appl. No. 10/307,165 Office Action dated Mar. 1, 2007.
U.S. Appl. No. 10/307,165 Office Action dated Aug. 17, 2007.
U.S. Appl. No. 10/307,165 Office Action dated Aug. 18, 2006.
U.S. Appl. No. 10/307,276 Office Action dated Feb. 22, 2006.
U.S. Appl. No. 10/307,276 Office Action dated Apr. 9, 2007.
U.S. Appl. No. 10/307,276 Office Action dated Jul. 19, 2006.
U.S. Appl. No. 10/307,276 Office Action dated Oct. 29, 2007.
U.S. Appl. No. 11/061,956 Office Action dated May 9, 2008.
U.S. Appl. No. 11/061,956 Office Action dated May 23, 2006.
U.S. Appl. No. 11/061,956 Office Action dated Nov. 13, 2007.
U.S. Appl. No. 11/061,956 Office Action dated Dec. 21, 2006.
U.S. Appl. No. 11/245,710 Office Action dated Jun. 3, 2008.
U.S. Appl. No. 12/574,571 Office Action dated Dec. 14, 2011.
U.S. Appl. No. 12/756,093 Office Action dated Jul. 20, 2012.
US Notice of Allowance—U.S. Appl. No. 11/245,546 dated Apr. 1, 2011.
US Notice of Allowance—U.S. Appl. No. 11/245,710 dated Aug. 9, 2011.
US Notice of Allowance—U.S. Appl. No. 11/841,623 dated Jan. 28, 2010.
Voznyi, et al. A fluorimeteric enzyme assay for the diagnosis of MPS II (Hunter disease). J Inherit Metab Dis. 2001;24:675-80.
Wang, et al. Identification of the key amino acids of glial cell line-derived neurotrophic factor family receptor alpha1 involved in its biological function. J Biol Chem. Jan. 2, 2004;279(1):109-16.
Ward, E.S. Binding activities of a repertoire of single immunoglobulin variable domains secreted from *Escherichia coli*. Nature. Oct. 12, 1989;341(6242):484-5.
Weich, et al. Interleukin-3/erythropoietin fusion proteins: in vitro effects on hematopoietic cells. Exp Hematol. May 1993;21(5):647-55.

(56) References Cited

OTHER PUBLICATIONS

Whetstone, et al. Blood-spinal cord barrier after spinal cord injury: relation to revascularization and wound healing. J Neurosci Res. Oct. 15, 2003;74(2):227-39.
Wiesenhofer, et al. Glial cell line-derived neurotrophic factor (GDNF) and its receptor (GFR-α1) are strongly expressed in human gliomas. Acta Neuropathol. (Berl). 2000;99:131-37.
Wraith, et al. Mucopolysaccaridosis type II (Hunter syndrome): a clinical review and recommendations for treatment in the era of enzyme replacement therapy. Eur J Pediatr. Mar. 2008;167(3):267-77.
Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.
Wu, et al. Neuroprotection in Experimental Stroke with Targeted Neurotrophins. NeuroRX: The Journal of the American Society for Experimental NeuroTherapeutics. 2005;2(1):120-128.
Xue, et al. Intrastriatal administration of erythropoietin protects dopaminergic neurons and improves neurobehavioral outcome in a rat model of Parkinson's disease. Neuroscience. May 25, 2007;146(3):1245-58.
Yamashita, et al. Post-Occlusion Treatment with BDNF Reduces Infarct Size in a Model of Permanent Occlusion of the Middle Cerebral Artery in Rat. Metabolic Brain Disease 12 (4);1997:271-80.
Yan, et al. 1994. Distribution of Intracerebral Ventricularly Administered Neurotrophins in Rat Brain and Its Correlation with Trk Receptor Expression. Experimental Neurology 127: 23-36.
Yan, et al. 2007 Enduring vulnerability to reinstatement of methamphetamine-seeking behavior in glial-cell-line-derived neurotrophic factor mutant mice. FASEB J. Jul. 21(9):1994-2004.
Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-84.
Zhang, et al. 2003. Global Non-Viral Gene Transfer to the Primate Brain Following Intravenous Administration. Molecular Therapy 7 (1): 11-18.
Zhou, et al. Brain penetrating IgG-erythropoietin fusion protein is neuroprotective following intravenous treatment in Parkinson's disease in the mouse. Brain Res. Mar. 25, 2011;1382:315-20. Epub Jan. 26, 2011.
Zito, et al. Sulphatase activities are regulated by the interaction of sulphatase-modifying factor 1 with SUMF2, EMBO Rep 2005;6(7):655-660.
Albeck, et al. A non-invasive transport system for GDNF across the blood-brain barrier. Regeneration and Transplantation. Jul. 7, 1997; 8(9-10):2293-2298.
Board of Patent Appeals and Interferences (BPAI) Decision dated Jul. 22, 2010 from U.S. Appl. No. 11/061,956.
Jeffrey, et al. 26-10 Fab-digoxin complex. Affinity and specificity due to surface complementarity. Proc Natl. Acad. Sci USA. 1993; 90(21):10310-10314.
Notice of allowance dated Sep. 23, 2013 for U.S. Appl. No. 12/756,093.
Notice of allowance dated Sep. 25, 2013 for U.S. Appl. No. 13/862,250.
Notice of allowance dated Oct. 7, 2013 for U.S. Appl. No. 12/323,232.
Office action dated Oct. 22, 2013 for U.S. Appl. No. 12/901,481.
Office action dated Nov. 4, 2013 for U.S. Appl. No. 12/179,806.
Schuchman, et al. Human alpha-L-iduronidase: Purification and properties of the high uptake (higher molecular weight) and the low uptake (processed) forms. J. Bioi. Chem. 1984; 259(5):3132-3140.
Aronovich et al., "Molecular Genetic Defect Underlying α-L-Iduronidase," Am. Journ. Hum. Genet. 58: 75-85 (1996).
Auclair, et al. Repeated intrathecal injections of recombinant human 4-sulphatase remove dural storage in mature mucopolysaccharidosis VI cats primed with a short-course tolerisation regimen. Mol Genet Metab. Feb. 2010;99(2):132-41. doi: 10.1016/j.ymgme.2009.10.002. Epub Oct. 13, 2009.
Batzer, et al. Enhanced evolutionary PCR using oligonucleotides with inosine at the 3'-terminus. Nucleic Acid Res.1991;19:5081.
Begley et al., "Lysosomal storage diseases and the blood-brain barrier," Current Pharmaceutical Design, vol. 14, No. 16, pp. 1566-1580 (2008).
Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010.
Boado et al., "Genetic engineering of a lysosomal enzyme fusion protein for targeted delivery across the human blood-brain barrier," Biotechnology and Bioengineering, vol. 99, No. 2, pp. 475-484 (2008).
Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).
Boado et al., "Pharmacokinetics and brain uptake if a genetically engineered bifunctional fusion antibody targeting the mouse transferrin receptor," Molecular Pharmaceutics, vol. 7, No. 1, pp. 237-244 (2010).
Boado et al., Genetic Engineering of IgG-glucuronidase fusion proteins, J. Drug Targeting 18(3):205-11 (2010).
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008.10.020. Epub Oct. 29, 2008.
Crow, et al. Biochemical and histopathological studies on patients with mucopolysaccharidoses, two of whom had been treated by fibroblast transplantation. J Clin Pathol. 1983:36(4):415-30.
Degraaf, M. et al., "Expression of scFvs and scFv Fusion Proteins in Eukaryotic Cells." Methods in Biology, 2001, vol. 178: Antibody Phage Display: Methods and Protocols, p. 379-387.
De Pascalis, et al. Grafting of "abbreviated" complementarity-determining regions containing specificity-determining residues essential for ligand contact to engineer a less immunogenic humanized monoclonal antibody. J Immunol Sep. 15, 2002;169(6):3076-84.
EP10754139 Search Report dated Dec. 13, 2012.
EP10822810.7 Search Report dated Mar. 1, 2013.
EP11733492 Search Report dated Jul. 15, 2013.
Franco, et al. A cluster of sulfatase genes on Xp22.3: mutations in chondrodysplasia punctata (CDPX) and implications for warfarin embryopathy. Cell. Apr. 7, 1995;81(1):15-25.
Fu et al., "Neuroprotection in stroke in the mouse with intravenous erythropoietin-Trojan horse fusion protein," Brain Research, vol. 1369, Jan. 19, 2011.
Gehrmann, et al. Biochemical properties of recombinant human beta-glucuronidase synthesized in baby hamster kidney cells. Biochem J. Aug. 1, 1994;301 ( Pt 3):821-8.
He, et al. Identification and characterization of the molecular lesion causing mucopolysaccharidosis type I in cats. Mol Genet Metab. 1999; 67(2):106-12.
Hui et al., "Tumor Necrosis Factor Receptor-IgG Fusion Protein for Targeted Drug Delivery across the Human Blood-Brain Barrier," vol. 6, No. 5, pp. 1536-1543 (2009).
Huston, et al. Protein engineering of antibody binding sites: recovery of specific activity in an anti-digoxin single-chain Fv analogue produced in *Escherichia coli*. Proc Natl Acad Sci U S A. 1988; 85(16):5879-83.
Kakkis, et al. Overexpression of the human lysosomal enzyme alpha-L-iduronidase in Chinese hamster ovary cells. Protein Expr Purif 1994; 5(3):225-32.
Knaust, "Residues Critical for Formylglycine Formation and/or Catalytic Activity of Arylsulfatase A," American Chemical Society, 37:13941-13946 (1998).

(56) References Cited

OTHER PUBLICATIONS

Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).
Lu et al., "Genetic Engineering of a Bifunctional IgG fusion protein with iduronate-2-sulfatase," Bioconjugate Chemistry, 21(1) pp. 151-156 (2010).
Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.
MacCallum, et al. Antibody-antigen interactions: contact analysis and binding site topography. J Mol Biol. Oct. 11, 1996;262(5):732-45.
Nawashiro et al., "Neuroprotective effects of TNF binding protein in focal cerebral ischemia," Brain Research, vol. 778, No. 2, pp. 265-271 (1997).
NCBI GenBank Accession No. NM-000487 (Oct. 23, 2011).
Padlan, et al. Structure of an antibody-antigen complex: crystal structure of the HyHEL-10 Fab-lysozyme complex. Proc Natl Acad Sci U S A. Aug. 1989;86(15):5938-42.
Pardridge et al., "Biologic TNF[alpha]-inhibitors that cross the human blood-brain barrier," Bioengineered Bugs, Landes Bioscience, vol. 1, No. 4, pp. 231-234 (2010).
Pardridge et al., "Blood-brain barrier delivery of protein and non-viral gene therapeutics with molecular Trojan horses," Journal of Controlled Release, vol. 122, No. 3, pp. 345-348 (2007).
Pardridge, "Re-engineering biopharmaceuticals for delivery to brain with molecular Trojan horses," Bioconjugate Chemistry, vol. 18, No. 7, pp. 1327-1338 (2008).
Pardridge, et al. Human insulin receptor monoclonal antibody undergoes high affinity binding to human brain capillaries in vitro and rapid transcytosis through the blood-brain barrier in vivo in the primate. Pharm Res. 12(6):807-16 (1995).
Pardridge, et al. Transport of histone through the blood-brain barrier. J Pharmacol Exp Ther. Dec.;251(3):821-6. (1989).
Paul, W. Fundamental Immunology. 3rd Edition. 1993;292-95.
PCT/US2012/054520 International Search Report dated Feb. 22, 2013.
Polito et al., "IDS Crossing of the Blood-Brain Barrier Corrects CNS Defects in MPSII Mice," Amer. Journ. Human Genetics, vol. 85, No. 2, pp. 296-301 (2009).
Rempel, et al. A homology model for human α-L-Iduronidase: Insights into human disease. Mol. Genetics and Met. 2005; 85:28-37.
Rudikoff, et al. Single amino acid substitution altering antigen-binding specificity. Proc Natl Acad Sci U S A. Mar. 1982;79(6):1979-83.
Schoonjans, R. et al., "Fab Chains As an Efficient Heterodimerization Scaffold for the Production of Recombinant Bispecific and Trispecific Antibody Derivatives." The Journal of Immunology, 2000, 165 (12): 7050-7057.
Scott, et al. Human alpha-L-iduronidase: cDNA isolation and expression. Proc Natl Acad Sci U S A. Nov. 1, 1991;88(21):9695-9.
Shipley, et al. The role of glycosylation and phosphorylation in the expression of active human beta-glucuronidase. J Biol Chem. Jun. 5, 1993;268(16):12193-8.
Tobinick et al., "Perispinal etanercept for neuroinflammatory disorders," Drug Discovery Today, vol. 14, No. 3-4, pp. 168-177 (2009).
U.S. Appl. No. 12/179,806 Office Action dated Apr. 24, 2013.
U.S. Appl. No. 12/901,481 Office Action dated Jan. 9, 2013.
Unger, et al. Recombinant α-iduronidase: characterization of the purified enzyme and correction of mucopolysaccharidosis type I fibroblasts. Biochem J. 1994; 384:43-49.
U.S. Appl. No. 11/245,546 Office Action dated Jun. 27, 2011.
U.S. Appl. No. 13/141,682 Office Action dated Aug. 15, 2013.
U.S. Appl. No. 11/841,594 Notice of Allowance dated Apr. 2, 2013.
U.S. Appl. No. 13/609,099 Notice of Allowance dated Mar. 20, 2013.
U.S. Appl. No. 13/609,099 Office Action dated Nov. 26, 2012.
Whittaker, et al. Characterization of the functional insulin binding epitopes of the full-length insulin receptor. J Biol Chem. 2005;280(22):20932-6.
Wraith, J. Enzyme replacement therapy in mucopolysaccharidosis type I: progress and emerging difficulties. J Inherit Metab Dis. Apr. 2001;24(2):245-50.
Yip, et al. Three-dimensional structural interactions of insulin and its receptor. J Biol Chem. Jul. 25, 2003;278(30):27329-32.
Zhang, et al. 2001. Mediated efflux of IgG molecules from brain to blood across the blood-brain barrier. J Neuroimmunol. Mar. 1;114(1-2):168-72.
U.S. Appl. No. 14/144,460, filed Dec. 30, 2013, Pardridge et al.
Bachis, et al. 2003. Brain-Derived Neurotropic Factor Inhibits Human Immunodeficiency Virus-1/gp 120- Mediated Cerebellar Granule Cell Death by Preventing gp 120 Internalization. The Journal of Neuroscience 23 (13): 5712-22.
Benito, et al. Beta-galactosidase enzymatic activity as a molecular probe to detect specific antibodies. J Biol Chem. Aug. 30, 1996;271(35):21251-6.
Chen, et al. Cotranslational folding and calnexin binding during glycoprotein synthesis. Proc Natl Acad Sci U S A. Jul 3, 1995;92(14):6229-33.
Corchero, et al. The position of the heterologous domain can influence the solubility and proteolysis of beta-galactosidase fusion proteins in E. coli. J Biotechnol. Jul 31, 1996;48(3):191-200.
Duffy, et al. 1988. Human blood-brain barrier insulin-like growth factor receptor. Metabolism. Feb.;37(2):136-40.
Gennaro, 2000. Remington: The Science and Practice of Pharmacy. 20 ed.
Ibanez, et al. An extended surface of binding to Trk tyrosine kinase receptors in NGF and BDNF allows the engineering of a multifunctional pan-neurotrophin. EMBO J. Jun. 1993;12(6):2281-93.
Ibanez, Structure-function relationships in the neurotrophin family. J Neurobiol. Nov. 1994;25(11):1349-61.
Iwasaki, et al. Protective effect of interleukin-3 and erythropoietin on motor neuron death after neonatal axotomy. Neurol Res. Oct. 2002;24(7):643-6.
Jefferies, et al. Analysis of lymphopoietic stem cells with a monoclonal antibody to the rat transferrin receptor. Immunology. Feb. 1985;54(2):333-41.
Jethwa, et al. 2004. Neuromedin U has a physiological role in the regulation of food intake and partially mediates the effects of leptin. American Journal of Physiology-Endocrinology and Metabolism 289: E301-E305.
Jiang, et al. BDNF Variation and Mood Disorders: A Novel Functional Promoter Polymorphism and Val66Met are Associated with Anxiety but Have Opposing Effects. 2005. Neuropsychopharmacology 30:1353-61.
Josse, et al. Identification of residues essential for human paraoxonase (PON1) arylesterase/organophosphatase activities. Biochemistry. Mar. 2, 1999;38(9):2816-25.
Josse, et al. Oligomeric states of the detergent-solubilized human serum paraoxonase (PON1). J Biol Chem. Sep. 6, 2002;277(36):33386-97.
Josse, et al. The active site of human paraoxonase (PON1). J Appl Toxicol. Dec. 2001;21 Suppl 1:S7-11.
Juul, et al. Erythropoietin concentrations in cerebrospinal fluid of nonhuman primates and fetal sheep following high-dose recombinant erythropoietin, Biol. Neonate. 2004;85:138-144.
Kabat, et al., Sequences of Proteins of Immunological Interest. 5th Ed. Public Health Service, National Institutes of Health, Bethesda, Md. 1991;pp. 647-649.
Karlin, et al. Applications and statistics for multiple high-scoring segments in molecular sequences. Proc. Natl. Acad. Sci. USA. 1993;90:5873-87.
Kashmiri, et al. SDR grafting—a new approach to antibody humanization. Methods. May 2005;36(1):25-34.
Kastin, et al. Glial cell line-derived neurotrophic factor does not enter normal mouse brain. Neuroscience Letters. 2003;340:239-41.
Kido, et al. 2000. Neuroprotective effects of brain-derived neurotropic factor in eyes with NMDA-induced neuronal death. Brain Research 884:59-67.

(56) References Cited

OTHER PUBLICATIONS

Kim, et al. Decreased paraoxonase-1 activity is a risk factor for ischemic stroke in Koreans. Biochem Biophys Res Commun. Dec. 7, 2007;364(1):157-62.

Kim, et al. N-terminal domains of native multidomain proteins have the potential to assist de novo folding of their downstream domains in vivo by acting as solubility enhancers. Protein Sci. Apr. 2007;16(4):635-43.

Kim, et al., Continuous Brain-derived Neurotropic Factor (BDNF) Infusion After Methylprednisolone Treatment in Severe Spinal Cord Injury. Journal of Korean Medical Science 2004;19: 113-22.

Kitagawa, et al. Reduction of Ischemic Brain Injury by Topical Application of Glial Cell Line—Derived Neurotrophic Factor After Permanent Middle Cerebral Artery Occlusion in Rats. Stroke. 1998;29:1417-22.

Kobayashi, et al. Intracerebral Infusion of Glial Cell Line-Derived Neurotrophic Factor Promotes Striatal Neurogenesis After Stroke in Adult Rats Stroke. 2006;37:2361-67.

Koehne, et al. Vascular endothelial growth factor and erythropoietin concentrations in cerebrospinal fluid of children with hydrocephalus. Childs Nerv Syst. Apr. 2002;18(3-4):137-41.

Krewson, et al. Distribution of nerve growth factor following direct delivery to brain interstitium. Brain Research 680: 196-206 (1995).

Kurihara, et al. Imaging Brain Tumors by Targeting Peptide Radiopharmaceuticals through the Blood-Brain Barrier. Cancer Research 59: 6159-63 (1999).

Lang, et al. Randomized controlled trial of intraputamenal glial cell line-derived neurotrophic factor infusion in Parkinson disease. Annals of Neurology. 2006;59:45966.

Lapchak, et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.

Lappi, et al. Expression and activities of a recombinant basic fibroblast growth factorsaporin fusion protein. J Biol Chem. Apr. 29, 1994;269(17):12552-8.

Lazar, et al. Transforming growth factor alpha: mutation of aspartic acid 47 and leucine 48 results in different biological activities. Mol Cell Biol. Mar. 1988;8(3):1247-52.

Lee, et al., Imaging Brain Amyloid of Alzheimer Disease In Vivo in Transgenic Mice With an Aβ Peptide Radiopharmaceutical. Journal of Cerebral Blood Flow and Metabolism 2002;22: 223-31.

Lenz, et al. Stoichiometric and catalytic scavengers as protection against nerve agent toxicity: a mini review. Toxicology. Apr. 20, 2007;233(1-3):31-9.

Lewin, B. Genes IV. Oxford University Press. 1990. p. 810.

Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.

Lin, et al. GDNF: a glial cell line-derived neurotrophic factor for midbrain dopaminergic neurons. Science. 1993;260:1130-32.

Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.

Lu, et al. Cationic Liposome-Mediated GDNF Gene Transfer after Spinal Cord Injury. Journal of Neurotrauma. 2002;19:1081-1090.

Ma, et al. Erythropoietin protects PC12 cells from beta-amyloid(25-35)-induced apoptosis via PI3K/Akt signaling pathway. Neuropharmacology. May-Jun. 2009;56(6-7):1027-34.

Martell, et al. Efficacy of transferrin receptor-targeted immunotoxins in brain tumor cell lines and pediatric brain tumors. Cancer Res. Mar. 15, 1993;53(6):1348-53.

Matis, et al. Erythropoietin in spinal cord injury. Eur Spine J. Mar. 2009;18(3):314-23.

Menzies, et al. Contributions of ions and albumin to the formations and resolution of ischemic brain edema. Journal of Neurosurgery 78: 257-266. (1993).

Messer, et al. Role for GDNF in biochemical and behavioral adaptations to drugs of abuse. Neuron. Apr. 2000;26(1):247-57.

Mori, et al. Differential expression patterns of TrkB ligands in the macaque monkey brain. Developmental Neuroscience 15: 2507-11 (2004).

Muenzer, et al. A phase II/III clinical study of enzyme replacement therapy with idursulfase in mucopolysaccharidosis II (Hunter syndrome). Genet Med Aug. 2006;8(8):465-73.

Muenzer, et al. Advances in the treatment of mucopolysaccharidosis type I. N Engl J Med. May 6, 2004;350(19):1932-4.

NCBI Reference Sequence: NM-000202.5 Homo sapiens iduronate 2-sulfatase (IDS), transcript variant 1, mRNA. 1992. http://www.ncbi.nlm.nih.gov/nuccore/NM000202.5.

Needleman, et al. A general method applicable to the search for similarities in the amino acid sequence of two proteins. J. Mol. Biol. 1970;48:443-53.

Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.

Ng, et al. Predicting the effects of amino acid substitutions on protein function. Annual Review of Genomics and Human Genetics. 2006;7:61-80.

Notice of allowance dated Jan. 22, 2014 for U.S. Appl. No. 12/323,232.

Notice of allowance dated Dec. 13, 2013 for U.S. Appl. No. 13/862,250.

Notice of allowance dated Dec. 16, 2013 for U.S. Appl. No. 12/756,093.

Nutt, et al., Randomized, double-blind trial of glial cell line-derived neurotropic factor (GDNF) in PD. Neurology 2003;60: 69-73.

Office action dated Nov. 1, 2012 for U.S. Appl. No. 11/841,594.

Ohtsuka, et al. An alternative approach to deoxyoligonucleotides as hybridization probes by insertion of Deoxyinosine at Ambiguous Codon Positions. J. Biol. Chem. 1985;260:2605-08.

Orcutt, et al. A modular IgG-scFv bispecific antibody topology. Protein Eng Des Sel. Apr. 2010;23(4):221-8. doi: 10.1093/protein/gzp077. Epub Dec. 17, 2009.

Osbourn, et al. Directed selection of MIP-1 alpha neutralizing CCR5 antibodies from a phage display human antibody library. Nat Biotechnol. Aug. 1998;16(8):778-81.

Paragh, et al. Ciprofibrate increases paraoxonase activity in patients with metabolic syndrome. Br J Clin Pharmacol. Jun. 2006;61(6):694-701.

Pardridge, The Blood-Brain Barrier: Bottleneck in Brain Drug Development. NeuroRx: The Journal of the American Society for Experimental NeuroTherapeutics 2:3-14 (2005).

Pardridge, Blood-Brain Barrier Drug Targeting: The Future of Brain Drug Development. Molecular Interventions 3: 90-105 (2003).

Pardridge, Brain drug targeting: The future of brain drug development. Cambridge University Press (2001).

Pardridge, Drug Targeting to the Brain. Pharm Res 24:1733-44 (2007).

Pardridge, Neuroprotection in stroke: is it time to consider large-molecule drugs? Drug Discovery Today 6: 751-53 (2001).

Pardridge, Neurotrophins, neuroprotection and the blood-brain barrier. Current Opinion in Investigational Drugs 3 (12): 1753-57 (2002).

Pardridge, The Blood-Brain Barrier and Neurotherapeutics. NeuroRx: The Journal of the American Society for Experimental NeuroTherapeutics 2 (1): 1-2 (2005).

Pardridge, Tyrosine Hydroxylase Replacement in Experimental Parkinson's Disease with Transvascular Gene Therapy. NueuoRx: Journal of the American Society for Experimental NeuroTherapeutics. 2(1):129-138. (2005).

Qi, et al. Binding and cytotoxicity of conjugated and recombinant fusion proteins targeted to the gonadotropin-releasing hormone receptor. Cancer Res. Mar. 15, 2004;64(6):2090-5.

Smith, et al. Comparison of Biosequences. Adv. Appl. Math. 1981 1;482-89.

Thompson, et al. Improved binding of a bivalent single-chain immunotoxin results in increased efficacy for in vivo T-cell depletion. Protein Eng. Dec. 2001;14(12):1035-41.

(56) References Cited

OTHER PUBLICATIONS

Um, et al. A "classical" homodimeric erythropoietin receptor is essential for the antiapoptotic effects of erythropoietin on differentiated neuroblastoma SH-SY5Y and pheochromocytoma PC-12 cells. Cell Signal Mar. 2007;19(3):634-45.

Wu, et al. Simultaneous targeting of multiple disease mediators by a dual-variable-domain immunoglobulin. Nat Biotechnol. Nov. 2007;25(11):1290-7. Epub Oct. 14, 2007.

Office action dated Apr. 8, 2014 for U.S. Appl. No. 13/141,682.

* cited by examiner

1
ATGGCGCAGGTGCAGCTGCAGCAGTCTGGGGCTGAACTGGTGAAGCCTGGGGCTACAGTGAAGTTGTCCTGCA
AGGCTTCTGGCTACAGTTTCAACAGTCACTATATATATTGGGTGAAGCAGAGGCCTGGACAAGGCCTTGAGTG
GATTGGAGAGATTAATCCTAGCAATGGTGCTATGAACTTCAATGAGAAGTTCAAGAATAAGGCCACACTGACT
GTAGACAAATCCTCCAGCACAGCTTACATGCAGCTCAGCAGCCTGACATCTGAGGACTCTGCGGTCTATTATT
GTGTAAGGGACCCTACGTCTTACTGGGGCCAGGGGACTCTGGTCACTGTCTCTGCA
348

Figure 4
Nucleotide sequence of mAβ ScFv VH from pPC-mAβScFv
SEQ. ID No. 11

1
QVQLQQSGAELVKPGATVKLSCKASGYSFNSHYIYWVKQRPGQGLEWIG**EINPSNGAM
NFNEKFKNK**ATLTVDKSSSTAYMQLSSLTSEDSAVYYCVR*DPTSY*WGQGTLVTVSA
114

Figure 5
Amino acid sequence of mAβ ScFv VH from pPC-mAβScFv
SEQ ID No. 12

1
GATATCGTGATGACCCAAACTCCACTCTCCCTGCCTGTCAGTCTTGGAGATCAAGCCTCCATCTCTTGCAGAT
CTAGTCAGAGCCTTGTACACAGTTATGGAAACACCTATTTACATTGGTACCTGCAGAAGCCAGGCCAGTCTCC
AAAGCTCCTGATCTACAAAGTTTCCAACCGATTTTCTGGGGTCCCAGACAGGTTCAGTGGCAGTGGATCAGGG
ACAGATTTCACACTCAAGATCAGCAGAGTGGAGGCTGAGGATCTGGGAGTTTATTTCTGCTCTCAAAGTACAC
ATGTTCCGTACACGTTCGGAGGGGGGACCAAGCTGGAAATAAAACGG
339

Figure 6

Nucleotide sequence of mAβ ScFv VL from pPC-mAβScFv

SEQ. ID No. 13

1
DIVMTQTPLSLPVSLGDQASISCRSSQSLVHSYGNTYLHWYLQKPGQSPKLLIYKVSNRFSGVPDRFSGSGSG
TDFTLKISRVEAEDLGVYFCSQSTHVPYTFGGGTKLEIKR
113

Figure 7
Amino acid sequence of mAβ ScFv VL from pPC-mAβScFv
SEQ. ID No. 14

1
ATGGCGCAGGTCCAGCTGCAGCAGTCTGGGGCTGAACTGGTGAAGCCTGGGGCTACAGTGAAGTTGTCCTGCA
AGGCTTCTGGCTACAGTTTCAACAGTCACTATATATATTGGGTGAAGCAGAGGCCTGGACAAGGCCTTGAGTG
GATTGGAGAGATTAATCCTAGCAATGGTGCTATGAACTTCAATGAGAAGTTCAAGAATAAGGCCACACTGACT
GTAGACAAATCCTCCAGCACAGCTTACATGCAGCTCAGCAGCCTGACATCTGAGGACTCTGCGGTCTATTATT
GTGTAAGGGACCCTACGTCTTACTGGGGCCAGGGGACTCTGGTCACTGTCTCTGCAGCCAAAACGACACCCAA
GCTTGAAGAAGGTGAATTTTCAGAAGCACGCGTAGATATCGTGATGACCCAAACTCCACTCTCCCTGCCTGTC
AGTCTTGGAGATCAAGCCTCCATCTCTTGCAGATCTAGTCAGAGCCTTGTACACAGTTATGGAAACACCTATT
TACATTGGTACCTGCAGAAGCCAGGCCAGTCTCCAAAGCTCCTGATCTACAAAGTTTCCAACCGATTTTCTGG
GGTCCCAGACAGGTTCAGTGGCAGTGGATCAGGGACAGATTTCACACTCAAGATCAGCAGAGTGGAGGCTGAG
GATCTGGGAGTTTATTTCTGCTCTCAAAGTACACATGTTCCGTACACGTTCGGAGGGGGGACCAAGCTGGAAA
TAAAACGGGCTGATGCTGCGGCCGCTGGATCCGAACAAAAGCTGATCTCAGAAGAAGATCTATCCCATCATCA
CCATCATCATTAA
816

Figure 8

Nucleotide sequence of mAβ ScFv from pAP-mAβScFv

SEQ ID NO. 15

1
QVQLQQSGAELVKPGATVKLSCKASGYSFNSHYIYWVKQRPGQGLEWIGEINPSNGAMNFNEKFKNKATLTVD
KSSSTAYMQLSSLTSEDSAVYYCVRDPTSYWGQGTLVTVSA<u>AKTTPKLEEGEFSEARVD</u>IVMTQTPLSLPVSL
GDQASISCRSSQSLVHSYGNTYLHWYLQKPGQSPKLLIYKVSNRFSGVPDRFSGSGSGTDFTLKISRVEAEDL
GVYFCSQSTHVPYTFGGGTKLEIKRADAAAAGSEQKLISEEDLSHHHHHH
269

Figure 9

Amino acid sequence of mAβ ScFv from pAP-mAβScFv

SEQ ID NO. 16

1
ATGGACTGGACCTGGAGGGTGTTCTGCCTGCTTGCAGTGGCCCCCGGAGCCCACAGCCAGGTCCAGCTGCAGC
AGTCTGGGGCTGAACTGGTGAAGCCTGGGGCTACAGTGAAGTTGTCCTGCAAGGCTTCTGGCTACAGTTTCAA
CAGTCACTATATATATTGGGTGAAGCAGAGGCCTGGACAAGGCCTTGAGTGGATTGGAGAGATTAATCCTAGC
AATGGTGCTATGAACTTCAATGAGAAGTTCAAGAATAAGGCCACACTGACTGTAGACAAATCCTCCAGCACAG
CTTACATGCAGCTCAGCAGCCTGACATCTGAGGACTCTGCGGTCTATTATTGTGTAAGGGACCCTACGTCTTA
CTGGGGCCAGGGGACTCTGGTCACTGTCTCTGCAGCCAAAACGACACCCAAGCTTGAAGAAGGTGAATTTTCA
GAAGCACGCGTAGATATCGTGATGACCCAAACTCCACTCTCCCTGCCTGTCAGTCTTGGAGATCAAGCCTCCA
TCTCTTGCAGATCTAGTCAGAGCCTTGTACACAGTTATGGAAACACCTATTTACATTGGTACCTGCAGAAGCC
AGGCCAGTCTCCAAAGCTCCTGATCTACAAAGTTTCCAACCGATTTTCTGGGGTCCCAGACAGGTTCAGTGGC
AGTGGATCAGGGACAGATTTCACACTCAAGATCAGCAGAGTGGAGGCTGAGGATCTGGGAGTTTATTTCTGCT
CTCAAAGTACACATGTTCCGTACACGTTCGGAGGGGGGACCAAGCTGGAAATAAAACGGGCTGATGCTGCGGC
CGCTGGATCCGAACAAAAGCTGATCTCAGAAGAAGATCTATAA
846

Figure 10

Nucleotide sequence of mAβ ScFv from pCD-mAβScFv

SEQ ID NO. 17

1

MDWTWRVFCLLAVAPGAHSQVQLQQSGAELVKPGATVKLSCKASGYSFNSHYIYWVKQRPGQGLEWIGEINPS
NGAMNFNEKFKNKATLTVDKSSSTAYMQLSSLTSEDSAVYYCVRDPTSYWGQGTLVTVSAAKTTPKLEEGEFS
EARVDIVMTQTPLSLPVSLGDQASISCRSSQSLVHSYGNTYLHWYLQKPGQSPKLLIYKVSNRFSGVPDRFSG
SGSGTDFTLKISRVEAEDLGVYFCSQSTHVPYTFGGGTKLEIKRADAAAAGSEQKLISEEDL

281

Figure 11
Amino acid sequence of mAβ ScFv from pCD-mAβScFv
SEQ ID NO. 18

1

ATGGAATGCAGCTGGGTCATGCTCTTCCTCCTGTCAGGAACTGCAGGTGTCCATTGCCAGGTTCAGCTGCAGC
AGTCTGGACCTGAGCTGGTGAAGCCTGGGGCTTTAGTGAAGATATCCTGCAAGGCTTCTGGTTACACCTTCAC
AAACTACGATATACACTGGGTGAAGCAGAGGCCTGGACAGGGACTTGAGTGGATTGGATGGATTTATCCTGGA
GATGGTAGTACTAAGTACAATGAGAAATTCAAGGGCAAGGCCACACTGACTGCAGACAAATCCTCCAGCACAG
CCTACATGCACCTCAGCAGCCTGACTTCTGAGAAATCTGCAGTCTATTTCTGTGCAAGAGAGTGGGCTTACTG
GGGCCAAGGGACTCTGGTCACTGTCTCTGCAGCTAGCACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAAAGTTGAGCCCAAATCTTGTGACAAAACTCACACATGCCCACCGT
GCCCAGCACCTGAACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTACCGTG
TGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACC
CTGCCCCCATCCCGGGATGAGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAAA
GTTCACAGGTCCAGCTGCAGCAGTCTGGGGCTGAACTGGTGAAGCCTGGGGCTACAGTGAAGTTGTCCTGCAA
GGCTTCTGGCTACAGTTTCAACAGTCACTATATATATTGGGTGAAGCAGAGGCCTGGACAAGGCCTTGAGTGG
ATTGGAGAGATTAATCCTAGCAATGGTGCTATGAACTTCAATGAGAAGTTCAAGAATAAGGCCACACTGACTG
TAGACAAATCCTCCAGCACAGCTTACATGCAGCTCAGCAGCCTGACATCTGAGGACTCTGCGGTCTATTATTG
TGTAAGGGACCCTACGTCTTACTGGGGCCAGGGGACTCTGGTCACTGTCTCTGCAGCCAAAACGACACCCAAG
CTTGAAGAAGGTGAATTTTCAGAAGCACGCGTAGATATCGTGATGACCCAAACTCCACTCTCCCTGCCTGTCA
GTCTTGGAGATCAAGCCTCCATCTCTTGCAGATCTAGTCAGAGCCTTGTACACAGTTATGGAAACACCTATTT
ACATTGGTACCTGCAGAAGCCAGGCCAGTCTCCAAAGCTCCTGATCTACAAAGTTTCCAACCGATTTTCTGGG
GTCCCAGACAGGTTCAGTGGCAGTGGATCAGGGACAGATTTCACACTCAAGATCAGCAGAGTGGAGGCTGAGG
ATCTGGGAGTTTATTTCTGCTCTCAAAGTACACATGTTCCGTACACGTTCGGAGGGGGGACCAAGCTGGAAAT
AAAACGGTAA
2127

Figure 12

Nucleotide sequence of fusion antibody heavy chain from pCD-HC-mAβScFv

SEQ ID NO. 19

1

MECSWVMLFLLSGTAGVHCQVQLQQSGPELVKPGALVKISCKASGYTFTNYDIHWVKQRPGQGLEWIGWIYPG
DGSTKYNEKFKGKATLTADKSSSTAYMHLSSLTSEKSAVYFCAREWAYWGQGTLVTVSAASTKGPSVFPLAPS
SKSTSGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKSRWQQGNVF
SCSVMHEALHNHYTQKSLSLSPGKSSQVQLQQSGAELVKPGATVKLSCKASGYSFNSHYIYWVKQRPGQGLEW
IGEINPSNGAMNFNEKFKNKATLTVDKSSSTAYMQLSSLTSEDSAVYYCVRDPTSYWGQGTLVTVSAAKTTPK
LEEGEFSEARVDIVMTQTPLSLPVSLGDQASISCRSSQSLVHSYGNTYLHWYLQKPGQSPKLLIYKVSNRFSG
VPDRFSGSGSGTDFTLKISRVEAEDLGVYFCSQSTHVPYTFGGGTKLEIKR

Amino acid sequence of fusion antibody heavy chain from pCD-HC-mAβScFv

SEQ ID NO. 20

1

ATGGACTGGACCTGGAGGGTGTTCTGCCTGCTTGCAGTGGCCCCCGGAGCCCACAGCCAGGTTCAGCTGCAGC
AGTCTGGACCTGAGCTGGTGAAGCCTGGGGCTTTAGTGAAGATATCCTGCAAGGCTTCTGGTTACACCTTCAC
AAACTACGATATACACTGGGTGAAGCAGAGGCCTGGACAGGGACTTGAGTGGATTGGATGGATTTATCCTGGA
GATGGTAGTACTAAGTACAATGAGAAATTCAAGGGCAAGGCCACACTGACTGCAGACAAATCCTCCAGCACAG
CCTACATGCACCTCAGCAGCCTGACTTCTGAGAAATCTGCAGTCTATTTCTGTGCAAGAGAGTGGGCTTACTG
GGGCCAAGGGACTCTGGTCACTGTCTCTGCAGCTAGCACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAAAGTTGAGCCCAAATCTTGTGACAAAACTCACACATGCCCACCGT
GCCCAGCACCTGAACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTACCGTG
TGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACC
CTGCCCCCATCCCGGGATGAGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAAA
GTTCACAGGTCCAGCTGCAGCAGTCTGGGGCTGAACTGGTGAAGCCTGGGGCTACAGTGAAGTTGTCCTGCAA
GGCTTCTGGCTACAGTTTCAACAGTCACTATATATATTGGGTGAAGCAGAGGCCTGGACAAGGCCTTGAGTGG
ATTGGAGAGATTAATCCTAGCAATGGTGCTATGAACTTCAATGAGAAGTTCAAGAATAAGGCCACACTGACTG
TAGACAAATCCTCCAGCACAGCTTACATGCAGCTCAGCAGCCTGACATCTGAGGACTCTGCGGTCTATTATTG
TGTAAGGGACCCTACGTCTTACTGGGGCCAGGGGACTCTGGTCACTGTCTCTGCAGCCAAAACGACACCCAAG
CTTGAAGAAGGTGAATTTTCAGAAGCACGCGTAGATGTCGTGATGACCCAAACTCCACTCTCCCTGCCTGTCA
GTCTTGGAGATCAAGCCTCCATCTCTTGCAGATCTAGTCAGAGCCTTGTACACAGTTATGGAAACACCTATTT
ACATTGGTACCTGCAGAAGCCAGGCCAGTCTCCAAAGCTCCTGATCTACAAAGTTTCCAACCGATTTTCTGGG
GTCCCAGACAGGTTCAGTGGCAGTGGATCAGGGACAGATTTCACACTCAAGATCAGCAGAGTGGAGGCTGAGG
ATCTGGGAGTTTATTTCTGCTCTCAAAGTACACATGTTCCGTACACGTTCGGAGGGGGGACCAAGCTGGAAAT
AAAACGGTAA

Nucleotide sequence of fusion antibody heavy chain from pCD-HC-mAβScFv following I2V site-directed mutagenesis

SEQ ID NO. 21

1
MDWTWRVFCLLAVAPGAHSQVQLQQSGPELVKPGALVKISCKASGYTFTNYDIHWVKQRPGQGLEWIGWIYPG
DGSTKYNEKFKGKATLTADKSSSTAYMHLSSLTSEKSAVYFCAREWAYWGQGTLVTVSAASTKGPSVFPLAPS
SKSTSGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKSRWQQGNVF
SCSVMHEALHNHYTQKSLSLSPGKSSQVQLQQSGAELVKPGATVKLSCKASGYSFNSHYIYWVKQRPGQGLEW
IGEINPSNGAMNFNEKFKNKATLTVDKSSSTAYMQLSSLTSEDSAVYYCVRDPTSYWGQGTLVTVSAAKTTPK
LEEGEFSEARVD<u>V</u>VMTQTPLSLPVSLGDQASISCRSSQSLVHSYGNTYLHWYLQKPGQSPKLLIYKVSNRFSG
VPDRFSGSGSGTDFTLKISRVEAEDLGVYFCSQSTHVPYTFGGGTKLEIKR
708

Figure 15

Amino acid sequence of fusion antibody heavy chain from pCD-HC-mAβScFv following I2V site-directed mutagenesis

SEQ ID NO. 22

1
ATGGACTGGACCTGGAGGGTGTTCTGCCTGCTTGCAGTGGCCCCGGAGCCCACAGCCAGGTTCAGCTGCAGC
AGTCTGGACCTGAGCTGGTGAAGCCTGGGGCTTTAGTGAAGATATCCTGCAAGGCTTCTGGTTACACCTTCAC
AAACTACGATATACACTGGGTGAAGCAGAGGCCTGGACAGGGACTTGAGTGGATTGGATGGATTTATCCTGGA
GATGGTAGTACTAAGTACAATGAGAAATTCAAGGGCAAGGCCACACTGACTGCAGACAAATCCTCCAGCACAG
CCTACATGCACCTCAGCAGCCTGACTTCTGAGAAATCTGCAGTCTATTTCTGTGCAAGAGAGTGGGCTTACTG
GGGCCAAGGGACTCTGGTCACTGTCTCTGCAGCTAGCACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAAAGTTGAGCCCAAATCTTGTGACAAAACTCACACATGCCCACCGT
GCCCAGCACCTGAACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTACCGTG
TGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACC
CTGCCCCCATCCCGGGATGAGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAAA
GTTCACAGGTCCAGCTGCAGCAGTCTGGGGCTGAACTGGTGAAGCCTGGGGCTACAGTGAAGTTGTCCTGCAA
GGCTTCTGGCTACAGTTTCAACAGTCACTATATATATTGGGTGAAGCAGAGGCCTGGACAAGGCCTTGAGTGG
ATTGGAGAGATTGCTCCTAGCAATGGTGCTATGAACTTCAATGAGAAGTTCAAGAATAAGGCCACACTGACTG
TAGACAAATCCTCCAGCACAGCTTACATGCAGCTCAGCAGCCTGACATCTGAGGACTCTGCGGTCTATTATTG
TGTAAGGGACCCTACGTCTTACTGGGGCCAGGGGACTCTGGTCACTGTCTCTGCAGCCAAAACGACACCCAAG
CTTGAAGAAGGTGAATTTTCAGAAGCACGCGTAGATGTCGTGATGACCCAAACTCCACTCTCCCTGCCTGTCA
GTCTTGGAGATCAAGCCTCCATCTCTTGCAGATCTAGTCAGAGCCTTGTACACAGTTATGGAAACACCTATTT
ACATTGGTACCTGCAGAAGCCAGGCCAGTCTCCAAAGCTCCTGATCTACAAAGTTTCCAACCGATTTTCTGGG
GTCCCAGACAGGTTCAGTGGCAGTGGATCAGGGACAGATTTCACACTCAAGATCAGCAGAGTGGAGGCTGAGG
ATCTGGGAGTTTATTTCTGCTCTCAAAGTACACATGTTCCGTACACGTTCGGAGGGGGGACCAAGCTGGAAAT
AAAACGGTAA
2127

Figure 16

Nucleotide sequence of fusion antibody heavy chain from pCD-HC-mAβScFv following N497A
site-directed mutagenesis

SEQ ID NO. 23

1
MDWTWRVFCLLAVAPGAHSQVQLQQSGPELVKPGALVKISCKASGYTFTNYDIHWVKQRPGQGLEWIGWIYPG
DGSTKYNEKFKGKATLTADKSSSTAYMHLSSLTSEKSAVYFCAREWAYWGQGTLVTVSAASTKGPSVFPLAPS
SKSTSGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKSRWQQGNVF
SCSVMHEALHNHYTQKSLSLSPGKSSQVQLQQSGAELVKPGATVKLSCKASGYSFNSHYIYWVKQRPGQGLEW
IGEIAPSNGAMNFNEKFKNKATLTVDKSSSTAYMQLSSLTSEDSAVYYCVRDPTSYWGQGTLVTVSAAKTTPK
LEEGEFSEARVDVVMTQTPLSLPVSLGDQASISCRSSQSLVHSYGNTYLHWYLQKPGQSPKLLIYKVSNRFSG
VPDRFSGSGSGTDFTLKISRVEAEDLGVYFCSQSTHVPYTFGGGTKLEIKR
708

Figure 17

Amino acid sequence of fusion antibody heavy chain from pCD-HC-mAβScFv following N497A site-directed mutagenesis

SEQ ID NO. 24

1

ATGGACTGGACCTGGAGGGTGTTCTGCCTGCTTGCAGTGGCCCCGGAGCCCACAGCCAGGTTCAGCTGCAGC
AGTCTGGACCTGAGCTGGTGAAGCCTGGGGCTTTAGTGAAGATATCCTGCAAGGCTTCTGGTTACACCTTCAC
AAACTACGATATACACTGGGTGAAGCAGAGGCCTGGACAGGGACTTGAGTGGATTGGATGGATTTATCCTGGA
GATGGTAGTACTAAGTACAATGAGAAATTCAAGGGCAAGGCCACACTGACTGCAGACAAATCCTCCAGCACAG
CCTACATGCACCTCAGCAGCCTGACTTCTGAGAAATCTGCAGTCTATTTCTGTGCAAGAGAGTGGGCTTACTG
GGGCCAAGGGACTCTGGTCACTGTCTCTGCAGCTAGCACCAAGGGCCCATCGGTCTTCCCCCTGGCACCCTCC
TCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAAAGTTGAGCCCAAATCTTGTGACAAAACTCACACATGCCCACCGT
GCCCAGCACCTGAACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTACCGTG
TGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACC
CTGCCCCCATCCCGGGATGAGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAAA
GTTCACAGGTCCAGCTGCAGCAGTCTGGGGCTGAACTGGTGAAGCCTGGGGCTACAGTGAAGTTGTCCTGCAA
GGCTTCTGGCTACAGTTTCAACAGTCACTATATATATTGGGTGAAGCAGAGGCCTGGACAAGGCCTTGAGTGG
ATTGGAGAGATTAATCCTGCCAATGGTGCTATGAACTTCAATGAGAAGTTCAAGAATAAGGCCACACTGACTG
TAGACAAATCCTCCAGCACAGCTTACATGCAGCTCAGCAGCCTGACATCTGAGGACTCTGCGGTCTATTATTG
TGTAAGGGACCCTACGTCTTACTGGGGCCAGGGGACTCTGGTCACTGTCTCTGCAGCCAAAACGACACCCAAG
CTTGAAGAAGGTGAATTTTCAGAAGCACGCGTAGATGTCGTGATGACCCAAACTCCACTCTCCCTGCCTGTCA
GTCTTGGAGATCAAGCCTCCATCTCTTGCAGATCTAGTCAGAGCCTTGTACACAGTTATGGAAACACCTATTT
ACATTGGTACCTGCAGAAGCCAGGCCAGTCTCCAAAGCTCCTGATCTACAAAGTTTCCAACCGATTTTCTGGG
GTCCCAGACAGGTTCAGTGGCAGTGGATCAGGGACAGATTTCACACTCAAGATCAGCAGAGTGGAGGCTGAGG
ATCTGGGAGTTTATTTCTGCTCTCAAAGTACACATGTTCCGTACACGTTCGGAGGGGGGACCAAGCTGGAAAT
AAAACGGTAA

Nucleotide sequence of fusion antibody heavy chain from pCD-HC-mAβScFv following S499A site-directed mutagenesis

SEQ ID NO. 25

1
MDWTWRVFCLLAVAPGAHSQVQLQQSGPELVKPGALVKISCKASGYTFTNYDIHWVKQRPGQGLEWIGWIYPG
DGSTKYNEKFKGKATLTADKSSSTAYMHLSSLTSEKSAVYFCAREWAYWGQGTLVTVSAASTKGPSVFPLAPS
SKSTSGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKSRWQQGNVF
SCSVMHEALHNHYTQKSLSLSPGKSSQVQLQQSGAELVKPGATVKLSCKASGYSFNSHYIYWVKQRPGQGLEW
IGEINPANGAMNFNEKFKNKATLTVDKSSSTAYMQLSSLTSEDSAVYYCVRDPTSYWGQGTLVTVSAAKTTPK
LEEGEFSEARVDVVMTQTPLSLPVSLGDQASISCRSSQSLVHSYGNTYLHWYLQKPGQSPKLLIYKVSNRFSG
VPDRFSGSGSGTDFTLKISRVEAEDLGVYFCSQSTHVPYTFGGGTKLEIKR
708

Figure 19

Amino acid sequence of fusion antibody heavy chain from pCD-HC-mAβScFv following S499A site-directed mutagenesis

SEQ ID NO. 26

Figure 20

6746 nucleotide sequence of antibody fusion protein tandem vector (SEQ ID NO. 27)

```
GTTGACATTGATTATTGACTAGTTATTAATAGTAATCAATTACGGGGTCATTAGTTCATAGCCCATATATGGAGTTCCGCGTTACATAACTTACGGTAAAT
GGCCCGCCTGGCTGACCGCCCAACGACCCCCGCCCATTGACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTACGCCCCCTATTGACGTCAATGACGGTAAATGGCCCGCCT
GGCATTATGCCCAGTACATGACCTTATGGGACTTTCCTACTTGGCAGTACATCTACGTATTAGTCATCGCTATTACCATGGTGATGCGGTTTTGGCAGTAC
ATCAATGGGCGTGGATAGCGGTTTGACTCACGGGGATTTCCAAGTCTCCACCCCATTGACGTCAATGGGAGTTTGTTTTGGCACCAAAATCAACGGGACTT
TCCAAAATGTCGTAACAACTCCGCCCCATTGACGCAAATGGGCGGTAGGCGTGTACGGTGGAGGTCTATATAAGCAGAGCTCTCTGGCTAACTAGAGAAC
CCACTGCTTACTGGCTTATCGAAATTAATACGACTCACTATAGGGAGACCCAAGCTGGCTAGCGTTTAAACTTAAGCTTGGTACCGAGCTCGGATCCACTA
GTCCAGTGTGGTGGAATTCTGCAGGCCGCCACCATGGAGACCCCCGCCCAGCTGCTGTTCCTGTTGCTGCTTTGGCTTCCAGATACTACCGGCGACATCCA
GATGACCCAGTCTCCATCCTCCTTATCTGCCTCTCTGGGAGAAAGAGTCAGTCTCACTTGTCGGGCAAGTCAGGACATTGGTGGTAACTTATACTGGCTTC
AGCAGGGACCAGATGGAACTATTAAACGCCTGATCTACGCCACATCCAGTTTAGATTCTGGTGTCCCCAAAAGGTTCAGTGGCAGTAGGTCTGGGTCAGAT
TATTCTCTCACCATCAGCAGCCTTGAGTCTGAAGATTTTGTAGACTATTACTGTCTACAGTATTCTAGTTCTCCGTGGACGTTCGGTGGAGGCACAAAGAT
GGAAATAAAACGAACTGTGGCTGCACCATCTGTCTTCATCTTCCCGCCATCTGATGAGCAGTTGAAATCTGGAACTGCCTCTGTTGTGTGCCTGCTGAATA
ACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGACAGACTACGAGAAACACAAAGTCTACGCCTGCGAAGTCACCCATCAGGGCCTGAGCTCGCCCGT
CACAAAGAGCTTCAACAGGGGAGAGTGTTAGCTCGAGTCTAGAGGGCCCGTTTAAACCCGCTGATCAGCCTCGACTGTGCCTTCTAGTTGCCAGCCATCTG
TTGTTTGCCCCTCCCCCGTGCCTTCCTTGACCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGGCAGGACAGCAAGGGGGAGGATTGGGAAGACAATAGCAGGCATGCTGGGGATGCGGTGGGCTCTATGGCTTC
TGAGGCGGAAAGAACCAGCCGATGTACGGGCCAGATATACGCGTTGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGACCGCCCAACGACCCCCGCCCATTGACGTCAATAATGACGTATGT
TCCCATAGTAACGCCAATAGGGACTTTCCATTGACGTCAATGGGTGGAGTATTTACGGTAAACTGCCCACTTGGCAGTACATCAAGTGTATCATATGCCAA
GTACGCCCCCTATTGACGTCAATGACGGTAAATGGCCCGCCTGGCATTATGCCCAGTACATGACCTTATGGGACTTTCCTACTTGGCAGTACATCTACGTA
TTAGTCATCGCTATTACCATGGTGATGCGGTTTTGGCAGTACATCAATGGGCGTGGATAGCGGTTTGACTCACGGGGATTTCCAAGTCTCCACCCCATTGA
CGTCAATGGGAGTTTGTTTTGGCACCAAAATCAACGGGACTTTCCAAAATGTCGTAACAACTCCGCCCCATTGACGCAAATGGGCGGTAGGCGTGTACGGT
GGGAGGTCTATATAAGCAGAGCTCTCTGGCTAACTAGAGAACCCACTGCTTACTGGCTTATCGAAATTAATACGACTCACTATAGGGAGACCCAAGCTGGC
TAGCGTTTAAACGGGCCCTCTAGACTCGAGCGGCCGCCACTGTGCTGGAGCGCCACCATGGACTGGACCTGGAGGGTGTTCTGCCTGCTTGCAGTGGCCC
CCGGAGCCCACAGCCAGGTTCAGCTGCAGCAGTCTGGACCTGAGCTGGTGAAGCCTGGGGCTTTAGTGAAGATATCCTGCAAGGCTTCTGGTTACACCTTC
ACAAACTACGATATACACTGGGTGAAGCAGAGGCCTGGACAGGGACTTGAGTGGATTGGATGGATTTATCCTGGAGATGGTAGTACTAAGTACAATGAGAA
ATTCAAGGGCAAGGCCACACTGACTGCAGACAAATCCTCCAGCACAGCCTACATGCAGCTCAGCAGCCTGACTTCTGAGAAATCTGCAGTCTATTTCTGTG
CAAGAGAGTGGGCTTACTGGGGCCAAGGGACTCTGGTCACTGTCTCTGCAGCTAGCACCAAGGGCCCATCGGTCTTCCCCCTGGCACCCTCCTCCAAGAGC
ACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCA
CACCTTCCCGGCTGTCCTACAGTCCTCAGGACTCTACTCCCTCAGCAGCGTGGTGACCGTGCCCTCCAGCAGCTTGGGCACCCAGACCTACATCTGCAACG
TGAATCACAAGCCCAGCAACACCAAGGTGGACAAGAAAGTTGAGCCCAAATCTTGTGACAAAACTCACACATGCCCACCGTGCCCAGCACCTGAACTCCTG
GGGGGACCGTCAGTCTTCCTCTTCCCCCCAAAAACCCAAGGACACCCTCATGATCTCCCGGACCCCTGAGGTCACATGCGTGGTGGTGGACGTGAGCCACGA
AGACCCTGAGGTCAAGTTCAACTGGTACGTGGACGGCGTGGAGGTGCATAATGCCAAGACAAAGCCGCGGGAGGAGCAGTACAACAGCACGTACCGTGTGG
TCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGATGAGCTGACCAAGAACCAGGTCAGCCTGACCTGCCTGGTCAA
AGGCTTCTATCCCAGCGACATCGCCGTGGAGTGGGAGAGCAATGGGCAGCCGGAGAACAACTACAAGACCACGCCTCCCGTGCTGGACTCCGACGGCTCCT
TCTTCCTCTACAGCAAGCTCACCGTGGACAAGAGCAGGTGGCAGCAGGGGAACGTCTTCTCATGCTCCGTGATGCATGAGGCTCTGCACAACCACTACACG
CAGAAGAGCCTCTCCCTGTCTCCGGGTAAAAGTTCACAGGTCCAGCTGCAGCAGTCTGGGGCTGAACTGGTGAAGCCTGGGGCTACAGTGAAGTTGTCCTG
CAAGGCTTCTGGCTACAGTTTCAACAGTCACTATATATATTGGGTGAAGCAGAGGCCTGGACAAGGCCTTGAGTGGATTGGAGAGATTAATCCTAGCAATG
GTGCTATGAACTTCAATGAGAAGTTCAAGAATAAGGCCACACTGACTGTAGACAAATCCTCCAGCACAGCTTACATGCAGCTCAGCAGCCTGACATCTGAG
GACTCTGCGGTCTATTATTGTGTAAGGGACCCTACGTCTTACTGGGGCCAGGGGACTCTGGTCACTGTCTCTGCAGCCAAAACGACACCCAAGCTTGAAGA
AGGTGAATTTTCAGAAGCACGCGTAGATGTCGTGATGACCCAAACTCCACTCTCCCTGCCTGTCAGTCTTGGAGATCAAGCCTCCATCTCTTGCAGAATCTA
GTCAGAGCCTTGTACACAGTTATGGAAACACCTATTTACATTGGTACCTGCAGAAGCCAGGCCAGTCTCCAAAGCTCCTGATCTACAAAGTTTCCAACCGA
TTTTCTGGGGTCCCAGACAGGTTCAGTGGCAGTGGATCAGGGACAGATTTCACACTCAAGATCAGCAGAGTGGAGGCTGAGGATCTGGGAGTTTATTTCTG
CTCTCAAAGTACACATGTTCCGTACACGTTCGGAGGGGGACCAAGCTGGAAATAAAACGGTAAACCCGAGCTCGGTACCAAGCTTAAGTTTAAACCGCTG
ATCAGCCTCGACTGTGCCTTCTAGTTGCCAGCCATCTGTTGTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGGGGTGGGGCAGGACAGCAAGGGGGAGGATTGGGAAGACAAT
AGCAGGCATGCTGGGGATGCGGTGGGCTCTATGGCTTCTGAGGCGGAAAGAACCAGGGGAGGTACCGAGCTCTTACGCGTGCTAGCTCGAGATCTGCATCT
CAATTAGTCAGCAACCATAGTCCCGCCCCTAACTCCGCCCATCCCGCCCCTAACTCCGCCCAGTTCCGCCCATTCTCCGCCCCATGGCTGACTAATTTTTT
TTATTTATGCAGAGGCCGAGGCCGCCTCGGCCTCTGAGCTATTCCAGAAGTAGTGAGGAGGCTTTTTTGGAGGCCTAGGCTTTTGCAAAAAGCTTATCGAT
TCTAGAAGCCGCCACCATGGTTCGACCATTGAACTGCATCGTCGCCGTGTCCCAAAATATGGGGATTGGCAAGAACGGAGACCTACCCTGGCCTCCGCTCA
GGAACGAGTTCAAGTACTTCCAAAGAATGACCACAACCTCTTCAGTGGAAGGTAAACAGAATCTGGTGATTATGGGTAGGAAAACCTGGTTCTCCATTCCT
GAGAAGAATCGACCTTTAAAGGACAGATTAATATAGTTCTCAGTAGAGAACTCAACACGAGGAGCTCATTTTCTTGCCAAAAGTTTGGATGA
TGCCTTAAGACTTATTGAACAACCGGAATTGGCAAGTAAAGTAGACATGGTTTGGATAGTCGGACGGCAGTTCTGTTTACCAGGAAGCCATGAATCAACCAG
GCCACCTCAGACTCTTTGTGACAAGGATCATGCAGGAATTTGAAAGTGACACGTTTTTCCCAGAAATTGATTTGGGGAAATATAAACTTCTCCCAGAATAC
CCAGGCGTCCTCTCTGAGGTCCAGGAGGAAAAAGGCATCAAGTATAAGTTTGAAGTCTACGAGAAGAAAGACTAACAGGAAGATGCTTTCAAGTTCTCTGC
TCCCCTCCTAAAGCTATGCATTTTTATAAGACCATGGGACTTTTGCTGGCTTTAGATCGTTCGCGGGACGTCCTTTGTTTACGTCCCGTCGGCGCTGAATC
CCGCGGACGACCCCTCGCGGGGCCGCTTGGGACTCTCTCGTCCCCTTCTCCGTCTGCCGTTCCAGCCGACCACGGGCGCACCTCTCTTTACGCGGTCTCC
CCGTCTGTGCCTTCTCATCTGCCGGTCCGTGTGCACTTCGCTTCACCTCTGCACGTTGCATGGAGACCACCGTGAACGCCCATCAGATCCTGCCCAAGGTC
TTACATAAGAGGACTCTTGGACTCCCAGCAATGTCAACGACCGACCTTGAGGCCTACTTCAAAGACTGTGTTTAAGGACTGGGAGGAGCTGGGGGAGCGA
GATTAGGTTAAAGGTCTTTGTATTAGGAGGCTGTAGGCATAAATTGGTCTGCGCACCAGCACCATGCAACTTTTTCACCTCTGCCTAATCATCTCTTGTAC
ATGTCCCACTGTTCAAGCCTCCAAGCTGTGCCTTGGGTGGCTTTGGGGCATGGACATTGACCCTTATAAAGAATTTGGAGCTACTGTGAGTTACTCTCGT
TTTTGCCTTCTGACTTCTTTCCTTCCGTCAGAGATCCTCTACGCCGGACGCATCGTGGCCGGCATCACCGGCGCCACAGGTGCGGTTGCTGGCGCCTATAT
CGCCGACATCACCGATGGGGAAGATCGGGCTCGCCACTTCGGGCTCATGAGCGCTTGTTTCGGCGTGGGTATGGTGGCAGGCCCCGTGCCGGGGGACTGT
TGGGCGCCATCTCCTTGCATGCACCATTCCTTGCGGCGGCGGTGCTCAACGGCCTCAACCTACTACTGGGCTGCTTCCTAATGCAGGAGTCGCATAAGGGA
GAGCG
6671
```

1
MDWTWRVFCLLAVAPGAHSQVQLQQSGPELVKPGALVKISCKASGYTFTNYDIHWVKQRPGQGLEWIG**WIYPG
DGSTKYNEKFKGKATLTADKSSSTAYMHLSSLTSEKSAVYFCAREWAY**WGQGTLVTVSAASTKGPSVFPLAPS
SKSTSGGTAALGCLVKDYFPEPVTVSWNSGALTSGVHTFPAVLQSSGLYSLSSVVTVPSSSLGTQTYICNVNH
KPSNTKVDKKVEPKSCDKTHTCPPCPAPELLGGPSVFLFPPKPKDTLMISRTPEVTCVVVDVSHEDPEVKFNW
YVDGVEVHNAKTKPREEQY<u>NST</u>YRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKSRWQQGNVF
SCSVMHEALHNHYTQKSLSLSPGKSSQVQLQQSGAELVKPGATVKLSCKASGYSFNSHYIYWVKQRPGQGLEW
IGEINPSNGAMNFNEKFKNKATLTVDKSSSTAYMQLSSLTSEDSAVYYCVRDPTSYWGQGTLVTVSAAKTTPK
LEEGEFSEARVDVVMTQTPLSLPVSLGDQASISCRSSQSLVHSYGNTYLHWYLQKPGQSPKLLIYKVSNRFSG
VPDRFSGSGSGTDFTLKISRVEAEDLGVYFCSQSTHVPYTFGGGTKLEIKR
708

Figure 21

Amino acid sequence of signal peptide and HIRMAb heavy chain (SEQ ID NO. 28)

1
METPAQLLFLLLLWLPDTTGDIQMTQSPSSLSASLGERVSLTCRASQDIGGNLYWLQQGPDGTIKRLIYATSSLDSGVPK
RFSGSRSGSDYSLTISSLESEDFVDYYCLQYSSSPWTFGGGTKMEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC
234

Figure 22

Amino acid sequence of signal peptide and HIRMAb light chain (SEQ ID NO. 29)

1

MVRPLNCIVAVSQNMGIGKNGDLPWPPLRNEFKYFQRMTTTSSVEGKQNLVIMGRKTWFSIPEKNRPLKDRIN

IVLSRELKEPPRGAHFLAKSLDDALRLIEQPELASKVDMVWIVGGSSVYQEAMNQPGHLRLFVTRIMQEFESD

TFFPEIDLGKYKLLPEYPGVLSEVQEEKGIKYKFEVYEKKD

187

Figure 23
Amino acid sequence of DHFR
(SEQ ID NO. 30)

Genetic engineering of antibody fusion protein tandem vector

Domain structure of antibody fusion protein heavy chain

SEQUENCE LISTING

<160> NUMBER OF SEQ ID NOS: 69

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aattttcaga agcacgcgta gatatcktgm tsacccaawc tcca    44

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gaagatggat ccagcggccg cagcatcagc    30

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagccggcca tggcgcaggt scagctgcag sag    33

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccagggccca gtggatagac aagcttgggt gtcgtttt    38

<210> SEQ ID NO 5
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atcctcgagg ccgccaccat ggactggacc tggagggtgt tctgcctgct tgcagtggcc    60
cccggagccc acagccaggt ccagctgcag    90

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgcagctgg acctggctgt gggctccggg ggccactgca agcaggcaga acaccctcca    60
ggtccagtcc atggtggcgg cctcgaggat    90

<210> SEQ ID NO 7
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 7
atcctcgagg ccgccacc                                                      18

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatgaattct tatagatctt cttctga                                            27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cacaggtcca gctgcagcag t                                                  21

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttaccgtttt atttccagct tggtc                                              25

<210> SEQ ID NO 11
<211> LENGTH: 348
<212> TYPE: DNA
<213> ORGANISM: Mus sp.

<400> SEQUENCE: 11
atggcgcagg tgcagctgca gcagtctggg gctgaactgg tgaagcctgg ggctacagtg        60
aagttgtcct gcaaggcttc tggctacagt ttcaacagtc actatatata ttgggtgaag       120
cagaggcctg gacaaggcct tgagtggatt ggagagatta atcctagcaa tggtgctatg       180
aacttcaatg agaagttcaa gaataaggcc acactgactg tagacaaatc ctccagcaca       240
gcttacatgc agctcagcag cctgacatct gaggactctg cggtctatta ttgtgtaagg       300
gaccctacgt cttactgggg ccaggggact ctggtcactg tctctgca                    348

<210> SEQ ID NO 12
<211> LENGTH: 114
<212> TYPE: PRT
<213> ORGANISM: Mus sp.

<400> SEQUENCE: 12

Gln Val Gln Leu Gln Gln Ser Gly Ala Glu Leu Val Lys Pro Gly Ala
 1               5                  10                  15

Thr Val Lys Leu Ser Cys Lys Ala Ser Gly Tyr Ser Phe Asn Ser His
            20                  25                  30

```
Tyr Ile Tyr Trp Val Lys Gln Arg Pro Gly Gln Gly Leu Glu Trp Ile
        35                  40                  45

Gly Glu Ile Asn Pro Ser Asn Gly Ala Met Asn Phe Asn Glu Lys Phe
 50                  55                  60

Lys Asn Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Val Arg Asp Pro Thr Ser Tyr Trp Gly Gln Gly Thr Leu Val Thr Val
                100                 105                 110

Ser Ala

<210> SEQ ID NO 13
<211> LENGTH: 339
<212> TYPE: DNA
<213> ORGANISM: Mus sp.

<400> SEQUENCE: 13
gatatcgtga tgacccaaac tccactctcc ctgcctgtca gtcttggaga tcaagcctcc      60
atctcttgca gatctagtca gagccttgta cacagttatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
tacacgttcg gaggggggac caagctggaa ataaaacgg                           339

<210> SEQ ID NO 14
<211> LENGTH: 113
<212> TYPE: PRT
<213> ORGANISM: Mus sp.

<400> SEQUENCE: 14

Asp Ile Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Tyr Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Lys Leu Glu Ile Lys
                100                 105                 110

Arg

<210> SEQ ID NO 15
<211> LENGTH: 816
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 15
atggcgcagg tccagctgca gcagtctggg gctgaactgg tgaagcctgg ggctacagtg      60
```

```
aagttgtcct gcaaggcttc tggctacagt ttcaacagtc actatatata ttgggtgaag    120
cagaggcctg gacaaggcct tgagtggatt ggagagatta atcctagcaa tggtgctatg    180
aacttcaatg agaagttcaa gataaggcc acactgactg tagacaaatc ctccagcaca    240
gcttacatgc agctcagcag cctgacatct gaggactctg cggtctatta ttgtgtaagg    300
gaccctacgt cttactgggg ccaggggact ctggtcactg tctctgcagc caaaacgaca    360
cccaagcttg aagaaggtga attttcagaa gcacgcgtag atatcgtgat gacccaaact    420
ccactctccc tgcctgtcag tcttggagat caagcctcca tctcttgcag atctagtcag    480
agccttgtac acagttatgg aaacacctat ttacattggt acctgcagaa gccaggccag    540
tctccaaagc tcctgatcta caaagtttcc aaccgatttt ctggggtccc agacaggttc    600
agtggcagtg gatcagggac agatttcaca ctcaagatca gcagagtgga ggctgaggat    660
ctggagtttt atttctgctc tcaaagtaca catgttccgt acacgttcgg agggggacc    720 aagctggaaa taaaacgggc tgatgctgcg gccgctggat ccgaacaaaa gctgatctca    780
gaagaagatc tatcccatca tcaccatcat cattaa                              816
```

<210> SEQ ID NO 16
<211> LENGTH: 269
<212> TYPE: PRT
<213> ORGANISM: Artificial Sequence
<220> FEATURE:
<223> OTHER INFORMATION: Description of Artificial Sequence: Synthetic construct

<400> SEQUENCE: 16

```
Gln Val Gln Leu Gln Gln Ser Gly Ala Glu Leu Val Lys Pro Gly Ala
 1               5                  10                  15

Thr Val Lys Leu Ser Cys Lys Ala Ser Gly Tyr Ser Phe Asn Ser His
            20                  25                  30

Tyr Ile Tyr Trp Val Lys Gln Arg Pro Gly Gln Gly Leu Glu Trp Ile
        35                  40                  45

Gly Glu Ile Asn Pro Ser Asn Gly Ala Met Asn Phe Asn Glu Lys Phe
    50                  55                  60

Lys Asn Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Asp Pro Thr Ser Tyr Trp Gly Gln Gly Thr Leu Val Thr Val
            100                 105                 110

Ser Ala Ala Lys Thr Thr Pro Lys Leu Glu Glu Gly Glu Phe Ser Glu
        115                 120                 125

Ala Arg Val Asp Ile Val Met Thr Gln Thr Pro Leu Ser Leu Pro Val
    130                 135                 140

Ser Leu Gly Asp Gln Ala Ser Ile Ser Cys Arg Ser Ser Gln Ser Leu
145                 150                 155                 160

Val His Ser Tyr Gly Asn Thr Tyr Leu His Trp Tyr Leu Gln Lys Pro
                165                 170                 175

Gly Gln Ser Pro Lys Leu Leu Ile Tyr Lys Val Ser Asn Arg Phe Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Leu Gly Val Tyr Phe Cys
    210                 215                 220
```

```
Ser Gln Ser Thr His Val Pro Tyr Thr Phe Gly Gly Thr Lys Leu
225                 230                 235                 240

Glu Ile Lys Arg Ala Asp Ala Ala Ala Gly Ser Glu Gln Lys Leu
            245                 250                 255

Ile Ser Glu Glu Asp Leu Ser His His His His His His
            260                 265
```

<210> SEQ ID NO 17
<211> LENGTH: 846
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 17

```
atggactgga cctggagggt gttctgcctg cttgcagtgg cccccggagc ccacagccag      60
gtccagctgc agcagtctgg ggctgaactg gtgaagcctg ggctacagt gaagttgtcc     120 tgcaaggctt ctggctacag tttcaacagt cactatatat attgggtgaa gcagaggcct    180
ggacaaggcc ttgagtggat tggagagatt aatcctagca atggtgctat gaacttcaat    240
gagaagttca gaataaggc cacactgact gtagacaaat cctccagcac agcttacatg     300
cagctcagca gcctgacatc tgaggactct gcggtctatt attgtgtaag ggaccctacg    360
tcttactggg gccaggggac tctggtcact gtctctgcag ccaaaacgac acccaagctt    420
gaagaaggtg aatttttcaga agcacgcgta gatatcgtga tgacccaaac tccactctcc    480
ctgcctgtca gtcttggaga tcaagcctcc atctcttgca gatctagtca gagccttgta    540
cacagttatg aaacacctta tttcattgg tacctgcaga agccaggcca gtctccaaag     600
ctcctgatct acaaagtttc caaccgattt tctggggtcc cagacaggtt cagtggaagt    660
ggatcaggga cagatttcac actcaagatc agcagagtgg aggctgagga tctgggagtt    720
tatttctgct ctcaaagtac acatgttccg tacacgttcg gagggggac caagctggaa    780 ataaaacggg ctgatgctgc ggccgctgga tccgaacaaa agctgatctc agaagaagat    840
ctataa                                                              846
```

<210> SEQ ID NO 18
<211> LENGTH: 281
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

```
Met Asp Trp Thr Trp Arg Val Phe Cys Leu Leu Ala Val Ala Pro Gly
1               5                   10                  15

Ala His Ser Gln Val Gln Leu Gln Gln Ser Gly Ala Glu Leu Val Lys
            20                  25                  30

Pro Gly Ala Thr Val Lys Leu Ser Cys Lys Ala Ser Gly Tyr Ser Phe
        35                  40                  45

Asn Ser His Tyr Ile Tyr Trp Val Lys Gln Arg Pro Gly Gln Gly Leu
    50                  55                  60

Glu Trp Ile Gly Glu Ile Asn Pro Ser Asn Gly Ala Met Asn Phe Asn
65                  70                  75                  80

Glu Lys Phe Lys Asn Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
```

```
                  100                 105                 110
Tyr Tyr Cys Val Arg Asp Pro Thr Ser Tyr Trp Gly Gln Gly Thr Leu
        115                 120                 125

Val Thr Val Ser Ala Ala Lys Thr Thr Pro Lys Leu Glu Glu Gly Glu
        130                 135                 140

Phe Ser Glu Ala Arg Val Asp Ile Val Met Thr Gln Thr Pro Leu Ser
145                 150                 155                 160

Leu Pro Val Ser Leu Gly Asp Gln Ala Ser Ile Ser Cys Arg Ser Ser
                165                 170                 175

Gln Ser Leu Val His Ser Tyr Gly Asn Thr Tyr Leu His Trp Tyr Leu
            180                 185                 190

Gln Lys Pro Gly Gln Ser Pro Lys Leu Leu Ile Tyr Lys Val Ser Asn
        195                 200                 205

Arg Phe Ser Gly Val Pro Asp Arg Phe Ser Gly Ser Gly Ser Gly Thr
        210                 215                 220

Asp Phe Thr Leu Lys Ile Ser Arg Val Glu Ala Glu Asp Leu Gly Val
225                 230                 235                 240

Tyr Phe Cys Ser Gln Ser Thr His Val Pro Tyr Thr Phe Gly Gly Gly
                245                 250                 255

Thr Lys Leu Glu Ile Lys Arg Ala Asp Ala Ala Ala Gly Ser Glu
            260                 265                 270

Gln Lys Leu Ile Ser Glu Glu Asp Leu
        275                 280

<210> SEQ ID NO 19
<211> LENGTH: 2127
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19
atggaatgca gctgggtcat gctcttcctc ctgtcaggaa ctgcaggtgt ccattgccag      60
gttcagctgc agcagtctgg acctgagctg gtgaagcctg gggctttagt gaagatatcc     120
tgcaaggctt ctggttacac cttcacaaac tacgatatac actgggtgaa gcagaggcct     180
ggacagggac ttgagtggat tggatggatt tatcctggag atggtagtac taagtacaat     240
gagaaattca gggcaaggc cacactgact gcagacaaat cctccagcac agcctacatg      300
cacctcagca gcctgacttc tgagaaatct gcagtctatt tctgtgcaag agagtgggct     360
tactggggcc aagggactct ggtcactgtc tctgcagcta gcaccaaggg cccatcggtc     420
ttccccctgg caccctcctc caagagcacc tctgggggca gcgcct ggctgcctg          480 gtcaaggact acttccccga accggtgacg gtgtcgtgga actcaggcgc cctgaccagc     540
ggcgtgcaca ccttcccggc tgtcctacag tcctcaggac tctactccct cagcagcgtg     600
gtgaccgtgc cctccagcag cttgggcacc cagacctaca tctgcaacgt gaatcacaag     660
cccagcaaca ccaaggtgga caagaaagtt gagcccaaat cttgtgacaa aactcacaca     720
tgcccaccgt gcccagcacc tgaactcctg ggggaccgt cagtcttcct cttccccca      780 aaacccaagg acaccctcat gatctcccgg acccctgagg tcacatgcgt ggtggtggac     840
gtgagccacg aagaccctga ggtcaagttc aactggtacg tggacggcgt ggaggtgcat     900
aatgccaaga caaagccgcg ggaggagcag tacaacagca cgtaccgtgt ggtcagcgtc     960
ctcaccgtcc tgcaccagga ctggctgaat ggcaaggagt acaagtgcaa ggtctccaac    1020
```

-continued

```
aaagccctcc cagccccat cgagaaaacc atctccaaag ccaaagggca gccccgagaa    1080
ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaaagtt cacaggtcca gctgcagcag tctggggctg aactggtgaa gcctggggct    1440
acagtgaagt tgtcctgcaa ggcttctggc tacagtttca acagtcacta tatatattgg    1500
gtgaagcaga ggcctggaca aggccttgag tggattggag agattaatcc tagcaatggt    1560
gctatgaact tcaatgagaa gttcaagaat aaggccacac tgactgtaga caaatcctcc    1620
agcacagctt acatgcagct cagcagcctg acatctgagg actctgcggt ctattattgt    1680
gtaagggacc ctacgtctta ctggggccag gggactctgg tcactgtctc tgcagccaaa    1740
acgacaccca gcttgaaga aggtgaattt tcagaagcac gcgtagatat cgtgatgacc    1800
caaactccac tctccctgcc tgtcagtctt ggagatcaag cctccatctc ttgcagatct    1860
agtcagagcc ttgtacacag ttatggaaac acctatttac attggtacct gcagaagcca    1920
ggccagtctc caaagctcct gatctacaaa gtttccaacc gattttctgg ggtcccagac    1980
aggttcagtg gcagtggatc agggacagat ttcacactca agatcagcag agtggaggct    2040
gaggatctgg gagtttattt ctgctctcaa agtacacatg ttccgtacac gttcggaggg    2100
gggaccaagc tggaaataaa acggtaa                                         2127
```

<210> SEQ ID NO 20
<211> LENGTH: 708
<212> TYPE: PRT
<213> ORGANISM: Artificial Sequence
<220> FEATURE:
<223> OTHER INFORMATION: Description of Artificial Sequence: Synthetic construct

<400> SEQUENCE: 20

```
Met Glu Cys Ser Trp Val Met Leu Phe Leu Leu Ser Gly Thr Ala Gly
  1               5                  10                  15

Val His Cys Gln Val Gln Leu Gln Gln Ser Gly Pro Glu Leu Val Lys
             20                  25                  30

Pro Gly Ala Leu Val Lys Ile Ser Cys Lys Ala Ser Gly Tyr Thr Phe
         35                  40                  45

Thr Asn Tyr Asp Ile His Trp Val Lys Gln Arg Pro Gly Gln Gly Leu
     50                  55                  60

Glu Trp Ile Gly Trp Ile Tyr Pro Gly Asp Gly Ser Thr Lys Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
```

```
                          165                 170                 175
Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
        210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ser Ser
    450                 455                 460

Gln Val Gln Leu Gln Gln Ser Gly Ala Glu Leu Val Lys Pro Gly Ala
465                 470                 475                 480

Thr Val Lys Leu Ser Cys Lys Ala Ser Gly Tyr Ser Phe Asn Ser His
                485                 490                 495

Tyr Ile Tyr Trp Val Lys Gln Arg Pro Gly Gln Gly Leu Glu Trp Ile
            500                 505                 510

Gly Glu Ile Asn Pro Ser Asn Gly Ala Met Asn Phe Asn Glu Lys Phe
        515                 520                 525

Lys Asn Lys Ala Thr Leu Thr Val Asp Lys Ser Ser Ser Thr Ala Tyr
    530                 535                 540

Met Gln Leu Ser Ser Leu Thr Ser Glu Asp Ser Ala Val Tyr Tyr Cys
545                 550                 555                 560

Val Arg Asp Pro Thr Ser Tyr Trp Gly Gln Gly Thr Leu Val Thr Val
                565                 570                 575

Ser Ala Ala Lys Thr Thr Pro Lys Leu Glu Glu Gly Glu Phe Ser Glu
            580                 585                 590
```

```
Ala Arg Val Asp Ile Val Met Thr Gln Thr Pro Leu Ser Leu Pro Val
        595                 600                 605

Ser Leu Gly Asp Gln Ala Ser Ile Ser Cys Arg Ser Ser Gln Ser Leu
610                 615                 620

Val His Ser Tyr Gly Asn Thr Tyr Leu His Trp Tyr Leu Gln Lys Pro
625                 630                 635                 640

Gly Gln Ser Pro Lys Leu Leu Ile Tyr Lys Val Ser Asn Arg Phe Ser
                645                 650                 655

Gly Val Pro Asp Arg Phe Ser Gly Ser Gly Ser Gly Thr Asp Phe Thr
                660                 665                 670

Leu Lys Ile Ser Arg Val Glu Ala Glu Asp Leu Gly Val Tyr Phe Cys
                675                 680                 685

Ser Gln Ser Thr His Val Pro Tyr Thr Phe Gly Gly Gly Thr Lys Leu
690                 695                 700

Glu Ile Lys Arg
705

<210> SEQ ID NO 21
<211> LENGTH: 2127
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
```

| | | | | | |
|---|---|---|---|---|---|
| atggactgga | cctggagggt | gttctgcctg | cttgcagtgg | cccccggagc | ccacagccag | 60 |
| gttcagctgc | agcagtctgg | acctgagctg | gtgaagcctg | ggctttagt | gaagatatcc | 120 |
| tgcaaggctt | ctggttacac | cttcacaaac | tacgatatac | actgggtgaa | gcagaggcct | 180 |
| ggacagggac | ttgagtggat | tggatggatt | tatcctggag | atggtagtac | taagtacaat | 240 |
| gagaaattca | gggcaaggc | cacactgact | gcagacaaat | cctccagcac | agcctacatg | 300 |
| cacctcagca | gcctgacttc | tgagaaatct | gcagtctatt | tctgtgcaag | agagtgggct | 360 |
| tactggggcc | aagggactct | ggtcactgtc | tctgcagcta | gcaccaaggg | cccatcggtc | 420 |
| ttccccctgg | caccctcctc | caagagcacc | tctggggca | cagcggccct | gggctgcctg | 480 |
| gtcaaggact | acttccccga | accggtgacg | gtgtcgtgga | actcaggcgc | cctgaccagc | 540 |
| ggcgtgcaca | ccttcccggc | tgtcctacag | tcctcaggac | tctactccct | cagcagcgtg | 600 |
| gtgaccgtgc | cctccagcag | cttgggcacc | cagacctaca | tctgcaacgt | gaatcacaag | 660 |
| cccagcaaca | ccaaggtgga | caagaaagtt | gagcccaaat | cttgtgacaa | aactcacaca | 720 |
| tgcccaccgt | gcccagcacc | tgaactcctg | gggggaccgt | cagtcttcct | cttcccccca | 780 |
| aaacccaagg | acaccctcat | gatctcccgg | acccctgagg | tcacatgcgt | ggtggtggac | 840 |
| gtgagccacg | aagaccctga | ggtcaagttc | aactggtacg | tggacggcgt | ggaggtgcat | 900 |
| aatgccaaga | caaagccgcg | ggaggagcag | tacaacagca | cgtaccgtgt | ggtcagcgtc | 960 |
| ctcaccgtcc | tgcaccagga | ctggctgaat | ggcaaggagt | acaagtgcaa | ggtctccaac | 1020 |
| aaagccctcc | cagcccccat | cgagaaaacc | atctccaaag | ccaaagggca | gccccgagaa | 1080 |
| ccacaggtgt | acaccctgcc | cccatcccgg | gatgagctga | ccaagaacca | ggtcagcctg | 1140 |
| acctgcctgg | tcaaaggctt | ctatcccagc | gacatcgccg | tggagtggga | gagcaatggg | 1200 |
| cagccggaga | acaactacaa | gaccacgcct | cccgtgctgg | actccgacgg | ctccttcttc | 1260 |
| ctctacagca | agctcaccgt | ggacaagagc | aggtggcagc | aggggaacgt | cttctcatgc | 1320 |
| tccgtgatgc | atgaggctct | gcacaaccac | tacacgcaga | agagcctctc | cctgtctccg | 1380 |

```
ggtaaaagtt cacaggtcca gctgcagcag tctggggctg aactggtgaa gcctggggct   1440
acagtgaagt tgtcctgcaa ggcttctggc tacagtttca acagtcacta tatatattgg   1500
gtgaagcaga ggcctggaca aggccttgag tggattggag agattaatcc tagcaatggt   1560
gctatgaact tcaatgagaa gttcaagaat aaggccacac tgactgtaga caaatcctcc   1620
agcacagctt acatgcagct cagcagcctg acatctgagg actctgcggt ctattattgt   1680
gtaagggacc ctacgtctta ctggggccag gggactctgg tcactgtctc tgcagccaaa   1740
acgacaccca gcttgaagag gtgaatttt cagaagcac gcgtagatgt cgtgatgacc   1800
caaactccac tctccctgcc tgtcagtctt ggagatcaag cctccatctc ttgcagatct   1860
agtcagagcc ttgtacacag ttatggaaac acctatttac attggtacct gcagaagcca   1920
ggccagtctc caaagctcct gatctacaaa gtttccaacc gattttctgg ggtcccagac   1980
aggttcagtg gcagtggatc agggacagat ttcacactca agatcagcag agtggaggct   2040
gaggatctgg gagtttattt ctgctctcaa agtacacatg ttccgtacac gttcggaggg   2100
gggaccaagc tggaaataaa acggtaa                                       2127
```

<210> SEQ ID NO 22
<211> LENGTH: 708
<212> TYPE: PRT
<213> ORGANISM: Artificial Sequence
<220> FEATURE:
<223> OTHER INFORMATION: Description of Artificial Sequence: Synthetic construct

<400> SEQUENCE: 22

```
Met Asp Trp Thr Trp Arg Val Phe Cys Leu Leu Ala Val Ala Pro Gly
 1               5                  10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205
```

-continued

```
Gly Thr Gln Thr Tyr Ile Cys Asn Val Asn His Lys Pro Ser Asn Thr
            210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
                275                 280                 285
Lys Phe Asn Trp Tyr Val Asp Gly Val Glu Val His Asn Ala Lys Thr
            290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
            355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys Ser Ser
            450                 455                 460
Gln Val Gln Leu Gln Gln Ser Gly Ala Glu Leu Val Lys Pro Gly Ala
465                 470                 475                 480
Thr Val Lys Leu Ser Cys Lys Ala Ser Gly Tyr Ser Phe Asn Ser His
                485                 490                 495
Tyr Ile Tyr Trp Val Lys Gln Arg Pro Gly Gln Gly Leu Glu Trp Ile
            500                 505                 510
Gly Glu Ile Asn Pro Ser Asn Gly Ala Met Asn Phe Asn Glu Lys Phe
            515                 520                 525
Lys Asn Lys Ala Thr Leu Thr Val Asp Lys Ser Ser Ser Thr Ala Tyr
530                 535                 540
Met Gln Leu Ser Ser Leu Thr Ser Glu Asp Ser Ala Val Tyr Tyr Cys
545                 550                 555                 560
Val Arg Asp Pro Thr Ser Tyr Trp Gly Gln Gly Thr Leu Val Thr Val
                565                 570                 575
Ser Ala Ala Lys Thr Thr Pro Lys Leu Glu Glu Gly Glu Phe Ser Glu
            580                 585                 590
Ala Arg Val Asp Val Val Met Thr Gln Thr Pro Leu Ser Leu Pro Val
            595                 600                 605
Ser Leu Gly Asp Gln Ala Ser Ile Ser Cys Arg Ser Ser Gln Ser Leu
            610                 615                 620
Val His Ser Tyr Gly Asn Thr Tyr Leu His Trp Tyr Leu Gln Lys Pro
625                 630                 635                 640
```

```
Gly Gln Ser Pro Lys Leu Leu Ile Tyr Lys Val Ser Asn Arg Phe Ser
            645                 650                 655

Gly Val Pro Asp Arg Phe Ser Gly Ser Gly Ser Gly Thr Asp Phe Thr
            660                 665                 670

Leu Lys Ile Ser Arg Val Glu Ala Glu Asp Leu Gly Val Tyr Phe Cys
            675                 680                 685

Ser Gln Ser Thr His Val Pro Tyr Thr Phe Gly Gly Gly Thr Lys Leu
            690                 695                 700

Glu Ile Lys Arg
705

<210> SEQ ID NO 23
<211> LENGTH: 2127
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 23
atggactgga cctggagggt gttctgcctg cttgcagtgg cccccggagc ccacagccag      60
gttcagctgc agcagtctgg acctgagctg gtgaagcctg ggctttagt gaagatatcc     120 tgcaaggctt ctggttacac cttcacaaac tacgatatac actgggtgaa gcagaggcct    180
ggacagggac ttgagtggat tggatggatt tatcctggag atggtagtac taagtacaat    240
gagaaattca gggcaaggc cacactgact gcagacaaat cctccagcac agcctacatg     300
cacctcagca gcctgacttc tgagaaatct gcagtctatt tctgtgcaag agagtgggct    360
tactggggcc aagggactct ggtcactgtc tctgcagcta gcaccaaggg cccatcggtc    420
ttccccctgg caccctcctc caagagcacc tctgggggca gcggccct gggctgcctg     480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcctg gggggaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc    1260
ctctacagca agctcaccgt ggacaagagc aggtggcagc aggggaacgt cttctcatgc   1320
tccgtgatgc atgaggctct gcacaaccac tacacgcaga agagcctctc cctgtctccg   1380
ggtaaaagtt cacaggtcca gctgcagcag tctggggctg aactggtgaa gcctggggct   1440
acagtgaagt tgtcctgcaa ggcttctggc tacagtttca acagtcacta tatatattgg   1500
gtgaagcaga ggcctggaca aggccttgag tggattggag agattgctcc tagcaatggt   1560
gctatgaact tcaatgagaa gttcaagaat aaggccacac tgactgtaga caaatcctcc   1620
```

```
agcacagctt acatgcagct cagcagcctg acatctgagg actctgcggt ctattattgt    1680
gtaagggacc ctacgtctta ctggggccag gggactctgg tcactgtctc tgcagccaaa    1740
acgacaccca agcttgaaga aggtgaattt tcagaagcac gcgtagatgt cgtgatgacc    1800
caaactccac tctccctgcc tgtcagtctt ggagatcaag cctccatctc ttgcagatct    1860
agtcagagcc ttgtacacag ttatggaaac acctatttac attggtacct gcagaagcca    1920
ggccagtctc caaagctcct gatctacaaa gtttccaacc gattttctgg ggtcccagac    1980
aggttcagtg gcagtggatc agggacagat ttcacactca agatcagcag agtggaggct    2040
gaggatctgg gagtttattt ctgctctcaa agtacacatg ttccgtacac gttcggaggg    2100
gggaccaagc tggaaataaa acggtaa                                        2127
```

<210> SEQ ID NO 24
<211> LENGTH: 708
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 24

```
Met Asp Trp Thr Trp Arg Val Phe Cys Leu Leu Ala Val Ala Pro Gly
  1               5                  10                  15

Ala His Ser Gln Val Gln Leu Gln Gln Ser Gly Pro Glu Leu Val Lys
             20                  25                  30

Pro Gly Ala Leu Val Lys Ile Ser Cys Lys Ala Ser Gly Tyr Thr Phe
         35                  40                  45

Thr Asn Tyr Asp Ile His Trp Val Lys Gln Arg Pro Gly Gln Gly Leu
     50                  55                  60

Glu Trp Ile Gly Trp Ile Tyr Pro Gly Asp Gly Ser Thr Lys Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
                340                 345                 350
Lys Ala Lys Gly Gln Pro Arg Glu Pro Gln Val Tyr Thr Leu Pro Pro
                    355                 360                 365
Ser Arg Asp Glu Leu Thr Lys Asn Gln Val Ser Leu Thr Cys Leu Val
                        370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
                435                 440                 445
Asn His Tyr Thr Gln Lys Ser Leu Ser Leu Ser Pro Gly Lys Ser Ser
            450                 455                 460
Gln Val Gln Leu Gln Gln Ser Gly Ala Glu Leu Val Lys Pro Gly Ala
465                 470                 475                 480
Thr Val Lys Leu Ser Cys Lys Ala Ser Gly Tyr Ser Phe Asn Ser His
                485                 490                 495
Tyr Ile Tyr Trp Val Lys Gln Arg Pro Gly Gln Gly Leu Glu Trp Ile
                500                 505                 510
Gly Glu Ile Ala Pro Ser Asn Gly Ala Met Asn Phe Asn Glu Lys Phe
            515                 520                 525
Lys Asn Lys Ala Thr Leu Thr Val Asp Lys Ser Ser Ser Thr Ala Tyr
                530                 535                 540
Met Gln Leu Ser Ser Leu Thr Ser Glu Asp Ser Ala Val Tyr Tyr Cys
545                 550                 555                 560
Val Arg Asp Pro Thr Ser Tyr Trp Gly Gln Gly Thr Leu Val Thr Val
                    565                 570                 575
Ser Ala Ala Lys Thr Thr Pro Lys Leu Glu Glu Gly Glu Phe Ser Glu
                580                 585                 590
Ala Arg Val Asp Val Val Met Thr Gln Thr Pro Leu Ser Leu Pro Val
                595                 600                 605
Ser Leu Gly Asp Gln Ala Ser Ile Ser Cys Arg Ser Ser Gln Ser Leu
            610                 615                 620
Val His Ser Tyr Gly Asn Thr Tyr Leu His Trp Tyr Leu Gln Lys Pro
625                 630                 635                 640
Gly Gln Ser Pro Lys Leu Leu Ile Tyr Lys Val Ser Asn Arg Phe Ser
                    645                 650                 655
Gly Val Pro Asp Arg Phe Ser Gly Ser Gly Ser Gly Thr Asp Phe Thr
                660                 665                 670
Leu Lys Ile Ser Arg Val Glu Ala Glu Asp Leu Gly Val Tyr Phe Cys
            675                 680                 685
Ser Gln Ser Thr His Val Pro Tyr Thr Phe Gly Gly Gly Thr Lys Leu
```

Glu Ile Lys Arg
705

<210> SEQ ID NO 25
<211> LENGTH: 2127
<212> TYPE: DNA
<213> ORGANISM: Artificial Sequence
<220> FEATURE:
<223> OTHER INFORMATION: Description of Artificial Sequence: Synthetic construct

<400> SEQUENCE: 25

| | | | | | |
|---|---|---|---|---|---|
| atggactgga | cctggagggt | gttctgcctg | cttgcagtgg | cccccggagc | ccacagccag | 60 |
| gttcagctgc | agcagtctgg | acctgagctg | gtgaagcctg | ggctttagt | gaagatatcc | 120 |
| tgcaaggctt | ctggttacac | cttcacaaac | tacgatatac | actgggtgaa | gcagaggcct | 180 |
| ggacagggac | ttgagtggat | tggatggatt | tatcctggag | atggtagtac | taagtacaat | 240 |
| gagaaattca | agggcaaggc | cacactgact | gcagacaaat | cctccagcac | agcctacatg | 300 |
| cacctcagca | gcctgacttc | tgagaaatct | gcagtctatt | tctgtgcaag | agagtgggct | 360 |
| tactggggcc | aagggactct | ggtcactgtc | tctgcagcta | gcaccaaggg | cccatcggtc | 420 |
| ttccccctgg | caccctcctc | caagagcacc | tctgggggca | gcgggccct | gggctgcctg | 480 |
| gtcaaggact | acttccccga | accggtgacg | gtgtcgtgga | actcaggcgc | cctgaccagc | 540 |
| ggcgtgcaca | ccttcccggc | tgtcctacag | tcctcaggac | tctactccct | cagcagcgtg | 600 |
| gtgaccgtgc | cctccagcag | cttgggcacc | cagacctaca | tctgcaacgt | gaatcacaag | 660 |
| cccagcaaca | ccaaggtgga | caagaaagtt | gagcccaaat | cttgtgacaa | aactcacaca | 720 |
| tgcccaccgt | gcccagcacc | tgaactcctg | ggggaccgt | cagtcttcct | cttccccca | 780 |
| aaacccaagg | acaccctcat | gatctcccgg | acccctgagg | tcacatgcgt | ggtggtggac | 840 |
| gtgagccacg | aagaccctga | ggtcaagttc | aactggtacg | tggacggcgt | ggaggtgcat | 900 |
| aatgccaaga | caaagccgcg | ggaggagcag | tacaacagca | cgtaccgtgt | ggtcagcgtc | 960 |
| ctcaccgtcc | tgcaccagga | ctggctgaat | ggcaaggagt | acaagtgcaa | ggtctccaac | 1020 |
| aaagccctcc | cagcccccat | cgagaaaacc | atctccaaag | ccaaagggca | gccccgagaa | 1080 |
| ccacaggtgt | acaccctgcc | cccatcccgg | gatgagctga | ccaagaacca | ggtcagcctg | 1140 |
| acctgcctgg | tcaaaggctt | ctatcccagc | gacatcgccg | tggagtggga | gagcaatggg | 1200 |
| cagccggaga | acaactacaa | gaccacgcct | cccgtgctgg | actccgacgg | ctccttcttc | 1260 |
| ctctacagca | agctcaccgt | ggacaagagc | aggtggcagc | aggggaacgt | cttctcatgc | 1320 |
| tccgtgatgc | atgaggctct | gcacaaccac | tacacgcaga | agagcctctc | cctgtctccg | 1380 |
| ggtaaaagtt | cacaggtcca | gctgcagcag | tctggggctg | aactggtgaa | gcctggggct | 1440 |
| acagtgaagt | tgtcctgcaa | ggcttctggc | tacagtttca | acagtcacta | tatatattgg | 1500 |
| gtgaagcaga | ggcctggaca | aggccttgag | tggattggag | agattaatcc | tgccaatggt | 1560 |
| gctatgaact | tcaatgagaa | gttcaagaat | aaggccacac | tgactgtaga | caaatcctcc | 1620 |
| agcacagctt | acatgcagct | cagcagcctg | acatctgagg | actctgcggt | ctattattgt | 1680 |
| gtaagggacc | ctacgtctta | ctggggccag | gggactctgg | tcactgtctc | tgcagccaaa | 1740 |
| acgacaccca | gcttgaaga | aggtgaattt | tcagaagcac | gcgtagatgt | cgtgatgacc | 1800 |
| caaactccac | tctccctgcc | tgtcagtctt | ggagatcaag | cctccatctc | ttgcagatct | 1860 |
| agtcagagcc | ttgtacacag | ttatggaaac | acctatttac | attggtacct | gcagaagcca | 1920 |

-continued

```
ggccagtctc caaagctcct gatctacaaa gtttccaacc gatttctgg ggtcccagac    1980 aggttcagtg gcagtggatc agggacagat ttcacactca agatcagcag agtggaggct    2040
gaggatctgg gagtttattt ctgctctcaa agtacacatg ttccgtacac gttcggaggg    2100
gggaccaagc tggaaataaa acggtaa                                       2127
```

<210> SEQ ID NO 26
<211> LENGTH: 708
<212> TYPE: PRT
<213> ORGANISM: Artificial Sequence
<220> FEATURE:
<223> OTHER INFORMATION: Description of Artificial Sequence: Synthetic construct

<400> SEQUENCE: 26

```
Met Asp Trp Thr Trp Arg Val Phe Cys Leu Leu Ala Val Ala Pro Gly
  1               5                  10                  15

Ala His Ser Gln Val Gln Leu Gln Gln Ser Gly Pro Glu Leu Val Lys
             20                  25                  30

Pro Gly Ala Leu Val Lys Ile Ser Cys Lys Ala Ser Gly Tyr Thr Phe
         35                  40                  45

Thr Asn Tyr Asp Ile His Trp Val Lys Gln Arg Pro Gly Gln Gly Leu
     50                  55                  60

Glu Trp Ile Gly Trp Ile Tyr Pro Gly Asp Gly Ser Thr Lys Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
```

```
                    325                 330                 335
Lys Val Ser Asn Lys Ala Leu Pro Ala Pro Ile Glu Lys Thr Ile Ser
                340                 345                 350
Lys Ala Lys Gly Gln Pro Arg Glu Pro Gln Val Tyr Thr Leu Pro Pro
            355                 360                 365
Ser Arg Asp Glu Leu Thr Lys Asn Gln Val Ser Leu Thr Cys Leu Val
        370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
                420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys Ser Ser
        450                 455                 460
Gln Val Gln Leu Gln Gln Ser Gly Ala Glu Leu Val Lys Pro Gly Ala
465                 470                 475                 480
Thr Val Lys Leu Ser Cys Lys Ala Ser Gly Tyr Ser Phe Asn Ser His
                485                 490                 495
Tyr Ile Tyr Trp Val Lys Gln Arg Pro Gly Gln Gly Leu Glu Trp Ile
                500                 505                 510
Gly Glu Ile Asn Pro Ala Asn Gly Ala Met Asn Phe Asn Glu Lys Phe
            515                 520                 525
Lys Asn Lys Ala Thr Leu Thr Val Asp Lys Ser Ser Ser Thr Ala Tyr
        530                 535                 540
Met Gln Leu Ser Ser Leu Thr Ser Glu Asp Ser Ala Val Tyr Tyr Cys
545                 550                 555                 560
Val Arg Asp Pro Thr Ser Tyr Trp Gly Gln Gly Thr Leu Val Thr Val
                565                 570                 575
Ser Ala Ala Lys Thr Thr Pro Lys Leu Glu Glu Gly Glu Phe Ser Glu
                580                 585                 590
Ala Arg Val Asp Val Val Met Thr Gln Thr Pro Leu Ser Leu Pro Val
            595                 600                 605
Ser Leu Gly Asp Gln Ala Ser Ile Ser Cys Arg Ser Ser Gln Ser Leu
        610                 615                 620
Val His Ser Tyr Gly Asn Thr Tyr Leu His Trp Tyr Leu Gln Lys Pro
625                 630                 635                 640
Gly Gln Ser Pro Lys Leu Leu Ile Tyr Lys Val Ser Asn Arg Phe Ser
                645                 650                 655
Gly Val Pro Asp Arg Phe Ser Gly Ser Gly Ser Gly Thr Asp Phe Thr
                660                 665                 670
Leu Lys Ile Ser Arg Val Glu Ala Glu Asp Leu Gly Val Tyr Phe Cys
            675                 680                 685
Ser Gln Ser Thr His Val Pro Tyr Thr Phe Gly Gly Gly Thr Lys Leu
        690                 695                 700
Glu Ile Lys Arg
705

<210> SEQ ID NO 27
<211> LENGTH: 6671
<212> TYPE: DNA
<213> ORGANISM: Artificial Sequence
<220> FEATURE:
```

<223> OTHER INFORMATION: Description of Artificial Sequence: Synthetic construct

<400> SEQUENCE: 27

```
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctctc tggctaacta     600
gagaacccac tgcttactgg cttatcgaaa ttaatacgac tcactatagg gagacccaag     660
ctggctagcg tttaaactta agcttggtac cgagctcgga tccactagtc cagtgtggtg     720
gaattctgca ggccgccacc atggagaccc cgcccagct gctgttcctg ttgctgcttt      780
ggcttccaga tactaccggc gacatccaga tgacccagtc tccatcctcc ttatctgcct     840
ctctgggaga aagagtcagt ctcacttgtc gggcaagtca ggacattggt ggtaacttat     900
actggcttca gcagggacca gatgaactaa ttaaacgcct gatctacgcc acatccagtt     960
tagattctgg tgtccccaaa aggttcagtg gcagtaggtc tgggtcagat tattctctca    1020
ccatcagcag ccttgagtct gaagattttg tagactatta ctgtctacag tattctagtt    1080
ctccgtggac gttcggtgga ggcacaaaga tggaaataaa acgaactgtg gctgcaccat    1140
ctgtcttcat cttcccgcca tctgatgagc agttgaaatc tggaactgcc tctgttgtgt    1200
gcctgctgaa taacttctat cccagagagg ccaaagtaca gtggaaggtg gataacgccc    1260
tccaatcggg taactcccag gagagtgtca cagagcagga cagcaaggac agcacctaca    1320
gcctcagcag caccctgacg ctgagcaaag cagactacga gaaacacaaa gtctacgcct    1380
gcgaagtcac ccatcagggc ctgagctcgc ccgtcacaaa gagcttcaac aggggagagt    1440
gttagctcga gtctagaggg cccgtttaaa cccgctgatc agcctcgact gtgccttcta    1500
gttgccagcc atctgttgtt tgcccctccc ccgtgccttc cttgaccctg gaaggtgcca    1560
ctcccactgt cctttcctaa taaaatgagg aaattgcatc gcattgtctg agtaggtgtc    1620
attctattct ggggggtggg gtggggcagg acagcaaggg ggaggattgg gaagacaata    1680
gcaggcatgc tggggatgcg gtgggctcta tggcttctga ggcggaaaga accagccgat    1740
gtacgggcca gatatacgcg ttgacattga ttattgacta gttattaata gtaatcaatt    1800
acggggtcat tagttcatag cccatatatg gagttccgcg ttacataact tacggtaaat    1860
ggcccgcctg gctgaccgcc caacgacccc cgcccattga cgtcaataat gacgtatgtt    1920
cccatagtaa cgccaatagg gactttccat tgacgtcaat gggtggagta tttacggtaa    1980
actgcccact tggcagtaca tcaagtgtat catatgccaa gtacgccccc tattgacgtc    2040
aatgacggta aatggcccgc ctggcattat gcccagtaca tgaccttatg gactttcct    2100
acttggcagt acatctacgt attagtcatc gctattacca tggtgatgcg gttttggcag    2160
tacatcaatg ggcgtggata gcggtttgac tcacggggat ttccaagtct ccaccccatt    2220
gacgtcaatg ggagtttgtt ttggcaccaa aatcaacggg actttccaaa atgtcgtaac    2280
```

```
aactccgccc cattgacgca aatgggcggt aggcgtgtac ggtgggaggt ctatataagc    2340
agagctctct ggctaactag agaacccact gcttactggc ttatcgaaat taatacgact    2400 cactatagggg agacccaagc tggctagcgt ttaaacgggc cctctagact cgagcggccg    2460
ccactgtgct ggagccgcca ccatggactg gacctggagg gtgttctgcc tgcttgcagt    2520
ggcccccgga gcccacagcc aggttcagct gcagcagtct ggacctgagc tggtgaagcc    2580 tggggctttta gtgaagatat cctgcaaggc ttctggttac accttcacaa actacgatat    2640
acactgggtg aagcagaggc ctggacaggg acttgagtgg attggatgga tttatcctgg    2700
agatggtagt actaagtaca atgagaaatt caagggcaag gccacactga ctgcagacaa    2760
atcctccagc acagcctaca tgcacctcag cagcctgact tctgagaaat ctgcagtcta    2820
tttctgtgca agagagtggg cttactgggg ccaagggact ctggtcactg tctctgcagc    2880
tagcaccaag ggcccatcgg tcttcccccct ggcaccctcc tccaagagca cctctggggg    2940
cacagcggcc ctgggctgcc tggtcaagga ctacttcccc gaaccggtga cggtgtcgtg    3000
gaactcaggc gccctgacca gcggcgtgca ccttcccg gctgtcctac agtcctcagg    3060
actctactcc ctcagcagcg tggtgaccgt gccctccagc agcttgggca cccagaccta    3120
catctgcaac gtgaatcaca agcccagcaa caccaaggtg gacaagaaag ttgagcccaa    3180
atcttgtgac aaaactcaca catgcccacc gtgcccagca cctgaactcc tggggggacc    3240
gtcagtcttc ctcttccccc caaaacccaa ggacaccctc atgatctccc ggaccctga    3300 ggtcacatgc gtggtggtgg acgtgagcca cgaagaccct gaggtcaagt tcaactggta    3360
cgtggacggc gtggaggtgc ataatgccaa gacaaagccg cgggaggagc agtacaacag    3420
cacgtaccgt gtggtcagcg tcctcaccgt cctgcaccag gactggctga atggcaagga    3480
gtacaagtgc aaggtctcca acaaagccct cccagccccc atcgagaaaa ccatctccaa    3540
agccaaaggg cagccccgag aaccacaggt gtacaccctg cccccatccc gggatgagct    3600
gaccaagaac caggtcagcc tgacctgcct ggtcaaaggc ttctatccca gcgacatcgc    3660
cgtggagtgg gagagcaatg ggcagccgga gaacaactac aagaccacgc ctcccgtgct    3720
ggactccgac ggctccttct tcctctacag caagctcacc gtggacaaga gcaggtggca    3780
gcaggggaac gtcttctcat gctccgtgat gcatgaggct ctgcacaacc actacacgca    3840
gaagagcctc tccctgtctc cgggtaaaag ttcacaggtc cagctgcagc agtctggggc    3900
tgaactggtg aagcctgggg ctacagtgaa gttgtcctgc aaggcttctg gctacagttt    3960
caacagtcac tatatatatt gggtgaagca gaggcctgga caaggccttg agtggattgg    4020
agagattaat cctagcaatg gtgctatgaa cttcaatgag aagttcaaga ataaggccac    4080
actgactgta gacaaatcct ccagcacagc ttacatgcag ctcagcagcc tgacatctga    4140
ggactctgcg gtctattatt gtgtaaggga ccctacgtct tactgggggcc aggggactct    4200 ggtcactgtc tctgcagcca aaacgacacc caagcttgaa gaaggtgaat tttcagaagc    4260
acgcgtagat gtcgtgatga cccaaactcc actctccctg cctgtcagtc ttggagatca    4320
agcctccatc tcttgcagat ctagtcagag ccttgtacac agttatggaa acacctattt    4380
acattggtac ctgcagaagc caggccagtc tccaaagctc ctgatctaca agtttccaa    4440 ccgattttct ggggtcccag acaggttcag tggcagtgga tcaggacag atttcacact    4500 caagatcagc agagtggagg ctgaggatct gggagtttat ttctgctctc aaagtacaca    4560
tgttccgtac acgttcggag gggggaccaa gctggaaata aaacggtaaa cccgagctcg    4620
gtaccaagct taagtttaaa ccgctgatca gcctcgactg tgccttctag ttgccagcca    4680
```

```
tctgttgttt gccccctcccc cgtgccttcc ttgaccctgg aaggtgccac tcccactgtc    4740
ctttcctaat aaaatgagga aattgcatcg cattgtctga gtaggtgtca ttctattctg    4800
gggggtgggg tggggcagga cagcaagggg gaggattggg aagacaatag caggcatgct    4860
ggggatgcgg tgggctctat ggcttctgag gcggaaagaa ccaggggagg taccgagctc    4920
ttacgcgtgc tagctcgaga tctgcatctc aattagtcag caaccatagt cccgccccta    4980
actccgccca tcccgcccct aactccgccc agttccgccc attctccgcc ccatggctga    5040 ctaattttt ttatttatgc agaggccgag gccgcctcgg cctctgagct attccagaag    5100
tagtgaggag gcttttttgg aggcctaggc ttttgcaaaa agcttatcga ttctagaagc    5160
cgccaccatg gttcgaccat tgaactgcat cgtcgccgtg tcccaaaata tggggattgg    5220
caagaacgga gacctaccct ggcctccgct caggaacgag ttcaagtact ccaaagaat    5280 gaccacaacc tcttcagtgg aaggtaaaca gaatctggtg attatgggta ggaaaacctg    5340
gttctccatt cctgagaaga tcgacctttt aaaggacaga attaatatag ttctcagtag    5400
agaactcaaa gaaccaccac gaggagctca ttttcttgcc aaaagtttgg atgatgcctt    5460
aagacttatt gaacaaccgg aattggcaag taaagtagac atggtttgga tagtcggagg    5520
cagttctgtt taccaggaag ccatgaatca accaggccac ctcagactct tgtgacaag    5580 gatcatgcag gaatttgaaa gtgacacgtt tttcccagaa attgatttgg ggaaatataa    5640
acttctccca gaatacccag gcgtcctctc tgaggtccag gaggaaaaag gcatcaagta    5700
taagtttgaa gtctacgaga agaaagacta acaggaagat gctttcaagt tctctgctcc    5760
cctcctaaag ctatgcattt ttataagacc atgggacttt tgctggcttt agatccttcg    5820
cgggacgtcc tttgtttacg tcccgtcggc gctgaatccc gcggacgacc cctcgcgggg    5880
ccgcttggga ctctctcgtc cccttctccg tctgccgttc cagccgacca cggggcgcac    5940
ctctctttac gcggtctccc cgtctgtgcc ttctcatctg ccggtccgtg tgcacttcgc    6000
ttcacctctg cacgttgcat ggagaccacc gtgaacgccc atcagatcct gcccaaggtc    6060
ttacataaga ggactcttgg actcccagca atgtcaacga ccgaccttga ggcctacttc    6120
aaagactgtg tgtttaagga ctgggaggag ctggggagg agattaggtt aaaggtctt    6180 gtattaggag gctgtaggca taaattggtc tgcgcaccag caccatgcaa ctttttcacc    6240
tctgcctaat catctcttgt acatgtccca ctgttcaagc ctccaagctg tgccttgggt    6300 ggcttgggg catggacatt gacccttata aagaatttgg agctactgtg gagttactct    6360 cgttttgcc ttctgacttc tttccttccg tcagagatcc tctacgccgg acgcatcgtg    6420
gccggcatca ccggcgccac aggtgcggtt gctggcgcct atatcgccga catcaccgat    6480
ggggaagatc gggctcgcca cttcgggctc atgagcgctt gtttcggcgt gggtatggtg    6540
gcaggccccg tggccggggg actgttgggc gccatctcct tgcatgcacc attccttgcg    6600
gcggcggtgc tcaacggcct caacctacta ctgggctgct tcctaatgca ggagtcgcat    6660
aagggagagc g                                                         6671
```

<210> SEQ ID NO 28
<211> LENGTH: 708
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

-continued

```
Met Asp Trp Thr Trp Arg Val Phe Cys Leu Leu Ala Val Ala Pro Gly
 1               5                  10                  15

Ala His Ser Gln Val Gln Leu Gln Gln Ser Gly Pro Glu Leu Val Lys
             20                  25                  30

Pro Gly Ala Leu Val Lys Ile Ser Cys Lys Ala Ser Gly Tyr Thr Phe
         35                  40                  45

Thr Asn Tyr Asp Ile His Trp Val Lys Gln Arg Pro Gly Gln Gly Leu
     50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
             85                  90                  95

Thr Ala Tyr Met His Leu Ser Ser Leu Thr Ser Glu Lys Ser Ala Val
             100                 105                 110

Tyr Phe Cys Ala Arg Glu Trp Ala Tyr Trp Gly Gln Gly Thr Leu Val
         115                 120                 125

Thr Val Ser Ala Ala Ser Thr Lys Gly Pro Ser Val Phe Pro Leu Ala
     130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
             165                 170                 175

Ala Leu Thr Ser Gly Val His Thr Phe Pro Ala Val Leu Gln Ser Ser
             180                 185                 190

Gly Leu Tyr Ser Leu Ser Ser Val Val Thr Val Pro Ser Ser Ser Leu
         195                 200                 205

Gly Thr Gln Thr Tyr Ile Cys Asn Val Asn His Lys Pro Ser Asn Thr
     210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
             245                 250                 255

Leu Phe Pro Pro Lys Pro Lys Asp Thr Leu Met Ile Ser Arg Thr Pro
             260                 265                 270

Glu Val Thr Cys Val Val Val Asp Val Ser His Glu Asp Pro Glu Val
         275                 280                 285

Lys Phe Asn Trp Tyr Val Asp Gly Val Glu Val His Asn Ala Lys Thr
     290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
             325                 330                 335

Lys Val Ser Asn Lys Ala Leu Pro Ala Pro Ile Glu Lys Thr Ile Ser
             340                 345                 350

Lys Ala Lys Gly Gln Pro Arg Glu Pro Gln Val Tyr Thr Leu Pro Pro
         355                 360                 365

Ser Arg Asp Glu Leu Thr Lys Asn Gln Val Ser Leu Thr Cys Leu Val
     370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
             405                 410                 415

Gly Ser Phe Phe Leu Tyr Ser Lys Leu Thr Val Asp Lys Ser Arg Trp
             420                 425                 430
```

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys Ser Ser
        450                 455                 460

Gln Val Gln Leu Gln Gln Ser Gly Ala Glu Leu Val Lys Pro Gly Ala
465                 470                 475                 480

Thr Val Lys Leu Ser Cys Lys Ala Ser Gly Tyr Ser Phe Asn Ser His
                485                 490                 495

Tyr Ile Tyr Trp Val Lys Gln Arg Pro Gly Gln Gly Leu Glu Trp Ile
            500                 505                 510

Gly Glu Ile Asn Pro Ser Asn Gly Ala Met Asn Phe Asn Glu Lys Phe
        515                 520                 525

Lys Asn Lys Ala Thr Leu Thr Val Asp Lys Ser Ser Thr Ala Tyr
    530                 535                 540

Met Gln Leu Ser Ser Leu Thr Ser Glu Asp Ser Ala Val Tyr Tyr Cys
545                 550                 555                 560

Val Arg Asp Pro Thr Ser Tyr Trp Gly Gln Gly Thr Leu Val Thr Val
                565                 570                 575

Ser Ala Ala Lys Thr Thr Pro Lys Leu Glu Glu Gly Glu Phe Ser Glu
            580                 585                 590

Ala Arg Val Asp Val Val Met Thr Gln Thr Pro Leu Ser Leu Pro Val
        595                 600                 605

Ser Leu Gly Asp Gln Ala Ser Ile Ser Cys Arg Ser Ser Gln Ser Leu
610                 615                 620

Val His Ser Tyr Gly Asn Thr Tyr Leu His Trp Tyr Leu Gln Lys Pro
625                 630                 635                 640

Gly Gln Ser Pro Lys Leu Leu Ile Tyr Lys Val Ser Asn Arg Phe Ser
                645                 650                 655

Gly Val Pro Asp Arg Phe Ser Gly Ser Gly Ser Gly Thr Asp Phe Thr
            660                 665                 670

Leu Lys Ile Ser Arg Val Glu Ala Glu Asp Leu Gly Val Tyr Phe Cys
        675                 680                 685

Ser Gln Ser Thr His Val Pro Tyr Thr Phe Gly Gly Gly Thr Lys Leu
    690                 695                 700

Glu Ile Lys Arg
705

<210> SEQ ID NO 29
<211> LENGTH: 234
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 29

Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

```
Arg Phe Ser Gly Ser Arg Ser Gly Ser Asp Tyr Ser Leu Thr Ile Ser
                85                  90                  95
Ser Leu Glu Ser Glu Asp Phe Val Asp Tyr Tyr Cys Leu Gln Tyr Ser
            100                 105                 110
Ser Ser Pro Trp Thr Phe Gly Gly Gly Thr Lys Met Glu Ile Lys Arg
        115                 120                 125
Thr Val Ala Ala Pro Ser Val Phe Ile Phe Pro Pro Ser Asp Glu Gln
130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
210                 215                 220
Val Thr Lys Ser Phe Asn Arg Gly Glu Cys
225                 230

<210> SEQ ID NO 30
<211> LENGTH: 187
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Met Val Arg Pro Leu Asn Cys Ile Val Ala Val Ser Gln Asn Met Gly
1               5                   10                  15
Ile Gly Lys Asn Gly Asp Leu Pro Trp Pro Pro Leu Arg Asn Glu Phe
            20                  25                  30
Lys Tyr Phe Gln Arg Met Thr Thr Thr Ser Ser Val Glu Gly Lys Gln
        35                  40                  45
Asn Leu Val Ile Met Gly Arg Lys Thr Trp Phe Ser Ile Pro Glu Lys
50                  55                  60
Asn Arg Pro Leu Lys Asp Arg Ile Asn Ile Val Leu Ser Arg Glu Leu
65                  70                  75                  80
Lys Glu Pro Pro Arg Gly Ala His Phe Leu Ala Lys Ser Leu Asp Asp
                85                  90                  95
Ala Leu Arg Leu Ile Glu Gln Pro Glu Leu Ala Ser Lys Val Asp Met
            100                 105                 110
Val Trp Ile Val Gly Gly Ser Ser Val Tyr Gln Glu Ala Met Asn Gln
        115                 120                 125
Pro Gly His Leu Arg Leu Phe Val Thr Arg Ile Met Gln Glu Phe Glu
130                 135                 140
Ser Asp Thr Phe Phe Pro Glu Ile Asp Leu Gly Lys Tyr Lys Leu Leu
145                 150                 155                 160
Pro Glu Tyr Pro Gly Val Leu Ser Glu Val Gln Glu Glu Lys Gly Ile
                165                 170                 175
Lys Tyr Lys Phe Glu Val Tyr Glu Lys Lys Asp
            180                 185

<210> SEQ ID NO 31
```

<211> LENGTH: 154
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31

```
cgagcggccg ccactgtgct ggatattcca ccatggactg gacctggagg gtgttctgcc    60
tgcttgcagt ggccccggga gcccacagcc aggttcagct gcagcagtct ggacctgagc   120
tggtgaagcc tggggcttta gtgaagatat cctg                               154
```

<210> SEQ ID NO 32
<211> LENGTH: 154
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32

```
caggatatct tcactaaagc cccaggcttc accagctcag gtccagactg ctgcagctga    60
acctggctgt gggctccggg ggccactgca agcaggcaga acaccctcca ggtccagtcc   120
atggtggaat atccagcaca gtggcggccg ctcg                               154
```

<210> SEQ ID NO 33
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33

```
caggtacagc tgcagcagtc tggatctgag ctgatgaagc ctggggcctc agtacagata    60
tcctgcaagg ctact                                                    75
```

<210> SEQ ID NO 34
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34

```
ctcaaggcca tgtccaggtc tctgctttac ccactcaatc cagtagtcac tgaatgtgta    60
gccagtagcc ttgcaggata tctgtac                                       87
```

<210> SEQ ID NO 35
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35

```
cagagacctg gacatggcct tgagtggatt ggagatattt tatgtggaac tggtagaact    60
agatacaatg agaagttaaa agcaatg                                       87
```

<210> SEQ ID NO 36
<211> LENGTH: 88

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cagatgtcag gctgcttagt tgcatgaagg ctgtgttgga ggatgtatct gcagtgaatg    60
tggccattgc ttttaacttc tcattgta                                      88

<210> SEQ ID NO 37
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgcaactaag cagcctgaca tctgaggact cagcagtcta ttactgtgca agatcggcat    60
catatggtga ttacgctgac tactggg                                       87

<210> SEQ ID NO 38
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttcaagcttg ggtgtcgttt tggctgagga gactgtgaga gtggtgccat ggccccagta    60
gtcagcgtaa tcaccat                                                  77

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
caggtacagc tgcagcagtc tgga                                          24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttcaagcttg ggtgtcgttt tggc                                          24

<210> SEQ ID NO 41
<211> LENGTH: 381
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 41
caggtacagc tgcagcagtc tggatctgag ctgatgaagc ctggggcctc agtacagata    60
```

```
tcctgcaagg ctactggcta cacattcagt gactactgga ttgagtgggt aaagcagaga      120
cctggacatg gccttgagtg gattggagat attttatgtg gaactggtag aactagatac      180
aatgagaagt taaaagcaat ggccacattc actgcagata catcctccaa cacagccttc      240
atgcaactaa gcagcctgac atctgaggac tcagcagtct attactgtgc aagatcggca      300
tcatatggtg attacgctga ctactggggc catggcacca ctctcacagt ctcctcagcc      360
aaaacgacac ccaagcttga a                                                 381
```

<210> SEQ ID NO 42
<211> LENGTH: 127
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 42

```
Gln Val Gln Leu Gln Gln Ser Gly Ser Glu Leu Met Lys Pro Gly Ala
 1               5                  10                  15

Ser Val Gln Ile Ser Cys Lys Ala Thr Gly Tyr Thr Phe Ser Asp Tyr
            20                  25                  30

Trp Ile Glu Trp Val Lys Gln Arg Pro Gly His Gly Leu Glu Trp Ile
        35                  40                  45

Gly Asp Ile Leu Cys Gly Thr Gly Arg Thr Arg Tyr Asn Glu Lys Leu
    50                  55                  60

Lys Ala Met Ala Thr Phe Thr Ala Asp Thr Ser Ser Asn Thr Ala Phe
65                  70                  75                  80

Met Gln Leu Ser Ser Leu Thr Ser Glu Asp Ser Ala Val Tyr Tyr Cys
                85                  90                  95

Ala Arg Ser Ala Ser Tyr Gly Asp Tyr Ala Asp Tyr Trp Gly His Gly
            100                 105                 110

Thr Thr Leu Thr Val Ser Ser Ala Lys Thr Thr Pro Lys Leu Glu
        115                 120                 125
```

<210> SEQ ID NO 43
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
tacaagcttg aagaaggtga attttcagaa gcacgcgtag atatcgacat agtgatgacc      60
cagtctcaca aattca                                                       76
```

<210> SEQ ID NO 44
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
gcagtactca catcctgact ggccttgcat gttatgctga ctctgtctcc tactgatgtg      60
gacatgaatt tgtgagactg ggtcatca                                          88
```

<210> SEQ ID NO 45

```
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggccagtcag gatgtgagta ctgctgtagc atggtatcaa caaaaacctg ggcaatctcc    60
taaactactc atttcctggg catccaca                                       88

<210> SEQ ID NO 46
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tggtgagagt ataatctgtc ccagatccac tgccagtgaa gcgatcgggt actcctgtgt    60
gccgtgtgga tgcccaggaa atgagtag                                       88

<210> SEQ ID NO 47
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ctgggacaga ttatactctc accatcagta gtgtgcaggc tgaagaccta gcactttatt    60
actgtcagca acattatacc actcccct                                       88

<210> SEQ ID NO 48
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatgcggccg cagcgtcagc tttcagctcc agtttggttc cagcaccgaa cgtgagggga    60
gtggtataat gttgctga                                                  78

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tacaagcttg aagaaggtga attttc                                         26

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 50
gatgcggccg cagcgtcagc tttc                                          24

<210> SEQ ID NO 51
<211> LENGTH: 386
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 51
tacaagcttg aagaaggtga attttcagaa gcacgcgtag atatcgacat agtgatgacc    60
cagtctcaca aattcatgtc cacatcagta ggagacagag tcagcataac atgcaaggcc   120
agtcaggatg tgagtactgc tgtagcatgg tatcaacaaa aacctgggca atctcctaaa   180
ctactcattt cctgggcatc cacacggcac acaggagtac ccgatcgctt cactggcagt   240
ggatctggga cagattatac tctcaccatc agtagtgtgc aggctgaaga cctagcactt   300
tattactgtc agcaacatta taccactccc ctcacgttcg gtgctggaac caaactggag   360
ctgaaagctg acgctgcggc cgcatc                                       386

<210> SEQ ID NO 52
<211> LENGTH: 128
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 52

Tyr Lys Leu Glu Glu Gly Glu Phe Ser Glu Ala Arg Val Asp Ile Asp
 1               5                  10                  15

Ile Val Met Thr Gln Ser His Lys Phe Met Ser Thr Ser Val Gly Asp
             20                  25                  30

Arg Val Ser Ile Thr Cys Lys Ala Ser Gln Asp Val Ser Thr Ala Val
         35                  40                  45

Ala Trp Tyr Gln Gln Lys Pro Gly Gln Ser Pro Lys Leu Leu Ile Ser
     50                  55                  60

Trp Ala Ser Thr Arg His Thr Gly Val Pro Asp Arg Phe Thr Gly Ser
 65                  70                  75                  80

Gly Ser Gly Thr Asp Tyr Thr Leu Thr Ile Ser Ser Val Gln Ala Glu
                 85                  90                  95

Asp Leu Ala Leu Tyr Tyr Cys Gln Gln His Tyr Thr Thr Pro Leu Thr
            100                 105                 110

Phe Gly Ala Gly Thr Lys Leu Glu Leu Lys Ala Asp Ala Ala Ala Ala
        115                 120                 125

<210> SEQ ID NO 53
<211> LENGTH: 903
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 53
atcctcgagg ccgccaccat ggactggacc tggagggtgt tctgcctgct tgcagtggcc    60
cccggagccc acagccaggt ccaggttcag ctgcagcagt ctggatctga gctgataaag   120
cctggggcct cagtgcagat atcctgcaag gctactggct acacattcag tgactactgg   180

```
attgagtggg taaagcagag gcctggacat ggccttgagt ggattggaga tattttatgt    240
ggaactggta gaactagata caatgagaag ttaaaggcca tggccacatt cactgcagat    300
acatcctcca acacagcctt catgcaactc agcagcctga catctgagga ctctgccgtc    360
tattactgtg caagatcggc gtcatatggt gattacgctg actactgggg ccatggcacc    420
actctcacag tctcctcagc caaaacgaca cccaagcttg aagaaggtga attttcagaa    480
gcacgcgtag atatcgacat tgtgatgacc cagtctcaca aattcatgtc cacatcagta    540
ggagacaggg tcagcatcac ctgcaaggcc agtcaggatg tgagtactgc tgtagcctgg    600
tatcaacaaa aaccagggca atctcctaaa ctactcattt cctgggcatc cacccggcac    660
actggagtcc ctgatcgctt cacaggcagt ggatctggga cagattatac tctcaccatc    720
agcagtgtgc aggctgaaga cctggcactt tattactgtc agcaacatta taccactccc    780
ctcacgttcg gtgctgggac caagctggag ctgaaagctg atgctgcggc cgctggatcc    840
gaacaaaagc tgatctcaga agaagatcta tcccatcatc accatcatca ttaagaattc    900
atc                                                                  903
```

```
<210> SEQ ID NO 54
<211> LENGTH: 291
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 54
```

Met Asp Trp Thr Trp Arg Val Phe Cys Leu Leu Ala Val Ala Pro Gly
 1               5                  10                  15

Ala His Ser Gln Val Gln Val Gln Leu Gln Gln Ser Gly Ser Glu Leu
            20                  25                  30

Met Lys Pro Gly Ala Ser Val Gln Ile Ser Cys Lys Ala Thr Gly Tyr
        35                  40                  45

Thr Phe Ser Asp Tyr Trp Ile Glu Trp Val Lys Gln Arg Pro Gly His
    50                  55                  60

Gly Leu Glu Trp Ile Gly Asp Ile Leu Cys Gly Thr Gly Arg Thr Arg
65                  70                  75                  80

Tyr Asn Glu Lys Leu Lys Ala Met Ala Thr Phe Thr Ala Asp Thr Ser
                85                  90                  95

Ser Asn Thr Ala Phe Met Gln Leu Ser Ser Leu Thr Ser Glu Asp Ser
            100                 105                 110

Ala Val Tyr Tyr Cys Ala Arg Ser Ala Ser Tyr Gly Asp Tyr Ala Asp
        115                 120                 125

Tyr Trp Gly His Gly Thr Thr Leu Thr Val Ser Ser Ala Lys Thr Thr
    130                 135                 140

Pro Lys Leu Glu Glu Gly Glu Phe Ser Glu Ala Arg Val Asp Ile Asp
145                 150                 155                 160

Ile Val Met Thr Gln Ser His Lys Phe Met Ser Thr Ser Val Gly Asp
                165                 170                 175

Arg Val Ser Ile Thr Cys Lys Ala Ser Gln Asp Val Ser Thr Ala Val
            180                 185                 190

Ala Trp Tyr Gln Gln Lys Pro Gly Gln Ser Pro Lys Leu Leu Ile Ser
        195                 200                 205

Trp Ala Ser Thr Arg His Thr Gly Val Pro Asp Arg Phe Thr Gly Ser
    210                 215                 220

```
Gly Ser Gly Thr Asp Tyr Thr Leu Thr Ile Ser Ser Val Gln Ala Glu
225                 230                 235                 240

Asp Leu Ala Leu Tyr Tyr Cys Gln Gln His Tyr Thr Thr Pro Leu Thr
                245                 250                 255

Phe Gly Ala Gly Thr Lys Leu Glu Leu Lys Ala Asp Ala Ala Ala Ala
            260                 265                 270

Gly Ser Glu Gln Lys Leu Ile Ser Glu Glu Asp Leu Ser His His His
        275                 280                 285

His His His
    290

<210> SEQ ID NO 55
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cagctgaagg gaacaacata tggagtctgc tcaaaagctt tcaaattcgc taggactccc    60
gctgacac                                                            68

<210> SEQ ID NO 56
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tgcagggacc gtctgttcca gtatattgca gttccaacac cacagttcca tgtccagtgt    60
cagcgggagt cctagcgaat                                                80

<210> SEQ ID NO 57
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atactggaac agacggtccc tgcaaagtgc ccatttcttc cgtagcttcc ctgaatgacc    60
tcacacctgt tggaagactg                                                80

<210> SEQ ID NO 58
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcaatcaaaa ccttcgagtt ggctgtggct acagacacaa atggattcac ggtcaccagt    60
cttccaacag gtgtgaggtc                                                80

<210> SEQ ID NO 59
<211> LENGTH: 80
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 59
agccaactcg aaggttttga ttgaactcga acccccgttt ggtgactctt acatcgtggt    60
gggaagagga gaacagcaga                                                80

<210> SEQ ID NO 60
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gtagcggccg cagcatcagc tccagatttg tgccagtgat ggtttatctg ctgttctcct    60
cttcccacca                                                           70

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cagctgaagg gaacaacata tggag                                          25

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gtagcggccg cagcatcagc tccag                                          25

<210> SEQ ID NO 63
<211> LENGTH: 338
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 63
cagctgaagg gaacaacata tggagtctgc tcaaaagctt tcaaattcgc taggactccc    60
gctgacactg gacatggaac tgtggtgttg gaactgcaat atactggaac agacggtccc   120
tgcaaagtgc ccatttcttc cgtagcttcc ctgaatgacc tcacacctgt tggaagactg   180
gtgaccgtga atccatttgt gtctgtagcc acagccaact cgaaggtttt gattgaactc   240 gaaccccgt ttggtgactc ttacatcgtg gtgggaagag gagaacagca gataaaccat   300
cactggcaca aatctggagc tgatgctgcg gccgctac                           338

<210> SEQ ID NO 64
<211> LENGTH: 112
<212> TYPE: PRT
<213> ORGANISM: Artificial Sequence
<220> FEATURE:
```

<223> OTHER INFORMATION: Description of Artificial Sequence: Synthetic
      construct

<400> SEQUENCE: 64

```
Gln Leu Lys Gly Thr Thr Tyr Gly Val Cys Ser Lys Ala Phe Lys Phe
 1               5                  10                  15

Ala Arg Thr Pro Ala Asp Thr Gly His Gly Thr Val Val Leu Glu Leu
            20                  25                  30

Gln Tyr Thr Gly Thr Asp Gly Pro Cys Lys Val Pro Ile Ser Ser Val
        35                  40                  45

Ala Ser Leu Asn Asp Leu Thr Pro Val Gly Arg Leu Val Thr Val Asn
    50                  55                  60

Pro Phe Val Ser Val Ala Thr Ala Asn Ser Lys Val Leu Ile Glu Leu
65                  70                  75                  80

Glu Pro Pro Phe Gly Asp Ser Tyr Ile Val Val Gly Arg Gly Glu Gln
                85                  90                  95

Gln Ile Asn His His Trp His Lys Ser Gly Ala Asp Ala Ala Ala Ala
            100                 105                 110
```

<210> SEQ ID NO 65
<211> LENGTH: 707
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 65

```
Met Asp Trp Thr Trp Arg Val Phe Cys Leu Leu Ala Val Ala Pro Gly
 1               5                  10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
```

```
                225                 230                 235                 240
Cys Pro Pro Cys Pro Ala Pro Glu Leu Leu Gly Gly Pro Ser Val Phe
            245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
            275                 280                 285
Lys Phe Asn Trp Tyr Val Asp Gly Val Glu Val His Asn Ala Lys Thr
            290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
            325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
            355                 360                 365
Ser Arg Asp Glu Leu Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
            405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys Ser Ser
    450                 455                 460
Gln Val Gln Leu Gln Gln Ser Gly Ser Glu Leu Met Lys Pro Gly Ala
465                 470                 475                 480
Ser Val Gln Ile Ser Cys Lys Ala Thr Gly Tyr Thr Phe Ser Asp Tyr
            485                 490                 495
Trp Ile Glu Trp Val Lys Gln Arg Pro Gly His Gly Leu Glu Trp Ile
            500                 505                 510
Gly Asp Ile Leu Cys Gly Thr Gly Arg Thr Arg Tyr Asn Glu Lys Leu
            515                 520                 525
Lys Ala Met Ala Thr Phe Thr Ala Asp Thr Ser Ser Asn Thr Ala Phe
            530                 535                 540
Met Gln Leu Ser Ser Leu Thr Ser Glu Asp Ser Ala Val Tyr Tyr Cys
545                 550                 555                 560
Ala Arg Ser Ala Ser Tyr Gly Asp Tyr Ala Asp Tyr Trp Gly His Gly
            565                 570                 575
Thr Thr Leu Thr Val Ser Ser Ala Lys Thr Thr Pro Lys Leu Glu Glu
            580                 585                 590
Gly Glu Phe Ser Glu Ala Arg Val Asp Ile Val Met Thr Gln Ser His
            595                 600                 605
Lys Phe Met Ser Thr Ser Val Gly Asp Arg Val Ser Ile Thr Cys Lys
            610                 615                 620
Ala Ser Gln Asp Val Ser Thr Ala Val Ala Trp Tyr Gln Gln Lys Pro
625                 630                 635                 640
Gly Gln Ser Pro Lys Leu Leu Ile Ser Trp Ala Ser Thr Arg His Thr
            645                 650                 655
```

-continued

```
Gly Val Pro Asp Arg Phe Thr Gly Ser Gly Ser Gly Thr Asp Tyr Thr
            660                 665                 670

Leu Thr Ile Ser Ser Val Gln Ala Glu Asp Leu Ala Leu Tyr Tyr Cys
            675                 680                 685

Gln Gln His Tyr Thr Thr Pro Leu Thr Phe Gly Ala Gly Thr Lys Leu
            690                 695                 700

Glu Leu Lys
705

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Gln Lys Leu Ile Ser Glu Glu Asp Leu
1               5                   10

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcggccgctg gatcccatca tcaccatcat cattaagaat tc                         42

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 68

His His His His His His
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 69

His His His His His
1               5
```

GENETICALLY ENCODED MULTIFUNCTIONAL COMPOSITIONS BIDIRECTIONALLY TRANSPORTED BETWEEN PERIPHERAL BLOOD AND THE CNS

RELATED APPLICATIONS

This application claims the benefit of U.S. Provisional Patent Application No. 60/822,825, entitled "Agents for Blood-Brain Barrier Delivery," filed Aug. 18, 2006, the contents of which are incorporated by reference in their entirety.

STATEMENT AS TO FEDERALLY SPONSORED RESEARCH

This invention was made with the support of the United States government under Grant number R43-NS-051857 by the National Institutes of Health. The United States Government may have certain rights in the invention.

REFERENCE TO A SEQUENCE LISTING SUBMITTED ON A DISKETTE AND INCORPORATION BY REFERENCE OF THE CONTENTS OF THE DISKETTE

A compact disc (PC/MS-DOS PATENTIN 3.3), containing the Sequence Listing for SEQ ID NO:1 through SEQ ID NO: 69 disclosed herein, and in computer readable form, as well as a paper copy of the Sequence Listing, are submitted herewith, are hereby referred to herein, and are hereby incorporated by reference herein in their entireties, including the contents thereof.

BACKGROUND OF THE INVENTION

The blood-brain barrier (BBB) is an endothelial tissue that surrounds and protects the CNS by excluding potentially toxic substances present in blood from entry into the brain while allowing selective entry of nutrients and other blood components. Unfortunately, the blood-brain barrier also prevents systemically administered protein therapeutic agents such as recombinant antibodies from entry into the CNS. Thus, the blood-brain barrier imposes a serious practical limitation on the usefulness of protein therapeutics for the treatment of CNS disorders. The present invention represents an advance in providing accessibility of the CNS for genetically encoded protein pharmaceuticals whose ability to cross the blood-brain barrier is limited.

SUMMARY OF THE INVENTION

In one aspect provided herein is a nucleic acid encoding a fusion protein comprising the amino acid sequence of: (a) an immunoglobulin CH2 region, a CH3 region, and a VH region, where the VH region is from a first immunoglobulin directed to an endogenous BBB receptor mediated transport system; or (b) an immunoglobulin light chain amino acid sequence comprising a CL region and a VL region, where the CL region is from the first immunoglobulin; and a ScFv from a second immunoglobulin, wherein the ScFv is covalently linked to the carboxyl terminus of the CH3 region or to the carboxyl terminus of the CL region.

In some embodiments, the just mentioned nucleic acid is part of a tandem expression vector that includes: a first promoter sequence operably linked to an open reading frame corresponding to the above-mentioned nucleic acid encoding a fusion protein, and a second promoter operably linked to a second open reading frame encoding an immunoglobulin CH2 region, a CH3 region, and a VH region from the first immunoglobulin or a CL region and a VL region from the first immunoglobulin. In some embodiments provided herein is a cell that contains the just-described tandem expression vector.

In some embodiments, the endogenous BBB receptor mediated transport system to which the first immunoglobulin is directed is an insulin receptor, a transferrin receptor, a leptin receptor, a lipoprotein receptor, or an IGF receptor. In some embodiments, the endogenous BBB receptor mediated transport system to which the first immunoglobulin is directed is to the insulin receptor.

In some embodiments, the ScFv is directed to a pathological substance present in the brain, and the pathological substance is associated with a brain disorder. In some embodiments, the referred-to brain disorder is Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, and multiple sclerosis. In some embodiments, the referred to pathological substance is a protein. In some embodiments, the pathological substance that is a protein is A$\beta$ amyloid, $\alpha$ synuclein, huntingtin protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is A$\beta$ amyloid.

In another aspect provided herein is a composition containing a first portion capable of crossing the BBB from the blood to the brain via a first receptor mediated BBB transport system; a second portion capable of crossing the BBB from the brain to the blood via a second receptor-mediated BBB transport system; and a third portion capable of interacting with a pathological substance associated with a brain disorder.

In some embodiments, the first and second portions of the above-described composition are part of an antibody structure. In some embodiments, the third portion of the just-mentioned compositions includes a ScFv. In some embodiments, the ScFv is a ScFv to A$\beta$ amyloid. In some embodiments, the VH region of the ScFv comprises a CDR1 amino acid sequence at least 60% identical to amino acids 26-35 of SEQ ID NO:12, a CDR2 amino acid sequence at least 60% identical to amino acids 50-66 of SEQ ID NO:12, or a CDR3 amino acid sequence at least 60% identical to amino acids 99-103 of SEQ ID NO:12. In some embodiments, the VL region of the ScFv comprises a CDR1 amino acid sequence at least 60% identical to amino acids 24-39 of SEQ ID NO:14, a CDR2 amino acid sequence at least 60% identical to amino acids 55-61 of SEQ ID NO:14, or a CDR3 amino acid sequence at least 60% identical to amino acids 94-102 of SEQ ID NO: 14.

In a further aspect provided herein is a composition capable of achieving an average volume of distribution in the brain of the therapeutic antibody structure or diagnostic antibody structure of at least about 30 to about 100 µl/gram of the subject's brain following peripheral administration.

In some embodiments, the therapeutic antibody structure or diagnostic antibody structure is linked to a structure capable of crossing the blood-brain barrier. In some embodiments, the structure capable of crossing the blood-brain barrier is capable of crossing the blood-brain barrier from blood to brain and from brain to blood. In some embodiments, the structure capable of crossing the blood-brain barrier is an antibody to a receptor mediated transport system.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4. Nucleotide sequence (SEQ ID NO: 11) of the VH of the murine anti-Aβ MAb derived by PCR from the murine hybridoma secreting the anti-Aβ MAb. The sequence was determined by DNA sequencing of the pPC-mAβ-VH plasmid (FIG. 1A).

FIG. 5. Amino acid sequence (SEQ ID NO: 12) of the VH of the murine anti-Aβ MAb derived by PCR from the murine hybridoma secreting the anti-Aβ MAb. The amino acid sequence is deduced from the nucleotide sequence (SEQ ID NO: 11). The amino acids underlined matched with the amino acid sequence of tryptic peptides obtained from the heavy chain of the anti-Aβ MAb isolated from the murine hybridoma. The amino acid sequences of CDR1, CDR2, and CDR3 of the anti-Aβ MAb heavy chain VH are in bold font.

FIG. 6. Nucleotide sequence (SEQ ID NO: 13) of the VL of the murine anti-Aβ MAb derived by PCR from the murine hybridoma secreting the anti-Aβ MAb. The sequence was determined by DNA sequencing of the pPC-mAβ-VL plasmid (FIG. 1A).

FIG. 7. Amino acid sequence (SEQ ID NO: 14) of the VH of the murine anti-Aβ MAb derived by PCR from the murine hybridoma secreting the anti-Aβ MAb. The amino acid sequence is deduced from the nucleotide sequence (SEQ ID NO: 13). The 11 amino acids at the amino terminus of the deduced sequence matched the amino acids observed with direct amino acid sequencing of the light chain of the hybridoma generated murine anti-Aβ MAb, except a valine (V) residue was observed at position 2 of the light chain of the anti-Aβ MAb derived from the mouse hybridoma. The amino acid sequences of CDR1, CDR2, and CDR3 of the anti-Aβ MAb light chain VL are in bold font.

FIG. 8. Nucleotide sequence (SEQ ID NO: 15) of the anti-Aβ ScFv cDNA encoded by the prokaryotic expression plasmid. The sequence was determined by DNA sequencing of the pPC-mAβScFv plasmid (FIG. 1A).

FIG. 9. Amino acid sequence (SEQ ID NO: 16) of the anti-Aβ ScFv cDNA encoded by the prokaryotic expression plasmid, and includes a poly-histidine (H) tail, and the 9E10 epitope (EQKLISEEDL) (SEQ ID NO:66) at the carboxyl terminus. The sequence was determined by DNA sequencing of the pPC-mAβScFv plasmid (FIG. 1A). The amino acid sequence is deduced from the nucleotide sequence (SEQ ID NO: 15). The 17-amino acid linker separating the VH and VL is underlined.

FIG. 10. Nucleotide sequence (SEQ ID NO: 17) of the anti-Aβ ScFv cDNA encoded by the eukaryotic expression plasmid. The sequence was determined by DNA sequencing of the pCD-mAβScFv plasmid (FIG. 1B).

FIG. 11. Amino acid sequence (SEQ ID NO: 18) of the anti-Aβ ScFv cDNA encoded by the eukaryotic expression plasmid. The poly-histidine (H) tail at the carboxyl terminus has been removed. The mAβScFv is now downstream of a 19-amino acid IgG signal peptide, and the signal peptide sequence is underlined. The amino acid sequence is deduced from the nucleotide sequence (SEQ ID NO: 17).

FIG. 12. Nucleotide sequence (SEQ ID NO: 19) of the fusion gene comprised of the anti-Aβ ScFv cDNA fused to the 3'-end of the cDNA encoding the chimeric HIRMAb heavy chain encoded by the eukaryotic expression plasmid. The sequence was determined by DNA sequencing of the pCD-HC-mAβScFv plasmid (FIG. 2).

FIG. 13. Amino acid sequence (SEQ ID NO: 20) of the HC-mAβScFv fusion protein, where the anti-Aβ ScFv is fused to the carboxyl terminus of the chimeric HIRMAb heavy chain (HC) via a S-S linker, and S=serine. The HC-mAβScFv fusion protein is downstream of a 19-amino acid IgG signal peptide, and the signal peptide sequence is underlined. The amino acid sequence is deduced from the nucleotide sequence (SEQ ID NO: 19).

FIG. 14. Nucleotide sequence (SEQ ID NO: 21) of the site-directed mutagenized fusion gene comprised of the anti-Aβ ScFv cDNA fused to the 3'-end of the cDNA encoding the chimeric HIRMAb heavy chain encoded by the eukaryotic expression plasmid, pCD-HC-mAβScFv plasmid (FIG. 2). The 'A' nucleotide has been mutagenized to a 'G' nucleotide at position 1789; the site is underlined in the figure. This change in nucleotide sequence results in the I2V amino acid change in the first framework region of the VL of the mAbScFv, as shown in FIG. 15.

FIG. 15. Amino acid sequence (SEQ ID NO: 22) of the site-directed mutagenized HC-mAβScFv fusion protein. PCR amplification of the VL of the mAβScFv produced a cDNA, which encoded isoleucine (I) at the 2 position of the first framework region of the VL; the mutagenized nucleotide is underlined in the figure. However, direct amino acid sequence analysis of the amino terminus of the murine anti-Aβ MAb showed a valine (V) at this position. The isoleucine residue at this site was changed to a valine by site-directed mutagenesis, and this change is called I2V. The amino acid sequence is deduced from the nucleotide sequence (SEQ ID NO: 21).

FIG. 16. Nucleotide sequence (SEQ ID NO: 23) of the site-directed mutagenized fusion gene comprised of the anti-Aβ ScFv cDNA fused to the 3'-end of the cDNA encoding the chimeric HIRMAb heavy chain encoded by the eukaryotic expression plasmid, pCD-HC-mAβScFv plasmid (FIG. 2). The 'AA' nucleotides have been mutagenized to 'GC' nucleotides at positions 1546-1547; the site is underlined in the figure. This change in nucleotide sequence results in the N497A amino acid change in the second complementarity determining region (CDR) of the VH of the mAbScFv, as shown in FIG. 17.

FIG. 17. Amino acid sequence (SEQ ID NO: 24) of the site-directed mutagenized HC-mAβScFv fusion protein. A predicted N-linked glycosylation site was found in CDR2 of the VH of the anti-Aβ MAb; the mutagenized site is underlined in the figure. The asparagine (N) residue at position 497 was changed to an alanine (A) residue, and this change is called N497A. The amino acid sequence is deduced from the nucleotide sequence (SEQ ID NO: 23).

FIG. 18. Nucleotide sequence (SEQ ID NO: 25) of the site-directed mutagenized fusion gene comprised of the anti-Aβ ScFv cDNA fused to the 3'-end of the cDNA encoding the chimeric HIRMAb heavy chain encoded by the eukaryotic expression plasmid, pCD-HC-mAβScFv plasmid (FIG. 2). The 'AG' nucleotides have been mutagenized to 'GC' nucleotides at positions 1552-1553; the site is underlined in the figure. This change in nucleotide sequence results in the S499A amino acid change in the second CDR of the VH of the mAbScFv, as shown in FIG. 19.

FIG. 19. Amino acid sequence (SEQ ID NO: 26) of the site-directed mutagenized HC-mAβScFv fusion protein. A predicted N-linked glycosylation site was found in CDR2 of the VH of the anti-Aβ MAb; the mutagenized site is underlined in the figure. The serine (S) residue at position 499 was changed to an alanine (A) residue, and this change is called S499A. The amino acid sequence is deduced from the nucleotide sequence (SEQ ID NO: 25).

FIG. 20. Nucleotide sequence (SEQ ID NO: 27) of the tandem vector encoding the intact antibody fusion protein comprised of the chimeric HIRMAb light chain (LC) and a fusion protein heavy chain (HC), where the mAβScFv was fused to the chimeric HIRMAb heavy chain. The tandem vector encodes for murine dihydrofolate reductase (DHFR). The individual expression cassettes of the tandem vector are shown in FIG. 24. From the 5'-end to the 3'-end, the LC gene, the HC fusion gene, and the DHFR gene are contained in 3 separate expression cassettes on the tandem vector; and the open reading frames of each of these 3 expression cassettes are underlined in the figure.

FIG. 21. Amino acid sequence (SEQ ID NO: 28) of the IgG signal peptide followed by the chimeric HIRMAb heavy chain followed by the Ab ScFv. The amino acid sequence is deduced from the nucleotide sequence in FIG. 20. The amino acid sequences of the CDR1, CDR2, and CDR3 of the anti-HIRMAb heavy chain VH are in bold font. The constant region glycosylation site, NST, is underlined.

FIG. 22. Amino acid sequence (SEQ ID NO: 29) of the light chain encoded by the tandem vector. The amino acid sequence is deduced from the nucleotide sequence in FIG. 20. The amino acid sequences of the CDR1, CDR2, and CDR3 of the anti-HIRMAb light chain VL are in bold font.

FIG. 23. Amino acid sequence (SEQ ID NO: 30) of the DHFR encoded by the tandem vector. The amino acid sequence is deduced from the nucleotide sequence in FIG. 20.

DETAILED DESCRIPTION OF THE INVENTION

Figure 1A:
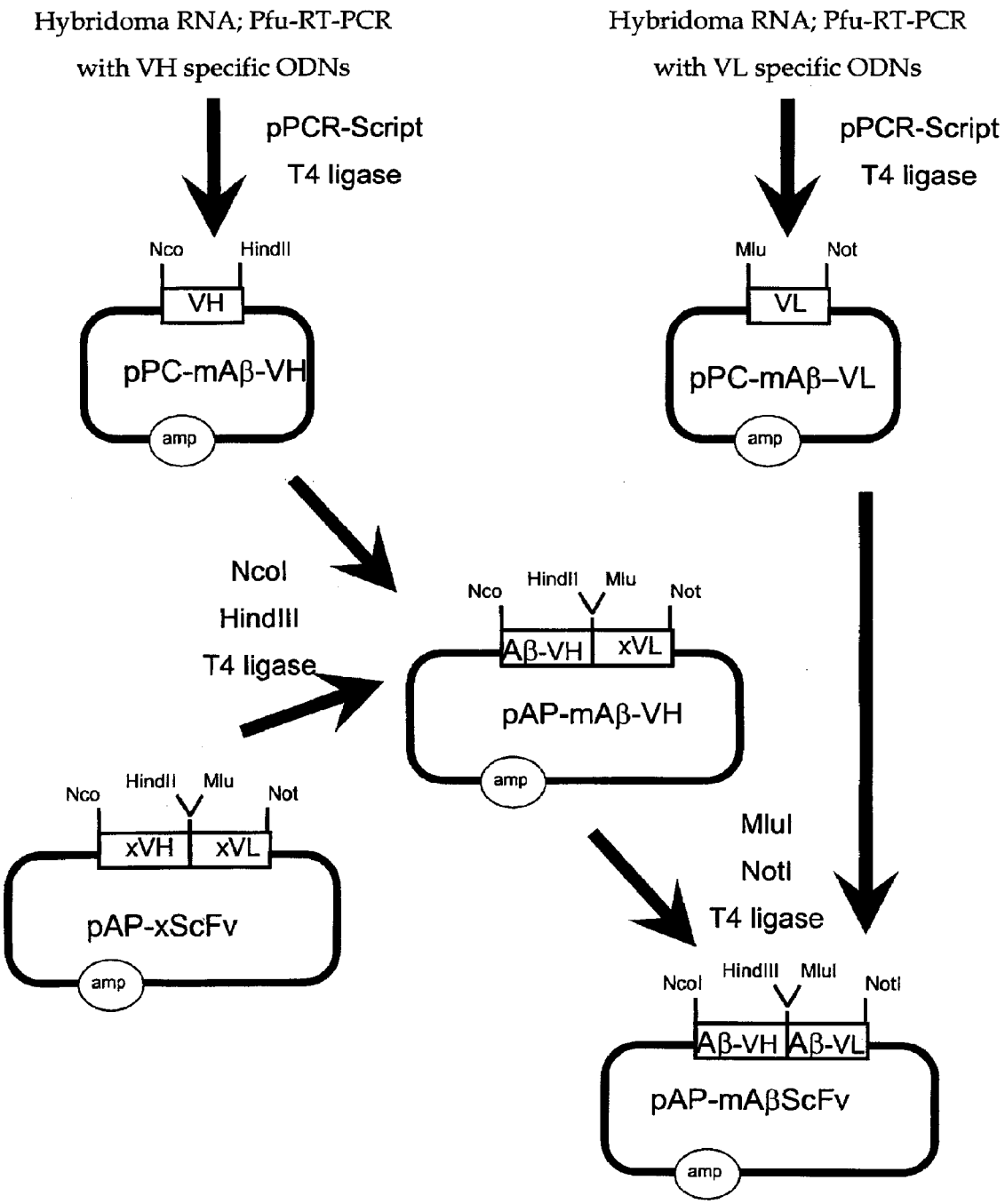
FIG. 1A. Diagram showing genetic engineering of a prokaryotic expression vector encoding a single chain Fv (ScFv) antibody against the Aβ peptide of AD. The ScFv is derived from a murine (m) antibody against Aβ, and is designated the mAβScFv. The ScFv is comprised of a variable region of the heavy chain (VH) and a variable region of the light chain (VL) originating from the murine MAb against the Aβ peptide. The VH and VL are joined by a linker to form the ScFv. The gene encoding the VH cDNA is produced by the polymerase chain reaction (PCR) from RNA isolated from the murine hybridoma secreting the anti-Aβ antibody, using oligodeoxynucleotide (ODN) primers that are specific for the mouse VH isotype; following PCR, the VH gene is ligated into the pPC plasmid with T4 ligase. The gene encoding the VL cDNA is produced by PCR from RNA isolated from the murine hybridoma secreting the anti-Aβ antibody, using ODN primers that are specific for the mouse VL isotype; following PCR, the VL gene is ligated into the pPC plasmid with T4 ligase.

The blood-brain barrier is a limiting factor in the delivery of many peripherally-administered agents to the central nervous system, including therapeutic or diagnostic monoclonal antibodies. The present invention addresses three factors that are important in delivering a composition, e.g., an antibody composition such as a pharmaceutical or diagnostic, across the BBB to the CNS: 1) Modification of the composition, e.g., antibody to allow it to flow into the brain through the BBB from peripheral blood; 2) Modification of the composition, e.g., antibody to allow it to flow out of the brain across the BBB into peripheral blood; and 3) Retention of activity of the composition, e.g., antibody once across the BBB and in brain. Various aspects of the invention address these factors, by providing nucleic acids encoding fusion structures (e.g., fusion antibody proteins) and compositions containing such fusion structures, which are capable of transport across the BBB and distribution throughout the brain.

Accordingly, in one aspect provided herein is a nucleic acid encoding a fusion protein comprising the amino acid sequence of: (a) an immunoglobulin CH2 region, a CH3 region, and a VH region, where the VH region is from a first immunoglobulin directed to an endogenous BBB receptor mediated transport system; or (b) an immunoglobulin light chain amino acid sequence comprising a CL region and a VL region, where the CL region is from the first immunoglobulin; and a ScFv from a second immunoglobulin, wherein the ScFv is covalently linked to the carboxyl terminus of the CH3 region or to the carboxyl terminus of the CL region.

In another aspect provided herein is a composition containing a first portion capable of crossing the BBB from the blood to the brain via a first receptor mediated BBB transport system; a second portion capable of crossing the BBB from the brain to the blood via a second receptor-mediated BBB transport system; and a third portion capable of interacting with a pathological substance associated with a brain disorder.

In a further aspect provided herein is a composition capable of achieving an average volume of distribution in the brain of the therapeutic antibody structure or diagnostic antibody structure of at least about 30 to about 100 µl/gram of the subject's brain following peripheral administration.

A listing of the abbreviations of terms used herein (e.g., orf, PrP, and ScFv) is provided at the end of the Detailed Description section.

As used herein, an "agent" includes any substance that is useful in producing an effect, including a physiological or biochemical effect in an organism. A "therapeutic agent" is a substance that produces or is intended to produce a therapeutic effect, i.e., an effect that leads to amelioration, prevention, and/or complete or partial cure of a disorder. A "therapeutic effect," as that term is used herein, also includes the production of a condition that is better than the average or normal condition in an individual that is not suffering from a disorder, i.e., a supranormal effect such as improved cognition, memory, mood, or other characteristic attributable at least in part to the functioning of the CNS, compared to the normal or average state. An "antibody therapeutic agent" is an antibody that produces a therapeutic effect in the CNS.

As used herein, an "antibody that is active in the central nervous system (CNS)" includes antibodies that have an effect when administered to the CNS. The effect may be a therapeutic effect or a non-therapeutic effect, e.g., a diagnostic effect or an effect useful in research. If the effect is a therapeutic effect, then the antibody is also a therapeutic antibody. If the effect is a diagnostic effect, then the antibody is also a diagnostic antibody. An antibody may be simultaneously a diagnostic and a therapeutic antibody.

As used herein, "capable of" (e.g., "capable of crossing the BBB") refers to an operational functional property of a structure (e.g., protein, antibody, compound, or composition) conferred by one or more structural features (i.e., intrinsic features) of the structure.

"Treatment" or "treating" as used herein includes achieving a therapeutic benefit and/or a prophylactic benefit. By therapeutic benefit is meant eradication or amelioration of the underlying disorder or condition being treated. For example, in an individual with a neurological disorder, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a neurological disorder), or decreasing the likelihood of occurrence of a condition. As used herein, "treating" or "treatment" includes prophylaxis.

As used herein, the term "effective amount" can be an amount sufficient to effect beneficial or desired results, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions of the CNS include dementia, neurodegenerative diseases as described herein, suboptimal memory or cognition, mood disorders, general CNS aging, or other undesirable conditions. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention will be determined by a patient's attending physician or veterinarian. Such amounts are readily ascertained by one of ordinary skill in the art and will a therapeutic effect when administered in accordance with the present invention. Factors which influence what a therapeutically effective amount will be include, the specific activity of the therapeutic agent being used, the type of disorder (e.g., acute vs. chronic neurological disorder), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human. In some embodiments, the subject suffers from a neurological disorder.

In some embodiments, an agent is "administered peripherally" or "peripherally administered" As used herein, these terms refer to any form of administration of an agent, e.g., a therapeutic antibody, to an individual that is not direct administration to the CNS, i.e., that brings the agent in contact with the non-brain side of the blood-brain barrier. "Peripheral administration," as used herein, includes intravenous, subcutaneous, intramuscular, intraperitoneal, transdermal, inhalation, transbuccal, intranasal, rectal, and oral administration.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in *Remington's Pharmaceutical Sciences*, Gennaro, A R, ed., 20th edition, 2000: Williams and Wilkins PA, USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-

1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptide nucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc. . . . ) in a sample. In another example, a polypeptide is purified if it is substantially removed from or concentrated in its natural environment. Methods for purification and isolation of nucleic acids and peptides are well known in the art.

In one aspect, the invention provides nucleic acids that encode multifunctional proteins capable of crossing the blood-brain barrier (BBB). Compositions comprising such multifunctional proteins are useful in transporting agents, e.g., antibodies, from the peripheral blood and across the blood-brain barrier into the CNS. In addition, in some aspects, compositions and methods of the invention utilize structures that are further capable of crossing the BBB from the CNS to the blood. As used herein, the "blood-brain barrier" refers to the barrier between the peripheral circulation and the brain and spinal cord which is formed by tight junctions within the brain capillary endothelial plasma membranes, creates an extremely tight barrier that restricts the transport of molecules into the brain, even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to herein as the blood-brain barrier or BBB.

The BBB is a limiting step in the development of new neurotherapeutics, diagnostics, and research tools for the brain and CNS. Essentially 100% of large molecule therapeutics such as recombinant proteins, antisense drugs, gene medicines, monoclonal antibodies, or RNA interference (RNAi)-based drugs, do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route delivers therapeutic proteins such as antibody pharmaceuticals only to the ependymal surface of the brain, not into brain parenchyma, which is typical for drugs given by the ICV route. The IC administration of a pharmaceutical only delivers drug to the local injection site, owing to the low efficiency of drug diffusion within the brain. The CED of pharmaceuticals results in preferential fluid flow through the white matter tracts of brain, which can lead to demyelination, and astrogliosis.

The present invention offers an alternative to these highly invasive and generally unsatisfactory methods for bypassing the BBB, allowing agents, e.g., antibody pharmaceuticals to cross the BBB from the peripheral blood and, in some embodiments, allowing the agent or the agent in modified form (e.g., antibody bound to antigen) to cross the BBB from the brain to the blood. Without wishing to be bound by theory, it is thought that it is based on the use of endogenous transport systems present in the BBB to provide a mechanism to transport a desired substance from the peripheral blood to the CNS.

In some embodiments, the invention provides nucleic acids that code for proteins or peptides that form a complex of molecular weight greater than about 1000 Daltons that is capable of crossing the BBB from the blood to the brain and crossing the BBB from the brain to the blood of the invention. In certain embodiments, the invention provides a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain. The first immunoglobulin can be directed to an endogenous BBB receptor mediated transport system, e.g., the insulin receptor, transferrin receptor, leptin receptor, lipoprotein receptor, or the IGF receptor. In some embodiments, the endogenous BBB receptor mediated transport system is the insulin BBB receptor mediated transport system. The ScFv can be directed to a pathological substance present in the brain, where the pathological substance is associated with a brain disorder such as Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. The pathological substance is can be protein, nucleic acid, carbohydrate, carbohydrate polymer, lipid, glycolipid, small molecule, or a combination thereof. In some embodiments, the pathological substance is a protein, e.g., Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the pathological protein is Aβ amyloid. In some embodiments, the VH region of the ScFv contains a comprises a sequence that is at least about 80, 90, 95, or 99% identical to SEQ ID NO: 12. In some embodiments, the VL region of the ScFv contains a sequence that is at least 80, 90, 95, or 99% identical to SEQ ID NO: 14.

The inventor further provides a vector containing a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain.

The invention further provides a cell containing a vector containing a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain. In some embodiments the cell is a eukaryotic cell. In some embodiments, the cell is a Chinese hamster ovary cell.

In some embodiments, the invention provides nucleic acid sequences that are at least about 60, 70, 80, 90, 95, 99, or 100% identical to a particular nucleotide sequence. For example, in some embodiments the invention provides a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain, where the VH region of the ScFv contains at least one, two, or three of: (i) a CDR1 sequence that is at least about 60, 70, 80, 90, 95, 99, or 100% identical to the sequence of amino acids 26-35 of SEQ ID NO: 12; (ii) a CDR2 sequence that is at least about 60, 70, 80, 90, 95, 99, or 100% identical to the sequence of amino acids 50-66 of SEQ ID NO: 12; and (iii) a CDR3 sequence that is at least about 60, 70, 80, 90, 95, 99, or 100% identical to the sequence of amino acids 99-103 of SEQ ID NO: 12.

In some embodiments the invention provides a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain, where the VL region of the ScFv contains at least one, two, or three of:

(i) a CDR1 sequence that is at least about 60, 70, 80, 90, 95, 99, or 100% identical to the sequence of amino acids 24-39 of SEQ ID NO: 14; (ii) a CDR2 sequence that is at least about 60, 70, 80, 90, 95, 99, or 100% identical to the sequence of amino acids 55-61 of SEQ ID NO: 14; and (iii) a CDR3 sequence that is at least about 60, 70, 80, 90, 95, 99, or 100% identical to the sequence of amino acids 94-102 of SEQ ID NO: 14.

In some embodiments, the invention provides a nucleic acid containing a first sequence that is at least about 60, 70, 80, 90, 95, 99, or 100% identical to nucleotides 58-2127 of SEQ ID NO: 19 and a second sequence that is at least about 60, 70, 80, 90, 95, 99, or 100% identical to nucleotides 801-1442 of SEQ ID NO: 27.

For sequence comparison, of two nucleic acids, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. The BLAST algorithm is typically performed with the "low complexity" filter turned off. The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The invention provides nucleic acids that code for any of the peptides of the invention. In some embodiments, the invention provides a single nucleic acid sequence containing a gene coding for a light chain of a targeting immunoglobulin and a gene coding for a fusion protein, where the fusion protein includes a heavy chain of the targeting immunoglobulin covalently linked to an antibody pharmaceutical. In some embodiments, the peptide is a therapeutic peptide. In some embodiments the antibody pharmaceutical is directed against aggregated protein such as Aβ. In some embodiments, the anti-Aβ antibody pharmaceutical is a ScFv. In some embodiments, the targeting immunoglobulin is an IgG. In some embodiments, the targeting IgG is a MAb, such as a chimeric MAb. The targeting antibody can be an antibody to a transport system, e.g., an endogenous BBB receptor-mediated transport system such as the endogenous BBB receptor-mediated insulin transport system. In some embodiments, the endogenous BBB receptor-mediated insulin transport system is a human endogenous BBB receptor-mediated insulin transport system and wherein the pharmaceutical to which the immunoglobulin heavy chain is covalently linked is an anti-Aβ ScFv. Any suitable peptide, neurotherapeutic peptide, ScFv, antibody, monoclonal antibody, or chimeric antibody, as described herein, may be coded for by the nucleic acid, combined as a fusion protein and coded for in a single nucleic acid sequence. As is well-known in the art, owing to the degeneracy of the genetic code, any combination of suitable codons may be used to code for the desired fusion protein. In addition, other elements useful in recombinant technology, such as promoters, termination signals, and the like, may also be included in the nucleic acid sequence. Such elements are well-known in the art. In addition, all nucleic acid sequences described and claimed herein include the complement of the sequence.

In some embodiments that code for an anti-Aβ ScFv, as a component of the fusion protein, the ScFv contains a sequence that is about 60, 70, 80, 90, 95, 99, or 100% identical to the sequence of amino acids 20-263 of SEQ ID NO: 18. In some embodiment, the ScFv contains a sequence of the VH part that is about 60, 70, 80, 90, 95, 99, or 100% identical to the sequence of amino acids 1-114 of SEQ ID NO: 12. In some embodiment, the ScFv contains a sequence of the VL part that is about 60, 70, 80, 90, 95, 99, or 100% identical to the sequence of amino acids 1-113 of SEQ ID NO: 14. In some embodiment, the ScFv contains a sequence of the linker peptide joining the VH and the VL part that is about 60, 70, 80, 90, 95, 99, or 100% identical to the sequence of amino acids 115-131 of SEQ ID NO: 16. In some embodiments, the ScFv is linked at its amino terminus to carboxy terminus of the heavy chain of the targeting immunoglobulin, e.g., MAb. The heavy chain of the targeting MAb can comprise a sequence that is about 60, 70, 80, 90, 95, 99 or 100% identical to amino acids 20-462 of SEQ ID NO: 28. In some embodiments, the light chain of the targeting immunoglobulin, e.g., MAb, comprises a sequence that is about 60, 70, 80, 90, 95, 99 or 100% identical to amino acids 21-234 of SEQ ID NO: 29. The nucleic acid can further contain a nucleic acid sequence that codes for a peptide linker between the heavy chain of the MAb and the therapeutic antibody. In some embodiments, the linker is S-S. The nucleic acid may further contain a nucleic acid sequence coding for a signal peptide, wherein the signal peptide is linked to the heavy chain. Any suitable signal peptide, as known in the art or subsequently developed, may be used. In some embodiments, the signal peptide attached to the heavy chain comprises a sequence that is about 60, 70, 80, 90, 95, 99, or 100% identical to amino acids 1-19 of SEQ ID NO: 28. In some embodiments, the nucleic acid contains a nucleic acid sequence coding for another signal peptide, wherein the other signal peptide is linked to the light chain. The signal peptide linked to the light chain can comprise a sequence that is about 60, 70, 80, 90, 95, 99, or 100% identical to amino acids 1-20 of SEQ ID NO: 29. The nucleic acid can contain a nucleic acid sequence coding for a selectable marker. In some embodiments the selectable marker is DHFR. The sequence of the DHFR can be about 60, 70, 80, 90, 95, 99, or 100% identical to amino acids 1-187 of SEQ ID NO: 30.

In certain embodiments, the invention provides a nucleic acid comprising a first sequence that codes for an antibody pharmaceutical, e.g., a ScFv against Aβ, in the same open reading frame as a second sequence that codes for a targeting immunoglobulin component. The targeting immunoglobulin component can be, e.g., a light chain or a heavy chain, e.g., that is at least about 60, 70, 80, 90, 95, 99, or 100% identical to nucleotides 801-1442 of SEQ ID NO: 27 and a second sequence that is at least about 60, 70, 80, 90, 95, 99, or 100% identical to nucleotides 2540-3868 of SEQ ID NO: 27. In some embodiments, the nucleic acid also contains a third sequence that is at least about 60, 70, 80, 90, 95, 99, or 100% identical to nucleotides 3874-4606 of SEQ ID NO: 27. In some embodiments, the nucleic acid further contains a fourth sequence that codes for a first signal peptide and a fifth sequence that codes for a second signal peptide. In some embodiments, the fourth sequence is at least about 60, 70, 80, 90, 95, 99, or 100% identical to nucleotides 741-800 of SEQ ID NO: 27 and the fifth sequence is at least about 60, 70, 80, 90, 95, 99, or 100% identical to nucleotides 2438-2539 of SEQ ID NO: 27. In some embodiments, the nucleic acid further contains a sequence that codes for a selectable marker, such as dihydrofolate reductase (DHFR). In some embodiments, the sequence that codes for the DHFR is at least about 60, 70, 80, 90, 95, 99, or 100% identical to nucleotides 5618-5728 of SEQ ID NO: 27.

The invention also provides vectors. The vector can contain any of the nucleic acid sequences described herein. In some embodiments, the invention provides a single tandem expression vector containing nucleic acid coding for an antibody heavy chain fused to an antibody pharmaceutical, e.g., a ScFv, and nucleic acid coding for a light chain of the antibody, all incorporated into a single piece of nucleic acid, e.g., a single piece of DNA. The single tandem vector can also include one or more selection and/or amplification genes. A method of making an exemplary vector of the invention is provided in the Examples, and in FIG. 24. However, any suitable techniques, as known in the art, may be used to construct the vector.

The use of a single tandem vector has several advantages over previous techniques. The transfection of a eukaryotic cell line with immunoglobulin G (IgG) genes generally involves the co-transfection of the cell line with separate plasmids encoding the heavy chain (HC) and the light chain (LC) comprising the IgG. In the case of an IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The approach to manufacturing the fusion protein utilized in certain embodiments of the invention is the production of a cell line that is permanently transfected with a single plasmid DNA that contains all the required genes on a single strand of DNA, including the HC-fusion protein gene, the LC gene, the selection gene, e.g. neo, and the amplification gene, e.g. the dihydrofolate reductase gene. As shown in the diagram of the fusion protein tandem vector in FIG. 24, the HC-fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

Thus, in some embodiments the invention provides a vector containing a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain.

The invention further provides cells that incorporate one or more of the vectors of the invention. The cell may be a prokaryotic cell or a eukaryotic cell. In some embodiments, the cell is a eukaryotic cell. In some embodiments, the cell is a mouse myeloma hybridoma cell. In some embodiments, the cell is a Chinese hamster ovary (CHO) cell. Exemplary methods for incorporation of the vector(s) into the cell are given in the Examples. However, any suitable techniques, as known in the art, may be used to incorporate the vector(s) into the cell. In some embodiments, the invention provides a cell capable of expressing an immunoglobulin fusion protein, where the cell is a cell into which has been permanently introduced a single tandem expression vector, where both the immunoglobulin light chain gene and the gene for the immunoglobulin heavy chain fused to the antibody pharmaceutical, are incorporated into a single piece of nucleic acid, e.g., DNA. In some embodiments, the invention provides a cell capable of expressing an immunoglobulin fusion protein, where the cell is a cell into which has been permanently introduced a single tandem expression vector, where both the immunoglobulin heavy chain gene and the gene for the immunoglobulin light chain fused to the antibody pharmaceutical, are incorporated into a single piece of nucleic acid, e.g., DNA. The introduction of the tandem vector may be by, e.g., permanent integration into the chromosomal nucleic acid, or by, e.g., introduction of an episomal genetic element.

Thus, in some embodiments the invention further provides a cell containing a vector containing a single nucleic acid sequence containing a first sequence coding for a some or all of a light chain of a first immunoglobulin operably linked to a second sequence coding for some or all of a heavy chain of the first immunoglobulin, where either the first sequence further codes for a ScFv derived from a second immunoglobulin that is expressed as a fusion protein of the ScFv covalently linked to the light chain or the second sequence further codes for a ScFv derived from a second immunoglobulin that is expressed as a fusion protein of the ScFv covalently linked to the heavy chain. In some embodiments the cell is a eukaryotic cell. In some embodiments, the cell is a Chinese hamster ovary cell.

In some embodiments, the invention provides compositions that include a structure that binds to a BBB receptor mediated transport system. The structure may be coupled to an active agent, e.g., an antibody pharmaceutical, diagnostic, or research moiety, for which transport across the BBB is desired, e.g., a neurotherapeutic agent. The compositions and methods of the invention may utilize any suitable structure that is capable of transport by the selected endogenous BBB receptor-mediated transport system, and that is also capable of attachment to the desired agent, e.g., antibody. In some embodiments, the targeting structure is itself an antibody. In some embodiment the targeting antibody is a monoclonal antibody (MAb), e.g., a chimeric MAb.

The BBB has been shown to have specific receptors that allow the transport from the blood to the brain of several macromolecules; these transporters are suitable as transporters for compositions of the invention. Endogenous BBB receptor-mediated transport systems useful in the invention include, but are not limited to, those that transport insulin, transferrin, insulin-like growth factors 1 and 2 (IGF1 and IGF2), leptin, and lipoproteins. In some embodiments, the invention utilizes a structure that is capable of crossing the BBB via the endogenous insulin BBB receptor-mediated transport system, e.g., the human endogenous insulin BBB receptor-mediated transport system.

One noninvasive approach for the delivery of agents to the CNS, and, in some embodiments, transport out of the CNS, is to attach the agent of interest to a structure, e.g., molecule that binds with receptors on the BBB. The structure then serves as a vector for transport of the agent across the BBB. Such structures are referred to herein as "molecular Trojan horses (MTH)." Typically, though not necessarily, a MTH is an exogenous peptide or peptidomimetic moiety (e.g., a MAb)

capable of binding to an endogenous BBB receptor mediated transport system that traverses the BBB on the endogenous BBB receptor-mediated transport system. In certain embodiments, the MTH can be an antibody to a receptor of the transport system, e.g., the insulin receptor. In some embodiments, the antibody is a monoclonal antibody (MAb). In some embodiments, the MAb is a chimeric MAb. Thus, despite the fact that antibodies in blood are normally are excluded from the brain, they can be an effective vehicle for the delivery of molecules into the brain parenchyma if they have specificity for receptors on the BBB.

Accordingly, antibodies are particularly useful in embodiments of the invention, especially MAbs. Certain receptor-specific MAbs may mimic the endogenous ligand and function as a MTH and traverse a plasma membrane barrier via transport on the specific receptor system. In certain embodiments, the MTH is a MAb to the human insulin receptor (HIR) on the human BBB. The HIR MAb binds an exofacial epitope on the human BBB HIR and this binding enables the MAb to traverse the BBB via a transport reaction that is mediated by the human BBB insulin receptor.

Current technologies permit a vast number of sequence variants of candidate HIR Abs or known HIR Abs to be readily generated be (e.g., in vitro) and screened for binding to a target antigen such as the ECD of the human insulin receptor or an isolated epitope thereof. See, e.g., Fukuda et al. (2006) "In vitro evolution of single-chain antibodies using mRNA display," *Nuc. Acid Res.*, 34(19) (published online) for an example of ultra high throughput screening of antibody sequence variants. See also, Chen et al. (1999), "In vitro scanning saturation mutagenesis of all the specificity determining residues in an antibody binding site," *Prot Eng*, 12(4): 349-356. An insulin receptor ECD can be purified as described in, e.g., Coloma et al. (2000) *Pharm Res*, 17:266-274, and used to screen for HIR Abs and HIR Ab sequence variants of known HIR Abs.

An "antibody" or "antibody construct," as those term are used herein, includes reference to any molecule, whether naturally-occurring, artificially induced, or recombinant, which has specific immunoreactive activity. Generally, though not necessarily, an antibody is a protein that includes two molecules, each molecule having two different polypeptides, the shorter of which functions as the light chains of the antibody and the longer of which polypeptides function as the heavy chains of the antibody. Normally, as used herein, an antibody will include at least one variable region from a heavy or light chain. Additionally, the antibody may comprise combinations of variable regions. The combination may include more than one variable region of a light chain or of a heavy chain. The antibody may also include variable regions from one or more light chains in combination with variable regions of one or more heavy chains. An antibody can be an immunoglobulin molecule obtained by in vitro or in vivo generation of the humoral response, and includes both polyclonal and monoclonal antibodies. Furthermore, the present invention includes antigen binding fragments of the antibodies described herein, such as Fab, Fab', F(ab)$_2$, and Fv fragments, fragments comprised of one or more CDRs, single-chain antibodies (e.g., single chain Fv fragments (ScFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain, all of which are encompassed by the terms "antibody" or "antibody structure." Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Synthetic methods of generating such fragments are also contemplated. Heavy and light chain monomers may similarly be produced by treating an intact antibody with a reducing agent, such as dithiothreitol or beta.-mercaptoethanol, or by using host cells transformed with DNA encoding either the desired heavy chain or light chain or both. An antibody immunologically reactive with a particular antigen can be generated in vivo or by recombinant methods such as selection of libraries of recombinant antibodies in phage or similar vectors.

A "chimeric" antibody includes an antibody derived from a combination of different mammals. The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas.

For use in humans, a chimeric MAb is preferred that contains enough human sequence that it is not significantly immunogenic when administered to humans, e.g., about 80% human and about 20% mouse, or about 85% human and about 15% mouse, or about 90% human and about 10% mouse, or about 95% human and 5% mouse, or greater than about 95% human and less than about 5% mouse. Chimeric antibodies to the human BBB insulin receptor with sufficient human sequences for use in the invention are described in, e.g., Coloma et al. (2000) *Pharm. Res.* 17: 266-274, which is incorporated by reference herein in its entirety. A more highly humanized form of the HIR MAb can also be engineered, and the humanized HIRMAb has activity comparable to the murine HIRMAb and can be used in embodiments of the invention. See, e.g., U.S. Patent Application Publication No. 20040101904, filed Nov. 27, 2002 incorporated by reference herein in its entirety.

Antibodies used in the invention may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

Accordingly, in some embodiments, a genetically engineered HIR MAb, with the desired level of human sequences, is fused to an agent for which transport across the BBB is desired, e.g. an antibody pharmaceutical, to produce a recombinant fusion protein that is a bi-functional molecule. The recombinant therapeutic antibody/HIRMAb is able to (i) cross the human BBB in the blood to brain direction, via transport on the BBB HIR, (ii) cross the human BBB in the brain to blood direction, via transport on the BBB FcR receptor, and (iii) bind the therapeutic antibody's target, e.g., the Aβ amyloid of AD, to cause neurotherapeutic effects once inside the brain, following peripheral administration.

The invention provides compositions and methods for transport of agents across the BBB from blood to CNS and/or from CNS to blood. One useful class of agents is antibody pharmaceuticals, which include therapeutic and diagnostic antibody structures. The antibody pharmaceutical agent for which transport across the BBB is desired may be any suitable antibody substance for introduction into the CNS. Generally, the agent is an antibody for which transport across the BBB is desired, which does not, in its native form, cross the BBB in significant amounts. The antibody agent may be, e.g., a therapeutic agent, a diagnostic agent, or a research agent. Diagnostic agents include antibody radiopharmaceuticals, such as an anti-Aβ antibody for imaging the Aβ amyloid burden in the brain of patients with AD. In some embodiments, the antibody pharmaceutical is a therapeutic agent, such as antibody that disaggregates the Aβ amyloid in the brain of patients with AD. Antibody agents useful in the invention are listed in Table 1.

TABLE 1

Treatment of Brain Disorders with Monoclonal Antibody Therapeutics

| Target for Monoclonal Antibody | Disease |
| --- | --- |
| Aβ amyloid | Alzheimer's disease |
| α-synuclein | Parkinson's disease |
| Huntingtin protein | Huntington's disease |
| PrP prion protein | Mad cow disease |
| West Nile envelope protein | West Nile virus encephalitis |
| tumor necrosis factor (TNF) related apoptosis inducing ligand (TRAIL) | Neuro-AIDS |
| Nogo A | Brain injury, spinal cord injury, stroke |
| HER2 | Metastatic breast cancer of brain |
| epidermal growth factor receptor (EGFR); hepatocyte growth factor (HGF) | Primary and metastatic cancer of brain |
| Oligodendrocyte surface antigen | Multiple sclerosis |

One type of agent of use in the invention is antibody agents. Many antibody agents, e.g., pharmaceuticals, are active (e.g., pharmacologically active) in brain but do not cross the blood-brain barrier. These factors are suitable for use in the compositions and methods of the invention and include an antibody that is directed against the Aβ amyloid peptide of Alzheimer's disease (AD) for the diagnosis or treatment of AD. In some embodiments, the antibody is directed against α-synuclein of Parkinson's disease (PD) for the diagnosis or treatment of PD. In some embodiments, the antibody is directed against the huntingtin protein of Huntington's disease (HD) for the diagnosis or treatment of HD. In some embodiments, the antibody is directed against the Prp protein of scrapie or mad cow disease for the diagnosis or treatment of human equivalents of scrapie. In some embodiments, the antibody is directed against an envelope protein of the West Nile virus for the diagnosis or treatment of West Nile encephalitis. In some embodiments, the antibody is directed against the tumor necrosis factor (TNF) related apoptosis inducing ligand (TRAIL) for the diagnosis or treatment of acquired immune deficiency syndrome (AIDS), which infects the brain. In some embodiments, the antibody is directed against the nogo A protein for the diagnosis or treatment of brain injury, spinal cord injury, or stroke. In some embodiments, the antibody is directed against the HER2 protein for the diagnosis or treatment of breast cancer metastatic to the brain. In some embodiments, the antibody is directed against oncogenic receptor proteins such as the epidermal growth factor receptor (EGFR) for the diagnosis or treatment of either primary brain cancer or metastatic cancer of the brain. In some embodiments, the antibody is directed against an oncogenic growth factor such as the epidermal growth factor (EGF) or the hepatocyte growth factor (HGF) for the diagnosis or treatment of either primary brain cancer or metastatic cancer of the brain. In some embodiments, the antibody is directed against an oligodendrocyte surface antigen for the diagnosis or treatment of demyelinating disease such as multiple sclerosis. Particularly useful in some embodiments of the invention utilizing ScFv forms of the antibody, e.g., therapeutic antibody, that are used as precursors for fusion proteins that cross the BBB are those that naturally form dimeric structures, similar to original antibody. Some embodiments of the invention provides a fusion protein constructed of ScFv derived from the antibody fused to one chain (e.g., a light or heavy chain) of a targeting antibody, e.g., of the HIRMAb. Typically, the molecular weight range of antibodies that may be fused to the molecular Trojan horse ranges from 1000 Daltons to 500,000 Daltons.

One particularly useful antibody pharmaceutical in embodiments of the invention is an antibody against the Aβ amyloid peptide of AD. The dementia of AD is caused by the progressive accumulation over many years of amyloid plaque. This plaque is formed by the aggregation of the Aβ amyloid peptide, which is a 40-43 amino acid peptide designated $A\beta^{1-40/43}$, which is derived from the proteolytic processing within the brain of the amyloid peptide precursor protein called APP.

A potential therapy for AD is any drug that can enter the brain and cause disaggregation of the amyloid plaque. Transgenic mice have been engineered which express mutant forms of the APP protein, and these mice develop amyloid plaque similar to people with AD. The amyloid plaque can be disaggregated with the application of anti-AD antibodies administered directly into the brain of the transgenic mice via either direct cerebral injection or via a cranial window. Following anti-Aβ antibody-mediated disaggregation of the amyloid plaque, the dystrophic nerve endings in the vicinity of the plaque begin to heal and form normal structures. The anti-Aβ antibody must be injected directly into the brain via needle because the antibody does not cross the BBB. Therefore, antibody administered in the blood cannot access the plaque in brain behind the BBB.

Antibody based therapies of AD include active or passive immunization against the Aβ peptide. In active immunization, the subject is immunized with the Aβ peptide along with an adjuvant such as Freund's adjuvant. Active immunization of transgenic mice resulted in a decrease in the amyloid burden in brain, which is evidence that the anti-Aβ peptide antibodies in the blood formed in the active immunization treatment were able to cross the BBB in the immunized mouse. It is well known that the administration of adjuvants such as Freunds adjuvant causes disruption of the BBB via an inflammatory response to the adjuvant administration. It is likely that active immunization in humans with AD will either not be effective, because (a) the adjuvant used in humans is not toxic, and the BBB is not disrupted, or (b) the adjuvant is toxic, and causes opening of the BBB via an inflammatory response to the adjuvant. Opening of the BBB allows the entry into brain of serum proteins such as albumin, and these proteins are toxic to brain cells. In passive immunization, an anti-Aβ peptide antibody is administered directly to the subject with brain amyloid, and this has been done in transgenic mice with brain amyloid similar to AD. However, the dose of anti-Aβ peptide antibody that must be administered to the mice is prohibitively high, owing to the lack of significant transport of antibody molecules in the blood to brain direction. Therefore, the limiting factor in either the active or passive immunization of either transgenic mice or of people with AD and brain amyloid is the BBB, and the lack of transport of antibody molecules across the BBB in the blood to brain direction.

As used herein, the term "anti-Aβ peptide antibody" includes the pharmaceutically acceptable salts, polymorphs, hydrates, solvates, biologically-active fragments, biologically active variants and stereoisomers of the precursor anti-Aβ peptide antibody, as well as agonist, mimetic, and antagonist variants of antibodies directed at alternative targets, which cross-react with the anti-Aβ peptide antibody, and polypeptide fusion variants thereof. Variants include one or more deletions, substitutions, or insertions in the sequence of the anti-Aβ peptide antibody precursor. When the targeting agent is also an antibody, e.g., a MAb such as HIRMAb is used, additional fusion protein variants can be produced with the substitution of amino acids within either the framework region (FR) or the complementarity determining region (CDR) of either the light chain or the heavy chain of the antibody, e.g., HIRMAb, as long as the fusion protein binds with high affinity to the endogenous receptor, e.g., HIR to promote transport across the human BBB. Additional fusion protein variants can be produced by changing the composition or length of the linker peptide separating the antibody pharmaceutical from the HIRMAb.

In some embodiments, the anti-Aβ peptide antibody is specific for $A\beta^{1-40}$, $A\beta^{1-42}$, or $A\beta^{1-43}$ peptide isoforms. Such isoform-specific anti-Aβ peptide antibodies are particularly useful where a ratio of Aβ peptide isoforms (e.g., $A\beta^{1-42}/A\beta^{1-40}$ ratio) is to be determined. Such peptide isoform ratio determinations are particularly useful for prognostic applications. For example, a high or increasing ratio of $A\beta^{1-42}/A\beta^{1-40}$ is indicative of Alzheimer's disease. See, e.g., Hansson et al. (2007), *Dement Geriatr Cogn Disord*, 23(5):316-320.

In some embodiments, the anti-Aβ peptide antibody is a ScFv antibody comprised of the variable region of the heavy chain (VH) and the variable region of the light chain (VL) derived from the original murine anti-Aβ peptide antibody produced by a hybridoma. The amino acid sequence of the VH of the anti-AD peptide antibody is given in SEQ ID NO: 12. The amino acid sequence of the VL of the anti-Aβ peptide antibody is given in SEQ ID NO: 14. The amino acid sequence of the VH of the anti-AD peptide antibody joined to the VL anti-Aβ peptide antibody via a 17 amino acid linker, and containing the epitope of the 9E 10 antibody and a polyhistidine (H) tail at the carboxyl terminus, is given in SEQ ID NO: 16. The amino acid sequence of the VH of the anti-Aβ peptide antibody joined to the VL anti-Aβ peptide antibody via a 17 amino acid linker, and containing the epitope of the 9E 10 antibody at the carboxyl terminus, and containing a 19 amino acid IgG signal peptide at the amino terminus, is given in SEQ ID NO: 18.

Figure 25:
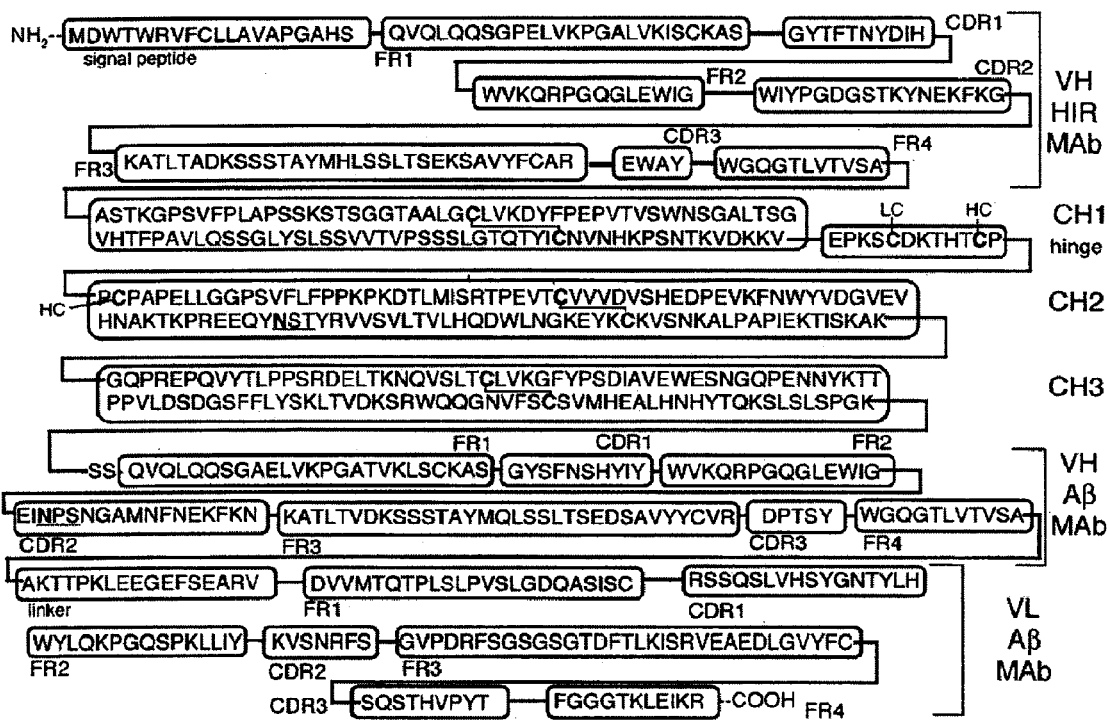
FIG. 25. Amino acid sequence of the 28 domains of the fusion antibody heavy chain (SEQ ID NO:22): (1) signal peptide, (2) framework region (FR) 1 of the heavy chain (HC) of the chimeric HIRMAb, (3) complementarity determining region (CDR) 1 of the HC of the chimeric HIRMAb, (4) FR2 of the HC of the chimeric HIRMAb, (5) CDR2 of the HC of the chimeric HIRMAb, (6) FR3 of the HC of the chimeric HIRMAb, (7) CDR3 of the HC of the chimeric HIRMAb, (8) FR4 of the HC of the chimeric HIRMAb, (9) CH1 region of the HC of the chimeric HIRMAb, (10) hinge region of the HC of the chimeric HIRMAb, (11) CH2 region of the HC of the chimeric HIRMAb; the constant region glycosylation site, NST (Asn-Ser-Thr) is underlined, (12) CH3 region of the HC of the chimeric HIRMAb, (13) Ser-Ser linker between the CH3 region of the HC of the chimeric HIRMAb and the beginning of the mAβScFv, (14) FR1 of the variable region of the HC (VH) of the mAβScFv, (15) CDR1 of the VH of the mAβScFv, (16) FR2 of the VH of the mAβScFv, (17) CDR2 of the VH of the mAβScFv, (18) FR3 of the VH of the mAβScFv, (19) CDR3 of the VH of the mAβScFv, (20) FR4 of the VH of the mAβScFv, (21) 17 amino acid linker between the VH and the variable region of the light chain (VL) of the mAβScFv, (22) FR1 of the VL of the mAβScFv b, (23) CDR1 of the VL of the mAβScFv, (24) FR2 of the VL of the mAβScFv, (25) CDR2 of the VL of the mAβScFv, (26) FR3 of the VL of the mAβScFv, (27) CDR3 of the VL of the mAβScFv, (28) FR4 of the VLH of the mAβScFv.

The VH of the anti-Aβ peptide ScFv antibody is comprised of 4 framework regions (FR), designated FR1, FR2, FR3, and FR4, and of 3 complementarity determining regions (CDR), designated CDR1, CDR2, and CDR3. The VL of the anti-Aβ peptide ScFv antibody is comprised of 4 FRs, designated FR1, FR2, FR3, and FR4, and of 3 CDRs, designated CDR1, CDR2, and CDR3. The relationship of these 14 sub-domains are depicted in FIG. 25. Amino acid substitutions in any of the 14 sub-domains could be made with retention of the anti-Aβ peptide binding properties.

Accordingly, anti-Aβ peptide antibodies useful in the invention include antibodies having at least about 60%, at least about 70%, at least about 80%, at least about 90%, at least about 95%, at least about 99%, or greater than 95% or greater than 99% sequence identity, e.g., 100% sequence identity, to the amino acid sequences disclosed herein.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:21 or SEQ ID NO: 29) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, SIAM *J. Appl Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

The present invention also includes peptides having a conservative amino acid change, compared with an amino acid sequence disclosed herein. Many such changes have been described specifically. More generally, for example, variants can be obtained that contain one or more amino acid substitutions of SEQ ID NO:22. In these variants, e.g., an alkyl amino acid is substituted for an alkyl amino acid in either the VH or VL of an anti-Aβ peptide antibody amino acid sequence, an aromatic amino acid is substituted for an aromatic amino acid in an anti-Aβ peptide antibody amino acid sequence, a sulfur-containing amino acid is substituted for a sulfur-containing amino acid in an anti-Aβ peptide antibody amino acid sequence, a hydroxy-containing amino acid is substituted for a hydroxy-containing amino acid in an anti-Aβ peptide antibody amino acid sequence, an acidic amino acid is substituted for an acidic amino acid in an anti-Aβ peptide antibody amino acid sequence, a basic amino acid is substituted for a basic amino acid in an anti-Aβ peptide antibody amino acid sequence, or a dibasic monocarboxylic amino acid is substituted for a dibasic monocarboxylic amino acid in an anti-Aβ peptide antibody amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Further, in designing conservative amino acid substitutions, mutation tolerance prediction programs can be used to greatly increase the number of functional sequence variants so generated. Various programs for predicting the effects of amino acid substitutions in a protein sequence on protein function are described in, e.g., Henikoff et al. (2006), "Predicting the Effects of Amino Acid Substitutions on Protein Function," Annu. Rev. Genomics Hum. Genet., 7:61-80. Such programs include, e.g., SIFT, PolyPhen, PANTHER PSEC, PMUT, and TopoSNP). These programs are available to the public on the world wide web.

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

Compositions of the invention are useful in one or more of: transporting an agent, e.g., an antibody, across the BBB in the blood to brain direction; transporting an agent, e.g., antibody, across the BBB in the brain to blood direction; and/or retaining activity of the agent, e.g., antibody, once transported across the BBB.

Structures useful in transporting an agent across the BBB in the blood to brain direction include structures capable of crossing the blood-brain barrier on an endogenous BBB receptor-mediated transporter, such as a transporter selected from the group consisting of the insulin transporter, the transferrin transporter, the leptin transporter, the LDL transporter, and the IGF receptor. In some embodiments, the endogenous BBB receptor-mediated transporter is selected from the group consisting of the insulin transporter and the transferrin transporter. In some embodiments, the endogenous BBB receptor-mediated transporter is the insulin transporter, e.g., the human insulin transporter. Thus, in embodiments in which the composition is an antibody fusion protein, the part of the antibody fusion protein that mediates transport across the BBB in the blood to brain direction is an immunoglobulin, and is an antibody to an endogenous BBB receptor-mediated transport system. In some embodiments, the endogenous BBB receptor-mediated transport system is selected from the group consisting of the BBB insulin receptor, the BBB transferrin receptor, the BBB leptin receptor, the BBB IGF receptor, or the BBB lipoprotein receptor. In some embodiments, the antibody is an antibody to the endogenous insulin BBB receptor-mediated transport system. Antibodies can be any suitable antibody as described herein. The structure capable of crossing the BBB can be an antibody, e.g., a MAb such as a chimeric MAb. The antibody can be an antibody to an endogenous BBB receptor-mediated transporter, as described herein.

Figure 26:
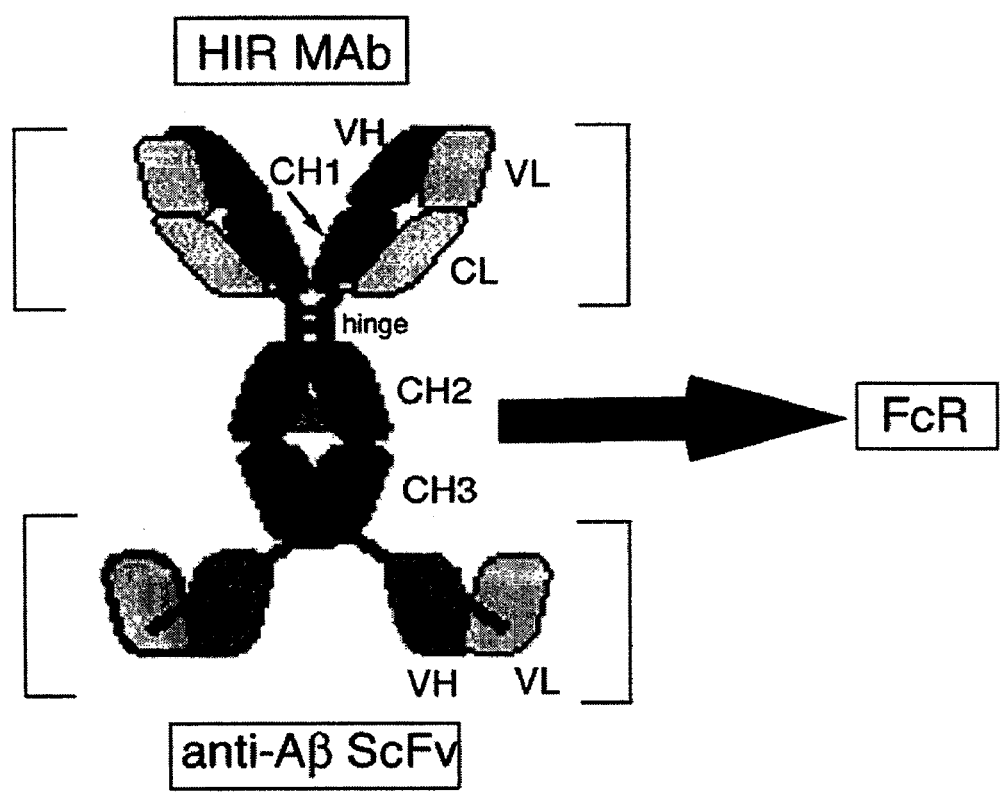
FIG. 26. Antibody fusion protein with 3 functionalities: (1) The CDRs of the chimeric HIRMAb bind to the BBB HIR to enable influx of the molecule from blood into brain across the BBB; (2) the CH2/CH3 interface of the Fc region binds to the FcR receptor to enable efflux of the molecule from brain back to blood across the BBB; (3) the mAβScFv fused to the CH3 region binds to the Aβ amyloid peptide of AD to cause clearance of amyloid from brain in AD. The role that each of these 3 functionalities plays in the clearance of brain amyloid in AD is shown in FIG. 27.

In some embodiments, the invention provides compositions, e.g., a fusion protein, that are capable of transport across the BBB from the CNS to the blood, e.g., compositions that can cross the BBB in both directions. Thus, in some embodiments the compositions also include a structure that is capable of crossing the BBB from the CNS to the blood. Any suitable structure that is capable of crossing the BBB from the CNS to the blood may be used. In some embodiments, the invention utilizes structures that are capable of crossing the BBB from the CNS to the blood via the Fc receptor. The BBB expresses an Fc receptor (FcR), and the neonatal FcR or FcRn, and this FcR mediates the unidirectional efflux of IgG molecules from brain to blood. See, e.g., Zhang, Y. and Pardridge, W. M. (2001): Mediated efflux of IgG molecules from brain to blood across the blood-brain barrier. J Neuroimmunol, 114: 168-172, and Schlachetzki, F., Zhu, C. and Pardridge, W. M. (2002): Expression of the neonatal Fc receptor (FcRn) at the blood-brain barrier. J Neurochem, 81: 203-206, incorporated herein by reference. The BBB FcR does not mediate the influx of IgG molecules from blood to brain. The FcR binds the IgG molecule at the interface of the CH2 and CH3 regions of the Fc part of the heavy chain. See, e.g., Martin, W. L., West, A. P., Jr., Gan, L. and Bjorkman, P. J. (2001): Crystal structure at 2.8 A of an FcRn/heterodimeric Fc complex: mechanism of pH-dependent binding. Mol Cell, 7: 867-877, incorporated herein by reference. Thus, in some embodiments, the interface of the CH2 and CH3 regions of the Fc part of the heavy chain serve as a structure that can transport compositions of the invention from the CNS to the blood across the BBB. For example, the interface of the CH2 and CH3 regions of the Fc part of the heavy chain, which is intact in the fusion antibody as illustrated in FIGS. 25 and 26, is such a structure It will be appreciated that the structure that crosses the BBB from the CNS to the blood, e.g., the interface of the CH2 and CH3 regions, may be part of the structure that crosses the BBB from the blood to the CNS, e.g., an antibody directed to a receptor-mediated BBB transport system, e.g., the HIR system.

Figure 27:
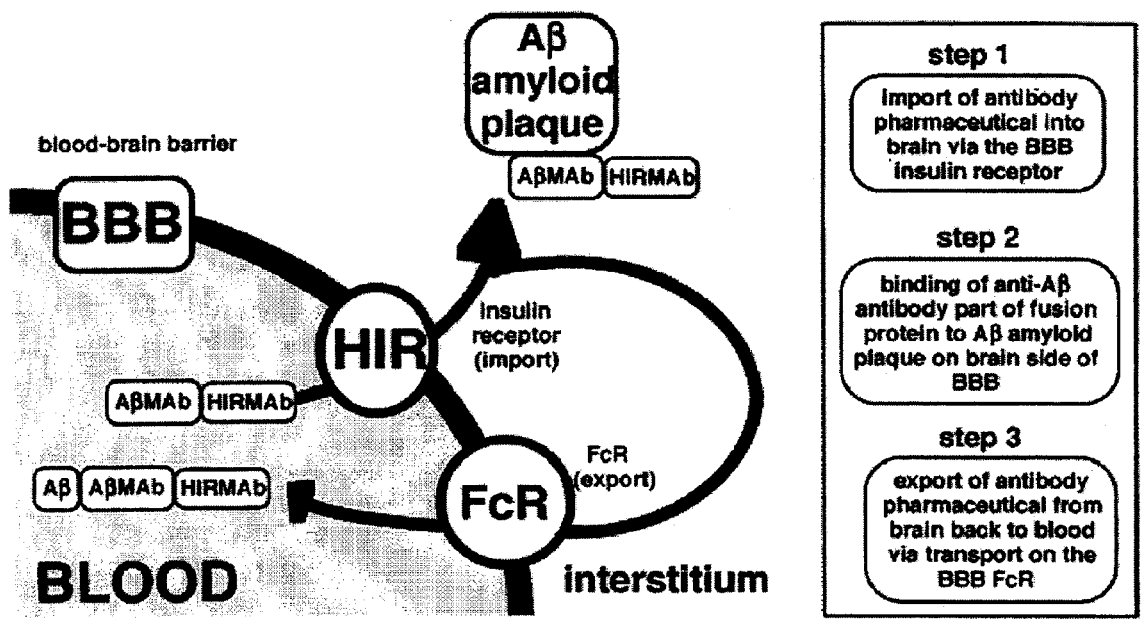
FIG. 27. The fusion protein clears amyloid from brain in AD via 3 sequential steps, and each of these 3 sequential steps uses 3 separate parts of the antibody fusion protein molecule as shown in FIG. 26. Step 1 is the influx of the fusion antibody from blood to brain across the BBB, which is mediated by binding of the fusion antibody to the BBB human insulin receptor (HIR). Step 2 is binding of the fusion antibody to the amyloid plaque in AD, which promotes disaggregation of the amyloid plaque, and this binding to the plaque is mediated by the mAβScFv part of the fusion antibody. Step 3 is the efflux of the fusion antibody from brain to blood across the BBB, which is mediated by binding of the fusion antibody to the BBB FcR receptor at the CH2-CH3 interface of the Fc region of the fusion antibody.

In embodiments used to treat aggregate diseases, were it not for the export of the fusion antibody from brain back to blood via the FcR, then there would be little or no clearance of the monomeric proteins from the protein aggregate. Many brain diseases are "aggregate" diseases, which are caused by the gradual deposition of aggregated protein in the brain. The aggregates of AD are formed by the Aβ amyloid peptide; the aggregates of PD are formed by α-synuclein and/or parkin; the aggregates of mad cow disease are formed by the Prp scrapie protein; the aggregates of HD are formed by the huntingtin protein. Antibodies against the monomers of these aggregates can dissolve the aggregate, as illustrated for Aβ aggregates in the Examples and in FIG. 41. Following binding of the aggregated protein by the fusion antibody, the complex of the fusion antibody and the aggregate precursor are exported out of brain and back to blood across the BBB, as shown in FIG. 27.

The Examples show that the fusion antibody binds the HIR with high affinity, and that the fusion antibody crosses the BBB via this receptor. However, once the fusion antibody binds the aggregated protein in brain, the fusion antibody must be able to efflux from brain back to blood, as depicted in FIG. 27.

In some embodiments, the structure that is capable of crossing the BBB utilizes an endogenous BBB receptor mediated transport system, such as a system that utilizes the insulin receptor, transferrin receptor, leptin receptor, LDL receptor, or IGF receptor. In some embodiments, the endogenous BBB receptor mediated transport system is the insulin BBB receptor mediated transport system. In some embodiments, the structure that is capable of crossing the BBB is an antibody, e.g., a monoclonal antibody (MAb) such as a chimeric MAb. The antibody can be a chimeric antibody with sufficient human sequence that it is suitable for administration to a human. The antibody can be glycosylated or nonglycosylated; in some embodiments, the antibody is glycosylated, e.g., in a glycosylation pattern produced by its synthesis in a CHO cell. In embodiments in which the structure is an antibody, the covalent linkage between the antibody and the neurotherapeutic agent may be a linkage between any suitable portion of the antibody and the antibody pharmaceutical agent, as long as it allows the antibody-agent fusion to cross the blood-brain barrier and the antibody pharmaceutical agent to retain a therapeutically useful portion of its activity within the CNS. In certain embodiments, the covalent link is between one or more light chains of the targeting antibody and the antibody pharmaceutical agent.

In some embodiments, more than one type of structure capable of crossing the BBB, e.g., molecular Trojan horse, may be used. The different structures may be covalently attached to a single antibody pharmaceutical agent, e.g., a single ScFv such as the anti-Aβ ScFv, or multiple ScFv's, or any combination thereof. Thus, for example, in some embodiments either with the same ScFv attached to each MTH or a different ScFv attached, or combinations of ScFv attached. Thus the antibody pharmaceutical can be fused to multiple molecular Trojan horses that undergo receptor-mediated transport across the blood-brain barrier, including monoclonal antibodies to the insulin receptor, transferrin receptor, insulin-like growth factor (IGF) receptor, or the low density lipoprotein (LDL) receptor or the endogenous ligand, including insulin, transferrin, the IGFs, or LDL. Ligands that traverse the blood-brain barrier via absorptive-mediated transport may also be used as molecular Trojan horses including cationic proteins, or carbohydrate bearing proteins that bind to membrane lectins. The molecular weight range of molecular Trojan horses is 1000 Daltons to 500,000 Daltons.

The covalent linkage between the structure capable of crossing the BBB and the antibody pharmaceutical agent may be direct (e.g., a peptide bond between the terminal amino acid of one peptide and the terminal amino acid of the other peptide to which it is linked) or indirect, via a linker. If a linker is used, it may be any suitable linker, e.g., a peptide linker. If a peptide linker is used, it may be 1, 2, 3, 4, 5, 6, 7, 8, 9, 10, or more than 10 amino acids in length. In some embodiments, a two amino acid linker is used. In some embodiments, the linker has the sequence ser-ser. The covalent linkage may be cleavable, however this is not a requirement for activity of the system in some embodiments; indeed, an advantage of these embodiments of the present invention is that the fusion protein, without cleavage, is partially or fully active both for transport and for activity once across the BBB.

In some embodiments, a noncovalent attachment may be used. An example of noncovalent attachment of the MTH, e.g., MAb, to the large molecule therapeutic neuroprotective factor is avidin/streptavidin-biotin attachment. Such an approach is further described in U.S. Pat. No. 6,287,792, entitled "Drug delivery of antisense oligodeoxynucleotides and peptides to tissues in vivo and to cells using avidin-biotin technology, which is hereby incorporated by reference in its entirety.

The agents transported across the BBB may be any suitable agent for which such transport is desired in one or both directions. For example, the agent may be a therapeutic, diagnostic, or research agent. Particularly useful agents for transport include antibodies, e.g., antibody pharmaceuticals that are active in the CNS.

The antibody pharmaceutical that is active in the CNS can be a neurotherapeutic agent, e.g., an antibody that disaggregates insoluble protein in the brain. In some embodiments, the antibody pharmaceutical is directed against the Aβ amyloid peptide of Alzheimer's disease (AD) for the diagnosis or treatment of AD. In some embodiments, the antibody pharmaceutical is directed against α-synuclein of Parkinson's disease (PD) for the diagnosis or treatment of PD. In some embodiments, the antibody pharmaceutical is directed against the huntingtin protein of Huntington's disease (HD) for the diagnosis or treatment of HD. In some embodiments, the antibody pharmaceutical is directed against the Prp protein of scrapie or mad cow disease for the diagnosis or treatment of human equivalents of scrapie. In some embodiments, the antibody pharmaceutical is directed against an envelope protein of the West Nile virus for the diagnosis or treatment of West Nile encephalitis. In some embodiments, the antibody pharmaceutical is directed against the tumor necrosis factor (TNF) related apoptosis inducing ligand (TRAIL) for the diagnosis or treatment of acquired immune deficiency syndrome (AIDS), which infects the brain. In some embodiments, the antibody pharmaceutical is directed against the nogo A protein for the diagnosis or treatment of brain injury, spinal cord injury, or stroke. In some embodiments, the antibody pharmaceutical is directed against the HER2 protein for the diagnosis or treatment of breast cancer metastatic to the brain. In some embodiments, the antibody pharmaceutical is directed against an oncogenic receptor proteins such as the epidermal growth factor receptor (EGFR) for the diagnosis or treatment of either primary brain cancer or metastatic cancer of the brain. In some embodiments, the antibody pharmaceutical is directed against an oncogenic growth factor such as the epidermal growth factor (EGF) or the hepatocyte growth factor (HGF) for the diagnosis or treatment of either primary brain cancer or metastatic cancer of the brain. In some embodiments, the antibody pharmaceutical is directed against an oligodendrocyte surface antigen for the diagnosis or treatment of demyelinating disease such as multiple sclerosis. The structure capable of crossing the BBB and the neurotherapeutic agent are covalently linked by a peptide linker in some embodiments.

Particularly useful antibody structures are ScFvs. In some embodiments, more than one molecule of the same therapeutic ScFv agent is attached to the structure that crosses the BBB. For example, in compositions of the invention where an ScFv is attached to an antibody, one molecule of the ScFv is attached to each heavy chain, naturally producing a homodimer structure. This is desired if a dimeric configuration of the ScFv is required for high antigen avidity. However, if a dimeric configuration is not required, then 2 different ScFv molecules with 2 different antigen specificities could be fused to the heavy chain of the targeting antibody. A naturally occurring homo-dimeric structure between two ScFv molecules is formed when the ScFv is fused to a carboxyl terminus of the CH3 region of an IgG molecule, as illustrated in FIG. 26. Without being bound by theory, it is thought that this may account for the unexpected finding of essentially 100% of activity of binding of the fusion antibody to the Aβ amyloid peptide (see, e.g., FIG. 34).

In some embodiments, more than one type of ScFv agent can be attached to the structure that is capable of crossing the blood-brain barrier. In some embodiments, 2, 3, 4, 5, 6, 7, 8, 9, 10, or more than 10 different ScFv agents may be attached to the structure that is capable of crossing the blood-brain barrier. In certain embodiments, 2 different ScFv are attached to an antibody to an endogenous BBB receptor-mediated transport system. Any combination of ScFv may be used. Certain ScFv's may form hetero-dimeric structures, and in some embodiments the invention provides a fusion protein constructed of one ScFv monomer fused to one chain (e.g., heavy chain) of an antibody, e.g., of the HIRMAb, and another ScFv monomer fused to the second chain of the antibody. Typically, the molecular weight range of recombinant ScFv's that may be fused to the molecular Trojan horse ranges from 1000 Daltons to 500,000 Daltons.

Compositions that Cross the BBB from Blood to CNS and from CNS to Blood.

In one aspect, the invention provides a composition that includes (i) a first portion capable of crossing the BBB from the blood to the brain via a first receptor-mediated BBB transport system; associated with (ii) a second portion capable of crossing the BBB from the brain to the blood via a second receptor-mediated BBB transport system. In some embodiments, the composition further contains (iii) a third portion capable of interacting with a central nervous system component. The composition can contain a protein, e.g., an antibody construct. In some embodiments, the first portion is capable of crossing the BBB on an endogenous BBB receptor mediated transport system that is the insulin receptor, transferrin receptor, leptin receptor, lipoprotein receptor, or the IGF receptor. In some embodiments, the endogenous BBB receptor mediated transport system is the insulin BBB receptor mediated transport system. In some embodiments, the second receptor-mediated BBB transport system includes the Fc receptor system. In some embodiments, the first and second portions are part of an antibody structure, e.g, the second portion comprises the CH2-CH3 region of the antibody structure. In some embodiments, the third portion comprises an antibody, antibody fragment, or ScFv. In embodiments containing a third portion capable of interacting with a central nervous system component, the central nervous system component can be a pathological substance associated with a brain disorder, e.g., Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. The pathological substance may one or more of a protein, nucleic acid, carbohydrate, carbohydrate polymer, lipid, glycolipid, small molecule, or combinations thereof. In some embodiments, the pathological substance is a protein, e.g., Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid In some embodiments, the invention provides a composition that includes (i) a first portion capable of crossing the BBB from the blood to the brain via a first receptor-mediated BBB transport system; associated with (ii) a second portion capable of crossing the BBB from the brain to the blood via a second receptor-mediated BBB transport system; and (iii) a third portion capable of interacting with a central nervous system component, where the first portion and the second portions are part of an antibody, and the third portion is a ScFv. The antibody can be directed to an endogenous BBB receptor-mediated transport system, e.g., the insulin BBB receptor mediated transport system such as the human insulin receptor mediated transport system. In some embodiments, the ScFv is a ScFv to Aβ amyloid peptide of AD.

In some embodiments, the invention provides compositions containing a fusion protein, where the targeting MAb is an antibody to the human insulin BBB receptor mediated transport system linked to an anti-Aβ ScFv. The ScFv is linked via its amino terminus to the carboxy terminus of the heavy chain of the antibody by a ser-ser linker. The antibody can be a chimeric antibody with sufficient human sequence that it is suitable for administration to a human. In some embodiments, the invention provides compositions containing a fusion MAb with a heavy chain-ScFv fusion protein and a separate covalently linked light chain, where the light chain is at least about 60%, or about 70%, or about 80%, or about 90%, or about 95%, or about 99% identical to, or is substantially 100% identical to amino acids 21-234 of SEQ ID NO: 29, and the heavy chain-ScFv fusion is at least about 60%, or about 70%, or about 80%, or about 90%, or about 95%, or about 99% identical to, or is substantially 100% identical to amino acids 20-708 of SEQ ID NO: 22.

The invention also provides compositions containing an antibody pharmaceutical that is covalently linked to a chimeric MAb to the human BBB insulin receptor. In some embodiments, the heavy chain of the MAb is covalently linked to the pharmaceutical antibody to form a fusion protein. The antibody pharmaceutical can be any antibody pharmaceutical described herein, i.e., any antibody pharmaceutical for which transport across the BBB is desired. In some embodiments, the antibody pharmaceutical is antibody against aggregated protein in brain, e.g., Aβ amyloid as in AD.

Compositions that Cross the BBB in Both Directions and that are Capable of Interacting with a CNS Component.

In one aspect, the invention provides a composition containing (i) a first portion capable of crossing the BBB from the blood to the brain; (ii) a second portion capable of interacting with a central nervous system component; and (iii) a third portion capable of crossing the BBB from the brain to the blood, where the first, second, and third portions are linked and wherein the first, second, and third portions are not the same and do not share common structures. In some embodiments, the composition is a non-naturally-occurring composition. In some embodiments, the first and third portions include a protein, e.g. an antibody, such as a mAb. In some embodiments, the first, second, and third portions are covalently linked. In some embodiments, the first portion is capable of crossing the BBB from the blood to the brain via an endogenous BBB receptor mediated transport system, e.g., the insulin receptor, transferrin receptor, leptin receptor, lipoprotein receptor, or the IGF receptor. In some embodiments, the endogenous BBB receptor mediated transport system is the insulin BBB receptor mediated transport system. In some embodiments, the second portion includes an antibody, antibody fragment, or ScFv The central nervous system component with which the second portion interacts can include a pathological substance associated with a brain disorder, e.g., Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. In some embodiments, the pathological substance is of a type selected from the group consisting of proteins, nucleic acids, carbohydrates, carbohydrate polymers, lipids, glycolipids, and small molecules, e.g. a protein such as Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid. In some embodiments, the third portion includes a structure that is capable of crossing the BBB from the brain to the blood via a receptor mediated BBB transport system such as the Fc receptor system, e.g., a structure that is part of an antibody structure, such as the CH2-CH3 region of the antibody structure.

Compositions that Contain a ScFv that is Bonded to an Immunoglobulin and Retains Activity/Affinity.

In another aspect, the invention provides a composition containing a ScFv that binds an antigen, where (i) the ScFv is derived from a first immunoglobulin, (ii) the ScFv is bonded with a second immunoglobulin, wherein the second immunoglobulin is optionally an immunoglobulin that is modified from its native form; and (iii) the affinity of the ScFv for its antigen is more than about 10, 20, 30, 40, 50, 60, 70, 80, 90, 100, 110, or 120% of the first immunoglobulin from which the ScFv was derived. In some embodiments, the ScFv is covalently bonded to the second immunoglobulin, e.g., at its amino terminus to the second immunoglobulin, or at its carboxy terminus to the second immunoglobulin. The ScFv can be bonded to the carboxy terminus of the heavy chain or the light chain of the second immunoglobulin, e.g., to the carboxy terminus of the heavy chain of the second immunoglobulin. The ScFv can also be bonded to the amino terminus of the heavy or light chain of the second immunoglobulin. In some embodiments, the ScFv is bonded to the CH3 region of the heavy chain of the second immunoglobulin. In some embodiments, the second immunoglobulin has been modified so that its heavy chain is truncated, and the ScFv is bonded to the carboxy terminus of the truncated heavy chain. In some of these embodiments, the ScFv is bonded to the carboxy terminus of the truncated heavy chain, and the heavy chain has been truncated so that its carboxy terminus lies within a region of the native heavy chain selected from the group consisting of the CH1, hinge, CH2, and CH3 regions. In some embodiments, the ScFv is bonded to the amino terminus of the heavy chain or the light chain of the second immunoglobulin. In some embodiments, the ScFv is derived from an antibody directed against a pathological substance present in the brain, where the pathological substance is associated with a brain disorder, e.g., Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. The pathological substance can of a type selected from the group consisting of proteins, nucleic acids, carbohydrates, carbohydrate polymers, lipids, glycolipids, and small molecules, e.g., a protein such as Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen.

In the case of a ScFv antibody pharmaceutical agent (e.g., a ScFv against the Aβ peptide of AD), the ScFv can be covalently linked by its carboxy or amino terminus to the carboxy or amino terminus of the light chain (LC) or heavy chain (HC) of the targeting antibody. Any suitable linkage may be used, e.g., carboxy terminus of light chain to amino terminus of ScFv, carboxy terminus of heavy chain to amino terminus of ScFv, amino terminus of light chain to carboxy terminus of ScFv, amino terminus of heavy chain to carboxy terminus of ScFv, carboxy terminus of light chain to carboxy terminus of ScFv, carboxy terminus of heavy chain to carboxy terminus of ScFv, amino terminus of light chain to amino terminus of ScFv, or amino terminus of heavy chain to amino terminus of ScFv. In some embodiments, the linkage is from the carboxy terminus of the HC to the amino terminus of the ScFv, where the VH precedes the VL of the ScFv. In other embodiments, the VL could precede the VH of the ScFv. It will be appreciated that a linkage between terminal amino acids is not required, and any linkage which meets the requirements of the invention may be used; such linkages between non-terminal amino acids of peptides are readily accomplished by those of skill in the art.

In some embodiments, the invention utilizes a ScFv against the Aβ amyloid peptide of AD. Strikingly, it has been found that fusion proteins of these forms of the ScFv retain normal or even greater than normal transport and activity. It is surprising that the affinity of the antibody fusion protein for the Aβ amyloid peptide is the same as the affinity of the original 150 kDa murine MAb against the Aβ amyloid peptide, because the fusion protein is comprised of a ScFv derived from the original murine MAb against the Aβ amyloid peptide. Generally, the affinity and/or avidity of a ScFv for the target antigen is reduced compared to the original MAb. High avidity for the target antigen is derived from the bivalent interaction between the intact 150 kDa MAb and the antigen. In contrast, the interaction of the ScFv and the antigen is monovalent. In addition, it is generally recognized that when a ScFv is fused to another antibody, the affinity of the ScFv for the target antigen is reduced. However, in the design of the fusion antibody depicted in FIG. 26, the bivalent interaction between the antigen and the ScFv is restored. The production of this new genetically engineered antibody fusion protein creates a tri-functional molecule that (i) binds with high affinity to the HIR to cause influx across the BBB from blood to brain, (ii) binds with high affinity to the FcR to cause efflux across the BBB from brain to blood, and (iii) binds with high affinity to the Aβ amyloid peptide of AD to cause disaggregation of amyloid plaque.

Strikingly, it has been found that multifunctional antibody fusion proteins of the invention, e.g., tri-functional fusion proteins, retain a high proportion of the activity of the separate portions, e.g., the portion that is capable of crossing the BBB and the portion that is active in the CNS. Accordingly, the invention further provides a fusion protein containing a structure capable of crossing the BBB in either direction, covalently linked to an antibody pharmaceutical that is active in the central nervous system (CNS), where the structure capable of crossing the blood-brain barrier and the antibody pharmaceutical that is active in the central nervous system each retain an average of at least about 10, 20, 30, 40, 50, 60, 70, 80, 90, 100, 110, or 120% of their activities, compared to their activities as separate entities. In some embodiments, the invention provides a fusion protein containing a structure capable of crossing the BBB, covalently linked to an antibody pharmaceutical that is active in the central nervous system (CNS), where the structure capable of crossing the blood-brain barrier and the antibody pharmaceutical that is active in the central nervous system each retain an average of at least about 50% of their activities, compared to their activities as separate entities. In some embodiments, the invention provides a fusion protein containing a structure capable of crossing the BBB, covalently linked to a antibody pharmaceutical that is active in the central nervous system (CNS), where the structure capable of crossing the blood-brain barrier and the antibody pharmaceutical that is active in the central nervous system each retain an average of at least about 60% of their activities, compared to their activities as separate entities. In some embodiments, the invention provides a fusion protein containing a structure capable of crossing the BBB, covalently linked to a antibody pharmaceutical that is active in the central nervous system (CNS), where the structure capable of crossing the blood-brain barrier and the antibody pharmaceutical that is active in the central nervous system each retain an average of at least about 70% of their activities, compared to their activities as separate entities. In some embodiments, the invention provides a fusion protein containing a structure capable of crossing the BBB, covalently linked to a antibody pharmaceutical that is active in the central nervous system (CNS), where the structure capable of crossing the blood-brain barrier and the antibody pharmaceutical that is active in the central nervous system each retain an average of at least about 80% of their activities, compared to their activities as separate entities. In some embodiments, the invention provides a fusion protein containing a structure capable of crossing the BBB, covalently linked to a antibody pharmaceutical that is active in the central nervous system (CNS), where the structure capable of crossing the blood-brain barrier and the antibody pharmaceutical that is active in the central nervous system each retain an average of at least about 90% of their activities, compared to their activities as separate entities. In some embodiments, the structure capable of crossing the blood-brain barrier retains at least about 10, 20, 30, 40, 50, 60, 70, 80, 90, 95, 99, or 100% of its activity, compared to its activity as a separate entity, and the antibody pharmaceutical that is active in the central nervous system retains at least about 10, 20, 30, 40, 50, 60, 70, 80, 90, 95, 99, or 100% of its activity, compared to its activity as a separate entity.

As used herein, "activity" includes physiological activity (e.g., ability to cross the BBB and/or therapeutic activity), and also binding affinity of the structures for their respective receptors or target antigens.

Transport of the structure capable of crossing the BBB across the BBB may be compared for the structure alone and for the structure as part of a fusion structure of the invention by standard methods. For example, pharmacokinetics and brain uptake of the fusion structure, e.g., fusion protein, by a model animal, e.g., a mammal such as a primate, may be used. Such techniques are illustrated in Example 10, which demonstrates the binding of the antibody fusion protein to the purified human insulin receptor. Similarly, standard models for the function of the antibody pharmaceutical, e.g. the therapeutic or protective function of a antibody therapeutic agent, may also be used to compare the function of the agent alone and the function of the agent as part of a fusion structure of the invention. See, e.g., Example 10, which demonstrates the activity of an murine anti-Aβ MAb alone and a ScFv derived from this murine anti-Aβ MAb, wherein the ScFv is bound to a fusion protein in a model system (Aβ peptide binding). In Example 10, Example 11, and Example 12, the fusion protein of the invention retained about 50-100% of the transport ability and the therapeutic function of its individual components, i.e., a structure capable of crossing the BBB (a MAb to the human insulin receptor) and an anti-Aβ ScFv antibody pharmaceutical.

Alternatively, functional assays may be used as a marker of activity. Transport of the fusion protein across the primate BBB in vivo is compared to the chimeric HIRMAb in Example 11. The blood pharmacokinetics, and the pattern of brain uptake of antibody fusion protein and the chimeric HIRMAb are, on average, nearly identical. Binding of the fusion antibody to the amyloid in autopsy sections of AD brain is compared for the murine anti-Aβ MAb and the fusion protein in Example 10, Example 13, and Example 14. The binding of either antibody to the amyloid plaque of AD is comparable. "Average" measurements are the average of at least three separate measurements.

Compositions for Transporting Antibodies from Brain to Blood

In another aspect, the invention provides a non-naturally-occurring composition comprising a portion that is capable of transporting an antibody structure from the brain to the blood across the BBB. In some embodiments, the transport is via the BBB FcR. In some embodiments, the antibody structure is a therapeutic or diagnostic antibody structure, such as a therapeutic or diagnostic antibody structure interacts with a pathological substance, wherein the pathological substance is associated with a brain disorder, e.g., Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. The pathological substance can be one or more of proteins, nucleic acids, carbohydrates, carbohydrate polymers, lipids, glycolipids, small molecules, or combinations thereof. In some embodiments, the pathological substance is a protein, e.g., Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid. The antibody structure can be a single chain Fv antibody (ScFv). The therapeutic antibody structure or diagnostic antibody structure can linked to a structure that is capable of crossing the blood-brain barrier (BBB). The portion that is capable of transporting an antibody structure from the brain to the blood across the BBB can interact with the Fc receptor.

The composition can further contain a portion that is capable of crossing the BBB from the blood to the brain, such as a portion that is capable of crossing the BBB crosses the BBB on an endogenous BBB receptor mediated transport system, e.g., the insulin receptor, transferrin receptor, leptin receptor, lipoprotein receptor, or the IGF receptor. In some embodiments, the endogenous BBB receptor mediated transport system is the insulin BBB receptor mediated transport system.

Compositions Containing ScFv Peptide Sequences.

In still another aspect, the invention provides a composition containing a ScFv, wherein the VH region of the ScFv comprises a sequence that is at least 80, 90, 95, or 99% identical to SEQ ID NO: 12. In some embodiments, the VL region of the ScFv contains a sequence that is at least 80, 90, 95, or 99% identical to SEQ ID NO: 14. The ScFv can linked to an Ab, e.g., a MAb. Ab or MAb is directed to an endogenous BBB receptor-mediated transport system, e.g., the insulin receptor, transferrin receptor, leptin receptor, lipoprotein receptor, or the IGF receptor. In some embodiments, the endogenous BBB receptor mediated transport system is the insulin BBB receptor mediated transport system. The linkage may be covalent. In some embodiments, the ScFv is linked to the carboxy terminus of the light chain of the Ab or MAb. In some embodiments, the ScFv is linked via its amino terminus to the carboxy terminus of the light chain of the Ab or MAb. In some embodiments, the ScFv is linked via its carboxy terminus to the carboxy terminus of the light chain of the Ab or MAb. In some embodiments, the ScFv is linked to the carboxy terminus of the heavy chain of the Ab or MAb. In some embodiments, the ScFv is linked via its amino terminus to the carboxy terminus of the heavy chain of the Ab or MAb. In some embodiments, the ScFv is linked via its carboxy terminus to the carboxy terminus of the heavy chain of the Ab or MAb.

In some embodiments, the invention provides a composition containing a ScFv where the VH region of the ScFv contains (i) a CDR1 sequence that is at least about 60, 70, 80, 90, 95, 99, or 100% identical to the sequence of amino acids 26-35 of SEQ ID NO: 12; (ii) a CDR2 sequence that is at least about 60, 70, 80, 90, 95, 99, or 100% identical to the sequence of amino acids 50-66 of SEQ ID NO: 12; and (iii) a CDR3 sequence that is at least about 60, 70, 80, 90, 95, 99, or 100% identical to the sequence of amino acids 99-103 of SEQ ID NO: 12.

In some embodiments, the invention provides a composition containing a ScFv where the VL region of the ScFv contains (i) a CDR1 sequence that is at least about 60, 70, 80, 90, 95, 99, or 100% identical to the sequence of amino acids 24-39 of SEQ ID NO: 14; (ii) a CDR2 sequence that is at least about 60, 70, 80, 90, 95, 99, or 100% identical to the sequence of amino acids 55-61 of SEQ ID NO: 14; and (iii) a CDR3 sequence that is at least about 60, 70, 80, 90, 95, 99, or 100% identical to the sequence of amino acids 94-102 of SEQ ID NO: 14.

Compositions Capable of Achieving Distribution of an Antibody in the Brain after Peripheral Administration.

In another aspect, the invention provides a composition containing a therapeutic antibody structure or diagnostic antibody structure, where the composition is capable of achieving an average volume of distribution in the brain of the neurotherapeutic antibody structure or diagnostic antibody structure of at least about 20, 30, 40, 50, 60, 70, 80, 80, 90, or 100 uL/gram brain following peripheral administration. In some embodiments, the therapeutic antibody structure or diagnostic antibody structure is capable of binding to a pathological substance present in the brain, where the pathological substance is associated with a brain disorder such as Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. In some embodiments, the pathological substance is a protein, nucleic acid, carbohydrate, carbohydrate polymer, lipid, glycolipid, small molecule, or combination thereof. In some embodiments, the pathological substance is a protein, e.g. AD amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid. In some embodiments, the therapeutic antibody structure is a single chain Fv antibody (ScFv). In some embodiments, the therapeutic antibody structure or diagnostic antibody structure is linked (e.g., covalently linked) to a structure that is capable of crossing the blood-brain barrier (BBB), such as a structure that is capable of crossing the BBB crosses the BBB on an endogenous BBB receptor mediated transport system, e.g., the insulin receptor, transferrin receptor, leptin receptor, lipoprotein receptor, or the IGF receptor. In some embodiments, the endogenous BBB receptor mediated transport system is the insulin BBB receptor mediated transport system. In some embodiments, the structure that is capable of crossing the BBB is capable of crossing the BBB from blood to brain and from brain to blood. In some of these embodiments, the structure that is capable of crossing the BBB is capable of crossing the BBB from blood to brain via a first receptor-mediated transport system and from brain to blood via a second receptor-mediated transport system. The first receptor-mediated transport system can be, e.g., the insulin receptor, transferrin receptor, leptin receptor, lipoprotein receptor, or the IGF receptor. In some embodiments, the first receptor mediated transport system is the insulin BBB receptor mediated transport system. In some embodiments, the second receptor-mediated transport system is the Fc-receptor-mediated transport system. The structure that is capable of crossing the BBB can be an antibody, e.g., a mAb as described herein.

Accordingly, in some embodiments, the invention provides compositions containing an antibody pharmaceutical agent covalently linked to a structure that is capable of crossing the blood-brain barrier (BBB), where the composition is capable of producing an average increase in brain volume of distribution of the antibody pharmaceutical of more than about 20, 30, 40, 50, 60, 70, 80, 80, 90, or 100 uL/gram brain following peripheral administration. The invention also provides compositions containing an antibody pharmaceutical that is covalently linked to a chimeric MAb to the human BBB insulin receptor. The invention further provides a fusion protein containing a structure capable of crossing the BBB, covalently linked to an antibody pharmaceutical that is active in the central nervous system (CNS), where the structure capable of crossing the blood-brain barrier and the antibody pharmaceutical that is active in the central nervous system each retain an average of at least about 10, 20, 30, 40, 50, 60, 70, 80, 90, 95, 99, 100, 110, or 120% of their activities, compared to their activities as separate entities. The invention also provides pharmaceutical compositions that contain one or more compositions of the invention and a pharmaceutically acceptable excipient.

In some embodiments, the invention provides compositions containing an antibody pharmaceutical agent covalently linked to a structure that is capable of crossing the blood-brain barrier (BBB), where the composition is capable of producing an average elevation of volume of distribution in the brain of the antibody pharmaceutical agent of at least about 20, 30, 40, 50, 60, 70, 80, 80, 90, or 100 uL/gram brain following peripheral administration.

"Elevation" of the agent is an increase in the brain volume of distribution of the pharmaceutical antibody compared to the concentration of the pharmaceutical antibody administered alone (i.e., not covalently linked to a structure that is capable of crossing the BBB) in different individuals. The individual in which the elevation is measured is a mammal, such as a rat, or, preferably, a primate, e.g., a monkey. An example of measurements of elevation of the level of a pharmaceutical antibody is given in FIG. 38.

The antibody pharmaceutical agent may be any suitable antibody agent, as described herein. In some embodiments, the antibody pharmaceutical is directed against the Aβ amyloid peptide of Alzheimer's disease (AD) for the diagnosis or treatment of AD. In some embodiments, the antibody pharmaceutical is directed against α-synuclein of Parkinson's disease (PD) for the diagnosis or treatment of PD. In some embodiments, the antibody pharmaceutical is directed against the huntingtin protein of Huntington's disease (HD) for the diagnosis or treatment of HD. In some embodiments, the antibody pharmaceutical is directed against the Prp protein of scrapie or mad cow disease for the diagnosis or treatment of human equivalents of scrapie. In some embodiments, the antibody pharmaceutical is directed against an envelope protein of the West Nile virus for the diagnosis or treatment of West Nile encephalitis. In some embodiments, the antibody pharmaceutical is directed against the tumor necrosis factor (TNF) related apoptosis inducing ligand (TRAIL) for the diagnosis or treatment of acquired immune deficiency syndrome (AIDS), which infects the brain. In some embodiments, the antibody pharmaceutical is directed against the nogo A protein for the diagnosis or treatment of brain injury, spinal cord injury, or stroke. In some embodiments, the antibody pharmaceutical is directed against the HER2 protein for the diagnosis or treatment of breast cancer metastatic to the brain. In some embodiments, the antibody pharmaceutical is directed against an oncogenic receptor proteins such as the epidermal growth factor receptor (EGFR) for the diagnosis or treatment of either primary brain cancer or metastatic cancer of the brain. In some embodiments, the antibody pharmaceutical is directed against an oncogenic growth factor such as the epidermal growth factor (EGF) or the hepatocyte growth factor (HGF) for the diagnosis or treatment of either primary brain cancer or metastatic cancer of the brain. In some embodiments, the antibody pharmaceutical is directed against an oligodendrocyte surface antigen for the diagnosis or treatment of demyelinating disease such as multiple sclerosis. In some embodiments, the antibody pharmaceutical is an ScFv against the Aβ peptide of AD, and contains a sequence that is at least about 60, 70, 80, 90, 95, 99, or 100% identical to the sequence of amino acids 465-708 of SEQ ID NO: 22. In some embodiments, the antibody pharmaceutical is an ScFv against the Aβ peptide of AD, and contains a VH domain with sequence that is at least about 60, 70, 80, 90, 95, 99, or 100% identical to the sequence of amino acids of SEQ ID NO: 12. In some embodiments, the antibody pharmaceutical is an ScFv against the Aβ peptide of AD, and contains a VL domain with sequence that is at least about 60, 70, 80, 90, 95, 99, or 100% identical to the sequence of amino acids of SEQ ID NO: 14. In some embodiments, the antibody pharmaceutical is an ScFv against the Aβ peptide of AD, and contains a VH domain with CDR1, CDR2, CDR3 sequences that are at least about 60, 70, 80, 90, 95, 99, or 100% identical to the sequence of amino acids 26-35, 50-66, and 99-103 of SEQ ID NO: 12, respectively. In some embodiments, the antibody pharmaceutical is an ScFv against the Aβ peptide of AD, and contains a VL domain with CDR1, CDR2, CDR3 sequences that are at least about 60, 70, 80, 90, 95, 99, or 100% identical to the sequence of amino acids 24-39, 55-61, and 94-102 of SEQ ID NO: 14, respectively. In some embodiments, the antibody pharmaceutical is an ScFv against the Aβ peptide of AD, and contains a VH domain with FR1, FR2, FR3, FR4 sequences that are at least about 60, 70, 80, 90, 95, 99, or 100% identical to the sequence of amino acids 1-25, 36-49, 67-98, 104-114 of SEQ ID NO: 12, respectively. In some embodiments, the antibody pharmaceutical is an ScFv against the Aβ peptide of AD, and contains a VL domain with FR1, FR2, FR3, FR4 sequences that are at least about 60, 70, 80, 90, 95, 99, or 100% identical to the sequence of amino acids 1-23, 40-54, 62-93, 103-113 of SEQ ID NO: 14, respectively.

In some embodiments, the invention provides compositions containing an antibody pharmaceutical agent covalently linked to a structure that is capable of crossing the BBB where the composition is capable of producing an average increase in brain volume of distribution of the antibody pharmaceutical of 20, 30, 40, 50, 60, 70, 80, 80, 90, or 100 uL/gram brain following peripheral administration, where the antibody pharmaceutical agent is a ScFv against aggregated protein and the structure that is capable of crossing the BBB is a targeting MAb to an endogenous BBB receptor mediated transport system. The targeting antibody can be glycosylated or nonglycosylated; in some embodiments, the antibody is glycosylated, e.g., in a glycosylation pattern produced by its synthesis in a CHO cell. In certain embodiments, the antibody pharmaceutical is an anti-Aβ ScFv. The targeting MAb can be an antibody to the insulin BBB receptor mediated transport system, e.g., a chimeric MAb. The targeting antibody can be a chimeric antibody with sufficient human sequence that it is suitable for administration to a human. In some embodiments, the insulin receptor is a human insulin receptor and the antibody pharmaceutical is a ScFv. In some embodiments, the ScFv contains a sequence that is at least about 60, 70, 80, 90, 95, 99, or 100% identical to the sequence of amino acids 1-244 of SEQ ID NO: 16. The ScFv can be covalently linked at its amino terminus to the carboxy terminus of the heavy chain of the targeting MAb, optionally with a linker between the termini, such as the two amino-acid linker ser-ser. In some embodiments, the heavy chain of the targeting MAb contains a sequence that is at least about 60, 70, 80, 90, 95, 99, or 100% identical to amino acids 20-462 of SEQ ID NO: 28. In some embodiments, the heavy chain of the targeting MAb contains a VH domain with CDR1, CDR2, CDR3 sequences that are at least about 60, 70, 80, 90, 95, 99, or 100% identical to the sequence of amino acids 45-54, 69-85, and 118-121 of SEQ ID NO: 28, respectively. In some embodiments, the heavy chain of the targeting MAb contains a VH domain with FR1, FR2, FR3, FR4 sequences that are at least about 60, 70, 80, 90, 95, 99, or 100% identical to the sequence of amino acids 20-44, 55-68, 86-117, 122-132 of SEQ ID NO: 28, respectively. In some embodiments, the light chain of the targeting MAb contains a sequence that is at least about 60, 70, 80, 90, 95, 99, or 100% identical to amino acids 21-234 of SEQ ID NO: 29. In some embodiments, the light chain of the targeting MAb contains a VL domain with CDR1, CDR2, CDR3 sequences that are at least about 60, 70, 80, 90, 95, 99, or 100% identical to the sequence of amino acids 44-54, 70-76, and 109-117 of SEQ ID NO: 29, respectively. In some embodiments, the light chain of the targeting MAb contains a VL domain with FR1, FR2, FR3, FR4 sequences that are at least about 60, 70, 80, 90, 95, 99, or 100% identical to the sequence of amino acids 21-43, 55-69, 77-108, 118-128 of SEQ ID NO: 29, respectively.

Compositions of MW Greater than about 1000 Daltons Capable of Crossing the BBB in Both Directions In yet another aspect, the invention provides composition of molecular weight greater than about 1000 Daltons that is capable of (i) crossing the BBB from the blood to the brain; and (ii) crossing the BBB from the brain to the blood. In some embodiments, the composition is further capable of interacting with a substance in the brain, e.g., a pathological substance associated with a brain disorder such as Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. The pathological substance can be of a type selected from the group consisting of proteins, nucleic acids, carbohydrates, carbohydrate polymers, lipids, glycolipids, small molecules, and combinations thereof. In some embodiments, the pathological substance is a protein, such as Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid.

Pharmaceutical Compositions

The invention also provides pharmaceutical compositions that contain one or more compositions of the invention and a pharmaceutically acceptable excipient. A thorough discussion of pharmaceutically acceptable carriers/excipients can be found in *Remington's Pharmaceutical Sciences*, Gennaro, A R, ed., 20th edition, 2000: Williams and Wilkins PA, USA. Pharmaceutical compositions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compositions of the invention are particular suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject.

The active therapeutic agents may be formulated within a mixture to comprise about 0.0001 to 1.0 milligrams, or about 0.001 to 0.1 milligrams, or about 1.0 to 100 milligrams or even about 0.01 to 1.0 grams per dose or so. Multiple doses can also be administered. In some embodiments, a dosage of about 5 to about 50 mg of a fusion protein of the invention is used as a unit dose for administration to a human, e.g., about 5 to about 50 mg of a fusion protein of Aβ ScFv and a HIR MAb.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and U.S. Pat. No. 5,527,288), pulmonary administration (See U.S. Pat. Nos. 6,361,760; 6,060,069; and U.S. Pat. No. 6,041,775), buccal administration (See U.S. Pat. No. 6,375,975; and U.S. Pat. No. 6,284,262), transdermal administration (See U.S. Pat. No. 6,348,210; and U.S. Pat. No. 6,322,808) and transmucosal administration (See U.S. Pat. No. 5,656,284). All such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions.

Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

In addition, the invention provides methods of manufacture. In some embodiments, the invention provides a method of manufacturing an immunoglobulin fusion protein, where the fusion protein contains an immunoglobulin heavy chain fused to a antibody pharmaceutical, by permanently introducing into a eukaryotic cell a single tandem expression vector, where both the immunoglobulin light chain gene and the gene for the immunoglobulin heavy chain fused to the antibody pharmaceutical, are incorporated into a single piece of nucleic acid, e.g., DNA. In some embodiments, the invention provides a method of manufacturing an immunoglobulin fusion protein, where the fusion protein contains an immunoglobulin light chain fused to a antibody pharmaceutical, by permanently introducing into a eukaryotic cell a single tandem expression vector, where both the immunoglobulin heavy chain gene and the gene for the immunoglobulin light chain fused to the antibody pharmaceutical, are incorporated into a single piece of nucleic acid, e.g., DNA. In some embodiments, the introduction of the vector is accomplished by permanent integration into the host cell genome. In some embodiments, the introduction of the vector is accomplished by introduction of an episomal genetic element containing the vector into the host cell. Episomal genetic elements are well-known in the art In some embodiments, the therapeutic agent is a antibody pharmaceutical. In some embodiments, the single piece of nucleic acid further includes one or more genes for selectable markers. In some embodiments, the single piece of nucleic acid further includes one or more amplification genes. In some embodiments, the immunoglobulin is an IgG, e.g., a MAb such as a chimeric MAb. The methods may further include expressing the immunoglobulin fusion protein, and/or purifying the immunoglobulin fusion protein. Exemplary methods for manufacture, including expression and purification, are given in the Examples.

However, any suitable techniques, as known in the art, may be used to manufacture, optionally express, and purify the proteins. These include non-recombinant techniques of protein synthesis, such as solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see Stewart et al. in *Solid Phase Peptide Synthesis* (1984), with the acid labile, urethane-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Synthesis* (1976) and, Stewart et al. in *Solid Phase Peptide Synthesis* (1984).

Solid phase synthesis is initiated by the coupling of the described C-terminal α-protected amino acid residue. Coupling requires activating agents, such as dicyclohexycarbodiimide with or without 1-hydroxybenzo-triazole, diisopropylcarbodiimide, or ethyldimethylaminopropylcarbodiimide. After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloro-methane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride cleaves the acid labile tertiary-butyloxycarbonyl (Boc) chemistry groups. Several nucleophilic scavengers, such as dimethylsulfide and anisole, are included to avoid side reactions especially on side chain functional groups.

Thus, in some embodiments, the invention provides a method of manufacturing an immunoglobulin fusion protein, where the fusion protein comprises an immunoglobulin heavy chain fused to an antibody structure or an immunoglobulin light chain fused to an antibody structure, by permanently introducing (e.g., integrating) into a eukaryotic cell a single tandem expression vector, where the gene for the fusion protein and another gene comprising the gene for the immunoglobulin light chain or the gene for the immunoglobulin heavy chain, are incorporated into a single piece of DNA. The fusion protein can contain an immunoglobulin heavy chain fused to an antibody structure, where both the gene for the fusion protein and the gene for the immunoglobulin light chain are incorporated into a single piece of DNA. The fusion protein can contain an immunoglobulin light chain fused to a therapeutic agent where both the gene for the fusion protein and the gene for the immunoglobulin heavy chain are incorporated into a single piece of DNA. In some embodiments, the permanently introducing is achieved by introducing a replicating episomal genetic element containing the tandem vector into the eukaryotic cell. In some embodiments, the antibody structure is a ScFv. The method may further include incorporating one or more genes for selectable markers in said single piece of DNA. The method may further include incorporating one or more amplification genes in said single piece of DNA. The immunoglobulin can be an IgG. The immunoglobulin can be an MAb. In some embodiments, the ScFv is directed against a pathological substance associated with a brain disorder. In some embodiments, the pathological substance is of a type selected from the group consisting of proteins, nucleic acids, carbohydrates, carbohydrate polymers, lipids, glycolipids, and small molecules. In some embodiments, the pathological substance is a protein. The method can further include expressing the immunoglobulin fusion protein. The method can further include purifying the immunoglobulin fusion protein.

The invention also provides methods. In some embodiments, the invention provides methods for transport of an antibody pharmaceutical active in the CNS across the BBB in an effective amount. In some embodiments, the invention provides therapeutic, diagnostic, or research methods.

Therapeutic Methods

The invention provides methods of treatment of CNS disorders or conditions by peripheral administration of an agent that does not normally cross the BBB, e.g., an antibody, in a composition that is capable of crossing the BBB from the blood to the brain. In some embodiments, the methods further include transport of the agent, e.g., the antibody (typically bound to antigen) from the brain to the blood. For treatment of aggregation diseases, the latter step can be important in allowing the disaggregated protein exit from the brain or CNS, without which the protein may reaggregate or cause other harm.

The compositions of the invention are effective in therapeutic methods of the invention, and any suitable composition described herein may be used in the methods.

Thus, in some embodiments, the invention provides a method of treating a CNS disorder by administering to an individual suffering from the disorder an effective amount of a composition containing a first structure capable of crossing the BBB from the blood to the brain, a second structure capable of interacting with a pathological substance associated with the disorder, and, optionally, a third structure capable of crossing the BBB from the brain to the blood. In some embodiments, the first and third structures (if a third structure is present) comprise an antibody, e.g., an antibody to an endogenous BBB receptor mediated transport system, as described herein. In some embodiments, the second structure comprises a ScFv, as described herein. The ScFv may be directed against a pathological substance associated with the disorder. In some embodiments, the pathological substance is of a type selected from the group consisting of proteins, nucleic acids, carbohydrates, carbohydrate polymers, lipids, glycolipids, and small molecules. In some embodiments, the pathological substance is a protein, e.g., A$\beta$ amyloid, $\alpha$-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is A$\beta$ amyloid. The method of administering can be any suitable method that introduces the agent into the peripheral circulation, e.g., oral, intravenous, intramuscular, subcutaneous, intraperitoneal, rectal, transbuccal, intranasal, transdermal, or inhalation. In some embodiments, the administering is intravenous, intramuscular, or subcutaneous. In some embodiments, the CNS disorder is an aggregate CNS disorder. In some embodiments, the CNS disorder is Alzheimer's disease, Parkinson's disease, Huntington's disease, bovine spongiform encephalopathy West Nile virus encephalitis, Neuro-AIDS, brain injury, spinal cord injury, metastatic cancer of the brain, metastatic breast cancer of the brain, primary cancer of the brain, or multiple sclerosis. In some embodiments, the CNS disorder is Alzheimer's disease. The individual can be an animal, e.g., a mammal. In some embodiments, the individual is a human. In some embodiments, the individual is administered a dose of the composition that is about 1 to about 100 mg.

In some embodiments of the invention, the methods involve administration of a composition that includes an antibody structure that is useful in therapy or diagnosis of the disorder of interest. Monoclonal antibody drug development illustrates the problems encountered when development of the delivery of agents active in the CNS, e.g., CNS drug development, is undertaken in the absence of a parallel program in delivery across the BBB, e.g., CNS drug delivery. The advances in the molecular neurosciences during the Decade of the Brain of the 1990s, and subsequently, led to identification of multiple targets in the brain for monoclonal antibody-based pharmaceuticals, including an antibody pharmaceutical directed against the A$\beta$ amyloid peptide of Alzheimer's disease (AD) for the diagnosis or treatment of AD; an antibody pharmaceutical directed against $\alpha$-synuclein of Parkinson's disease (PD) for the diagnosis or treatment of PD; an antibody pharmaceutical directed against the huntingtin protein of Huntington's disease (HD) for the diagnosis or treatment of HD; an antibody pharmaceutical directed against the Prp protein of scrapie or mad cow disease for the diagnosis or treatment of human equivalents of scrapie; an antibody pharmaceutical directed against an envelope protein of the West Nile virus for the diagnosis or treatment of West Nile encephalitis; an antibody pharmaceutical directed against the tumor necrosis factor (TNF) related apoptosis inducing ligand (TRAIL) for the diagnosis or treatment of acquired immune deficiency syndrome (AIDS), which infects the brain; an antibody pharmaceutical directed against the nogo A protein for the diagnosis or treatment of brain injury, spinal cord injury, or stroke; an antibody pharmaceutical directed against the HER2 protein for the diagnosis or treatment of breast cancer metastatic to the brain; an antibody pharmaceutical directed against an oncogenic receptor proteins such as the epidermal growth factor receptor (EGFR) for the diagnosis or treatment of either primary brain cancer or metastatic cancer of the brain; an antibody pharmaceutical directed against an oncogenic growth factor such as the epidermal growth factor (EGF) or the hepatocyte growth factor (HGF) for the diagnosis or treatment of either primary brain cancer or metastatic cancer of the brain; or an antibody pharmaceutical directed against an oligodendrocyte surface antigen for the diagnosis or treatment of demyelinating disease such as multiple sclerosis. In none of these cases, can the antibody pharmaceutical be developed as a neuropharmaceutical for human disease, because the antibodies do not cross the BBB.

Owing to the BBB problem, antibody therapeutics must be injected directly into the brain to achieve a therapeutic effect. It is not expected that antibody pharmaceuticals will have beneficial effects on brain disorders following the peripheral (intravenous, subcutaneous) administration of these molecules, because the molecules do not cross the BBB.

Antibody pharmaceuticals can be developed as drugs for the brain that are administered by peripheral routes of administration, providing the antibody is enabled to cross the BBB. Attachment of the antibody pharmaceutical, e.g. an anti-Aβ ScFv to a MTH, e.g., the chimeric HIRMAb, offers a new approach to the non-invasive delivery of antibody therapeutics to the CNS in animals, e.g., mammals such as humans for the treatment of acute brain and spinal cord conditions, such as focal brain ischemia, global brain ischemia, and spinal cord injury, and chronic treatment of neurodegenerative disease, including prion diseases, Alzheimer's disease, Parkinson's disease, Huntington's disease, or multiple sclerosis, for the treatment of brain infection, such as infection by the West Nile virus or the human immunodeficiency virus, and for the treatment of brain cancer, such as metastatic cancer to brain, or primary brain cancer.

Accordingly, in some embodiments the invention provides methods of transport of an antibody pharmaceutical active in the CNS from the peripheral circulation across the BBB in an effective amount, where the agent is covalently attached to a structure that crosses the BBB, and where the antibody pharmaceutical alone is not transported across the BBB in an effective amount. In some embodiments the invention provides methods of transport of antibody pharmaceuticals from the peripheral circulation across the BBB in a therapeutically effective amount, where the antibody pharmaceutical is covalently attached to a structure that crosses the BBB, and where the antibody pharmaceutical alone is not transported across the BBB in a therapeutically effective amount.

The invention also provides, in some embodiments, methods of treatment of disorders of the CNS by peripheral administration of an effective amount of a antibody pharmaceutical, e.g., an anti-aggregate antibody covalently linked to a structure that is capable of crossing the BBB, where the antibody pharmaceutical alone is not capable of crossing the BBB in an effective amount when administered peripherally. In some embodiments, the CNS disorder is an acute disorder, and, in some cases, may require only a single administration of the agent. In some embodiments, the CNS disorder is a chronic disorder and requires more than one administration of the agent.

In some embodiments, the effective amount, e.g., therapeutically effective amount is such that a concentration in the brain is reached of at least about 0.001, 0.01, 0.1, 0.5, 1, 2, 3, 4, 5, 6, 7, 8, 9, 10, 15, 20, 25, 30, 35, 40, 45, 50, 100, or more than 100 ng/gram brain. In some embodiments, a therapeutically effective amount, e.g., of a antibody pharmaceutical, is such that a brain level is achieved of about 0.1 to 1000, or about 1-100, or about 5-50 ng/g brain. In some embodiments, the antibody pharmaceutical is directed against the Aβ amyloid peptide of Alzheimer's disease (AD) for the diagnosis or treatment of AD. In some embodiments, the antibody pharmaceutical is directed against α-synuclein of Parkinson's disease (PD) for the diagnosis or treatment of PD. In some embodiments, the antibody pharmaceutical is directed against the huntingtin protein of Huntington's disease (HD) for the diagnosis or treatment of HD. In some embodiments, the antibody pharmaceutical is directed against the Prp protein of scrapie or mad cow disease for the diagnosis or treatment of human equivalents of scrapie. In some embodiments, the antibody pharmaceutical is directed against an envelope protein of the West Nile virus for the diagnosis or treatment of West Nile encephalitis. In some embodiments, the antibody pharmaceutical is directed against the tumor necrosis factor (TNF) related apoptosis inducing ligand (TRAIL) for the diagnosis or treatment of acquired immune deficiency syndrome (AIDS), which infects the brain. In some embodiments, the antibody pharmaceutical is directed against the nogo A protein for the diagnosis or treatment of brain injury, spinal cord injury, or stroke. In some embodiments, the antibody pharmaceutical is directed against the HER2 protein for the diagnosis or treatment of breast cancer metastatic to the brain. In some embodiments, the antibody pharmaceutical is directed against an oncogenic receptor proteins such as the epidermal growth factor receptor (EGFR) for the diagnosis or treatment of either primary brain cancer or metastatic cancer of the brain. In some embodiments, the antibody pharmaceutical is directed against an oncogenic growth factor such as the epidermal growth factor (EGF) or the hepatocyte growth factor (HGF) for the diagnosis or treatment of either primary brain cancer or metastatic cancer of the brain. In some embodiments, the antibody pharmaceutical is directed against an oligodendrocyte surface antigen for the diagnosis or treatment of demyelinating disease such as multiple sclerosis.

In some embodiments, the invention provides methods of treating a disorder of the CNS by peripherally administering to an individual in need of such treatment an effective amount of a antibody pharmaceutical, where the antibody pharmaceutical is capable of crossing the BBB to produce an average elevation of antibody pharmaceutical concentration in the brain of at least about 0.1, 1, 2, 3, 4, 5, 6, 7, 8, 9, 10, 15, 20, 25, 30, 35, 40, 45, 50, 100, or more than 100 ng/gram brain following said peripheral administration, and where the antibody pharmaceutical remains at the elevated level for about 1, 2, 3, 4, 5, 6, 7, 8, 9, 10, or more than 10 days after a single administration. In some embodiments, the antibody pharmaceutical remains at a level of greater than about 1 ng/g brain, or about 2 ng/g brain, or about 5 ng/g brain for about 2, 3, 4, 5, 6, 7, 8, 9, 10, or more than 10 days after a single administration. In some embodiments, the antibody pharmaceutical is an anti-Aβ ScFv.

In some embodiments, the invention provides methods of treating a disorder of the CNS by peripherally administering to an individual in need of such treatment an effective amount of a composition of the invention. The term "peripheral administration," as used herein, includes any method of administration that is not direct administration into the CNS, i.e., that does not involve physical penetration or disruption of the BBB. "Peripheral administration" includes, but is not limited to, intravenous intramuscular, subcutaneous, intraperitoneal, intranasal, transbuccal, transdermal, rectal, transalveolar (inhalation), or oral administration. Any suitable composition of the invention, as described herein, may be used. In some embodiments, the composition is a antibody pharmaceutical covalently linked to a chimeric HIR-MAb. In some embodiments, the antibody pharmaceutical is an anti-Aβ ScFv.

A "disorder of the CNS" or "CNS disorder," as those terms are used herein, encompasses any condition that affects the brain and/or spinal cord and that leads to suboptimal function. In some embodiments, the CNS disorder is an acute CNS disorder, such as brain injury, spinal cord injury, focal brain ischemia and global brain ischemia. In embodiments in which the disorder is an acute disorder, the composition is administered only once. In embodiments in which the disorder is an acute disorder, the composition is administered up to 10, 15, 20, 30, or more than 30 times. In some embodiments the composition is administered at a frequency of no greater than about once per week. In some embodiments, the CNS disorder is a chronic disorder. In some embodiments, the chronic disorder is selected from the group consisting of chronic neurodegenerative disease. In some embodiments where the disorder is a chronic neurodegenerative disease, the chronic neurodegenerative disease is prion diseases, Alzheimer's disease, Parkinson's disease, Huntington's disease, multiple sclerosis. In some embodiments, the chronic disorder is selected from the group consisting of chronic brain infection. In some embodiments where the disorder is a chronic brain infection, the chronic infection is West Nile virus or human immunodeficiency virus. In some embodiments, the chronic disorder is cancer. In some embodiments where the disorder is a cancer, the cancer is metastatic breast cancer to brain, metastatic cancer to brain, or primary brain cancer.

In some embodiments, the invention provides methods of treatment of the retina, or for treatment or prevention of blindness. The retina, like the brain, is protected from the blood by the blood-retinal barrier (BRB). The insulin receptor is expressed on both the BBB and the BRB, and the HIRMAb has been shown to deliver therapeutics to the retina via RMT across the BRB. An antibody against the vascular endothelial growth factor (VEGF) is protective in retinal disease, but it is necessary to inject the antibody directly into the eyeball, because antibody does not cross the BRB. In some embodiments, fusion proteins of the invention are used to treat retinal degeneration and blindness with a route of administration no more invasive than an intravenous or subcutaneous injection, because the HIRMAb delivers the antibody pharmaceutical across the BRB, so that the antibody is exposed to retinal neural cells from the blood compartment.

It will be appreciated that the compositions containing the antibody pharmaceuticals described herein may be further modified to transport a therapeutic substance to close proximity or contact with a pathological substance, e.g., such proximity or contact can be achieved by binding of the pharmaceutical antibody to the pathological substance. Such methods can involve coupling of any suitable substance to the composition that is capable of destroying or ameliorating the effect of the pathological substance while doing minimal or no damage to surrounding structures, e.g., an appropriate radionuclide, a toxin, or the like. Such methods of coupling and suitable substances are well-known in the art. It will be further appreciated that damage to surrounding areas can be kept to a minimum if the substance is further transported out of the CNS across the BBB as described herein.

Diagnostic Methods

The invention also provides diagnostic, prognostic, and treatment evaluation methods. In some embodiments, the invention provides a method of diagnosis, prognosis, or treatment evaluation by measurement of peripheral blood markers. In some embodiments, the invention provides a method of diagnosis, prognosis, or treatment evaluation by imaging of CNS structures associated with disease.

Thus, in some embodiments, the invention provides a method of diagnosis, prognosis, or evaluation of treatment of a CNS disorder by measuring the level of a composition in a body fluid of an individual, where the composition is capable of crossing the BBB from the blood to the brain, interacting with a pathological substance associated with a brain disorder, and crossing the BBB from the brain to the blood, and where the composition has been administered to the individual and has interacted with the pathological substance. In some embodiments, the brain disorder is Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, or multiple sclerosis. In some embodiments, the brain disorder is Alzheimer's disease. In some embodiments, the pathological substance is of a type selected from the group consisting of proteins, nucleic acids, carbohydrates, carbohydrate polymers, lipids, glycolipids, small molecules, or combinations thereof. In some embodiments, the pathological substance is a protein, e.g., Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid. The method may further include administering the composition to the individual. The composition may include an antibody, and may also include a ScFv. The body fluid in some embodiments is blood, serum, or plasma. Methods of measuring a marker in a body fluid are well-known, e.g., sandwich based ELISA may be used.

In some embodiments, the invention provides method of diagnosis, prognosis, or evaluation of treatment of a brain disorder by detecting a signal emitted by a composition in the CNS of an individual, where the composition includes an antibody that is capable of crossing the BBB from the blood to the brain and interacting with a pathological substance associated with a brain disorder. In some embodiments, the method further includes administering the composition to the individual. The composition may be constructed so as to emit a signal, e.g., to emit positrons, to give a radioactive signal, or to give a magnetic signal. In some embodiments, the composition is a radiopharmaceutical or a magnetopharmaceutical. In some embodiments, the composition is labeled with a substance that emits the signal. In some embodiments, the substance that emits the signal is selected from the group consisting of positron emitters, radionuclide, and magnetic substances. In some embodiments, the substance that emits the signal is a positron emitter. In some embodiments, the substance that emits the signal is a radionuclide. In some embodiments, the brain disorder is selected from the group consisting of Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, and multiple sclerosis. In some embodiments, the brain disorder is Alzheimer's disease. The pathological substance can be of a type selected from the group consisting of proteins, nucleic acids, carbohydrates, carbohydrate polymers, lipids, glycolipids, and small molecules. In some embodiments, the pathological substance is a protein, e.g., Aβ amyloid, α-synuclein, huntingtin Protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), or oligodendrocyte surface antigen. In some embodiments, the protein is Aβ amyloid. In some embodiments, the antibody comprises a ScFv.

Thus, diagnostic, prognostic, and treatment evaluation methods include the use of an antibody, e.g., positron emitter labeled, radiolabeled or magnetically labeled antibodies capable of transport across the BBB, such as the fusion of a diagnostic antibody to a targeting agent such as an MAb for an endogenous receptor in the BBB, followed by the positron, magnetic or radiolabelling of the fusion protein, followed by systemic administration, and external imaging of the localization within the brain of the antibody diagnostic. The fusion antibody can be labeled with a positron emitter for brain scanning using positron emission tomography (PET), or labeled with a radionuclide that could be detected with single photon emission computed tomography (SPECT), or magnetically labeled for MRI. For SPECT scanning, the fusion protein can be radiolabeled with 111-indium following conjugation to the fusion antibody of a suitable chelating agent. One such chelating agent is 1,4,7,10-tetraazacyclododecane-N,-N',N'',N'''-tetraacetic acid (DOTA). Administration is as described herein, and imaging may be achieved by methods well known in the art.

Formulations and Administration.

Any suitable formulation, route of administration, and dose of the compositions of the invention may be used. Formulations, doses, and routes of administration are determined by those of ordinary skill in the art with no more than routine experimentation. Compositions of the invention, e.g., fusion proteins are typically administered in a single dose, e.g., an intravenous dose, of about 0.01-1000 mg, or about 0.05-500 mg, or about 0.1-100 mg, or about 1-100 mg, or about 0.5-50 mg, or about 5-50 mg, or about 1, 2, 3, 4, 5, 6, 7, 8, 9, 10, 11, 12, 15, 20, 25, 30, 25, 40, 45, 50, 60, 70, 80, 90, or 100 mg. Typically, for the treatment of acute brain disease, such as stroke, cardiac arrest, spinal cord injury, or brain trauma, higher doses may be used, whereas for the treatment of chronic conditions such as Alzheimer's disease, Parkinson's disease, Huntington's disease, mad cow disease, MS, West Nile encephalitis, brain AIDS infection, or metastatic or primary brain cancer, lower, chronic dosing may be used. Oral administration can require a higher dosage than intravenous or subcutaneous dosing, depending on the efficiency of absorption and possible metabolism of the protein, as is known in the art, and may be adjusted from the foregoing based on routine experimentation.

For intravenous or subcutaneous administration, formulations of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

Figure 37:
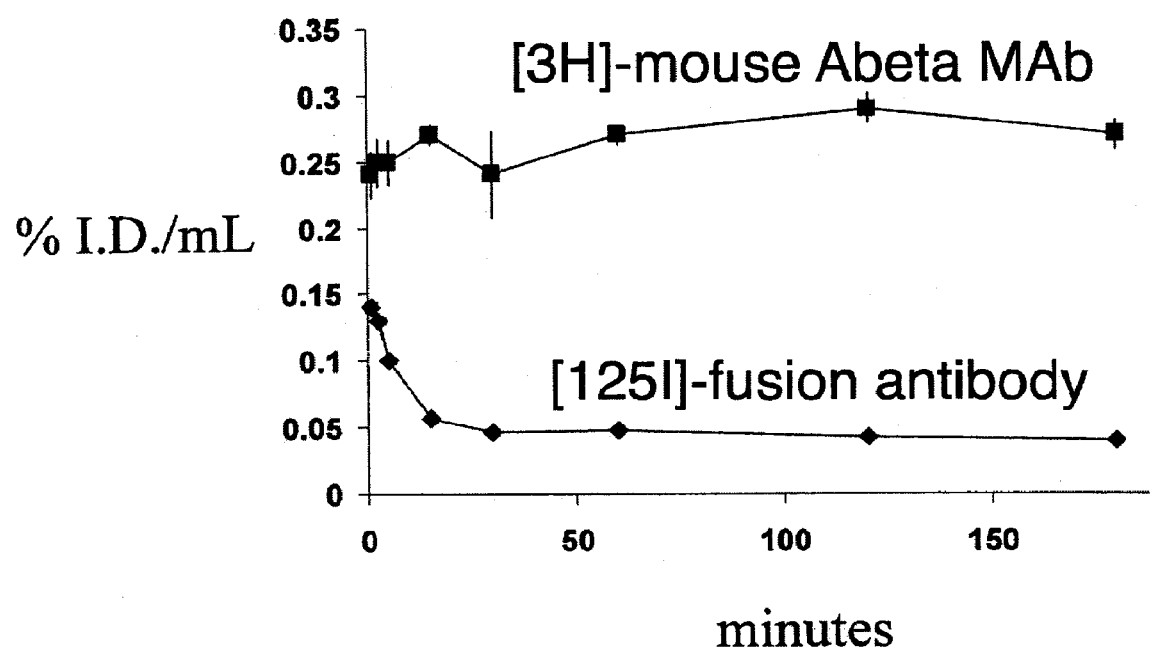
FIG. 37. In vivo pharmacokinetics in adult Rhesus monkey. The [$^{125}$I]-fusion antibody, and the [$^3$H]-mouse anti-Aβ antibody, were injected intravenously into the adult Rhesus monkey and serum concentrations [% of injected dose (I.D.)/mL] determined over a 3 hour period. There is no measurable clearance from blood of the [$^{125}$I]-mouse anti-Aβ antibody during this time period, whereas the fusion antibody is cleared from serum.
Figure 38:
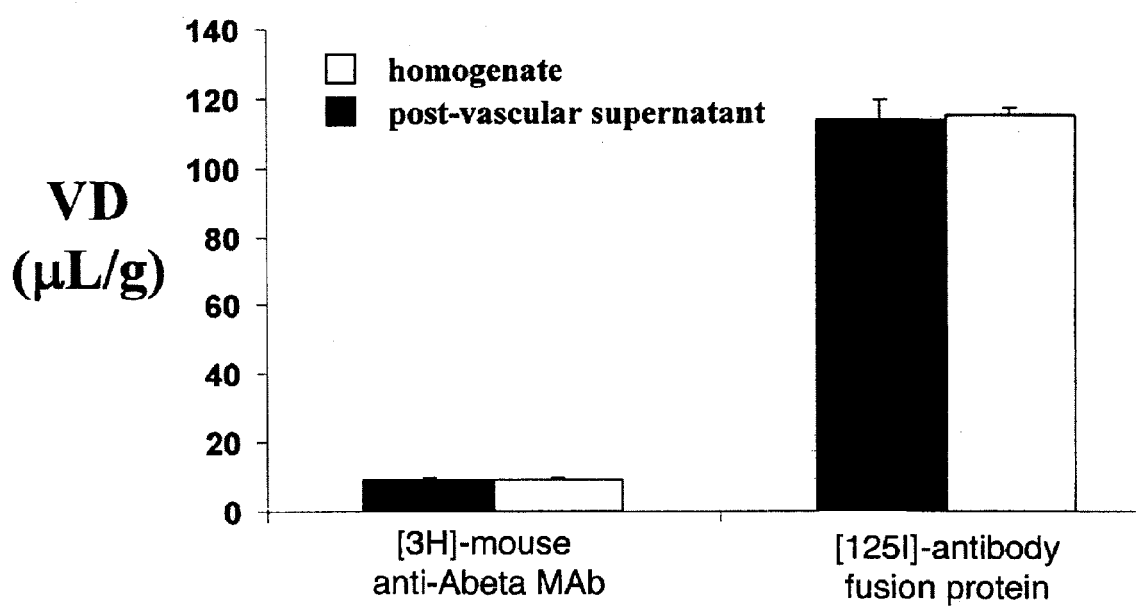
FIG. 38. Brain volume of distribution (VD) of the [$^3$H]-mouse anti-Aβ antibody and the [$^{125}$I]-fusion antibody in Rhesus monkey brain at 3 hours after a single intravenous injection of both labeled antibodies. The VD for both the homogenate and the post-vascular supernatant is shown. The VD for the [$^3$H]-mouse anti-Aβ antibody, 10 uL/g, is equal to the brain blood volume, and indicates this antibody is not transported across the primate BBB in vivo. The VD for the [$^{125}$I]-fusion antibody is >10-fold higher than for the [$^3$H]-mouse anti-Aβ antibody, in both the brain homogenate and the post-vascular supernatant, which indicates the [$^{125}$I]-fusion antibody is transported across the BBB from blood to brain.
Figure 41:
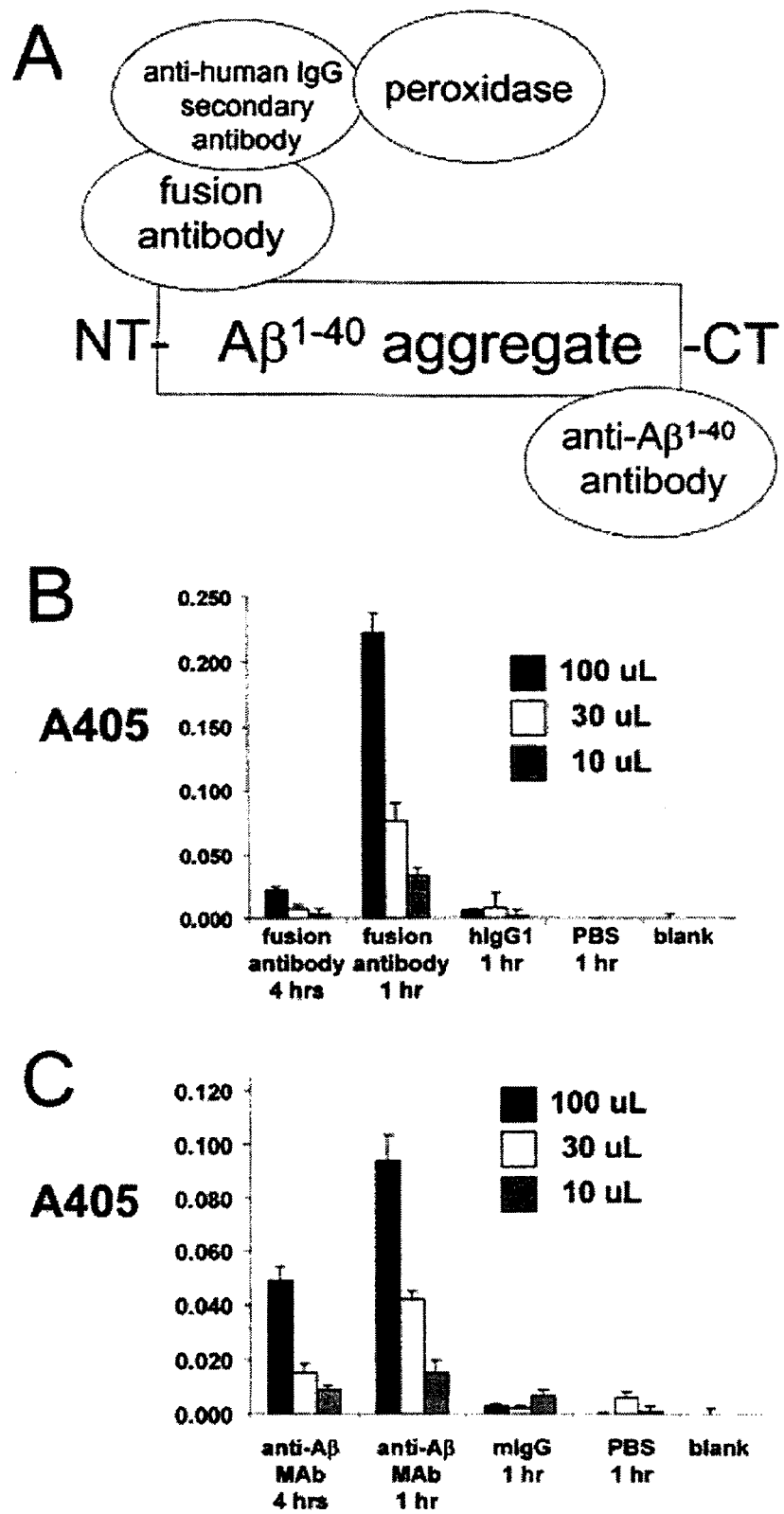
FIG. 41. (A) Outline of Aβ plaque disaggregation assay. The secondary antibody is an anti-human IgG for study of the fusion antibody, and is an anti-mouse IgG for study of the mouse anti-Aβ MAb. (B, C) Disaggreagation of Aβ amyloid in vitro by the fusion antibody (B) or by the mouse anti-AβMAb (C). Aβ$^{1-40}$ aggregates were formed over 6 days, followed by incubation with the fusion antibody, with human IgG1 (hIgG1), or with phosphate buffered saline (PBS) for either 1 or 4 hours at 37 C (B), or with the mouse anti-Aβ antibody, with non-immune mouse IgG, or PBS for either 1 or 4 hours at 37 C (C). In parallel, an antibody that binds to the carboxyl terminal region of the Aβ$^{1-40}$ peptide was plated in 96 well plates, as depicted in panel A. The anti-Aβ ScFv portion of the fusion antibody, or the mouse anti-Aβ MAb, binds to the amino terminal part of Aβ$^{1-40}$. Therefore, a positive ELISA signal is generated only if plaque is present. The data show that the fusion antibody, and the mouse anti-Aβ MAb, selectively bind to Aβ$^{1-40}$ plaque, and that this binding causes disaggregation over a 4 hour period.

Dosages for humans can be calculated from appropriate animal data. For example, human dosing of a ScFv-MAb fusion protein is based on pre-clinical pharmacokinetic studies, and these measurements have been performed in Rhesus monkeys. The in vitro disaggregation assay, FIG. 41, shows that a concentration of 250 ng/1 mL of anti-Aβ ScFv/ HIRMAb fusion protein causes rapid disaggregation of amyloid plaque. The studies in Rhesus monkey shows the brain volume of distribution of the anti-Aβ ScFv/HIRMAb fusion protein is 100 uL/gram brain (FIG. 38). Therefore, in order to achieve a brain concentration of 250 ng/gram brain, the corresponding plasma concentration of the anti-Aβ ScFv/ HIRMAb fusion protein must be 5 ug/mL. The concentration in blood of the anti-Aβ ScFv/HIRMAb fusion protein in a 7 kg primate is 0.05% ID/mL (FIG. 37). Therefore, the concentration in blood in a 70 kg human will be 0.005% I.D./mL. If the I.D.=100 mg in a human, then the blood level will be 5 ug/ml and the concentration of the anti-Aβ ScFv/HIRMAb fusion protein in human brain will be 250 ng/g, which will cause rapid disaggregation of amyloid plaque.

The antibody fusion protein can be formulated for chronic use for the treatment of a chronic CNS disorder, e.g., neurodegenerative disease, stroke or brain/spinal cord injury rehabilitation, or depression. Chronic treatment may involve daily, weekly, bi-weekly administration of the composition of the invention, e.g., fusion protein either intravenously, intramuscularly, or subcutaneous in formulations similar to that used for acute treatment. Alternatively, the composition, e.g., fusion protein may be formulated as part of a bio-degradable polymer, and administered on a monthly schedule.

Combination Therapies.

The composition of the invention, e.g., fusion protein may be administered as part of a combination therapy. The combination therapy involves the administration of a composition of the invention in combination with another therapy for the CNS disorder being treated. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

Other CNS disorder treatment agents that may be used in methods of the invention include, without limitation, thrombolytic therapy for stroke, cholinergic-directed therapy for Alzheimer's disease, dopamine restoration therapy for Parkinson's disease, RNA interference therapy for genetic disorders, cancer, or infections, and anti-convulsant therapy for epilepsy. Dosages, routes of administration, administration regimes, and the like for these agents are well-known in the art.

In some embodiments, the composition, e.g., antibody fusion protein is co-administered to the patient with another medication, either within the same formulation or as a separate composition. For example, the antibody fusion protein could be formulated with another fusion protein that is also designed to deliver across the human blood-brain barrier a recombinant protein other than an anti-Aβ ScFv. The fusion protein may be formulated in combination with other large or small molecules.

Compositions of the invention, e.g., fusion proteins, may be provided as a kit that includes the formulation, e.g., antibody fusion protein in a container and in suitable packaging. The composition can be provided in a dry powder form in solid form (i.e., lyophilized), in solution, or in suspension. If the composition is a protein, to the proteins may have been added emulsifiers, salts, preservatives, other proteins, nucleic acids, protease inhibitors, antibiotics, perfumes, polysaccharides, adhesive agents, polymers, microfibrils, oils, etc. The composition is packaged for transport, storage and/or use by a consumer. Such packaging of therapeutic compositions for transport, storage, and use is well-known in the art. Packaged compositions may include further components for the dispensing and storage of the composition, and may also include separately packaged diluent comprised of, e.g., sterile water or a suitable buffer, for solubilizing the formulation, e.g., fusion protein prior to administration to the patient. Kits of the invention may also include written materials, including instructions for use, results of clinical studies, desired outcome and expected course of treatment, information about precautions and side effects, and the like. The kits may optionally further contain other components, such as gloves, scissors, tape, implements for disposal of used vials and other waste, masks, antiseptic, antibiotics, and the like.

ABBREVIATIONS

9E10 MAb against 10-amino acid epitope of c-myc oncogene
AD Alzheimer's disease
ALS amyotrophic lateral sclerosis
anti-mAβScFv same as mAβScFv
AUC area under the plasma concentration curve
AUCss steady state AUC
Aβ amyloid peptide of AD
$A\beta^{1-40}$ 40 amino acid Aβ amyloid peptide of AD
$A\beta^{1-42}$ 42 amino acid Aβ amyloid peptide of AD
$A\beta^{1-43}$ 43 amino acid Aβ amyloid peptide of AD
BBB blood-brain barrier
BGH bovine growth hormone
Boc tert-butyloxycarbonyl
BRB blood-retinal barrier
CDR complementarity determining region
CED convection enhanced diffusion
CH1 first part of IgG constant region
CH2 second part of IgG constant region
CH3 third part of IgG constant region
CHO Chinese hamster ovary cell line
CLBA competitive ligand binding assay
CLss steady state systemic clearance
CMV cytomegalovirus
CNS central nervous system
COS CV-1 origin SV40 cell line
CT carboxyl terminus
Da Dalton
DHFR dihydrofolate reductase
DOTA 1,4,7,10-tetraazacyclododecane-N,-N',N'',N'''-tetraacetic acid
DPM disintegrations per minute
E envelope protein of WNV
ECD extracellular domain
EDC N-methyl-N'-3-(dimethylaminopropyl)carbodiimide hydrochloride
EGF epidermal growth factor
EGFR EGF receptor
ELISA enzyme linked immunosorbant assay
FcR Fc receptor
FcRn neonatal FcR
FR framework region
FWD forward
HC heavy chain
HC-1 HC of chimeric HIRMAb
HD Huntington's disease
HGF hepatocyte growth factor
HIR human insulin receptor
HIRMAb monoclonal antibody to human insulin receptor
HIR-HC heavy chain (HC) of HIRMAb
HIR-LC light chain (LC) of HIRMAb
HIRMAb-mAβScFv fusion protein of HIRMAb and mAβ-ScFv
HIV human immune deficiency virus
IC intra-cerebral
ICC immunocytochemistry
ICV intra-cerebroventricular
ID injected dose
IEF isoelectric focusing
IGF insulin-like growth factor
IgG immunoglobulin G
kb kilobase
IRMA immunoradiometric assay
LC light chain
LDL low density lipoprotein
MAb monoclonal antibody
mAβScFv murine ScFv against Aβ peptide
MRT mean residence time
MS multiple sclerosis
MTH molecular Trojan horse
MTX methotrexate
MW molecular weight
NHS N-hydroxy succinimide
NK new Kozak sequence
NT amino terminus
NSP new signal peptide
nt nucleotide
ODN oligodeoxynucleotide
orf open reading frame
pA poly-A signal
PBS phosphate buffered saline
PCR polymerase chain reaction
PD Parkinson's disease
PET positron emission tomography
PNA peptide nucleic acid
PRO promoter
Prp prion protein
RE restriction endonuclease
REV reverse
RMT receptor mediated transport
RNAi RNA interference
RT reverse transcriptase
SA streptavidin
ScFv single chain Fv antibody
ScFv-MAb fusion antibody of a tetrameric MAb and a ScFv
SCLC small cell lung cancer
SDM site-directed mutagenesis
SDS-PAGE sodium dodecyl sulfate polyacrylamide gel electrophoresis
SFM serum free medium
SPECT single photon emission computed tomography
TAA tumor-associated antigen
TNF tumor necrosis factor
TRAIL TNF-related apoptosis-inducing ligand
TV tandem vector
VD volume of distribution
VEGF vascular endothelial growth factor
VH variable region of heavy chain
VL variable region of light chain
Vss steady state systemic volume of distribution
WNV West Nile virus

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Genetic Engineering of a Eukaryotic Expression Plasmid Encoding an Anti-Aβ ScFv

Figure 1B:
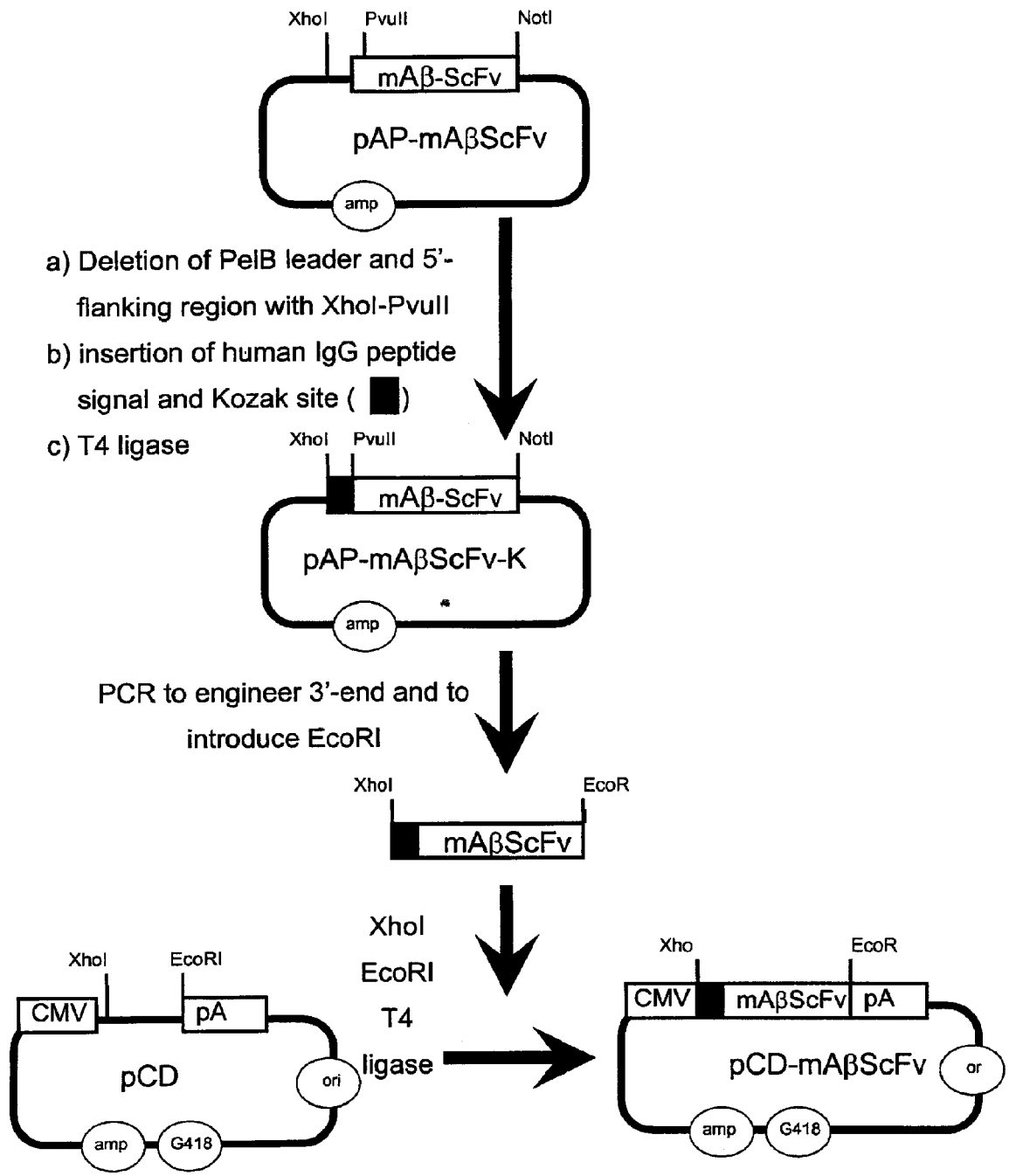
FIG. 1B. Diagram showing genetic engineering of a eukaryotic expression plasmid encoding mAβScFv cDNA with an IgG signal peptide and Kozak site. The eukaryotic expression plasmid contains the cytomegalovirus (CMV) promoter and a polyA (pA) transcription termination sequence.
Figure 3:
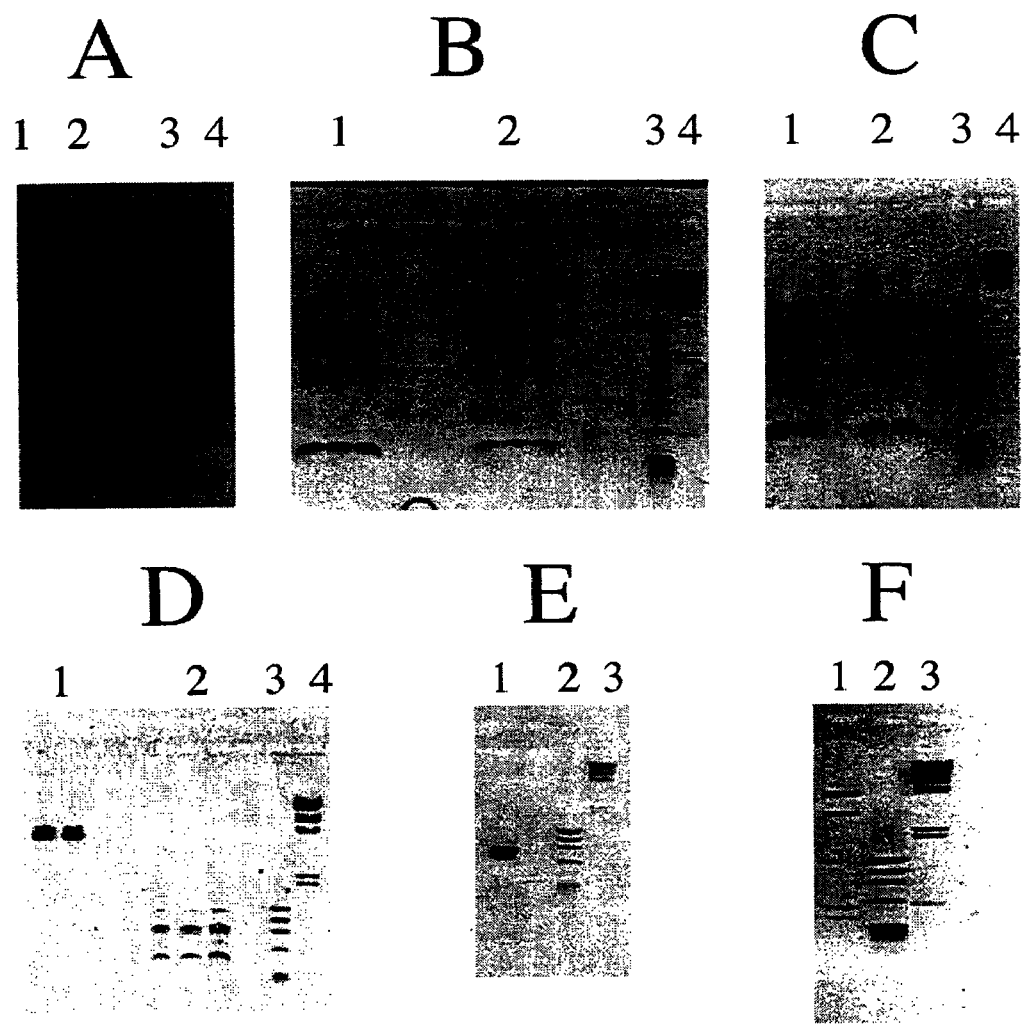
FIG. 3. Ethidium bromide staining agarose gels showing the size of various constructs and PCR amplified cDNAs that are intermediates in the construction of the fusion gene encoding the fusion antibody where the mAβScFv is fused at its amino terminus to the carboxyl terminus of the heavy chain of the chimeric HIRMAb. (A) Lanes 1 and 2, PCR amplified 0.4 kb mAβScFv VH cDNA and PCR amplified 0.4 kb mAβScFv VL cDNA, respectively. PolyA+RNA was isolated form the murine hybridoma expressing the anti-Aβ MAb, subjected to reverse transcription and PCR amplification with VH and VL specific ODN primers described in Table 2. Lane 3, molecular weight (MW) size standards ranging from 1.4-0.1 kb. Lane 4, MW size standards ranging from 23-2.0 kb. (B) Lane 1, NcoI and HindIII digestion of pPC-mAβ-VH showing the expected band size of ~0.4 kb corresponding to the VH of the anti-Aβ MAb, and the backbone vector (~3.0 kb). Lane 2, NcoI and HindIII digestion of pAP-xScFv cloning vector showing the expected band size of ~3.5 kb corresponding to the vector backbone, and the xVH (~0.4 kb), where xVH is the VH of a non-related ScFv contained in the original pAP-xScFv plasmid (FIG. 1A). Lanes 3 and 4 are same MW size standards as shown in panel A. (C) Lane 1, MluI and NotI digestion of pPC-mAβ-VL showing the expected band size of ~0.4 kb corresponding to the VL of the anti-AβMAb, and the backbone vector (~3.0 kb). Lane 2, MluI and NotI digestion of p-mAβ-VH showing the expected band size of ~3.5 kb corresponding to the plasmid backbone, and xVL (~0.4 kb), where xVL is the VL of a non-related ScFv contained in the original pAP-xScFv plasmid. Lanes 3 and 4 are same MW size standards as shown in panel A. (D) Lane 1, XhoI-EcoRI digestion of a eukaryotic expression plasmid, pCD, showing the expected band size of ~5.4 kb corresponding the linear backbone vector (total of 2 lanes). Lane 2, XhoI-EcoRI digestion of PCR generated mAβScFv cDNA showing the expected band size of ~0.8 kb (total of 3 lanes) and minor bands of lower and higher MW size. Lanes 3 and 4 are same MW size standards as shown in panel A. (E) Lane 1, PCR product showing the expected single band of ~0.8 kb corresponding to the mAβScFv cDNA to be used in the engineering of the HIRMAb-mAβScFv fusion antibody tandem expression vector. Lanes 2 and 3 are same MW size standards as shown in panel A. (F) HindIII restriction endonuclease mapping of the HIRMAb-mAβScFv fusion antibody tandem vector showing the expected bands of 6.5, 3.6, 0.5 and 0.4 kb, respectively. Lanes 2 and 3 are same MW size standards as shown in panel A.

The genetic engineering of a eukaryotic expression vector encoding a mouse single chain antibody to human Aβ peptide is outlined in FIG. 1. The final protein expression vector was designated pCD-mAβScFv (FIG. 1B). This vector was designed to produce a single chain Fv antibody (ScFv), comprised of both the variable region of the heavy chain (VH) and the variable region of the light chain (VL) of a mouse (m) monoclonal antibody to human Aβ peptide; this ScFv is designated 1 mAβScFv. The VH and VL are fused by a 17 amino acid linker to form the ScFv. The pCD-mAβScFv plasmid encodes the mAβScFv with a human IgG signal peptide (FIG. 11; amino acid residues 1-19 of SEQ ID NO. 18), and its expression is driven by the CMV promoter. The pCD-mAβ-ScFv expression vector also encompasses a full Kozak sequence domain (i.e. GCCGCCACCATGG; nucleotides 732-744 of SEQ ID NO. 27) prior to the ATG methionine initiation codon (ATG) (FIG. 1B). For the cloning of either the VH and VL cDNA of the mAβScFv, poly A+ RNA was isolated from the original murine hybridoma cell line and subjected to reverse transcription (RT) using oligo(dT)$_{12-18}$ and SuperScript II reverse transcriptase (Invitrogen, Carlsbad, Calif.) to form single stranded complementary DNA (scDNA). The VL cDNA was produced by polymerase chain reaction (PCR) using the VH or VL scDNA as template and the VL-specific forward (FWD) or reverse (REV) oligodeoxynucleotide (ODN) PCR primers (Table 2, SEQ ID NO. 1 and 2, respectively). VL forward and reverse ODN primers introduce MluI and NotI restriction endonuclease (RE) sites, respectively, for directional cloning into the prokaryote ScFv expression vector pAP-xScFv (FIG. 1A). The mAβ VH cDNA was obtained by PCR using the mAβscDNA as template and the VH-specific forward and reverse ODN PCR primers (Table 2, SEQ ID NO. 3 and 4, respectively). VH forward and reverse ODN primers introduce NcoI and HindIII RE sites, respectively, for directional cloning into the prokaryote ScFv expression vector pAP-xScFv (FIG. 1A). The PCR reactions were performed with PfuUltra DNA polymerase (Stratagene, La Jolla, Calif.), and PCR products were resolved by agarose gel electrophoresis (FIG. 3A). The expected major cDNA bands corresponding to the PCR amplified ~0.4 kilobase (kb) mAβ VL cDNA and PCR amplified ~0.4 kb mAβ VH cDNA are shown in FIG. 3A, lanes 1 and 2, respectively. The VH and VL bands were isolated from the agarose gels and subcloned into the pPCR-Script to form pPC-mAβ-VH and pPC-mAβ-VL (FIG. 1A) using the PCR-Script Amp Cloning Kit (Stratagene) for further characterization and DNA sequencing.

TABLE 2

Oligodeoxynucleotides used in the reverse transcription PCR cloning of the VH and VL domains of the mouse anti-Aβ antibody (mAβ), and in the engineering of the HIR-mAβ fusion antibody VL forward (SEQ ID NO. 1):
5'-AATTTTCAGAAGCACGCGTAGATATC(G/T)TG(A/C)T(G/C)ACC CAA(A/T)CTCCA-3'

TABLE 2-continued

Oligodeoxynucleotides used in the reverse transcription PCR cloning of the VH and VL domains of the mouse anti-Aβ antibody (mAβ), and in the engineering of the HIR-mAβ fusion antibody VL reverse (SEQ ID NO. 2):
5'-GAAGATGGATCCAGCGGCCGCAGCATCAGC-3'

VH forward (SEQ ID NO. 3):
5'-CAGCCGGCCATGGCGCAGGT(G/C)CAGCTGCAG(G/C)AG-3'

VH reverse (SEQ ID NO. 4):
5'-CCAGGGGCCAGTGGATAGACAAGCTTGGGTGTCGTTTT-3'

Human IgG peptide signal FWD (SEQ ID NO. 5):
5'ATCCTCGAGGCCGCCACCATGGACTGGACCTGGAGGGTGTTCTGCCTG
CTTGCAGTGGCCCCCGGAGCCCACAGCCAGGTCCAGCTGCAG-3'

Human IgG peptide signal REV (SEQ ID NO. 6):
5'CTGCAGCTGGACCTGGCTGTGGGCTCCGGGGGCCACTGCAAGCAGGCA
GAACACCCTCCAGGTCCAGTCCATGGTGGCGGCCTCGAGGAT-3'

Human IgG peptide signal XhoI PCR FWD (SEQ ID NO. 7):
5'-ATCCTCGAGGCCGCCACC-3'

Human IgG peptide signal EcoRI PCR REV (SEQ ID NO. 8):
5'-GATGAATTCTTATAGATCTTCTTCTGA-3'

Mature mAβ ScFv PCR FWD (SEQ ID NO. 9):
5'-phosphate-CACAGGTCCAGCTGCAGCAGT-3'

Mature mAβ ScFv PCR REV (SEQ ID NO. 10):
5'-phosphate-TTACCGTTTTATTTCCAGCTTGGTC-3'

Human IgG peptide signal HIR FWD (SEQ ID NO. 31):
CGAGCGGCCGCCACTGTGCTGGATATTCCACCATGGACTGGACCTGGAGG
GTGTTCTGCCTGCTTGCAGTGGCCCCCGGAGCCCACAGCCAGGTTCAGCT
GCAGCAGTCTGGACCTGAGCTGGTGAAGCCTGGGGCTTTAGTGAAGATAT
CCTG Human IgG peptide signal HIR REV (SEQ ID NO. 32):
CAGGATATCTTCACTAAAGCCCCAGGCTTCACCAGCTCAGGTCCAGACTG
CTGCAGCTGAACCTGGCTGTGGGCTCCGGGGGCCACTGCAAGCAGGCAGA
ACACCCTCCAGGTCCAGTCCATGGTGGAATATCCAGCACAGTGGCGGCCG
CTCG The nucleotide and deduced amino acid sequence of the mAβ VH are shown in FIGS. 4 (SEQ ID NO. 11) and 5 (SEQ ID NO. 12), respectively. The mAβ VH cDNA sequence was 100% confirmed in several isolated clones, and it is compatible with the consensus sequence for the mouse gamma heavy chain. The FR1-4 and CDR1-3 domain structure of the mAβ VH amino acid sequence in shown in FIG. 25. The nucleotide and deduced amino acid sequence of the mAβ VL are shown in FIGS. 6 (SEQ ID NO. 13) and 7 (SEQ ID NO. 14), respectively. The 1 mAβ VH cDNA sequence was 100% confirmed in several isolated clones, and it is compatible with the consensus sequence for the mouse kappa VL. The FR1-4 and CDR1-3 domain structure of the mAβ VL amino acid sequence is shown in FIG. 25.

The amino acids comprising the CDR1, CDR2, and CDR3 of the anti-Aβ MAb VH are in bold font in FIG. 5, and correspond to amino acids 26-35, 50-66, and 99-103, respectively of SEQ ID NO. 12. The amino acids comprising the CDR1, CDR2, and CDR3 of the anti-AD MAb VL are in bold font in FIG. 7, and correspond to amino acids 24-39, 55-61, and 94-102, respectively of SEQ ID NO. 14.

Both mAβ VH and VL cDNAs were subcloned into the prokaryote ScFv expression vector pAP-xScFv to create the intermediate mAβ-ScFv expression plasmid pAP-mAβScFv (FIG. 1A). The mAβ VH cDNA in pPC-mAβ-VH and the pAP-xScFv plasmid were digested with NcoI and HindIII.

The expected mAβ-VH of ~0.4 kb and the pAP-xScFv backbone of ~3.5 kb (FIG. 3B, lanes 1 and 2, respectively) were gel-purified. The mAβ-VH cDNA was ligated into the pAP-xScFv backbone at the same RE sites to form the intermediate plasmid pAP-mAβ-VH (FIG. 1A). The pAP-mAβ-VH plasmid was isolated and characterized by DNA sequence, which confirmed 100% the expected DNA sequence for mAβ-VH (FIG. 4, SEQ ID NO. 11). The engineering of the pAP-mAβ-ScFv was completed by insertion of the mAβ-VL into the pAP-mAβ-VH at MluI and NotI sites (FIG. 1A). Both pAP-mAβ-VH and the pPC-mAβ-VL clones were digested with MluI and NotI. The ~0.4 kb mAβ-VL cDNA and the ~3.5 kb pAP-mAβ-VH plasmid backbone (FIG. 3C, lanes 1 and 2, respectively) were gel-purified. The mAβ-VL cDNA was ligated into pAP-mAβ-VH to form the pAP-mAβ-ScFv (FIG. 1A). The pAP-mAβ-ScFv plasmid was isolated and validated by DNA sequencing. The nucleotide and deduced amino acid sequence of the pAP-mAβ-ScFv are shown in FIGS. 8 (SEQ ID NO. 15) and 9 (SEQ ID NO. 16), respectively. The regions corresponding to mAβ VH and VL cDNAs in pAP-mAβ-ScFv are 100% similar to the ones of the individual VH and VL genes shown FIGS. 4 and 6, respectively. The pAP-xScFv prokaryote expression vector introduces a c-myc epitope (FIG. 9, amino acid residues 255-265) and a 5-histidine (His$_5$) tag (SEQ ID NO:69) at the end of the VL region (FIG. 9).

The engineering of the mAβ-ScFv eukaryotic expression vector, clone pCD-mAβ-ScFv, is summarized in FIG. 1B and it was performed by (a) deletion of the prokaryote PelB leader sequence in pAP-mAβ-ScFv, (b) insertion of a human IgG signal peptide including a full Kozak sequence domain to form pAP-mAβ-ScFv-K, (c) PCR cloning of the mAβ-ScFv-K cDNA to introduce XhoI and EcoRI RE sites, and (d) subcloning of the PCR-generated XhoI-mAβ-ScFv-K-EcoRI cDNA into the eukaryote expression vector pCD to form the pCD-mAβ-ScFv plasmid. A DNA fragment of the prokaryote expression vector pAP-mAβ-ScFv, including the PelB leader sequence, was deleted with XhoI and PvuII, the latter located at the second amino acid of the mAβ-VH. The backbone vector was gel-purified. In parallel, ODNs corresponding to the artificial new human peptide signal (Table 2, human IgG peptide signal FWD and REV ODNs, respectively, SEQ ID NO. 5 and 6) were annealed at 65° C. and purified with Qiagen PCR extraction kit (Valencia, Calif.). The double stranded (ds) ODN was digested with XhoI and PvuII, purified with Qiagen PCR extraction kit and inserted at the same RE sites in the pAP-mAβ-ScFv-XhoI-PvuII vector to form the pAP-mAβ-ScFv-K intermediate plasmid (FIG. 1B). The dsODN inserts a full Kozak site and a human IgG signal peptide (amino acid residues 1-19, SEQ ID NO. 18). Positive clones were identified by RE mapping with EcoRI, a site that was present in the deleted DNA fragment of the pAP-mAβ-ScFv, but absent in the inserted human IgG signal peptide sequence. The mAβ-ScFv cDNA was further engineered to introduce XhoI and EcoRI RE sites by PCR for directional subcloning into the eukaryote expression vector pCD (FIG. 1B). The PCR cloning of the mAβ-ScFv cDNA was performed with the human IgG peptide signal XhoI PCR FWD and EcoRI PCR REV ODNs (Table 2, SEQ ID NO. 7 and 8, respectively). The REV ODN also introduces a TAA stop codon after the c-myc tag of the vector (FIG. 10). Both the PCR products and the pCD vector were digested with XhoI and EcoRI (FIG. 3D). The ~5.4 kb pCD and the ~0.8 kb mAβ-ScFv cDNA (FIG. 3D, lanes 1 and 2, respectively) were gel-purified and ligated at the same RE sites to form the pCD-mAβScFv expression vector (FIG. 1B). The pCD-mAβScFv clone was validated by DNA sequencing, and both the nucleotide and deduced amino acid sequences are shown in FIGS. 10 and 11 (SEQ ID NO. 17 and 18), respectively. The nucleotide and amino acid sequences corresponding to mAβ VH and VL cDNAs in pCD-mAβScFv (including the VH-VL linker) are 100% identical to the sequences in the pAP-mAβ-ScFv vector shown FIGS. 8 and 9, respectively. The pCD-mAβScFv vector does not have the His$_5$ tag (SEQ ID NO:69) (FIG. 11), so the TAA stop codon follows the end of the c-myc epitope (FIG. 10). The pCD-mAβScFv eukaryote expression plasmid is driven by the CMV promoter, has a full Kozak domain before the ATG initiation codon, and contains a human IgG signal peptide.

Example 2

Figure 2:
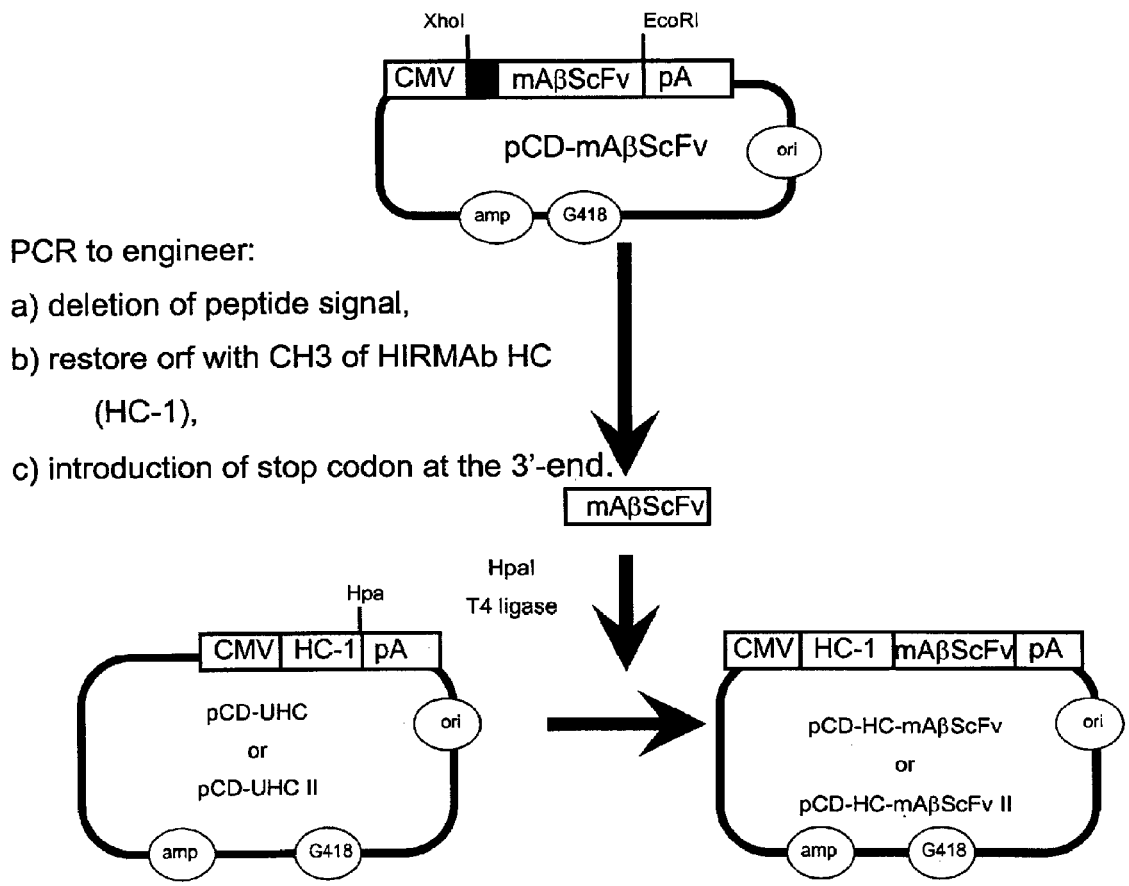
FIG. 2. Diagram showing the genetic engineering of a eukaryotic expression plasmid encoding the mAβScFv cDNA that is fused at its 5'-end to the 3'-end of the cDNA encoding the heavy chain (HC) of the chimeric HIRMAb (HC-1). Amp=ampicillin resistance gene; G418=neomycin resistance gene; ori=SV40 origin of replication; CMV=cytomegalovirus promoter; pA=poly A transcription termination sequence.

Genetic Engineering of a Eukaryotic Expression Plasmid Encoding a Fusion Protein of the Anti-Aβ ScFv and the Chimeric HIRMAb Heavy Chain The genetic engineering of the eukaryotic expression vector encoding for the heavy chain of the fusion antibody was performed as summarized in FIG. 2. The fusion antibody heavy chain is comprised of the mAβScFv, which is fused at its amino terminus to the carboxyl terminus of the heavy chain (HC) of the chimeric HIRMAb; the HC of the chimeric HIRMAb is designated HC-1 in FIG. 2. The engineering of this gene encoding the HC of the fusion antibody was done in 2 steps: (a) PCR cloning of the mAβScFv and (b) insertion of this cDNA into the universal HIR heavy chain expression vector, designated pCD-UHC (FIG. 2), to form the pCD-HC-mAβScFv plasmid (FIG. 2). In the pCD-UHC expression vector, the chimeric HIRMAb heavy chain (HC) cDNA is preceded by the CMV promoter and is followed by the bovine growth hormone (BGH) polyadenylation sequence (pA). The pCD-UHC has a single HpaI site at the end of the HIRMAb HC open reading frame (orf) for insertion of genes of interest and expression of HIRMAb HC fusion proteins. For the PCR cloning of the mature mAβScFv, the mature mAβScFv PCR FWD ODN (Table 2, SEQ ID NO. 9) was designed, so as to delete the human IgG peptide leader sequence from the mAβ-ScFv cDNA, while maintaining the orf at the CH3 region of the HIRMAb heavy chain of the pCD-UHC. This results in the insertion of a Ser-Ser linker between the end of the CH3 region of the HIR MAb heavy chain, and the mAβScFv cDNA. The mature mAβScFv REV PCR ODN (Table 2, SEQ ID NO. 10) was designed to delete the c-myc tag, and the linker [ADAAAAGS (amino acids 245-252, SEQ ID NO. 16; FIG. 9)], between the end of the mAβScFv cDNA and the c-myc tag, and to introduce a stop codon, TAA. Both PCR primers were 5'-phosphorylated for direct ligation into the pCD-UHC at the HpaI site. The PCR cloning of the mature mAβScFv cDNA was done using the pCD-mAβScFv DNA as template. Agarose gel electrophoresis of the PCR products showed the expected single band of ~0.8 kb corresponding to the mature mAβScFv cDNA (lane 1, FIG. 3E). The engineered mature mAβScFv was ligated at the HpaI site in pCD-UHC to form the pCD-HC-mAβScFv expression vector (FIG. 2). The pCD-HC-mAβScFv clone was validated by DNA sequencing, and both the nucleotide and deduced amino acid sequences are shown in FIGS. 12 and 13 (SEQ ID NO. 19 and 20), respectively. The nucleotide and amino acid sequence of the reconstructed carboxyl terminus at the CH3 region of the HIR mAb heavy chain confirmed a 2-amino acid linker (Ser-Ser) prior to the mature mAβScFv and the TAA stop codon, both introduced in the PCR cloning step (FIGS. 12 and 13)

Example 3

I2V Site-Directed Mutagenesis of the FR1 of the VH of the Anti-Aβ ScFv

Amino acid microsequencing analysis of the amino terminus of the light chain of the mAβ MAβ confirmed 11 residues, with the exception of the amino acid at position 2 of the light chain (FIG. 7). The PCR primers introduced a isoleucine (I or Ile) at position 2, whereas the hybridoma generated light chain contained a valine (V or Val) at position 2. The Ile residue was most likely introduced during the PCR cloning of the mAβ VL due to the use of degenerate primers used in the PCR amplification of this cDNA. It was necessary to perform site-directed mutagenesis (SDM) to change the I residue to a V residue at position 2, and this SDM is designated the I2V change. A new eukaryotic expression vector encoding for the heavy chain of the fusion antibody carrying the I2V VL mutant was constructed. The SDM was performed using the QuickChange II XL SDM kit (Stratagene) and standard protocol. SDM-ODNs were designed to introduced the mutation of interest, i.e. "A" for "G" at position 1789 (FIG. 12, SEQ ID NO. 19). ODNs for SDM also contain 15 nucleotides at each flanking region to anneal with the target sequence. SDM was completed using the pCD-HC-mAβScFv clone DNA as template to form pCD-HC-mAβScFv I2V, and the SDM clone was validated by DNA sequencing. The nucleotide and deduced amino acid sequences are shown in SEQ ID NOS: 21 and 22, respectively. Both the nucleotide and deduced amino acid sequences of pCD-HC-mAβScFv-I2V are identical to the ones of the parental clone pCD-HC-mAβScFv (FIGS. 12 and 13) with the exception of the SDM-introduced mutation, which is A1789G (FIG. 14, underlined "G" residue) and I597V (FIG. 15, underlined "V" residue).

Example 4

Genetic Engineering of Signal Peptide and Full Kozak Site of Fusion Protein Heavy Chain In order to optimize the expression of the fusion antibody heavy chain, the signal peptide (SP) of the chimeric HIRMAb heavy chain in pCD-UHC (FIG. 13, amino acid residues 1-19 of SEQ ID NO 20) was replaced by a new peptide signal, which had been used in the engineering of pCD-mAβScFv (FIGS. 1B and 11, amino acid residues 1-19 of SEQ ID NO 18). The full Kozak consensus sequence was also introduced prior to engineering of the new pCD-HC-mAbScFv II plasmid (FIG. 2). The signal peptide sequence of the chimeric HIRMAb expression vector, pCD-UHC, was deleted by double digestion with NotI and EcoRV, RE sites located in the pCD multiple cloning site and in the HIRMAb HC open reading frame. A DNA fragment comprised of 148 bp was replaced by an artificial dsODN that encompasses the human IgG peptide signal using the human IgG peptide signal HIR FWD ODN (Table 2, SEQ ID NO. 31) and the human IgG peptide signal HIR REV ODN (Table 2, SEQ ID NO. 32). Both the artificial dsODN and the pCD-UHC expression plasmid were digested with NotI and EcoRV and gel-purified. Engineering of the pCD-UHC with new signal peptide (NSP) continued with the ligation of the NSP into the pCD-UHC at the same RE sites to form the pCD-UHC-NSP vector. The full Kozak consensus sequence was then introduce by SDM using the QuickChange II XL SDM kit and standard protocol. SDM-ODNs were designed to introduce the mutation of interest (i.e. GCCGCCACC) and also contain 15 nucleotides at each flanking region to anneal with the target sequence. SDM was completed using the chimeric HIRMAb heavy chain in pCD-HC-NSP DNA as template to form pCD-HC-NSP new Kozak (NK) vector. The pCD-HC-NSP-NK was converted into a Universal HIRMAb heavy chain expression vector for fusion proteins (pCD-UHC-II, FIG. 2) by insertion of a HpaI RE site at the stop codon after the CH3 region by SDM. The SDM protocol was completed with the QuickChange II XL SDM kit and SDM-ODNs to introduce the HpaI RE site (i.e. GTTAAC). ODNs also contain 15 nucleotides at each flanking region to anneal with the target sequence. The genetic engineering of a new eukaryotic expression vector encoding for the heavy chain of the HIRMAb fusion antibody was performed using the optimized expression vector pCD-UHC-II as summarized in FIG. 2. The engineering of new fusion antibody heavy chain fusion gene was done in 2 steps, (a) PCR cloning of the mAβScFv cDNA and (b) insertion of this cDNA into the new universal HIRMAb heavy chain expression vector pCD-UHC-II to form pCD-HC-mAβScFv II (FIG. 2). The mAβScFv cDNA was obtained by PCR cloning using the pCD-HC-mAβScFv-I2V (SEQ ID NO:21) as template and the mAb ScFv PCR FWD and REV ODNs (Table 2, SEQ ID NO. 9 and 10, respectively). The engineered mAβScFv I2V cDNA was ligated at the HpaI site in pCD-UHC-II to form the pCD-HC-mAβScFv II expression vector. (FIG. 2). The pCD-HC-mAβ-ScFv II clone was validated by DNA sequencing, and both the nucleotide and deduced amino acid sequences are shown in FIGS. 14 and 15 (SEQ ID NO. 21 and 22), respectively. The nucleotide and amino acid sequence of the reconstructed carboxyl terminus at the CH3 region of the HIRMAb heavy chain, confirmed a 2-amino acid linker (Ser-Ser) prior to the mAβScFv I2V and the TAA stop codon, both introduced in the PCR cloning step (FIGS. 14 and 15). The NSP was also confirmed, i.e. nucleotides 1-57 (FIG. 14; SEQ ID NO 21) and amino acids 1-19 (FIG. 15; SEQ ID NO 22).

Example 5

N497a Site-Directed Mutagenesis of the CDR2 of the VH of the Anti-Aβ ScFv

Figure 24:
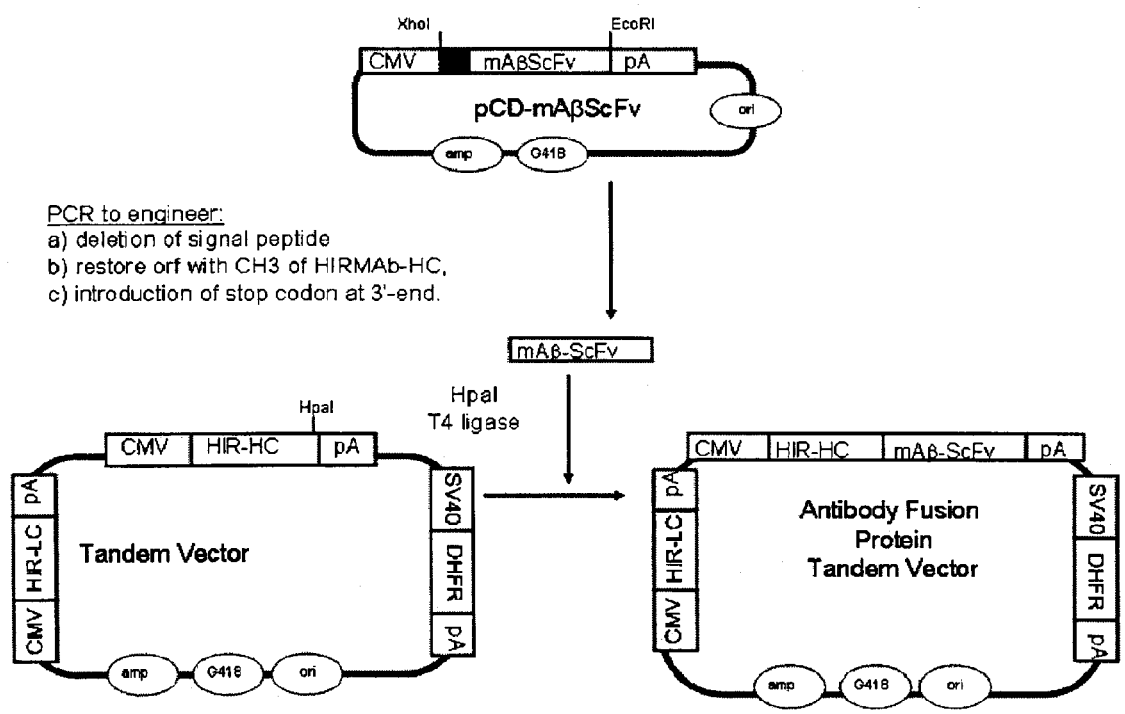
FIG. 24. Genetic engineering of the antibody fusion protein tandem vector. The cDNA encoding the mAβScFv is produced by PCR from the pCD-HC-mAβScFv-I2V plasmid, and ligated into the HpaI site of the tandem vector precursor. The tandem vector encodes the antibody fusion protein shown in FIG. 26. CMV=cytomegalovirus; HIR-LC=light chain (LC) of the anti-human insulin receptor (MR) MAb; HIR-HC=heavy chain (HC) of the anti-HIRMAb; pA=poly A transcription termination sequence SV40=SV40 promoter; DHFR=dihydrofolate reductase.

The mAβScFv has a predicted variable region N-glycosylation domain in the second CDR of the VH, which is underlined in FIG. 25, and which corresponds to the asparagine (N or Asn) residue at position 497 of the VH without the signal peptide shown in FIG. 24; if the signal peptide of the 1 mAβScFv is included, this Asn residue corresponds to position 516 of FIG. 15 and SEQ ID NO. 22. Because glycosylation of the variable region of an antibody may affect binding, the N-glycosylation domain of the mAβScFv was mutated in clone pCD-HC-mAbScFv II, which corresponds to SEQ ID NO. 21, to form new clone named pCD-HC-mAbScFv II-N497A; the mAβScFv part of the heavy chain of the fusion antibody produced by this clone expresses an alanine (A or Ala) residue at position 497 instead of the asparagine, and this SDM is designated N497A. The SDM of residue N497A was completed with standard protocol and the QuickChange II XL SDM kit. SDM-ODNs were designed to introduce the mutation of interest, i.e. "GC" nucleotides at positions 1546-1547 (FIG. 16, SEQ ID NO. 23) and contain 15 nucleotides at each flanking region to anneal with the target sequence. SDM was competed using the pCD-HC-mAbScFv II clone DNA as template (SEQ ID NO. 21), and the SDM clone was validated by DNA sequencing. The nucleotide and deduced amino acid sequences are shown in FIGS. 16 and 17 (SEQ ID NO. 23 and 24), respectively. Both the nucleotide and deduced amino acid sequences of pCD-HC-mAβScFv II N497A are identical to the ones of the parental clone pCD-HC-mAβScFv II with the exception of the SDM-introduced mutations, i.e. 1546GC 1547 (FIG. 16, underlined "GC" residues) and N497A (FIG. 17, underlined "A" residue). COS cells were dual transfected with pCD-HC-mAbScFv II-N497A plasmid, and the pCD-LC plasmid, where pCD-LC is a eukaryotic expression plasmid encoding the light chain of the HIRMAb. The fusion antibody with the N497A mutation was purified from the COS cell conditioned medium by protein A affinity chromatography. The affinity of the Ala-497 form of the antibody fusion protein for the Aβ$^{1-40}$ peptide was measured with an immunoradiometric assay (IMRA) as described below in Example 10. The IRMA showed the affinity of the Ala-497 fusion antibody for the Aβ$^{1-40}$ was characterized by a $K_I$ of 182±32 nM, which is decreased nearly 6-fold, as compared to the Asn-497 fusion antibody shown in FIG. 34 and Example 10. Therefore, the Asn residue at position 497 was left intact in all future investigations.

Example 6

S499A Site-Directed Mutagenesis of the CDR2 of the VH of the Anti-Aβ ScFv

As an alternative strategy to mutation of the variable region glycosylation site in the mAβScFv the serine residue (S or Ser) at position 499 was mutated to an alanine residue, and this mutation is designated the S499A mutation. The latter was mutated in clone pCD-HC-mAbScFv II (SEQ ID NO. 21) to form new clone named pCD-HC-mAbScFv II S499A. The SDM of this residue was completed with standard protocol and the QuickChange II XL SDM kit. SDM-ODNs were designed to introduce the mutation of interest, i.e. "GC" at positions 1552-1553 (FIG. 14, SEQ ID NO. 21) and contain 15 nucleotides at each flanking region to anneal with the target sequence. SDM was competed using the pCD-HC-mAβScFv II clone DNA as template, and the SDM clone was validated by DNA sequencing. The nucleotide and deduced amino acid sequences are shown in FIGS. 18 and 19 (SEQ ID NO. 25 and 26), respectively. Both the nucleotide and deduced amino acid sequences of pCD-HC-mAβScFv II S499A are identical to the ones of the parental clone pCD-HC-mAβScFv II with the exception of the SDM-introduced mutations, i.e. 1552GC1553 (FIG. 18, underlined "GC" residues) and S499A (FIG. 19, underlined "A" residue). COS cells were dual transfected with pCD-HC-mAbScFv II-S499A plasmid, and the pCD-LC plasmid. The secretion of the fusion antibody by the transfected cells was assayed by measurement of human IgG secreted to the medium. The level of secretion of the fusion antibody was unchanged following engineering of the S499A mutation. The fusion antibody with the S499A mutation was purified from the COS cell conditioned medium by protein A affinity chromatography. The affinity of the Ala-499 form of the antibody fusion protein for the Aβ$^{1-40}$ peptide was measured with an immunoradiometric assay (IMRA) as described below in Example 10. The IRMA showed the affinity of the Ala-499 fusion antibody for the Aβ$^{1-40}$ was characterized by a $K_I$ of 271±119 nM, which is decreased 8-fold, as compared to the Ser-499 fusion antibody shown in FIG. 34 and Example 10. Therefore, the Ser residue at position 499 was left intact in all future investigations.

Example 7

Substitution of Constant Region, Including Site-Directed Mutagenesis of Constant Region Glycosylation Site Similar to Examples 5 and 6, it is possible to perform site-directed mutagenesis of the consensus glycosylation site in the constant (C) region of the heavy chain of the fusion antibody. This consensus sequence is NST (Asn-Ser-Thr) of the CH2 region, which is underlined in FIGS. 21 and 25. Substitution of either the Asn Or the Ser or the Thr residue of this sequence can abolish the C-region glycosylation. Removal of the glycosylation of the C-region should have no effect on binding of the fusion antibody to either the HIR or the target antigen such as the Aβ peptide. Removal of the C-region carbohydrate has no effect on binding of IgG to Fc receptors (FcR), such as the neonatal FcR, also called the FcRn. The constant region used in the present examples is the C-region from the human IgG1 subclass. This C-region includes the hinge-CH1-CH2-CH3 regions shown in FIG. 25, in encompasses amino acid residues 133-462 of SEQ ID NO. 28. The IgG1 C-region could be substituted with the C-region of human IgG2, IgG3, or IgG4. The sub-domains, hinge, CH1, CH2, CH3, or CH4, could be interchanged between the different IgG subclasses.

Example 8

Genetic Engineering of Tandem Vector Expressing Antibody Fusion Protein

The genetic engineering of the eukaryotic expression tandem vector encoding for the fusion antibody was performed as summarized in FIG. 24. The tandem vector is comprised of several expression cassettes including: (a) the HIRMAb light chain (LC), (b) the HIRMAb heavy chain (HC) and (c) the dihydrofolate reductase (DHFR) expression cassettes. Both the LC and HC genes are driven by the CMV promoter and contain BGH polyadenylation sequences and human IgG signal peptide. The DHFR gene is regulated by the SV40 promoter and contains the hepatitis B polyadenylation sequence. All 3 genes have full Kozak sequences. The engineering of this fusion gene was done in 2 steps: (a) PCR cloning of the mAβScFv, and (b) insertion of this cDNA into the tandem vector to create the fusion antibody tandem vector (FIG. 24). The mAβScFv cDNA was obtained by PCR cloning using the pCD-HC-mAbScFv II (SEQ ID NO:21) as template and the mAβScFv PCR FWD and REV ODNs (Table 2, SEQ ID NO. 9 and 10, respectively). The engineered mature mAbScFv cDNA was ligated at the HpaI site of the tandem vector to form the fusion antibody tandem vector (FIG. 24). The fusion antibody tandem vector was validated by DNA sequencing, and the nucleotide sequence is shown in FIG. 20 (SEQ ID NO. 27). The deduced amino acid sequences for the fusion antibody HC, the HIRMAb LC, and DHFR genes are shown in FIGS. 21-23 (SEQ ID NO. 28-30), respectively. The nucleotide and amino acid sequence of the reconstructed carboxyl terminus at the CH3 region of the HIRMAb heavy chain confirmed a 2-amino acid (Ser-Ser) linker, preceding the mAβScFv and the TAA stop codon, following the mAβScFv, and both modifications were introduced in the PCR cloning step (FIG. 24). The LC expression casette is contained within nucleotides (nt) 1-1736 of FIG. 20 (SEQ ID NO 27), and is comprised of (a) a CMV promoter, nt 1-731, (b) a full Kozak sequence, nt 732-740, (c) the LC orf, nt 741-1445, and (d) a BGH polyadenylation sequence, nt 1446-1736. The HC expression casette is contained within nt 1760-4904 of FIG. 20 (SEQ ID NO 27), and is comprised of (a) a CMV promoter, nt 1760-2473, (b) a full Kozak sequence, nt 2474-2482, (c) the HC orf, nt 2483-4609, and (d) a BGH polyadenylation sequence, nt 4610-4904. The DHFR expression casette is contained within nt 4905-6671 of FIG. 20 (SEQ ID NO 27), and is comprised of (a) a SV40 promoter, nt 4905-5158, (b) a full Kozak sequence, nt 5159-5167, (c) the DHFR orf, nt 5168-5731, and (d) a hepatitis B polyadenylation sequence, nt 5732-6671.

The fusion antibody tandem vector (FIG. 24) was linearized with PvuI and electroporated into CHO DG44 cells followed by selection with G418 (500 ug/ml) and hypoxanthine-thymidine deficient medium for 3 weeks. Positive clones were detected in 96 well plates with a human IgG ELISA that uses 2 primary antibodies to both the human IgG1 HC and the human kappa LC. Cell lines of high copy number of the transgene were selected by graded increases in MTX to 600 nM. The G41/MTX selected cell lines were maintained in high density and continued to secrete human IgG. The transfected CHO cells were subjected to a round of limited dilutional cloning, and produced human IgG at a level of 10 mg/L in shake flasks. Following affinity purification the CHO cell derived fusion protein was analyzed by SDS-PAGE and human IgG Western blotting, and the fusion heavy chain and light chain migrated identical to that observed for the fusion antibody produced in COS cells and shown in FIG. 32.

Example 9

Diverse Structural Domains of Antibody Fusion Protein

The heavy chain of the fusion antibody is comprised of 28 domains as shown in FIG. 25. The 19-amino acid human IgG signal peptide is cleaved in the secretion of the fusion antibody from the intracellular compartment. The constant region of human IgG is comprised of 4 domains: CH1, hinge, CH2, and CH3. The variable region of the heavy chain (VH) of the chimeric HIRMAb is fused to the amino terminus of CH1; this VH is comprised of 4 framework regions (FR), designated FR1, FR2, FR3, and FR4, and 3 complementarity determining regions (CDR), designated CDR1, CDR2, and CDR3. A serine-serine (S-S) linker joins the carboxyl terminus of CH3 with the amino terminus of the VH of the anti-Aβ ScFv; the VH and the VL of the ScFv are also comprised each of 4 FR and 3 CDR regions. The VH and the VL of the anti-Aβ ScFv are joined by a 17-amino acid linker. This linker is formed by amino acid sequences from the human α-tubulin protein (Genbank CAA25855) to reduce immunogenicity in humans. The heavy chain shown in FIG. 25 covalently binds to the light chain of the chimeric HIRMAb, and to another fusion antibody heavy chain via disulfide bridges in the hinge region to form the hetero-tetrameric structure shown in FIG. 26. The fusion antibody depicted in FIG. 26 possesses 3 functionalities, each of which exerts a specific action in the clearance of Aβ amyloid aggregates in the brain of AD. As shown in FIG. 27, there are 3 steps in the clearance of aggregated protein from the blood. First, influx of the fusion antibody across the BBB from blood to brain via the HIR expressed at the BBB; this step is mediated by the HIRMAb part of the fusion antibody, or the "head" of the molecule shown in FIG. 26. Second, binding and disaggregation of the aggregated protein in brain; this step is mediated by the anti-Aβ ScFv part of the fusion antibody, or the "tail" of the molecule shown in FIG. 26. Third, efflux of the fusion antibody/aggregate protein complex from brain to blood across the BBB via the FcR expressed at the BBB; this step is mediated by binding of the CH2-CH3 parts of the constant region of the fusion antibody, or the "mid-section" of the molecule shown in FIG. 26.

Example 10

Eukaryotic Expression and Characterization of Anti-Aβ ScFv

Figure 28:
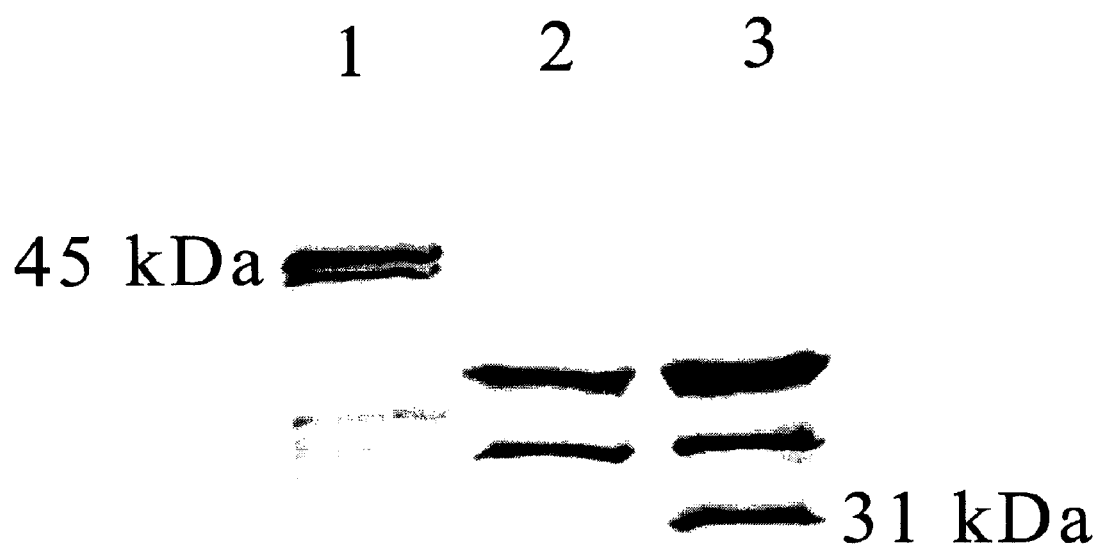
FIG. 28. Western blot with 9E10 MAb to C-terminal c-myc epitope of the single chain Fv (ScFv) antibody. (Lane 1): Fusion protein (45 kDa) of streptavidin (SA) and OX26 ScFv, used as a positive control. This OX26 ScFv-SA fusion protein is comprised of 3 domains: OX26 ScFv, SA, and c-myc C-terminal epitope, and was affinity purified from bacterial pellets. (Lane 2): Negative control: media conditioned by COS cells transfected with Lipofectamine and no plasmid DNA. The 9E 10 anti-c-myc MAb cross-reacts with 2 proteins of 35-37 kDa that are secreted by COS cells. Note the absence of the 29 kDa anti-Aβ ScFv in the media of COS cells not transfected with pCD-mAβScFv. (Lane 3): Anti-AβScFv obtained from media conditioned by COS cells transfected with Lipofectamine 2000 and pCD mAβScFv (FIG. 1B); the anti-Aβ ScFv has a molecular weight of 29 kDa, and is 16 kDa smaller in size than the OX26 ScFv-SA fusion protein in lane 1, owing to the presence of the 16 kDa SA moiety in the OX26 ScFv/SA fusion protein.

COS-1 cells were grown in serum free medium and transfected with pCD-mAβScFv (FIG. 1B) using Lipofectamine-2000. The conditioned medium was removed at 3 or 7 days. The medium conditioned by COS cells transfected with pCD-mAβScFv and Lipofectamine-2000 was concentrated with an Ultra-15 (Amicon) filtration unit with a 10 kDa molecular weight cutoff, and was solubilized in sodium dodecyl sulfate (SDS) sample buffer under reducing conditions, and applied to a 15% SDS-polyacrylamide gel for SDS-polyacrylamide gel electrophoresis (PAGE) followed by Western blotting with the 9E10 MAb. The 9E10 MAb binds to an epitope derived from the c-myc protein, and this epitope, EQKLI-SEEDL (SEQ ID NO: 66), is present at the carboxyl terminus of the anti-Aβ ScFv (FIG. 11). The positive control in the Western blot (FIG. 28, lane 1) is the OX26 ScFv/streptavidin (SA) fusion protein, which was affinity purified from bacterial pellets. The OX26 ScFv/SA fusion protein is comprised of 3 domains: (i) the 29 kDa OX26 ScFv, (ii) the 16 kDa SA monomer, and (iii) the C-terminal 10-amino acid c-myc epitope, which reacts. with the 9E10 MAb. The negative control in the Western blot (FIG. 28, lane 2) is media from COS cells exposed to Lipofectamine 2000, but no plasmid DNA. The anti-Aβ ScFv lacks the SA domain and is comprised of (i) the anti-Aβ ScFv (27 kDa), and (ii) the C-terminal 10-amino acid c-myc epitope (2 kDa), which reacts with the 9E10 MAb. The 9E10 MAb also cross-reacts with 2 proteins of 35-37 kDa that are secreted by non-transfected COS cells (FIG. 28, lane 2). The 29 kDa anti-Aβ ScFv is specifically secreted to the medium by the COS cells transfected with pCD-mAβScFv (FIG. 28, lane 3). This Western blot studied verified that the mAβScFv was secreted intact by the COS cells transfected with the pCD-mAβScFv.

The binding of the mAβScFv to the Aβ$^{1-40}$ amyloid peptide was verified with a specific ELISA. The Aβ$^{1-40}$ amyloid peptide was plated in 96-well plates, followed by the addition of the media conditioned by COS cells transfected with the pCD-mAβScFv plasmid and Lipofectamine-2000. The anti-A, ScFv contains a C-terminal 10-amino acid c-myc epitope, which is recognized by the 9E10 MAb (FIG. 29A). The 9E10 MAb is biotinylated, which enables quantitation of the sc 165 binding to Aβ$^{1-40}$ by a peroxidase detection system and A492 readings (FIG. 29A). This ligand binding assay showed the anti-AD ScFv binds well to the Aβ$^{1-40}$ amyloid peptide, whereas there is no signal when COS cell media is obtained from cells exposed only to Lipofectamine-2000 (FIG. 29B).

The binding of the anti-AD ScFv to the amyloid plaque of AD was verified with immunocytochemistry and sections of autopsy AD human brain. The concentrated conditioned medium obtained from COS cells transfected with the pCD-mAβScFv was used to test the functional activity of the anti-Aβ ScFv, with respect to binding to the Aβ plaque of AD. Frozen AD brain was used to prepare 10 um frozen sections, which were fixed in 2% paraformaldehyde. The COS cell medium was co-incubated with the 9E 10 MAb, which is a murine MAb that binds the 9E 10 epitope of the anti-Aβ ScFv, and the mixture was applied to the AD frozen sections. This 9E10 MAb will bind the c-myc epitope at the C-terminus of the anti-Aβ ScFv, similar to the Western blotting and binding assay format (FIG. 29A). The secondary antibody was a biotinylated horse-anti-mouse IgG, which binds the 9E 10 MAb, a mouse IgG1. The anti-Aβ ScFv strongly stained the amyloid plaque of autopsy AD sections, as shown in FIGS.

30A and 30C. No immune staining of amyloid plaque was observed with the negative controls, which included the 9E 10 MAb plus medium conditioned by COS cells exposed to lipofectamine 2000 but without transfection with pCD-mAβ-ScFv (FIG. 30B), or mouse IgG1, which is the isotype control of the 9E 10 MAb (FIG. 30D). The Aβ ligand binding assay and the AD immunocytochemistry (FIGS. 29-30) both show the anti-Aβ ScFv avidly binds the Aβ amyloid of Alzheimer's disease, and that this anti-Aβ ScFv could be used to produce a fusion protein with the chimeric HIRMAb, as outlined in FIG. 26.

Example 11

Figure 31:
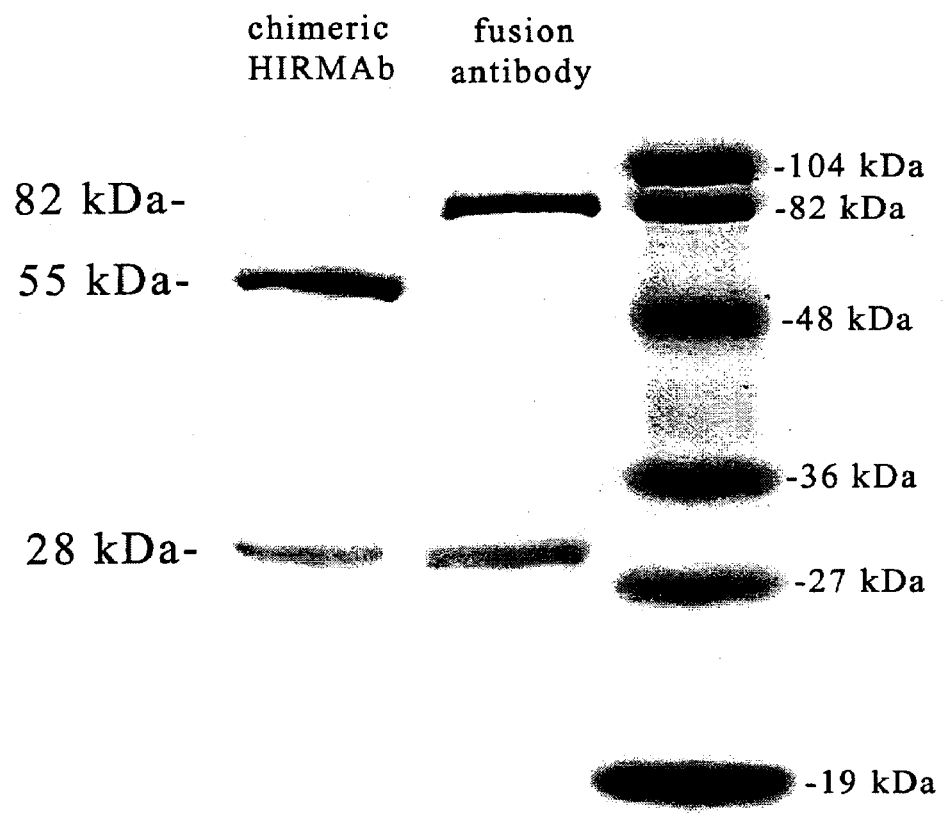
FIG. 31. Sodium dodecylsulfate polyacrylamide gel electrophoresis (SDS-PAGE) of protein A purified fusion antibody or chimeric HIRMAb under reducing conditions, and stained with Coomasie blue. The gel shows a side by side comparison of the sizes of the heavy and light chains of the chimeric HIRMAb, and the fusion antibody. Both are comprised of the same light chain, which is 28 kDa. The size of the heavy chain of chimeric HIRMAb is 55 kDa, whereas the size of the heavy chain of fusion antibody is 82 kDa. The heavy chain of the fusion antibody includes the 55 kDa heavy chain of chimeric HIRMAb fused to the 27 kDa anti-Aβ ScFv.

Eukaryotic Expression and Characterization of Anti-Aβ ScFv/Chimeric HIRMAb Fusion Protein COS cells were dual transfected with the pCD-HC-mAβ-ScFv (FIG. 2), which is the fusion protein heavy chain expression plasmid and with pCD-LC, which is the HIRMAb light chain expression plasmid using Lipofectamine 2000. Following 4 days of culture, the medium was harvested, and the AβScFv/chimeric HIRMAb fusion protein was purified by protein A affinity chromatography. The processing of the fusion antibody was examined by Western blotting, and the biofunctionality of the fusion antibody was examined with ligand binding assays directed at either the HIR or $A\beta^{1-40}$. The fusion antibody and the chimeric HIRMAb was subjected to SDS-PAGE under reducing conditions, and the gel was stained with Coomasie blue (FIG. 31). These results show the fusion antibody was purified to homogeneity on SDS-PAGE, and that the size of the light chain (LC) for both the fusion antibody and the chimeric HIRMAb are identical in size, as expected (FIG. 31). The heavy chain (HC) of the fusion antibody is 82 kDa, whereas the size of the HC of the chimeric HIRMAb is 55 kDa (FIG. 31). The difference in size, 27 kDa, is due to the fusion of the AβScFv to the HC of the fusion antibody.

Figure 32:
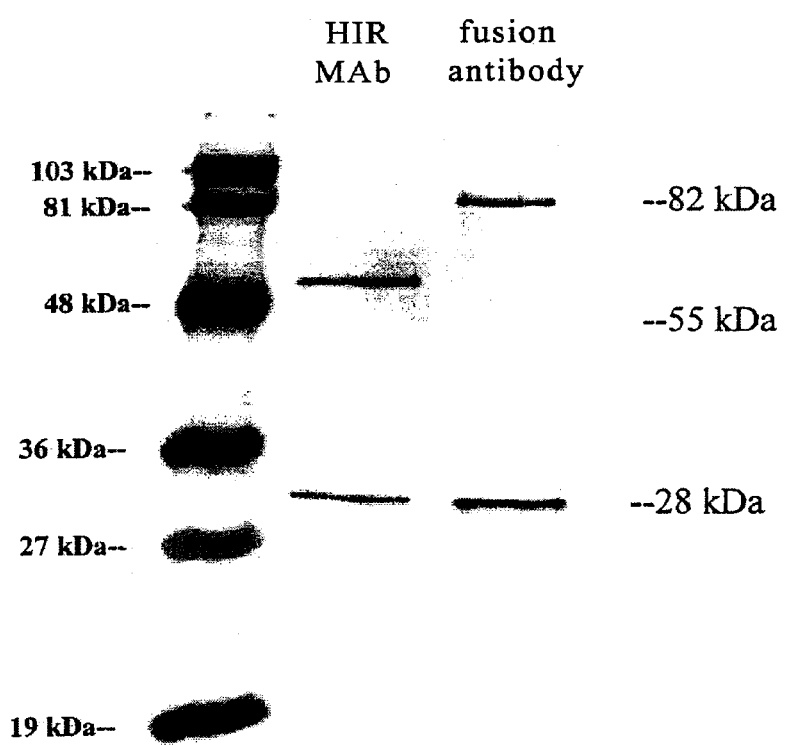
FIG. 32. Western blotting of protein A purified fusion antibody with an anti-human IgG primary antibody shows that the fusion antibody expressed in COS cells is processed and secreted intact with the expected molecular size. The blot shows a side by side comparison of the immunoreactivity of the chimeric HIRMAb, and the fusion antibody. Both are comprised of the same light chain, which is 28 kDa, as shown in the Western blot. The size of the heavy chain of chimeric HIRMAb is 55 kDa, whereas the size of the heavy chain of fusion antibody is 82 kDa. The heavy chain of the fusion antibody includes the 55 kDa heavy chain of chimeric HIRMAb fused to the 27 kDa anti-Aβ ScFv.

The SDS-PAGE was repeated, and following blotting to nitrocellulose, the blot was probed with a primary antibody to human IgG. The antibody detected identical size 28 kDa light chains in both the chimeric HIRMAb and the fusion antibody (FIG. 32), which is expected because the ScFv is fused to the heavy chain (FIG. 25). The size of the chimeric HIRMAb heavy chain was the expected 55 kDa (FIG. 32). The size of the fusion antibody heavy chain was 82 kDa (FIG. 32), which is the sum of the 55 kDa chimeric HIRMAb heavy chain, and the 27 kDa anti-Aβ ScFv.

Figure 33:
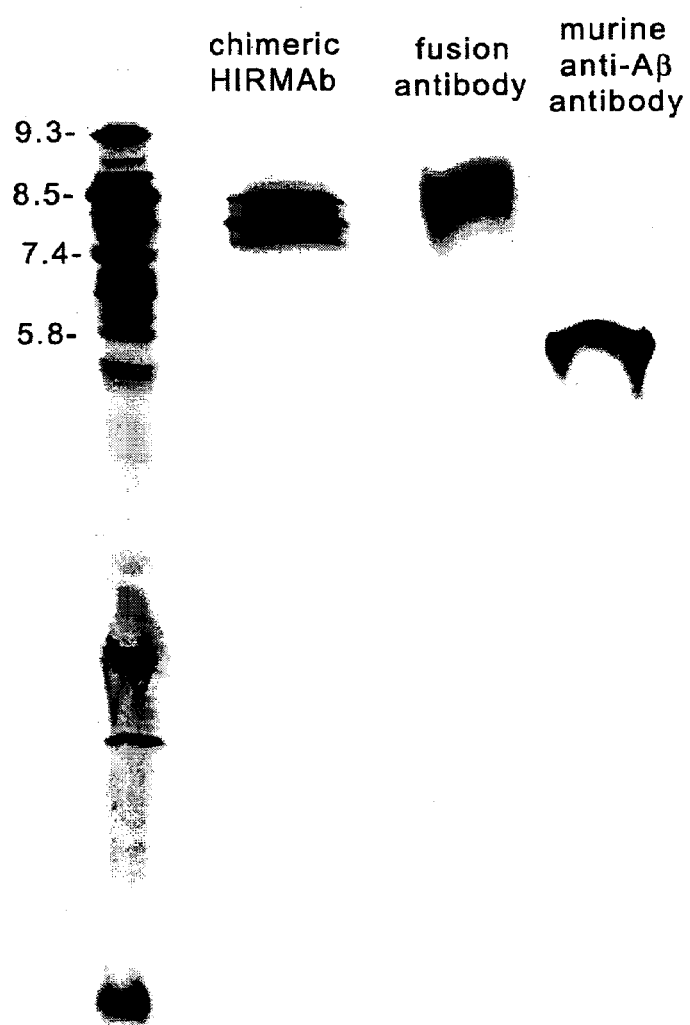
FIG. 33. Isoelectric focusing of isoelectric standards, the chimeric HIRMAb, the hybridoma generated murine anti-Aβ antibody, and the fusion antibody.

The isoelectric point (pI) of the fusion antibody, the chimeric HIRMAb, and the hybridoma generated anti-Aβ MAb was determined by isoelectric focusing (IEF), as shown in FIG. 33. The pI of the chimeric HIRMAb and the fusion protein wee nearly identical, about 8.5, whereas the pI of the murine anti-Aβ MAb was more acidic with a pI of about 6.8. The theoretical pI of the fusion antibody heavy chain is predicted to be 8.8, which matches the experimentally observed pI in FIG. 33.

Figure 34:
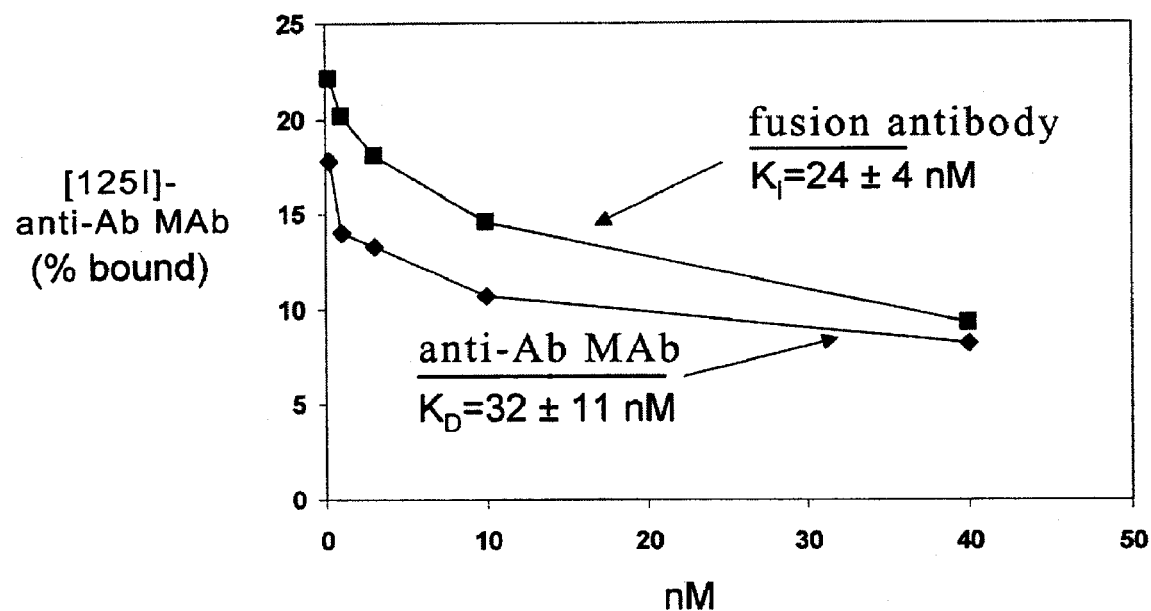
FIG. 34. $A\beta^{1-40}$ immunoradiometric assay (IRMA) measures the binding of the $[^{125}I]$-murine anti-Aβ MAb to $A\beta^{1-40}$ that is plated in wells of a 96-well plate. The murine anti-AD MAb is the original murine MAb against Aβ purified from hybridoma conditioned medium. In the absence of competitors of binding, approximately 20% of the total $[^{125}I]$-anti-Aβ MAb is bound to the $A\beta^{1-40}$. Both the murine anti-Aβ MAb and the fusion antibody bind to the $A\beta^{1-40}$, and the half saturation constant, $K_D$, is not significantly different. The affinity of the fusion antibody for $A\beta^{1-40}$ is equal to the affinity of the original murine anti-$A\beta^{1-40}$ MAb FIG. 35. The affinity of the chimeric HIRMAb, and the fusion antibody for the human insulin receptor (HIR) as determined by competitive ELISA, where the solid phase antigen is the affinity purified HIR extracellular domain (ECD) produced from CHO cells. The avidity for the HIR ECD of the fusion antibody, $ED_{50}=1.0\pm0.1$ nM, is comparable to that of the chimeric HIRMAb, $ED_{50}=0.53\pm0.02$ nM. There is no binding of human IgG1, the isotype control, to the HIR ECD.

The affinity of the fusion antibody for binding to $A\beta^{1-40}$ was compared to the same affinity of the murine hybridoma generated anti-Aβ MAb with an immunoradiometric assay (IMRA). In this assay, the $A\beta^{1-40}$ is plated in 96-well plates, and the binding of $[^{125}I]$-murine anti-Aβ MAb to the $A\beta^{1-40}$ is measured. The dissociation constant, $K_D$, of the murine anti-Aβ MAb binding to the $A\beta^{1-40}$ is 32±11 nM (FIG. 34). The $K_D$ of fusion protein binding to the $A\beta^{1-40}$ is 24±4 nM (FIG. 34). Therefore, the affinity of the fusion antibody for $A\beta^{1-40}$ is identical to that of the original 150 kDa hetero-tetrameric murine anti-Aβ MAb. This was a surprising finding, since the affinity of a ScFv for the target antigen is generally much lower than for the full, tetrameric MAb molecule. Owing to the bivalency of the tetrameric MAb, the affinity for the antigen is higher than the affinity of the monomeric ScFv. The high affinity of the ScFv moiety of the fusion antibody for $A\beta^{1-40}$ is attributed to the design of the fusion antibody molecule, which places the ScFv in a dimeric or bivalent conformation (FIG. 26).

Figure 35:
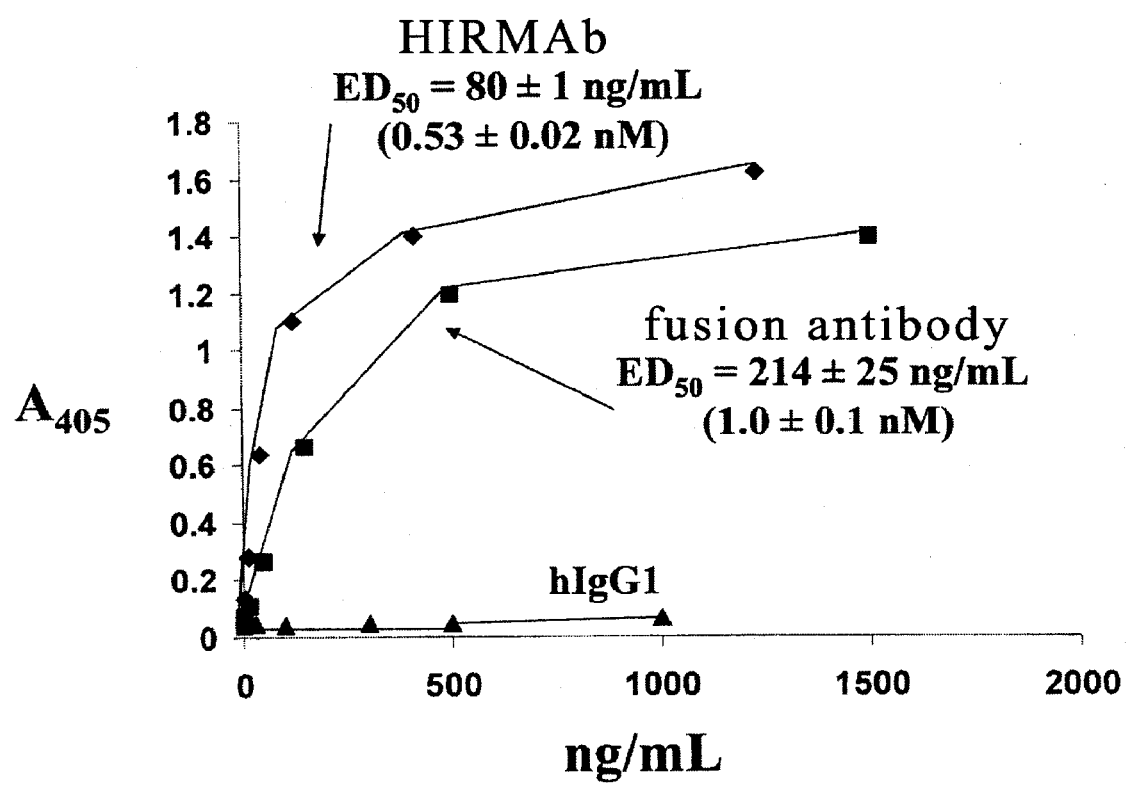
Figure 36:
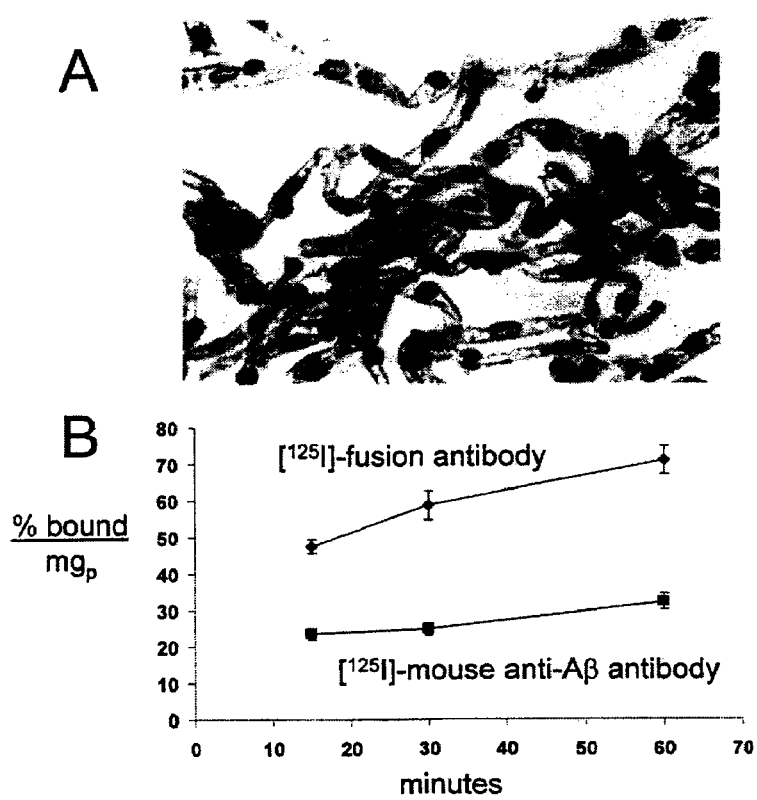
FIG. 36. Binding of fusion protein to the HIR on the human BBB. (A) Isolated capillaries are purified from human autopsy brain, and used as an in vitro model of binding to the human BBB HIR. (B) Specific binding of [$^{125}$I]-fusion antibody to human brain capillaries is time-dependent, whereas binding of the [$^{125}$I]-mouse anti-Aβ antibody is constant with time, and is non-specific.

The affinity of the fusion antibody for binding to the human insulin receptor (HIR) extracellular domain (ECD) was measured with an ELISA using affinity purified HIR ECD obtained from medium conditioned by CHO cells permanently transfected with the HIR ECD gene. As shown in FIG. 35, both the chimeric HIRMAb and the fusion antibody bind the HIR ECD with high affinity. The 50% saturation of binding, $ED_{50}$, is 0.53±0.02 nM for the chimeric HIRMAb. The $ED_{50}$ of fusion antibody binding to the HIR is 1.0±0.1 nM (FIG. 35). Therefore, the affinity of fusion antibody for the HIR is >50% of the affinity of the original chimeric HIRMAb. The HIR at the BBB is an heterotetrameric molecule comprised of two alpha and two beta chains. The binding of the $[^{125}I]$-fusion antibody to the intact HIR at the human BBB was demonstrated with a radio-receptor assay using isolated human brain capillaries (FIG. 36A), as an in vitro model of the human BBB. There is specific binding of the $[^{125}I]$-fusion antibody to human brain capillaries in a time-dependent process, whereas binding of the $[^{125}I]$-mouse anti-Aβ antibody is constant with time, and is non-specific (FIG. 36B).

Example 12

Influx Across the BBB from Blood to Brain of Anti-Aβ ScFv/Chimeric HIRMAb Fusion Antibody in Adult Rhesus Monkey In Vivo The fusion antibody was iodinated with $[^{125}I]$-iodine and chloramine T to a specific activity of 19 µCi/µg. In parallel, the murine anti-Aβ MAb was tritiated with $[^{3}H]$-N-succinimidyl proprionate to a specific activity of 0.42 µCi/ug. A 8 year old female Rhesus monkey, weighing 10.2 kg, was administered by a single intravenous injection a dose of 777 µCi of $[^{125}I]$-fusion antibody and 888 µCi of $[^{3}H]$-murine anti-Aβ MAb. Serum was collected at multiple time points over a 180 min period. The serum glucose of the anesthetized, overnight-fasted primate was constant throughout the 180 min study period, and averaged 90±2 mg %, which indicates that the administration of the fusion antibody caused no interference of the endogenous insulin receptor, and had no effect on glycemia control.

The serum removed from the anesthetized Rhesus monkey was analyzed for total radioactivity, and expressed as a % of injected dose (I.D.)/mL serum (FIG. 37). The $^{125}I$ radioactivity was counted in a gamma counter, and the $^{3}H$ radioactivity was counted in a liquid scintillation counter; the $^{125}I$ isotope emits radioactivity in the $^{3}H$ window and standard curves were prepared to eliminate $^{125}I$ spill-over into the $^{3}H$ channel. The serum % I.D./mL for the $[^{3}H]$-murine anti-Aβ MAb was constant at all time points, and averaged 0.25% I.D./mL (FIG. 37). The constant blood concentration of the $[^{3}H]$-murine anti-Aβ MAb indicated this MAb was not significantly cleared by the primate tissues in vivo, which is consistent with the known prolonged blood mean residence time (MRT) of monoclonal antibodies. In contrast, the serum % I.D./mL for the $[^{125}I]$-fusion antibody decreased rapidly to about 0.05% I.D./mL (FIG. 37), which is indicative of rapid clearance of the fusion antibody from blood via tissues expressing the insulin receptor. Although the HIRMAb does not react with the rodent insulin receptor, the HIRMAb does cross react with the insulin receptor in Old World primates such as the Rhesus monkey.

The serum concentration profile for the [$^{125}$I]-fusion antibody was fit to a 2-compartment pharmacokinetic (PK) model to yield the pharmacokinetics parameters listed in Table 3. The PK parameters for the [$^{125}$I]-fusion antibody are compared in Table 3 to the PK parameters in the adult Rhesus monkey for [$^{111}$In]-chimeric HIRMAb. The systemic clearance rate of the fusion antibody is no different from that of the chimeric HIRMAb, which indicates fusion of the ScFv to the heavy chain of the HIRMAb does not alter systemic clearance. Systemic clearance of either the chimeric HIRMAb or the fusion antibody is a function of antibody uptake by peripheral tissues, e.g. liver or spleen, which express high amounts of insulin receptor at the vascular barrier of the tissue. In fact, the CNS is virtually the only organ where the microvascular endothelium expresses significant amounts of insulin receptor. Clearance of the HIRMAb or the fusion antibody by organs, e.g. heart or skeletal muscle, that are perfused by capillaries with continuous endothelium that does not express insulin receptor, would not be expected to clear significant amounts of an antibody directed against the insulin receptor. In the case of liver or spleen, these organs are perfused by sinusoidal capillary compartments that are freely permeable to large molecules such as monoclonal antibodies. The HIRMAb or fusion antibody is rapidly exposed to the insulin receptor on parenchymal cells in liver or spleen, and uptake into these organs accounts for the rapid decrease in serum concentration of the HIRMAb or fusion antibody after intravenous injection (FIG. 37).

TABLE 3

Pharmacokinetic parameters for [$^{125}$H]-fusion antibody and [$^{111}$In]-chimeric HIRMAb

| Parameter | [$^{111}$In]-chimeric HIRMAb | [$^{125}$I]-fusion antibody |
|---|---|---|
| $A_1$ (% ID/ml) | 0.15 ± 0.01 | 0.11 ± 0.01 |
| $A_2$ (% ID/ml) | 0.10 ± 0.01 | 0.048 ± 0.019 |
| $k_1$ (min$^{-1}$) | 0.12 ± 0.02 | 0.16 ± 0.02 |
| $k_2$ (min$^{-1}$) | 0.0018 ± 0.0010 | 0.00090 ± 0.00033 |
| $t_{1/2}^1$ (min) | 5.8 ± 0.6 | 4.4 ± 0.4 |
| $t_{1/2}^2$ (min) | 380 ± 39 | 769 ± 282 |
| Vss (ml/kg) | 116 ± 11 | 200 ± 9 |
| AUCss (% IDmin/ml) | 55 ± 5 | 54 ± 16 |
| $CL_{ss}$ (ml/min/kg) | 0.22 ± 0.08 | 0.18 ± 0.05 |
| MRT (hours) | 8.9 ± 0.9 | 18.2 ± 6.7 |

$A_1$, $A_2$, $k_1$, and $k_2$ are the intercepts and slopes of the bi-exponential function describing the decay in plasma concentration with time.
$t_{1/2}^1$ and $t_{1/2}^2$ are computed from $k_1$ and $k_2$, respectively, and are the half-times of the decay curves for each exponent.
$CL_{ss}$, AUCss, Vss, and MRT are the steady state clearance, steady state area under the serum concentration curve, steady state systemic volume of distribution, and mean residence time, respectively, and are computed from $A_1$, $A_2$, $k_1$, and $k_2$ using standard pharmacokinetic formulations.

Figure 39:
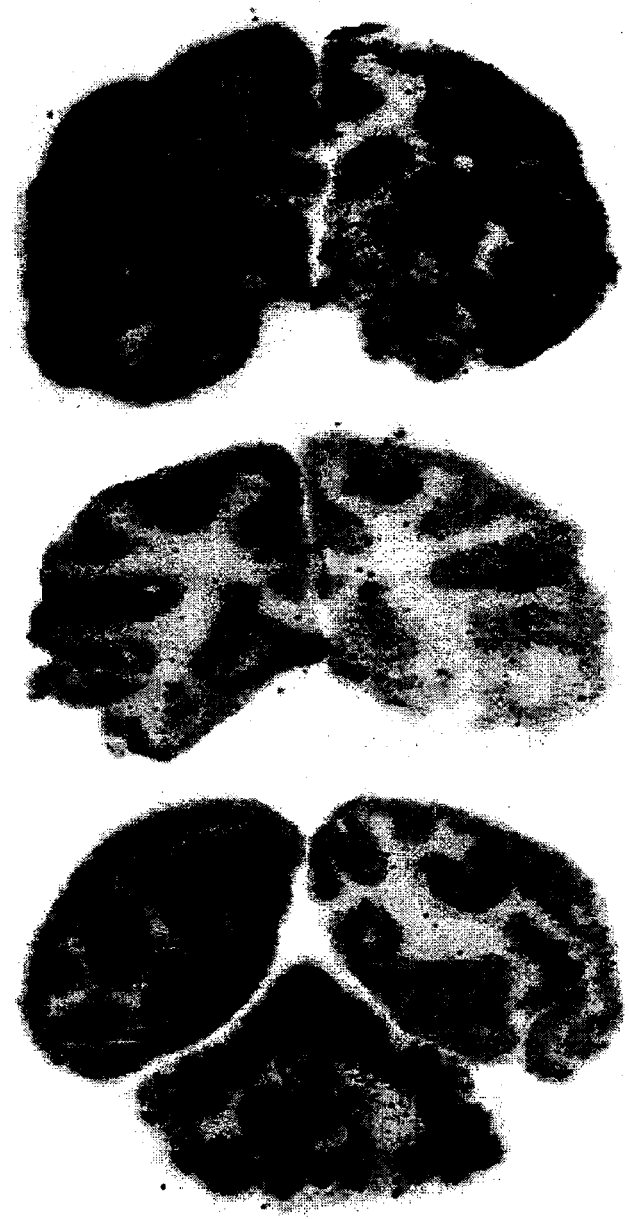
FIG. 39. Brain scans of adult Rhesus monkey at 3 hours after the intravenous administration of the [$^{125}$I]-fusion antibody demonstrates widespread distribution of the fusion antibody into the primate brain in vivo from blood. The top scan is the most frontal part of brain, and the bottom scan is the most caudal part of brain, and includes the cerebellum.

At 180 minutes after drug injection, the animal was euthanized, and brain radioactivity was analyzed with the capillary depletion method (FIG. 38). This method separates brain homogenate into a capillary pellet and a post-vascular supernatant. If the volume of distribution (VD) of the antibody in the post-vascular supernatant is high, then this is evidence that the antibody has crossed the BBB and entered into the brain interstitial and intracellular spaces. The VD has units of uL/gram brain and is the ratio of the concentration of the antibody in brain (DPM/g) divided by the concentration of the antibody in serum (DPM/uL) at the 180 terminal time point. The brain VD of the [$^3$H]-murine anti-Aβ MAb is 10 uL/gram brain in either the homogenate or the post-vascular supernatant (FIG. 38), and this VD is equal to the brain plasma volume. Therefore, the low VD of the [$^3$H]-murine anti-Aβ MAb is evidence that this MAb, similar to MAb's in general, does not cross the BBB. That is, the murine anti-Aβ MAb, in either the murine form, a chimeric form, or a humanized form, would not cross the human BBB, and could not be used as an amyloid clearing therapeutic for AD. The failure of the anti-Aβ MAb to cross the BBB, as shown by the data in FIG. 38, means this antibody therapeutic could not be developed as a drug for the diagnosis or treatment of AD. Similarly, other anti-Aβ MAb molecules do not cross the BBB, which is why there is no MAb-based therapeutic approved for the treatment of AD. In contrast, the fusion antibody rapidly crosses the primate BBB, as demonstrated by the high VD shown in FIG. 38. Further evidence that the fusion antibody freely crosses the BBB, and enters all parts of brain is the 3 hour brain scan of radioactivity in the Rhesus monkey brain (FIG. 39). The high brain uptake of the fusion antibody is due to the ability of this molecule to bind to the BBB insulin receptor from the blood compartment, and this binding to the BBB insulin receptor triggers receptor-mediated transport into the brain. The brain uptake of the fusion antibody is higher in gray matter, as compared to white matter, as shown in FIG. 39, because the vascular density in gray matter is much higher than in white matter of brain.

The in vivo brain uptake in Rhesus monkey shown in FIGS. 38-39, and the HIR binding assay in FIG. 35, indicates the fusion antibody is able to influx across the BBB in the blood to brain direction via the BBB insulin receptor. Therefore, the fusion antibody is shown to perform step 1 in the scheme outlined in FIG. 27. The fusion antibody is also able to perform steps 2 and 3 of the scheme in FIG. 27, as illustrated by the following examples.

Example 13

Figure 40:
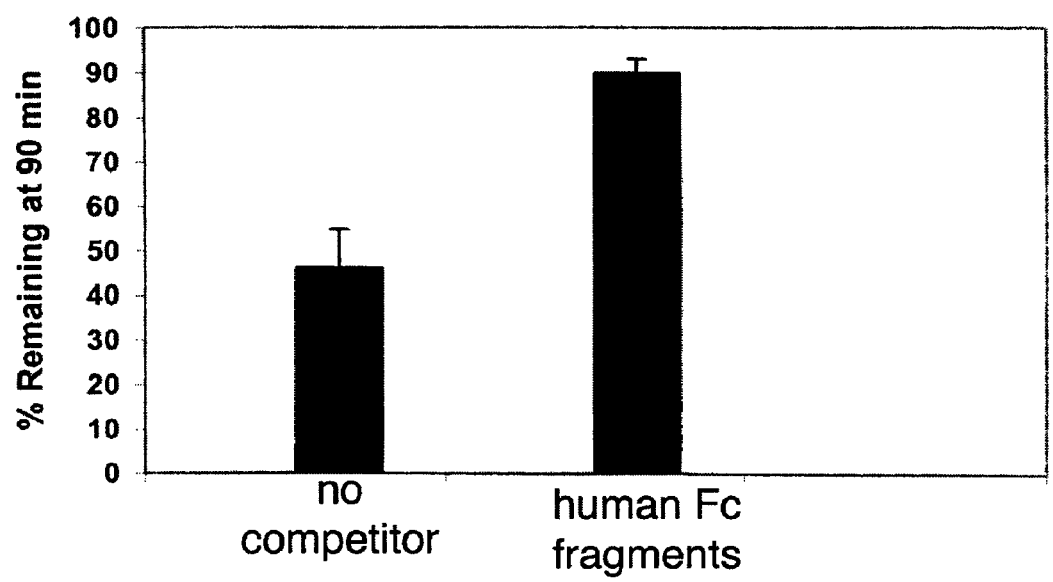
FIG. 40. Efflux from brain to blood of the [$^{125}$I]-fusion antibody in the adult rat. The [$^{125}$I]-fusion antibody was injected into the cortex under stereotaxic guidance, and the efflux of the fusion antibody from brain across the BBB was measured at 90 minutes after the injection. At this time nearly 60% of the injected fusion antibody had effluxed from brain. This efflux was completely blocked by the co-injection of human Fc fragments, which indicates the efflux is mediated by a Fc receptor at the BBB.

Efflux Across the BBB from Brain to Blood of Anti-Aβ ScFv/Chimeric HIRMAb Fusion Protein Mediated Via Fc Receptor in Adult Rat Brain In Vivo The [$^{125}$I]-fusion antibody (0.03 uCi in 0.3 uL) was injected into the cortex of the brain of the anesthetized adult rat under stereotaxic guidance per the standard protocol of the Brain Efflux Index technique. See, e.g., Zhang, Y. and Pardridge, W. M. (2001): Mediated efflux of IgG molecules from brain to blood across the blood-brain barrier. *J Neuroimmunol*, 114: 168-172, incorporated herein by reference. The fusion antibody was injected in the par2 region of the parietal cortex of brain, with the following stereotaxic coordinates: 0.2 mm anterior to bregma; 5.5 mm lateral to bregma; 4.5 mm deep from the dural surface. This region is far removed from the cerebrospinal fluid (CSF) tracts, and efflux of radioactivity from brain over time can only occur via efflux across the BBB from brain to blood. The rate of efflux of the [$^{125}$I]-fusion antibody from rat brain was followed over the next 90 minutes. During this time>50% of the injected dose of the [$^{125}$I]-fusion antibody had effluxed from brain (FIG. 40). In contrast, other large molecules efflux from rat brain with a half-time of about 10 hours. The rapid efflux of IgG molecules from brain is mediated by the BBB Fc receptor (FcR), including the neonatal form of FcR, also called the FcRn. The BBB FcR mediates the asymmetric efflux of IgG from brain to blood, but not the influx of IgG from blood to brain. The efflux of the [$^{125}$I]-fusion antibody from brain is mediated by the BBB FcR, because the efflux is completely blocked by human Fc fragments (FIG. 40). These observations indicate the rat BBB FcR recognizes human Fc, in the form either of human Fc fragments, or the human sequence comprising the CH2-CH3-region of the fusion antibody, which is depicted in FIG. 25. The rodent FcR is known to bind with high affinity to human IgG. See, e.g., Ober, R. J., Radu, C. G., Ghetie, V. and Ward, E. S. (2001): Differences in promiscuity for antibody-FcRn interactions across species: implications for therapeutic antibodies. *Int Immunol,* 13: 1551-1559, incorporated herein by reference.

The in vivo brain efflux in rat shown in FIG. 40 indicates the fusion antibody is able to efflux across the BBB in the brain to blood direction via the BBB Fc receptor. Therefore, the fusion antibody is shown to perform step 3 in the scheme outlined in FIG. 27. The fusion antibody is also able to perform step 2 of the scheme in FIG. 27, as illustrated by the following examples.

Example 14

Disaggregation of Aβ Plaque by Anti-Aβ ScFv/Chimeric HIRMAb Fusion Antibody

Aβ plaque was formed by incubating the $A\beta^{1-40}$ peptide in an orbital shaker at 37 C for 6 days, and the plaque was collected by centrifugation. An antibody against the carboxyl terminus (CT) of the $A\beta^{1-40}$ peptide was plated in 96-well dishes, as outlined if FIG. 41A. In parallel, the Aβ plaque was incubated for either 1 or 4 hours at 37 C with either the fusion antibody, human IgG1 (hIgG1), or phosphate buffered saline (PBS), as shown in FIG. 41B, or with the mouse anti-Aβ MAb, mouse IgG (mIgG), or PBS, as shown in FIG. 41C. The AD aggregate/fusion antibody, or Aβ aggregate/mouse anti-Aβ MAb complex was then added in increasing doses (10, 30, 100 uL, which is equivalent to 100, 300, 1000 ng/mL) to the immobilized anti-CT antibody, as outlined in FIG. 41A. The anti-Aβ ScFv part of the fusion antibody, or the mouse anti-Aβ MAb, binds an epitope on the $A\beta^{1-40}$ peptide near the amino terminus (NT). Therefore, if plaque is present, then a complex will form between anti-CT antibody, the plaque, the fusion antibody, and a secondary antibody coupled to peroxidase for detection of anti-Aβ antibody binding to plaque by ELISA. The secondary antibodies used for the studies in FIGS. 41B and 41C were anti-human and anti-mouse IgG, respectively. The study in FIG. 41 shows (a) that the fusion antibody selectively binds to Aβ plaque, (b) that a 4 hour incubation of Aβ plaque with the fusion antibody nearly completely disaggregates the Aβ plaque in a dose-dependent process, and (c) that the anti-Aβ plaque disaggregation properties of the fusion antibody are as high or higher than the anti-Aβ plaque disaggregation properties of the original murine anti-Aβ MAb.

Figure 29:
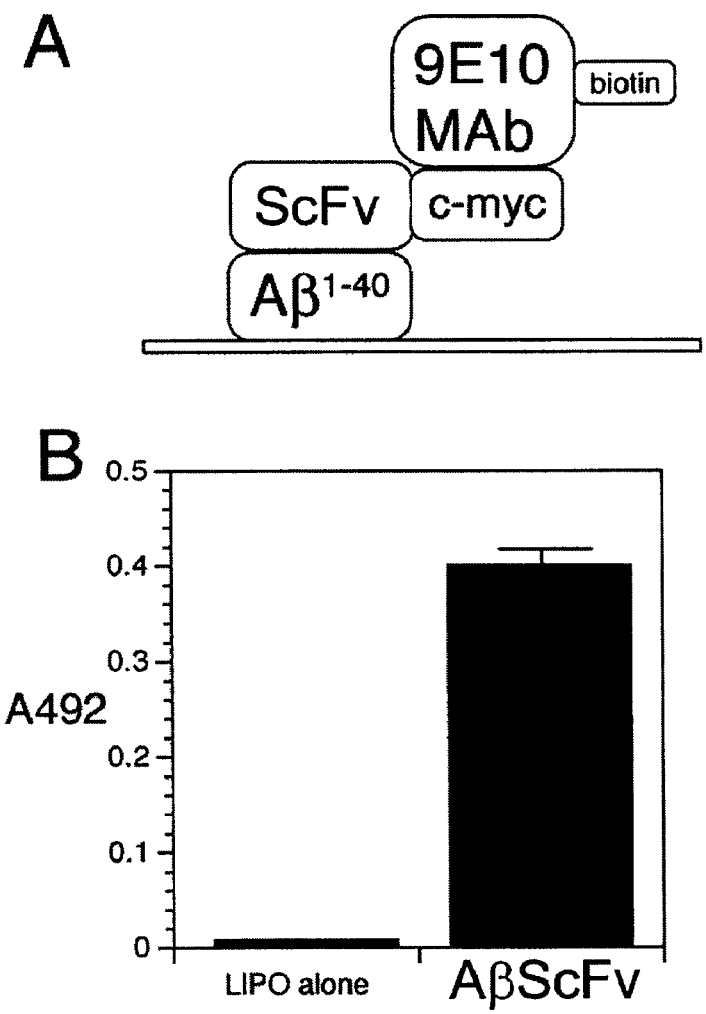
FIG. 29. (A) Structure of ELISA used to demonstrate binding of mAβScFv to $A\beta^{1-40}$ peptide, which is plated on a solid support. The mAβScFv binds to the amyloid peptide, and the 9E10 anti-c-myc MAb binds to the EQKLISEEDL (SEQ ID NO:66) epitope fused to the carboxyl terminus of the protein (FIG. 9). The 9E10 MAb is biotinylated, which enables detection with a conjugate of streptavidin and peroxidase. Medium conditioned by COS cells that were transfected with pCD-mAβScFv produced a high signal in the assay, whereas medium from COS cells exposed only to Lipofectamine (LIPO) produced no signal. The assay shows that the mAβScFv binds to the $A\beta^{1-40}$ peptide.
Figure 30:
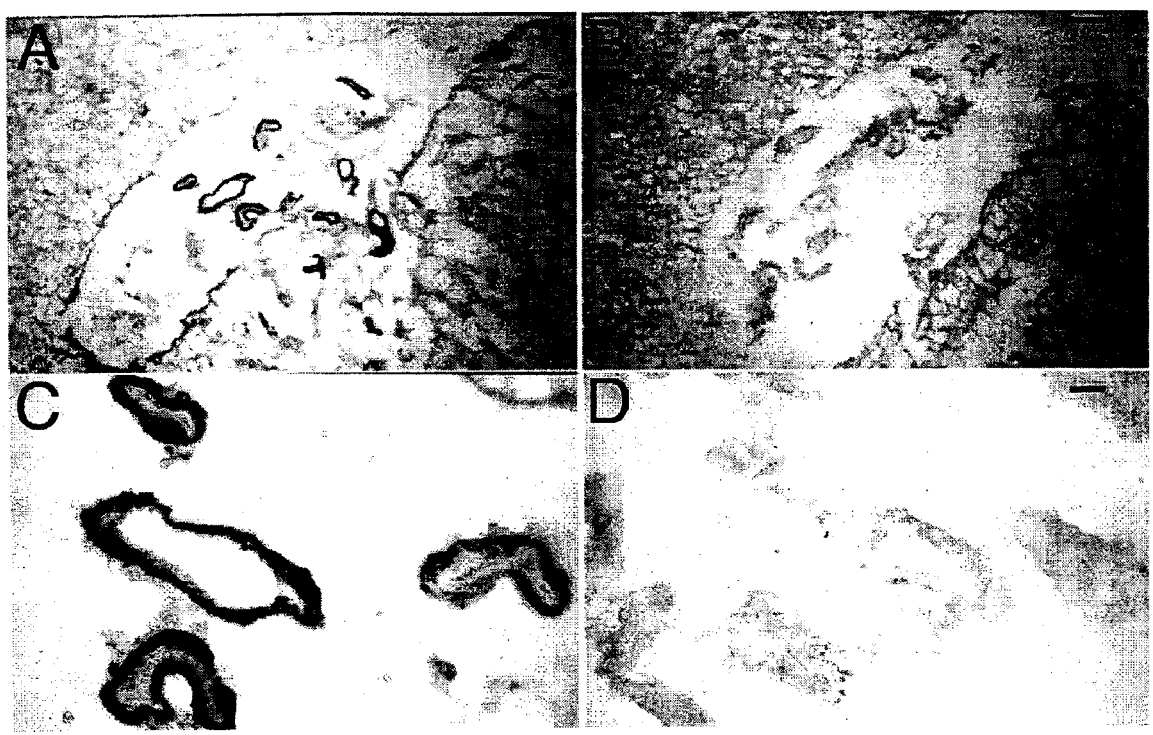
FIG. 30. Immunocytochemistry of frozen sections of AD autopsy brain, which were immune stained with medium conditioned by COS cells which were transfected with pCD-mAβScFv and expressing the mAβScFv (panels A and C), with medium conditioned by COS cells which were exposed only to Lipofectamine 2000 (panel B), or with the mouse IgG1 isotype control antibody (panel D). Magnification bar in panels A and B is 88 um; magnification bar in panels C and D is 35 um. The assay shows that the in mAβScFv binds to the Aβ amyloid plaque of AD.

The disaggregation of Aβ amyloid plaque shown in FIG. 41, and the Aβ binding data shown in FIGS. 29, 30, and 34, indicates the fusion antibody is able to bind the Aβ plaque of AD, and to disaggregate this plaque. Therefore, the fusion antibody is shown to perform step 2 in the scheme outlined in FIG. 27.

Example 15

Figure 42:
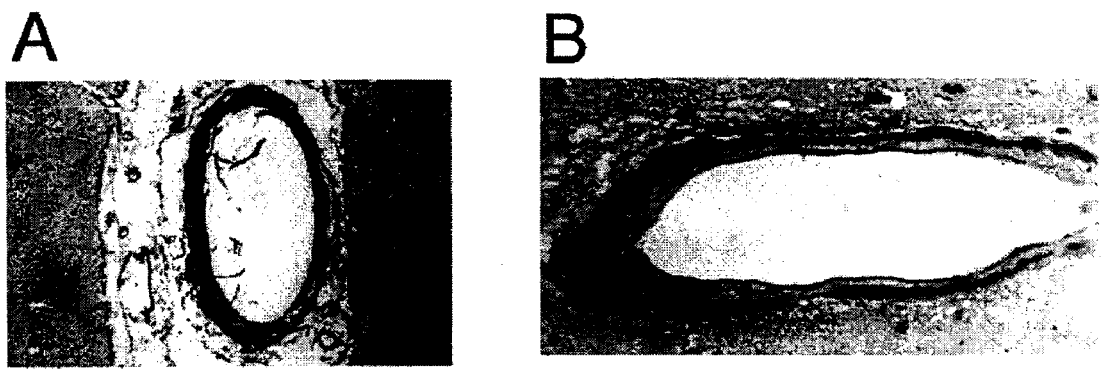
FIG. 42. (A) Film autoradiography of AD autopsy brain sections labeled with [$^{125}$I]-fusion antibody, showing binding of antibody to vascular amyloid plaque. (B) Immunocytochemistry of AD autopsy brain sections labeled with murine anti-Aβ MAb showing antibody binding to vascular amyloid of AD.

Anti-Aβ ScFv/Chimeric HIRMAb Fusion Protein Binds to Amyloid Plaque in Aizheimers Disease The fusion antibody was radiolabeled with 125-iodine and chloramine T and the [$^{125}$I]-fusion protein was applied to microtome sections of autopsy Alzheimer's disease (AD) brain for 2 hours. The slides were washed and coated in a darkroom with emulsion. After 1-2 weeks of exposure in the dark the slides were developed, fixed, washed, and photographed under bright field with a light microscope (FIG. 42A). In parallel, sections of the AD brain were immunostained with the hybridoma generated murine anti-AD MAb using peroxidase immunocytochemistry (FIG. 42B). The parallel immunocytochemistry and light microscopy of the emulsion autoradiography shows binding of the fusion protein radiopharmaceutical to the vascular amyloid plaque of AD, and this binding is comparable to that observed with immunocytochemistry and the murine antibody against Aβ (FIG. 42).

Figure 43:
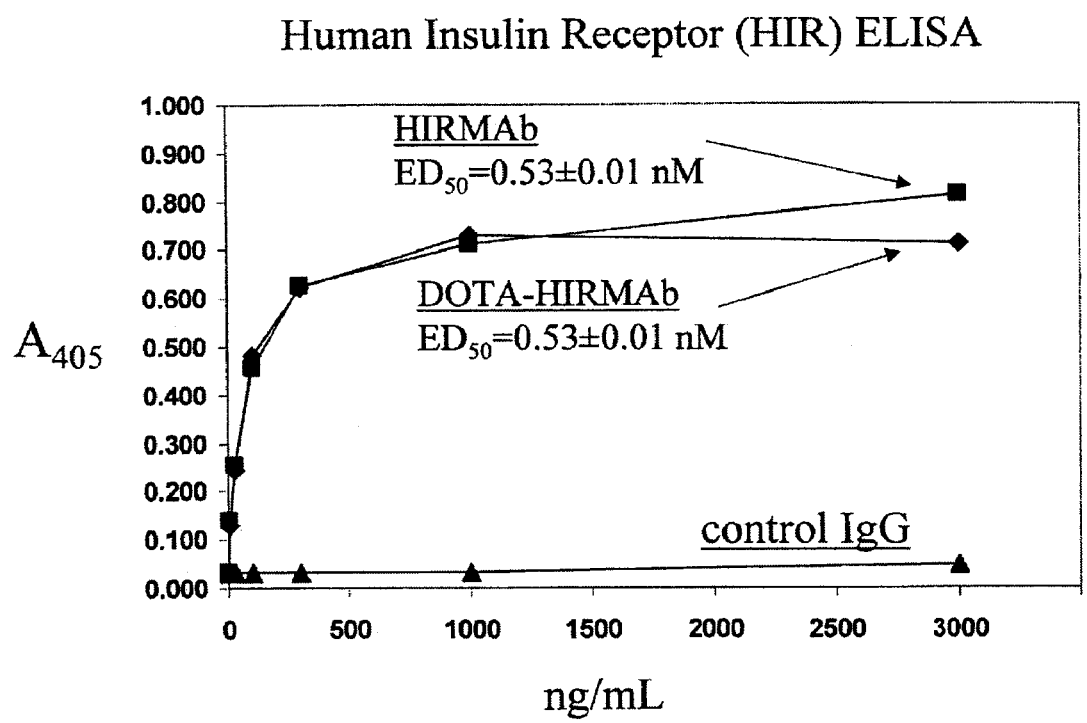
FIG. 43. Conjugation of 1,4,7,10-tetraazacyclododecane-N,-N',N'',N'''-tetraacetic acid (DOTA) to the HIRMAb does not inhibit binding of the antibody to the HIR extracellular domain, as shown by the HIR ELISA. The DOTA is a high affinity chelator of radionuclide metals, such as 111-indium, and enables production of a radiopharmaceutical for neurodiagnosis and brain scanning with the DOTA conjugated fusion antibody.

The fusion protein could be used as an antibody radiopharmaceutical for imaging the amyloid in brain of people suspected of having AD or people suspected of depositing in brain the Aβ amyloid of AD. The fusion antibody could be labeled with a positron emitter for brain scanning using positron emission tomography (PET), or could be labeled with a radionuclide that could be detected with single photon emission computed tomography (SPECT). For SPECT scanning, the fusion protein can be radiolabeled with 111-indium following conjugation to the fusion antibody of a suitable chelating agent. One such chelating agent is 1,4,7,10-tetraazacyclododecane-N,-N',N'',N'''-tetraacetic acid (DOTA). The HIRMAb was conjugated with DOTA. The DOTA was obtained from the Parish Chemical Company (Oren, Utah), and 16.2 mg of DOTA was dissolved in 0.81 ml of water, and 80 μl of 1 M NaOH was added so that the pH is 5.45. This pH has been shown to add approximately 2-10 DOTA chelator molecules/monoclonal antibody. This solution is cooled to 4° C., and 240 μl is removed (4.4 mg) and added to 2.33 mg of sulfo-NHS, where NHS=N-hydroxysuccinimide, which is obtained from Pierce Chemical Company. Then, 8 μl (0.21 mg) of N-methyl-N'-3-(dimethylaminopropyl)carbodiimide hydrochloride (EDC from Sigma) is added and stirred at 4° C. The pH is adjusted to 7.3 with 0.2 M $Na_2HPO_4$ (pH=9.2). The NHS-DOTA is then added to 8 mg of monoclonal antibody and incubated overnight at room temperature followed by purification of the DOTA conjugated antibody by gel filtration. The affinity of the HIRMAb for the HIR was measured with the ELISA as described in Example 10. The affinity of the DOTA conjugated antibody for the HIR is not significantly different from the unconjugated antibody, as shown in FIG. 43. DOTA-conjugated fusion antibodies can be prepared for radio-labeling with 111-indium and imaging of the target antigen in brain using standard external detection radio-imaging methods.

Example 16

Method of Manufacturing IgG Fusion Proteins

The transfection of a eukaryotic cell line with immunoglobulin G (IgG) genes generally involves the co-transfection of the cell line with separate plasmids encoding the heavy chain (HC) and the light chain (LC) comprising the IgG. In the case of an IgG fusion protein, the gene encoding the recombinant therapeutic protein may be fused to either the HC or LC gene. However, this co-transfection approach makes it difficult to select a cell line that has equally high integration of both the HC and LC-fusion genes, or the HC-fusion and LC genes. The preferred approach to manufacturing the fusion protein is the production of a cell line that is permanently transfected with a single plasmid DNA that contains all the required genes on a single strand of DNA, including the HC-fusion protein gene, the LC gene, the selection gene, e.g. neo, and the amplification gene, e.g. the dihydrofolate reductase gene. As shown in the diagram of the fusion protein tandem vector in FIG. 24, the HC-fusion gene, the LC gene, the neo gene, and the DHFR gene are all under the control of separate, but tandem promoters and separate but tandem transcription termination sequences. Therefore, all genes are equally integrated into the host cell genome, including the fusion gene of the therapeutic protein and either the HC or LC IgG gene.

Example 17

Treatment of Parkinsons Disease with a Fusion Antibody that Crosses the BBB

The neurodegeneration of Parkinson's disease (PD) is caused by the gradual accumulation of protein aggregates called Lewy bodies, which are derived from α-synuclein and parkin proteins. Accordingly, active immunization of patients with PD against proteins such as α-synuclein, or parkin, has been proposed. Active immunization of PD may likely encounter the same difficulties as in the active immunization of AD. If the BBB is not disrupted, then the anti-α-synuclein, or anti-parkin, antibodies in the blood that are generated with the immunization program will not cross the BBB, and not be able to access the protein aggregates in brain. Or, if the adjuvant administered in the active immunization program causes disruption of the BBB, then toxic side effects will be generated. A panel of monoclonal antibodies against α-synuclein or parkin can be generated, and the antibody that disaggregates Lewy bodies can be selected for production of a ScFv. A fusion antibody of the chimeric HIRMAb and the anti-α-synuclein ScFv can be produced for treatment of PD.

Example 18

Treatment of Huntington's Disease with a Fusion Antibody that Crosses the BBB

The neurodegeneration of Huntington's disease (HD) is caused by the gradual accumulation of protein aggregates, which are derived from the huntingtin protein. Active immunization of patients with HD against the huntingtin protein has been proposed. Active immunization of HD against the huntingtin protein may likely encounter the same difficulties as in the active immunization of AD. If the BBB is not disrupted, then the anti-huntingtin antibodies in the blood that are generated with the immunization program will not cross the BBB, and not be able to access the huntingtin aggregates in brain. Or, if the adjuvant administered in the active immunization program causes disruption of the BBB, then toxic side effects will be generated. A panel of monoclonal antibodies against the huntingtin protein can be generated, and the antibody that disaggregates huntingtin aggregates can be selected for production of an ScFv. A fusion antibody of the chimeric HIRMAb and the anti-huntingtin ScFv can be produced for treatment of HD.

Example 19

Treatment of Mad Cow Disease with a Fusion Antibody that Crosses the BBB

The neurodegeneration of mad cow disease is caused by the gradual accumulation of protein aggregates, which are derived from the prion protein (Prp). Active immunization of patients with mad cow disease against the prp protein has been proposed. Active immunization of patients with mad cow disease against the Prp protein may likely encounter the same difficulties as in the active immunization of AD. If the BBB is not disrupted, then the anti-prp antibodies in the blood that are generated with the immunization program will not cross the BBB, and not be able to access the prp aggregates in brain. Or, if the adjuvant administered in the active immunization program causes disruption of the BBB, then toxic side effects will be generated. A panel of monoclonal antibodies against the prp protein can be generated, and the antibody that disaggregates prp amyloid aggregates can be selected for production of an ScFv. A fusion antibody of the chimeric HIRMAb and the anti-prp ScFv can be produced for treatment of mad cow disease.

Example 20

Treatment of West Nile Encephalitis with a Fusion Antibody that Crosses the BBB

Figure 44:
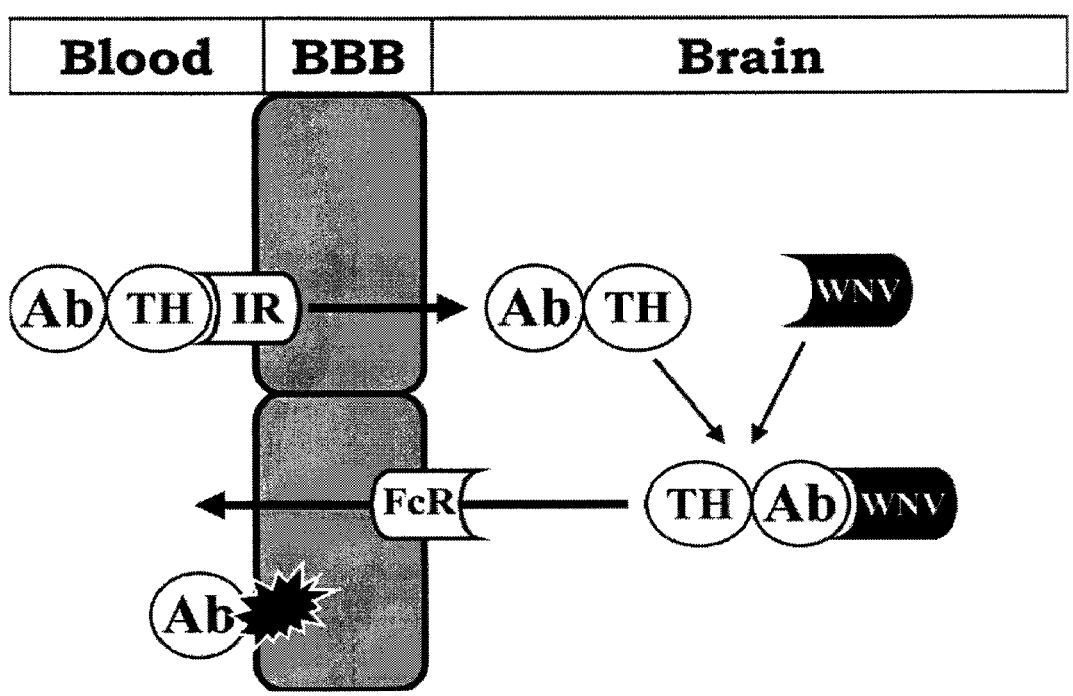
FIG. 44. The anti-WNV antibody (Ab) does not cross the blood-brain barrier (BBB). However, the anti-WNV Ab can cross the BBB following fusion to a molecular Trojan horse (TH), which is itself another antibody to the insulin receptor (IR). The TH undergoes receptor-mediated transport across the BBB via transport on the endogenous IR, and carries the anti-WNV Ab into the brain, where the Ab can neutralize the virus. The TH is also a ligand for the BBB Fc receptor (FcR), which allows for net export of the WNV from brain.

The West nile virus infects the brain and causes severe encephalitis. Antibodies directed against the envelope protein of the virus block viral replication. See, e.g., Chung, K. M., et al. (2006): "Antibodies against West Nile Virus (WNV) nonstructural protein NS 1 prevent lethal infection through Fc gamma receptor-dependent and -independent mechanisms," *J Virol*, 80: 1340-1351, incorporated herein by reference. However, such antibodies could not be used to treat the encephalitis of West nile virus infection, because the antibodies do not cross the BBB, as depicted in FIG. 44. Monoclonal antibodies against the West nile virus envelope (E) protein are particularly effective in neutralizing WNV infection of cells. A fusion antibody of the chimeric HIRMAb and the anti-envelope antibody can be produced for treatment of West Nile virus encephalitis. As depicted in FIG. 44, the fusion antibody first binds the BBB insulin receptor to trigger transport into brain, where the anti-WNV antibody part of the hybrid molecule then neutralizes the WNV in brain behind the BBB.

Figure 45:
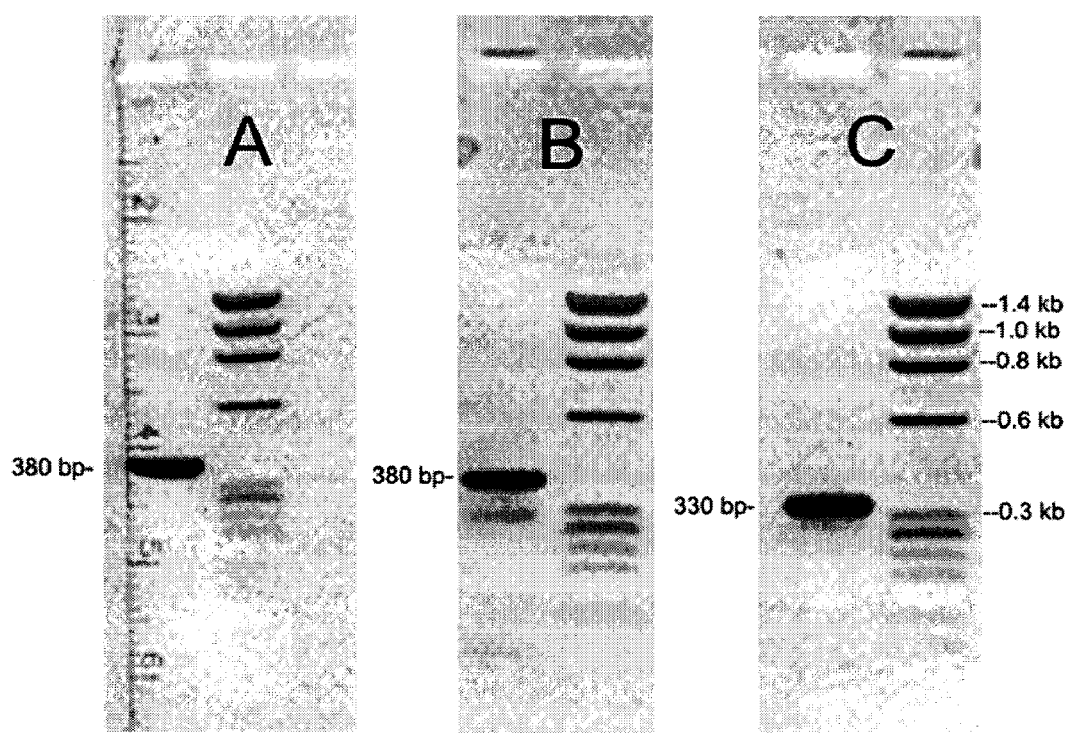
FIG. 45. Ethidium bromide stain of agarose gel electrophoresis of the PCR reaction following amplification of the anti-WNV VH (A), the anti-WNV VL (B), and the DIII (C). MW size standards on shown on the right. The VH, VL, and DIII cDNAs were produced by PCR with the ODNs shown in Tables 4, 5, and 6, respectively.

The synthetic gene encoding the VH of the E16 MAb against the E protein of the WNV was produced by PCR (FIG. 45A). The VH gene was constructed from a series of 8 oligodeoxynucleotides (ODNs), which were designed based on the sequence of the E16 MAb VH (Genbank DQ083997) and custom ordered, and the sequences of the ODNs producing the VH are given in Table 4, and in SEQ ID NOS 33-40. The sequences were designed so that there are alternating forward and reverse ODNs that cross-hybridize at the 5'- and 3'-termini of each ODN. The third letter codon is substituted to reduce the Tm of stable hairpin loops when needed. The overlapping ODNs are 75-88 nucleotides. (nt) with 24 nt overlap at each end. The synthetic VH gene is designed to include the appropriate restriction endonuclease (RE) sites, for subcloning of the VH into a single chain Fv (ScFv) expression vector, designated pCD-pScFv in FIG. 46. The VH of the E16 MAb was cloned by PCR as demonstrated by the ethidium bromide stain of an agarose gel following electrophoresis (FIG. 45A).

The PCR-generated anti-WNV VH cDNA (FIG. 45A) was subcloned into pCR-Script, maxi-prepped, and subjected to DNA sequencing in both directions with T7 and T3 sequencing primers. The results showed the VH gene was successfully cloned with the nucleotide sequence given in SEQ ID NO: 41. The predicted amino acid sequence of the anti-WNV VH is given in SEQ ID NO: 42 and in FIG. 47.

Figure 46:
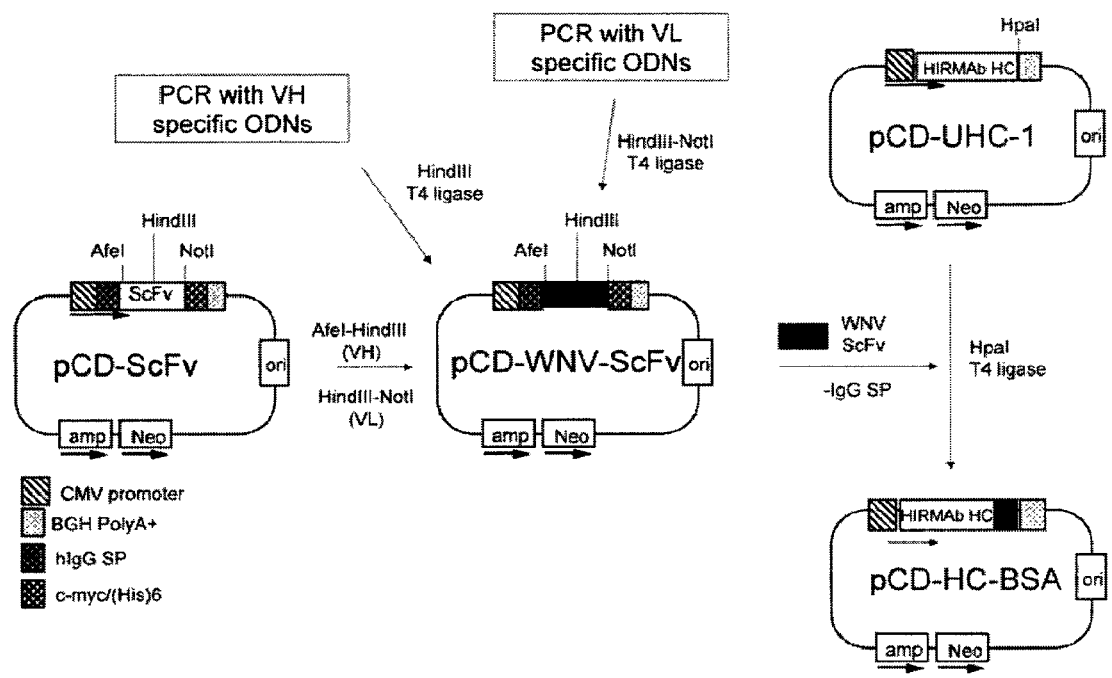
FIG. 46. Genetic engineering of COS cell expression plasmids for transient expression of anti-WNV ScFv, from pCD-WNV-ScFv, and anti-BSA heavy chain, from pCD-HC-BSA, respectively. The pCD-ScFv vector is an ScFv expression vector that enables fusion of a VH and VL via an intermediate 17-amino acid linker. 6×His tag disclosed as SEQ ID NO: 68.

In parallel, the gene encoding the VL of the E16 anti-WNV MAb was produced by PCR (FIG. 45B). The VL gene was constructed from a series of 8 ODNs, which were designed based on the sequence of the E16 MAb VL (Genbank DQ083998). The sequences of the custom ordered synthetic ODNs are given in Table 5, and in SEQ ID NOS 43-50. The synthetic VL gene is designed to include REs (HindIII, NotI) at the 5'- and 3'-termini for subcloning into the pCD-ScFv expression vector as shown in FIG. 46. The VL of the E16 MAb was cloned by PCR as demonstrated by the ethidium bromide stain of an agarose gel following electrophoresis (FIG. 45B).

The PCR-generated anti-WNV VL cDNA (FIG. 45B) was subcloned into pCR-Script, maxi-prepped, and subjected to DNA sequencing in both directions with T7 and T3 sequencing primers. The results showed the VL gene was successfully cloned with the nucleotide sequence given in SEQ ID NO: 51. The predicted amino acid sequence of the anti-WNV VL is given in SEQ ID NO: 52.

Having engineered the genes encoding the VH and VL of the anti-WNV antibody, it was then possible to engineer a new cDNA encoding a ScFv antibody, whereby the VH and VL formed a single polypeptide via a common peptide linker. To enable expression of the anti-WNV ScFv in host cells, an expression plasmid was engineered, designated pCD-ScFv. The pCD-ScFv vector is opened with AfeI and HindIII to release the non-related VH gene (FIG. 46). The VH generated by PCR (FIG. 45A) is digested with HindIII, and then ligated into the pCD-ScFv with T4 ligase, in frame with the eukaryotic signal peptide and the 17 amino acid linker joining the VH and VL in the pCD-ScFv vector (FIG. 46). The new pCD-ScFv, and the PCR generated VL, are digested with HindIII and NotI, and the VL is inserted into the vector with T4 ligase to produce pCD-WNV-ScFv, the anti-WNV ScFv expression vector (FIG. 46). Subcloning in the pCD-ScFv plasmid places the c-myc epitope of the 9E10 MAb at the carboxyl terminus of the ScFv; this epitope is comprised of the following 10-amino acid sequence: EQKLISEEDL (SEQ ID NO: 66). The presence of this sequence and the availability of the 9E10 anti-c-myc mouse MAb allows for detection of the anti-WNV ScFv by Western blotting. The pCD-ScFv expression plasmid also encodes a 6-histidine tag following the c-myc epitope, and the (His)6 (SEQ ID NO: 68) allows for purification by immobilized metal affinity chromatography following expression in COS cells. The nucleotide and amino acid sequence of the anti-WNV ScFV are given in SEQ ID NO: 53 and SEQ ID NO: 54, respectively (see FIG. 47 for amino acid sequence).

In order to assess the biological activity of the anti-WNV antibody, it was necessary to produce the portion of the E protein of the WNV that contains the epitope of the anti-WNV antibody. This epitope is contained within the DIII region between amino acids 296-401 of the viral E protein (Genbank NC001563). The DIII gene is produced by PCR, and was constructed from a series of 8 ODNs, which were designed and custom ordered, and the sequences of the ODNs producing the DIII gene are given in Table 6, and in SEQ ID NOS 55-62. The sequences were designed so that there are alternating forward and reverse ODNs that cross-hybridize at the 5'- and 3'-termini of each ODN. The PCR-generated DIII (FIG. 45C) was subcloned into pCR-Script, maxi-prepped, and subjected to DNA sequencing in both directions with T7 and T3 sequencing primers. The results showed the DIII gene was successfully cloned with the nucleotide sequence is given in SEQ ID NO: 63. The predicted amino acid sequence of the DIII protein is given in SEQ ID NO: 64.

The synthetic DIII gene is designed to include the appropriate restriction endonuclease (RE) sites, for subcloning of the DIII into a eukaryotic expression vector, designated pCD-DIII. For engineering of pCD-DIII, the pCD-ScFv (FIG. 46) is digested with NotI and EcoRI and gel purified to release the c-myc encoding sequence. In parallel, an artificial linker is produced with the following sequence: 5'-GCGGCCGCTG- GATCCCATCATCACCATCATCATTAAGAATTC-3' (SEQ ID NO: 67), and this linker is treated with NotI and EcoRI, and ligated into the opened pCD-ScFv to produce an intermediate plasmid, designated pCD-ScFvII. The latter is gel purified and digested with AfeI and NotI, and the NotI-digested DIII PCR product (FIG. 45C) is ligated into the intermediate plasmid to generate pCD-DIII.

Figure 47:
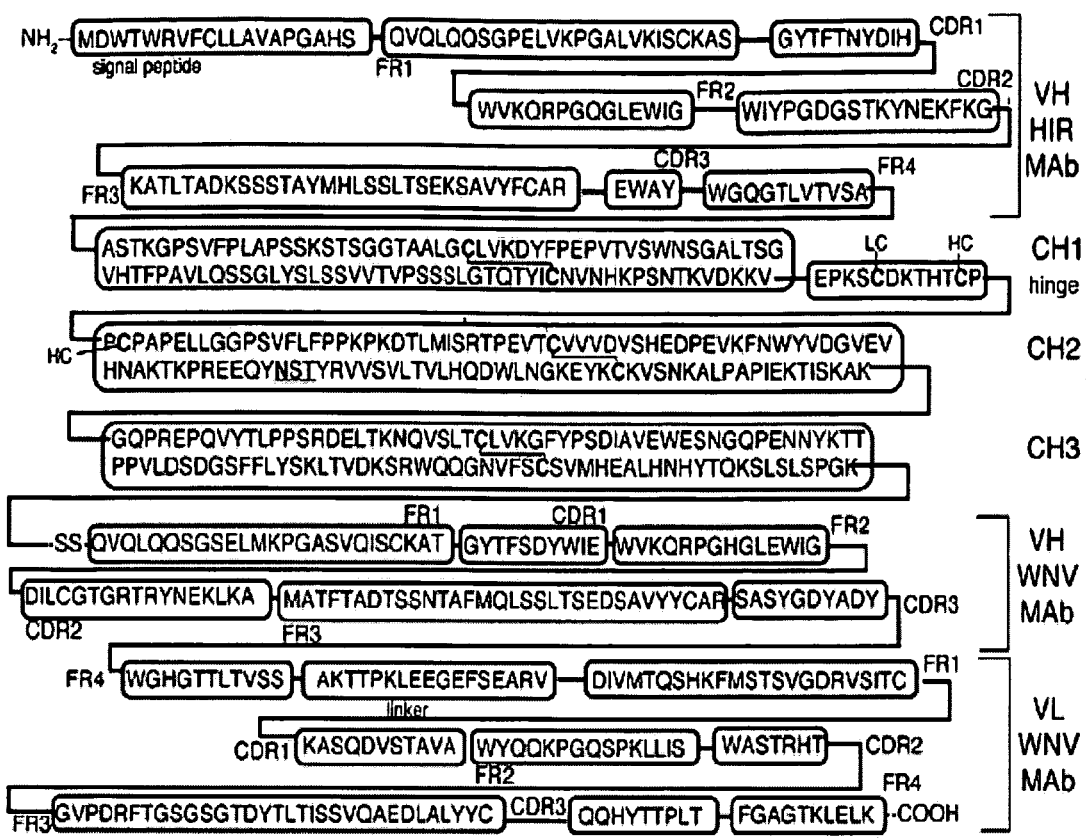
FIG. 47. Amino acid sequence of the heavy chain of the anti-WNV-fusion antibody (SEQ ID NO: 65), which is comprised of the following domains: (i) IgG signal peptide, (ii) HIRMAb heavy chain variable region (VH), (iii) human IgG1 constant region, which is comprised of 4 sub-domains: CH1, hinge, CH2, and CH3, (iv) linker separating the HIRMAb heavy chain and the anti-WNV ScFv, (v) the anti-WNV ScFv heavy chain variable region (VH), (vi) a 17 amino acid linker separating the ScFv VH and VL, and (vii) the anti-WNV ScFv light chain variable region (VL). The complementarity determining regions (CDRs) of the HIRMAb and the anti-WNV antibody are indicated in the figure.
Figure 48:
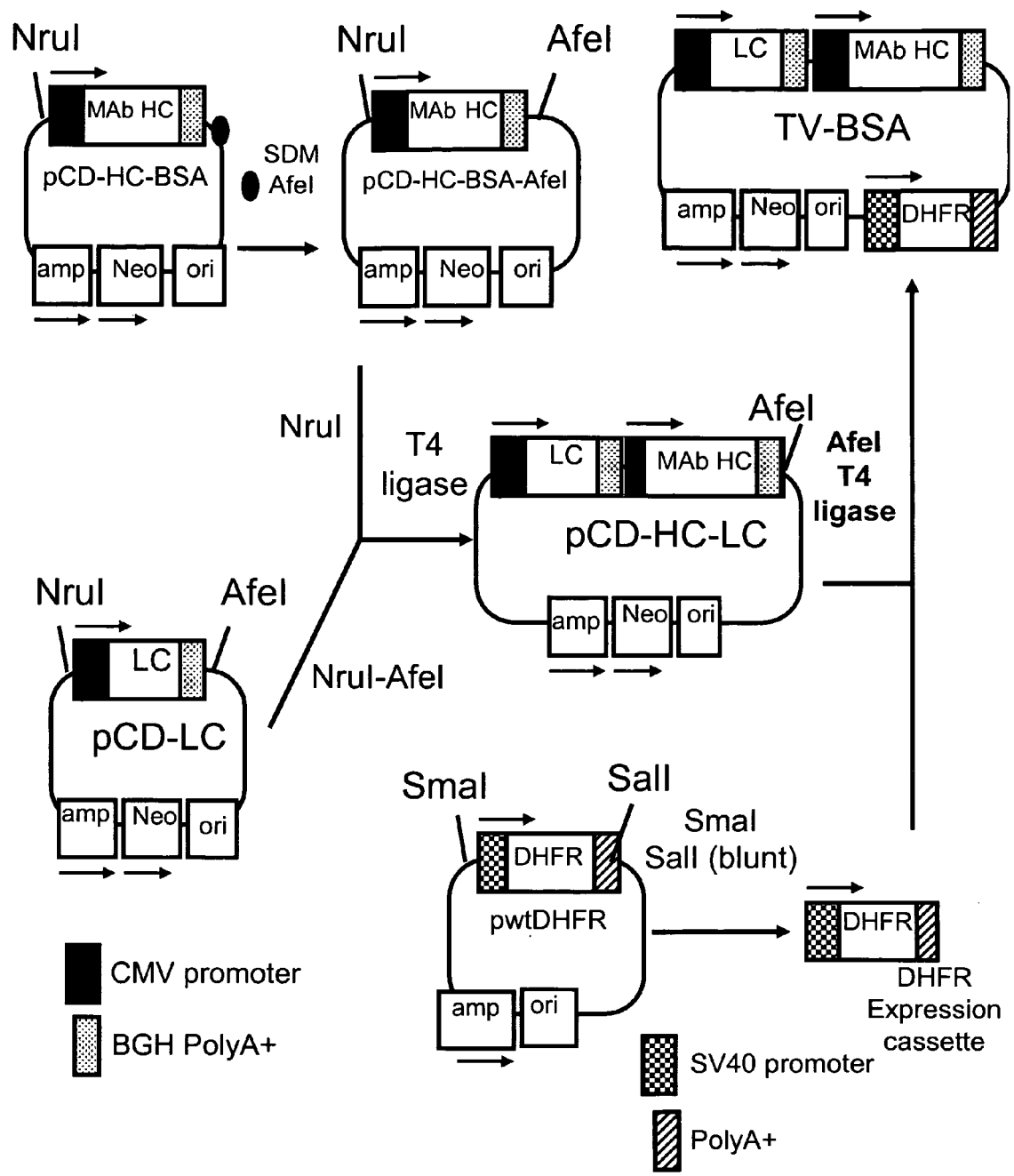
FIG. 48. Genetic engineering of CHO cell tandem vector for expression of the anti-WNV fusion antibody (BSA) from 3 precursor plasmids: the fusion heavy chain plasmid, pCD-HC-BSA, the light chain plasmid, pCD-LC, and the wild type (wt) dihydrofolate reductase (DHFR) plasmid, pwt DHFR.

The WNV ScFv cDNA, generated by PCR with the pCD-ScFv as template, and using primers that amplify only the ScFv and not the signal peptide, is subcloned into pCD-UHC to produce pCD-HC-BSA, as outlined in FIG. 46. The pCD-UHC encodes the heavy chain (HC) of the chimeric HIRMAb, under the influence of a human IgG signal peptide, and is linearized with HpaI (FIG. 46). This site is localized at the immediate 3'-end of the HC open reading frame, and enables fusion of the amino terminus of the anti-WNV ScFv to the carboxyl terminus of the CH3 domain of the human IgG1 constant region of the HIRMAb. The final heavy chain fusion protein is expressed by the pCD-HC-BSA vector shown in FIG. 46, which will encode the protein shown in FIG. 47. The amino acid sequence of the HC anti-WNV fusion heavy chain is given in SEQ ID NO: 65. The fusion heavy chain is comprised of the following domains, as shown in FIG. 47:

19 amino acid human IgG signal peptide
VH of the chimeric HIRMAb
Human IgG1 C-region comprised of the CH1, hinge, CH2, and CH3 regions
Ser-Ser linker
VH of the WNV MAb
17 amino acid linker
VL of the WNV MAb The intact fusion antibody that both crosses the BBB and neutralizes the WNV is a hetero-tetrameric molecule comprised of 2 heavy chains, shown in FIGS. 47, and 2 light chains, similar to the structure shown in FIG. 26. For permanent transfection of a eukaryotic host cell, for the manufacturing of the fusion antibody, Chinese hamster ovary (CHO) DG44 cells may be permanently transfected with separate expression plasmids encoding the fusion heavy chain (HC) and the HIRMAb light chain (LC). In addition, it is necessary to transfect the CHO cells with the dihydrofolate reductase (DHFR) gene to allow for isolation of high producing cell lines via amplification with methotrexate (MTX). In order to isolate a high producing CHO line, that has commercial value, and could meet market demand for the WNV BSA, it is necessary to include all 3 genes (HC, LC, DHFR) on a single piece of DNA, called a tandem vector (TV). The TV expressing the WNV fusion antibody is called TV-BSA, and is shown in FIG. 48. The TV-BSA is engineered from 3 precursor expression plasmids: pCD-HC, which is the HC fusion gene outlined in FIG. 46, pCD-LC, which is the HIRMAb LC expression plasmid, and pwtDHFR, which encodes the wild type (wt) murine DHFR. The TV-BSA will also encode the neomycin resistance gene (neo) for initial selection of transfected CHO lines with G418. The expression cassettes of the 3 genes include the following:

The HC cassette is comprised of the cytomegalovirus (CMV) promoter, followed by the HC fusion gene (which includes the ScFv fused to the 3'-end of the HIRMAb HC), followed by the bovine growth hormone (BGH) polyA termination sequence The LC cassette is comprised of the CMV promoter, followed by the LC gene, followed by the BGH polyA termination sequence The DHFR cassette is comprised of the simian virus (SV) 40 promoter, followed by the murine DHFR, followed by the hepatitis B virus (HBV) polyA termination sequence.

The starting point of the genetic engineering of TV-BSA is the pCD-HC-BSA, as outlined in FIG. 48. Site directed mutagenesis (SDM) of pCD-HC-BSA is performed to introduce an AfeI site at the end of the BGH polyA+ site of clone pCD-HC-BSA using the Stratagene QuickChange kit with ODN primers as per the manufacturer's instructions. The intermediate plasmid named pCD-HC-BSA-AfeI is digested with NruI and treated with alkaline phosphatase to prevent reclosing. The LC expression cassette is released from the pCD-LC vector by double digestion with NruI and AfeI and gel-purified. The LC cassette is subcloned into the pCD-HC-WNV-AfeI at the NruI site to form the pCD-HC-LC intermediate plasmid (FIG. 48). The DHFR expression cassette, under the influence of the SV40 promoter, is isolated from the pwtDHFR plasmid by SmaI-SalI digestion and gel-purified with Qiagen gel extraction kit. The SalI end is filled with T4 DNA polymerase. The wtDHFR expression cassette is ligated in the pCD-HC-LC at the AfeI site to form the TV-BSA (FIG. 48). The identification of both AfeI-SDM and intermediate positive clones, as well as confirmation of their orientation, is done by restriction endonuclease mapping and DNA sequencing.

Following the genetic engineering of the TV-BSA, and validation by DNA sequencing, CHO cells may be permanently transfected by electroporation. Following amplification with MTX, and dilutional cloning, a high producing cell line may be isolated, and propagated in a bioreactor for mass manufacturing of the fusion antibody against the WNV. This fusion antibody would be the first monoclonal antibody therapeutic engineered to cross the BBB and neutralize the WNV. Without the ability to cross the BBB, an anti-WNV MAb cannot access the WNV behind the BBB. Within the sanctuary of the brain, provided by the BBB, the WNV may replicate within the brain until encephalitis produces severe morbidity and mortality.

TABLE 4

Oligodeoxynucleotides (ODNs) for Production of the anti-WNV VH

1) FWD-1 (75-mer)
SEQ ID NO: 33
CAGGTaCAGCTGCAGCAGTCTGGATCTGAGCTGATGAAGCCTGGGGCCTC
AGTaCAGATATCCTGCAAGGCTACT 2) REV-1 (87-mer)
SEQ ID NO: 34
CTCAAGGCCATGTCCAGGtCTCTGCTTTACCCACTCAATCCAGTAGTCAC
TGAATGTGTAGCCAGTAGCCTTGCAGGATATCTGtAC 3) FWD-2 (87-mer)
SEQ ID NO: 35
CAGAGaCCTGGACATGGCCTTGAGTGGATTGGAGATATTTTATGTGGAAC
TGGTAGAACTAGATACAATGAGAAGTTAAAaGCaATG 4) REV-2 (88-mer)
SEQ ID NO: 36
CAGATGTCAGGCTGCTtAGTTGCATGAAGGCTGTGTTGGAGGATGTATCT
GCAGTGAATGTGGCCATtGCtTTTAACTTCTCATTGTA 5) FWD-3 (87-mer)
SEQ ID NO: 37
TGCAACTaAGCAGCCTGACATCTGAGGACTCaGCaGTCTATTACTGTGCA
AGATCGGCaTCATATGGTGATTACGCTGACTACTGGG 6) REV-3 (77-mer)
SEQ ID NO: 38
TTCAAGCTTGGGTGTCGTTTTGGCTGAGGAGACTGTGAGAGTGGTGCCAT
GGCCCCAGTAGTCAGCGTAATCACCAT TABLE 4-continued Oligodeoxynucleotides (ODNs) for Production of the anti-WNV VH 7) 5'-PCR FWD (24-mer)
SEQ ID NO: 39
5'-phosphate-CAGGTaCAGCTGCAGCAGTCTGGA 8) 3'-PCR-REV (24-mer)
SEQ ID NO: 40
TTCAAGCTTGGGTGTCGTTTTGGC Lower case indicates the 3rd letter codon nucleotide substituted to reduce the Tm of stable hairpin loops to 30-46° C. Overlapping ODNs are 76-88 nt long with 24 nt overlap at both ends. All ODNs were reconfirmed by reverse testing, wherein the cDNA was constructed from the ODNs, and the former translated. The translated protein was identical to the expected one.

Lower case indicates the 3rd letter codon nucleotide substituted to reduce the Tm of stable hairpin loops to 30-46° C. Overlapping ODNs are 76-88 nt long with 24 nt overlap at both ends. All ODNs were reconfirmed by reverse testing, wherein the cDNA was constructed from the ODNs, and the former translated. The translated protein was identical to the expected one.

TABLE 5

Oligodeoxynucleotides (ODNs) for production of the anti-WNV VL 1) 165-LV-FWD-1 (76-mer)
SEQ ID NO: 43
TACAAGCTTGAAGAAGGTGAATTTTCAGAAGCACGCGTAGATATCGACAT
aGTGATGACCCAGTCTCACAAATTCA 2) 165-LV-REV-1 (88-mer)
SEQ ID NO: 44
GCAGTACTCACATCCTGACTGGCCTTGCAtGTtATGCTGACtCTGTCTCC
TACTGATGTGGACATGAATTTGTGAGACTGGGTCATCA 3) 165-LV-FWD-2 (88-mer)
SEQ ID NO: 45
GGCCAGTCAGGATGTGAGTACTGCTGTAGCaTGGTATCAACAAAAACCtG
GGCAATCTCCTAAACTACTCATTTCCTGGGCATCCACa 4) 165-LV-REV-2 (88-mer)
SEQ ID NO: 46
TGGTGAGAGTATAATCTGTCCCAGATCCACTGCCaGTGAAGCGATCgGGt
ACTCCtGTGTGCCGtGTGGATGCCCAGGAAATGAGTAG 5) 165-LV-FWD-3 (88-mer)
SEQ ID NO: 47
CTGGGACAGATTATACTCTCACCATCAGtAGTGTGCAGGCTGAAGACCTa
GCACTTTATTACTGTCAGCAACATTATACCACTCCCCT 6) 165-LV-REV-3 (78-mer)
SEQ ID NO: 48
GATGCGGCCGCAGCgTCAGCTTTCAGCTCCAGtTTGGTtCCAGCACCGAA
CGTGAGGGGAGTGGTATAATGTTGCTGA 7) 5'-PCR 165-VL-F
SEQ ID NO: 49
TACAAGCTTGAAGAAGGTGAATTTTC 8) 3'-PCR 165-VL-R
SEQ ID NO: 50
GATGCGGCCGCAGCgTCAGCTTTC Lower case indicates the 3rd letter codon nucleotide substituted to reduce the Tm of stable hairpin loops to 30-46° C. Overlapping ODNs are 76-88 nt long with 24 nt overlap at both ends. All ODNs were reconfirmed by reverse testing, wherein the cDNA was constructed from the ODNs, and the former translated. The translated protein was identical to the expected one.

Lower case indicates the 3rd letter codon nucleotide substituted to reduce the Tm of stable hairpin loops to 30-46° C. Overlapping ODNs are 76-88 nt long with 24 nt overlap at both ends. All ODNs were reconfirmed by reverse testing, wherein the cDNA was constructed from the ODNs, and the former translated. The translated protein was identical to the expected one.

TABLE 6

Oliogodeoxynucleotides (ODNs) for production of DIII of WNV E protein

1) DIII-FWD-1 (68-MER)
SEQ ID NO: 55
CAGCTGAAGGGAACAACATATGGAGTCTGCTCAAAAGCTTT
CAAATTCGCTAGGACTCCCGCTGACAC

2) DIII-REV-1 (80-MER)
SEQ ID NO: 56
TGCAGGGACCGTCTGTTCCAGTATATTGCAGTTCCAACACC
ACAGTTCCATGTCCAGTGTCAGCGGGAGTCCTAGCGAAT

3) DIII-FWD-2 (80-MER)
SEQ ID NO: 57
ATACTGGAACAGACGGTCCCTGCAAAGTGCCCATTTCTTCC
GTAGCTTCCCTGAATGACCTCACACCTGTTGGAAGACTG

4) DIII-REV-2 (80-MER)
SEQ ID NO: 58
TCAATCAAAACCTTCGAGTTGGCTGTGGCTACAGACACAAA
TGGATTCACGGTCACCAGTCTTCCAACAGGTGTGAGGTC

5) DIII-FWD-3 (80-MER)
SEQ ID NO: 59
AGCCAACTCGAAGGTTTTGATTGAACTCGAACCCCCGTTTG
GTGACTCTTACATCGTGGTGGGAAGAGGAGAACAGCAGA

6) DIII-REV-3 (70-MER)
SEQ ID NO: 60
GTAGCGGCCGCAGCATCAGCTCCAGATTTGTGCCAGTGATG
GTTTATCTGCTGTTCTCCTCTTCCCACCA 7) 5'-PCR DIII-FWD (25-MER)
SEQ ID NO: 61
CAGCTGAAGGGAACAACATATGGAG 8) 5'-PCR DIII-REV (24-MER)
SEQ ID NO: 62
GTAGCGGCCGCAGCATCAGCTCCAG

Example 21

Treatment of Neuro-Aids with an Antibody that Crosses the BBB

The human immunodeficiency virus (HIV) causes acquired immune deficiency syndrome (AIDS), and the HIV infects the brain to cause dementia and other symptoms of neuro-AIDS. The tumor necrosis factor (TNF)-related apoptosis-inducing ligand (TRAIL) induces neuronal death in neuro-AIDS, and administration of an anti-TRAIL antibody blocks the neuronal apoptosis in the HIV-infected brain following systemic administration of lipopolysaccharide, which causes BBB disruption. However, disrupting the BBB is not a safe method for administration of antibodies to the brain, because serum proteins are toxic to the brain. A fusion antibody of the chimeric HIRMAb and the anti-TRAIL ScFv antibody can be produced for treatment of neuro-AIDS. The treatment of AIDS infection of the brain could also use an anti-carbohydrate, or anti-glycan antibody. Monoclonal antibodies against the carbohydrate portion of Schistosoma mansoni are potent inhibitors of HIV proliferation. A fusion antibody of the chimeric HIRMAb and the anti-glycan antibody can be produced for the treatment of viral infection of the brain, including HIV-1 infection of the brain.

Example 22

Treatment of Brain or Spinal Cord Injury or Stroke with Fusion Antibody that Crosses the BBB The recovery of the damaged brain following brain injury, spinal cord injury, or stroke is inhibited by a naturally occurring protein in the brain, nogo-A. Inhibition of nogo-A by a monoclonal antibody increases the functional recovery following brain damage. See, e.g., Buchli, A. D. and Schwab, M. E. (2005): Inhibition of Nogo: a key strategy to increase regeneration, plasticity and functional recovery of the lesioned central nervous system. Ann Med, 37: 556-567, incorporated herein by reference. The BBB is disrupted as the brain heals following injury, and systemically administered anti-nogo-A antibodies might penetrate the brain during this time window. However, the BBB closes following the period of BBB disruption, and during this time it is still necessary to inhibit endogenous nogo-A in the brain. A fusion antibody of the chimeric HIRMAb and an anti-nogo-A antibody can be produced for treatment of the recovery period from brain injury, spinal cord injury, or stroke.

Example 23

Treatment of Cancer Metastatic to the Brain with a Fusion Antibody that Crosses the BBB The growth of HER2-positive breast cancer cells is inhibited by a monoclonal antibody against HER2. Breast cancer often metastasizes to the brain, where the breast cancer cells reside behind the BBB. In this setting, the anti-HER2 antibodies are not able to inhibit growth of the breast cancer in the brain, because the antibodies do not cross the BBB. See, e.g., Duchnowska, R. and Szczylik, C. (2005): Central nervous system metastases in breast cancer patients administered trastuzumab. Cancer Treat Rev, 31: 312-318, incorporated herein by reference. A fusion antibody of the chimeric HIRMAb and an anti-HER2 antibody can be produced for treatment of metastatic breast cancer of the brain. Other epithelial cancers, such as small cell lung cancer (SCLC) express tumor-associated antigens (TAA) that are glycolipids or gangliosides. Monoclonal antibodies against the TAA glycolipids induce apoptosis and suppress cell growth of SCLC. A fusion antibody of the chimeric HIRMAb and an anti-glycolipid antibody can be produced for treatment of the metastatic cancer of the brain.

Example 24

Treatment of Brain Cancer with a Fusion Antibody that Crosses the BBB

The growth of brain cancer cells is stimulated by certain trophic factors such as epidermal growth factor (EGF) or hepatocyte growth factor (HGF). Inhibition of either EGF or HGF is a treatment strategy for brain cancer, and these growth factors are inhibited by growth factor-specific monoclonal antibodies. However, the antibodies do not cross the BBB, which is intact in brain cancer. Consequently, the systemic administration of an anti-trophic factor antibody does not suppress growth of intra-cranial brain cancer. See, e.g., Sampson, J. H., et al. (2000): Unarmed, tumor-specific monoclonal antibody effectively treats brain tumors. Proc Natl Acad Sci USA, 97: 7503-7508, incorporated herein by reference. A fusion antibody of the chimeric HIRMAb and an anti-growth factor antibody can be produced for treatment of brain cancer.

Example 25

Treatment of Multiple Sclerosis with a Fusion Antibody that Crosses the BBB Multiple sclerosis (MS) is associated with the loss of myelin in the brain. Therapy of MS aims to increase remyelination, which can be promoted by monoclonal antibodies directed against oligodendrocyte surface antigens. See, e.g., Warrington, A. E., et al. (2000): Human monoclonal antibodies reactive to oligodendrocytes promote remyelination in a model of multiple sclerosis. *Proc Natl Acad Sci USA*, 97: 6820-6825, incorporated herein by reference. Although the BBB may become disrupted in MS, this disruption is intermittent. A fusion antibody of the chimeric HIRMAb and an anti-human oligodendrocyte surface antigen antibody can be produced for treatment of MS.

Example 26

Treatment of Brain Disease with a Fusion Antibody that Crosses the BBB Preferentially in the Blood to Brain Direction In the treatment of brain aggregate disease, such as Alzheimers disease, Parkinsons disease, Huntingtons disease, or mad cow disease, the intent is to clear from the brain the aggregated protein, via efflux across the BBB via the BBB FcR (FIG. 27). However, in the case of other brain diseases, such as taught in Examples 20-25, the intent is to prolong the residence time of the antibody therapeutic in brain. In this case, the efflux of the fusion antibody from brain can be minimized by eliminating the part of the fusion antibody that is the binding site of the BBB FcR efflux system, which is found in the regions encompassing CH1, CH2, and CH3 shown in FIGS. 25 and 26. In this case, the genes encoding the heavy chain of the fusion antibody can be engineered so as to eliminate any or all parts of the CH 1, CH2, or CH3 regions of the heavy chain. The ScFv protein can be fused to the carboxyl terminus of the CH3 region, as outlined in FIGS. 25-26, or the ScFv protein can be fused to the carboxyl terminus of the hinge, CH1, or CH2 regions of the heavy chain.

Example 27

Diagnosis of Aizheimers Disease with a Blood Test Based on Measurement of Fusion Antibody-Aβ Complexes The administration of the fusion antibody to patients with AD is expected to lead to the formation in blood of complexes between the fusion antibody and the Aβ peptide, following efflux of the complex from brain to blood, as depicted in FIG. 27. Such complexes should form in greater quantities in the patient with amyloid build-up in the brain, which is specific for either AD, or pre-AD conditions, such as mild cognitive impairment. The amyloid in brain that causes AD is known to accumulate for years before the onset of symptoms. Therefore, the formation of increased complexes between the fusion antibody and Aβ, following the administration of the fusion antibody could lead not only to the detection of active AD, but also to the detection of individuals at risk for the later development of AD. The fusion antibody-Aβ complex in human blood could be quantitated with a sandwich based ELISA using standard methodology. In one such embodiment of the assay, an anti-Aβ antibody could be plated, followed by capture of the fusion antibody-Aβ complex. Since the fusion antibody binds to the amino terminal portion of Aβ, then the capture antibody would be selected so that there is binding to the carboxyl terminal portion of Aβ, similar to that used in the disaggregation assay shown in FIG. 42A, and discussed in Example 14. The second antibody in the sandwich assay could be an anti-human IgG antibody, as illustrated in FIG. 42A, and Example 14.

Example 28

Treatment of Brain Cancer with Fusion Antibody Radiopharmaceuticals

Brain cancers over-express certain surface antigens as compared to normal brain, and one approach to the radiotherapy of brain cancer is the administration of a MAb therapeutic that is conjugated with a radionuclide, such as $^{211}$At-labelled anti-tenascin MAb. See, e.g., McLendon R. E. et al. (1999): Radiotoxicity of systemically administered 211 At-labeled human/mouse chimeric monoclonal antibody: a long-term survival study with histologic analysis. *Int. J. Radiation Oncology Biol. Phys.* 45: 491-499, incorporated herein by reference. To facilitate transport of the MAb therapeutic across the BBB, a radionuclide-conjugated fusion antibody can be produced, which is comprised of the chimeric HIRMAb and a MAb directed against a brain tumor-associated antigen. The exposure of normal brain to the radiation can be eliminated by conjugating the fusion antibody with a non-radioactive radionuclide, such as $^{10}$B. Following administration of the $^{10}$B-labeled fusion antibody, and efflux of the antibody from normal brain, the brain tumor may be selectively irradiated with low energy thermal neutrons, which generates local alpha ray-irradiation of the brain cancer. See, e.g., Barth, R. F. et al. (1999): Boron neutron capture therapy of brain tumors: an emerging therapeutic modality. *Neurosurg.* 44: 433-451, incorporated herein by reference.

While preferred embodiments of the present invention have been shown and described herein, it is to be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A nucleic acid encoding a fusion antibody that:
   (i) comprises a first antibody and a second antibody, wherein the first antibody is an ScFv that is covalently linked to the carboxy terminus of either the heavy or light chain of the second antibody;
   (ii) is capable of crossing the blood-brain barrier (BBB) from the blood to the brain by binding to an endogenous BBB receptor-mediated transport system;
   (iii) comprises an Fc region that enables crossing the BBB from the brain to the blood by binding to an Fc receptor; and
   (iv) interacts with a pathological substance associated with a brain disorder, wherein the ScFv retains an average of at least about 20% of its activity compared to its activity as a separate entity.

2. The nucleic acid of claim 1, wherein the second antibody comprises a $CH_2$ region, a $CH_3$ region, and a VH region.

3. The nucleic acid of claim 2, wherein the ScFv is covalently linked to the carboxyl terminus of the $CH_3$ region.

4. The nucleic acid of claim 2, wherein the VH region is a VH region derived from an antibody that binds to an endogenous receptor of the BBB.

5. The nucleic acid of claim 4, wherein the VH region is derived from an antibody that is generated in vivo or by a recombinant method.

6. The nucleic acid of claim 5, wherein the recombinant method comprises selection of libraries of recombinant antibodies in phage or vectors.

7. The nucleic acid of claim 1, wherein the ScFv is generated in vivo or by a recombinant method.

8. The nucleic acid of claim 7, wherein the recombinant method comprises selection of libraries of recombinant antibodies in phage or vectors.

9. The nucleic acid of claim 1, wherein the ScFv interacts with a pathological substance associated with a brain disorder.

10. The nucleic acid of claim 1, wherein the second antibody interacts with a pathological substance associated with a brain disorder.

11. The nucleic acid of claim 1, wherein the endogenous BBB receptor-mediated transport system is selected from the group consisting of an insulin receptor, transferrin receptor, leptin receptor, lipoprotein receptor, and an insulin-like growth factor (IGF) receptor.

12. The nucleic acid of claim 11, wherein the endogenous BBB receptor-mediated transport system is the insulin receptor.

13. The nucleic acid of claim 1, wherein the brain disorder is a disorder selected from the group consisting of Alzheimer's disease, Parkinson's disease, Huntington's disease, bovine spongiform encephalopathy, West Nile virus encephalitis, Neuro-AIDS, brain injury, spinal cord injury, metastatic cancer of the brain, metastatic breast cancer of the brain, primary cancer of the brain, and multiple sclerosis.

14. The nucleic acid of claim 1, wherein the pathological substance is a protein.

15. The nucleic acid of claim 14, wherein the protein is selected from the group consisting of Aβ amyloid, α-synuclein, huntingtin protein, PrP prion protein, West Nile envelope protein, tumor necrosis factor (TNF) related apoptosis inducing ligand (TRAIL), Nogo A, HER2, epidermal growth factor receptor (EGFR), hepatocyte growth factor (HGF), and oligodendrocyte surface antigen.

16. The nucleic acid of claim 14, wherein the protein is Aβ amyloid.

17. The nucleic acid of claim 1, comprising the nucleotide sequence of SEQ ID NO: 11.

18. The nucleic acid of claim 1, comprising the nucleotide sequence of SEQ ID NO: 13.

19. The nucleic acid of claim 1, comprising the nucleotide sequence of SEQ ID NO: 15 or SEQ ID NO: 17.

20. The nucleic acid of claim 1, comprising the nucleotide sequence of SEQ ID NO: 19, SEQ ID NO: 21, SEQ ID NO: 23, or SEQ ID NO: 25.

21. The nucleic acid of claim 1, comprising the nucleotide sequence of SEQ ID NO: 27.

22. A tandem expression vector comprising (i) a first promoter sequence operably linked to an open reading frame corresponding to the nucleic acid sequence of claim 2; and (ii) a second promoter operably linked to a second open reading frame encoding an immunoglobulin light chain amino acid sequence comprising a CL region and a VL region.

23. A cell comprising the tandem expression vector of claim 22.

* * * * *

UNITED STATES PATENT AND TRADEMARK OFFICE
CERTIFICATE OF CORRECTION

| | | |
|---|---|---|
| PATENT NO. | : 8,759,297 B2 | Page 1 of 1 |
| APPLICATION NO. | : 11/841541 | |
| DATED | : June 24, 2014 | |
| INVENTOR(S) | : William M. Pardridge et al. | |

It is certified that error appears in the above-identified patent and that said Letters Patent is hereby corrected as shown below:

In the Specification:

In Column 1, line 20, replace "may have" with --has--

Signed and Sealed this
Ninth Day of September, 2014

Michelle K. Lee
*Deputy Director of the United States Patent and Trademark Office*